(12) United States Patent
Bjornson et al.

(10) Patent No.: US 9,617,310 B2
(45) Date of Patent: Apr. 11, 2017

(54) INHIBITORS OF HEPATITIS C VIRUS

(71) Applicant: Gilead Sciences, Inc., Foster City, CA (US)

(72) Inventors: Kyla L. Bjornson, San Lorenzo, CA (US); Kapil K. Karki, Foster City, CA (US); John O. Link, San Francisco, CA (US); Hyung-jung Pyun, Fremont, CA (US); Adam J. Schrier, Redwood City, CA (US); Kirk L. Stevens, Bothell, WA (US); James G. Taylor, San Mateo, CA (US); Randall W. Vivian, San Mateo, CA (US); Jeff Zablocki, Los Altos, CA (US); Sheila Zipfel, San Mateo, CA (US)

(73) Assignee: Gilead Sciences, Inc., Foster City, CA (US)

( * ) Notice: Subject to any disclaimer, the term of this patent is extended or adjusted under 35 U.S.C. 154(b) by 63 days.

(21) Appl. No.: 14/214,477

(22) Filed: Mar. 14, 2014

(65) Prior Publication Data

US 2014/0274884 A1 Sep. 18, 2014

Related U.S. Application Data

(60) Provisional application No. 61/798,961, filed on Mar. 15, 2013.

(51) Int. Cl.
| | |
|---|---|
| *C07D 498/22* | (2006.01) |
| *A61K 31/437* | (2006.01) |
| *A61K 31/519* | (2006.01) |
| *A61K 31/4985* | (2006.01) |
| *A61P 31/14* | (2006.01) |
| *C07K 7/64* | (2006.01) |
| *C07D 487/00* | (2006.01) |
| *C07D 487/02* | (2006.01) |
| *C07D 203/02* | (2006.01) |

(52) U.S. Cl.
CPC ............. *C07K 7/64* (2013.01); *A61K 31/437* (2013.01); *A61K 31/519* (2013.01); *C07D 203/02* (2013.01); *C07D 487/00* (2013.01); *C07D 487/02* (2013.01); *C07D 498/22* (2013.01)

(58) Field of Classification Search
None
See application file for complete search history.

(56) References Cited

U.S. PATENT DOCUMENTS

| | | | |
|---|---|---|---|
| 7,041,698 B2 | 5/2006 | Ripka et al. | |
| 7,879,797 B2 | 2/2011 | Holloway et al. | |
| RE42,375 E | 5/2011 | Nakajima et al. | |
| 7,973,040 B2 * | 7/2011 | Harper | C07K 5/0808 514/250 |
| 8,030,307 B2 | 10/2011 | Moore et al. | |
| 8,080,654 B2 | 12/2011 | Harper et al. | |
| 8,106,059 B2 | 1/2012 | Holsinger et al. | |
| 8,106,187 B2 | 1/2012 | Scalone et al. | |
| 8,119,592 B2 | 2/2012 | Beigelman et al. | |
| 8,163,693 B2 | 4/2012 | Chen et al. | |
| 8,163,921 B2 | 4/2012 | Sin et al. | |
| 8,178,491 B2 * | 5/2012 | Cho et al. | 514/3.7 |
| 8,178,520 B2 | 5/2012 | Di Francesco et al. | |
| 8,211,891 B2 | 7/2012 | Gai et al. | |
| 8,216,999 B2 | 7/2012 | Holloway et al. | |
| 8,263,549 B2 | 9/2012 | Moore et al. | |
| 8,349,869 B2 | 1/2013 | Simmen et al. | |
| 8,362,035 B2 | 1/2013 | Berkenbusch et al. | |
| 8,420,596 B2 | 4/2013 | Ku et al. | |
| 8,431,733 B2 | 4/2013 | Dener | |
| 8,445,430 B2 | 5/2013 | Zhang et al. | |

(Continued)

FOREIGN PATENT DOCUMENTS

| | | |
|---|---|---|
| EP | 1343807 B1 | 4/2009 |
| EP | 1924593 B9 | 9/2009 |

(Continued)

OTHER PUBLICATIONS

Arasappan, et al., "Discovery of Narlaprevir (SCH 900518): A Potent, Second Generation HCV NS3 Serine Protease Inhibitor," *ACS Med. Chem. Lett.*, 1: 64-69 (2010).
Chen, et al., "Discovery of Small Molecule Inhibitors of HCV N53-4A Protease as Potential Therapeutic Agents against HCV Infection," *Current Medicinal Chemistry*, 12, 2317-2342 (2005).
Ciesek, et al., "Second-wave Protease Inhibitors: Choosing an Heir," *Clin Liver Dis*, doi: 10.1016/j.cld.2011.05.014 (2011).
Cummings, et al., "Induced-Fit Binding of the Macrocyclic Noncovalent Inhibitor TMC435 to its HCV NS3/NS4A Protease Target," *Angew. Chem. Int. Ed.*, 49: 1652-1655 (2010).

(Continued)

*Primary Examiner* — Marcela M Cordero Garcia
*Assistant Examiner* — Catherine Mader
(74) *Attorney, Agent, or Firm* — Sheppard Mullin Richter & Hampton LLP

(57) ABSTRACT

Compounds of formula I:

or pharmaceutically acceptable salts thereof, wherein the various substituents are defined herein, methods of using said compounds, and pharmaceutical compositions containing said compounds.

4 Claims, No Drawings

(56) References Cited

U.S. PATENT DOCUMENTS

| | | |
|---|---|---|
| 8,461,107 B2 | 6/2013 | Liverton et al. |
| 8,530,497 B2 | 9/2013 | Yang et al. |
| 8,563,505 B2 | 10/2013 | Hiebert et al. |
| 2004/0077551 A1 | 4/2004 | Campbell et al. |
| 2007/0027071 A1 | 2/2007 | Holloway et al. |
| 2009/0005387 A1 | 1/2009 | Niu et al. |
| 2009/0258891 A1 | 10/2009 | Di Francesco et al. |
| 2009/0269305 A1 | 10/2009 | Seiwert et al. |
| 2009/0274652 A1 | 11/2009 | Sin et al. |
| 2009/0274657 A1 | 11/2009 | Gai et al. |
| 2010/0003214 A1 | 1/2010 | Gai et al. |
| 2010/0029666 A1 | 2/2010 | Harper et al. |
| 2010/0099695 A1 | 4/2010 | Liverton et al. |
| 2010/0124545 A1 | 5/2010 | Zhang et al. |
| 2010/0150866 A1 | 6/2010 | Wang et al. |
| 2010/0160403 A1 | 6/2010 | Link et al. |
| 2010/0183551 A1 | 7/2010 | Harper et al. |
| 2010/0298210 A1 | 11/2010 | Liverton et al. |
| 2011/0002884 A1 | 1/2011 | McCauley et al. |
| 2011/0028494 A1 | 2/2011 | Holloway et al. |
| 2011/0123496 A1 | 5/2011 | Gai et al. |
| 2011/0224134 A1 | 9/2011 | Harper et al. |
| 2012/0034187 A1 | 2/2012 | Llinas-Brunet et al. |
| 2012/0070416 A1 | 3/2012 | Or et al. |
| 2012/0094897 A1 | 4/2012 | Buckman et al. |
| 2012/0095211 A1 | 4/2012 | Buckman et al. |
| 2012/0101031 A1 | 4/2012 | Chen et al. |
| 2012/0101032 A1 | 4/2012 | Buckman et al. |
| 2012/0101049 A1 | 4/2012 | Chen et al. |
| 2012/0121624 A1 | 5/2012 | Liverton et al. |
| 2012/0190866 A1 | 7/2012 | Cho et al. |
| 2012/0230949 A1 | 9/2012 | Perrone et al. |
| 2012/0232247 A1 | 9/2012 | Song et al. |
| 2013/0017991 A1 | 1/2013 | Niu et al. |
| 2013/0115190 A1 | 5/2013 | Hiebert et al. |
| 2013/0129671 A1 | 5/2013 | Sun et al. |
| 2013/0131105 A1 | 5/2013 | Petter et al. |
| 2013/0142754 A1 | 6/2013 | Rajamani et al. |
| 2013/0144036 A1 | 6/2013 | Gai et al. |
| 2013/0178413 A1 | 7/2013 | McCauley et al. |
| 2013/0274463 A1 | 10/2013 | Chen et al. |
| 2014/0017198 A1 | 1/2014 | Bjornson et al. |

FOREIGN PATENT DOCUMENTS

| | | |
|---|---|---|
| EP | 2331552 B1 | 6/2011 |
| EP | 2331553 B1 | 5/2013 |
| EP | 2079480 B1 | 6/2013 |
| EP | 2382198 B1 | 7/2013 |
| EP | 2250174 B1 | 8/2013 |
| WO | WO 03/099316 A1 | 12/2003 |
| WO | WO 2004/093798 A2 | 11/2004 |
| WO | WO 2004/094452 A2 | 11/2004 |
| WO | WO 2005/051410 A1 | 6/2005 |
| WO | WO 2006/020276 A2 | 2/2006 |
| WO | WO 2006/020276 A3 | 2/2006 |
| WO | WO 2006/119061 A2 | 11/2006 |
| WO | WO 2007/001406 A2 | 1/2007 |
| WO | WO 2007/014926 A1 | 2/2007 |
| WO | WO 2007/015824 A2 | 2/2007 |
| WO | WO 2007/015824 A3 | 2/2007 |
| WO | WO 2007/016441 A1 | 2/2007 |
| WO | WO 2007/044893 A2 | 4/2007 |
| WO | WO 2007/044933 A1 | 4/2007 |
| WO | WO 2007/131966 A1 | 11/2007 |
| WO | WO 2007/148135 A1 | 12/2007 |
| WO | WO 2008/005511 A2 | 1/2008 |
| WO | WO 2008/051475 A2 | 5/2008 |
| WO | WO 2008/051477 A2 | 5/2008 |
| WO | WO 2008/051514 A2 | 5/2008 |
| WO | WO 2008/057208 A2 | 5/2008 |
| WO | WO 2008/057209 A1 | 5/2008 |
| WO | WO 2008/134397 A1 | 11/2008 |
| WO | WO 2008/137779 A2 | 11/2008 |
| WO | WO 2008/141227 A1 | 11/2008 |
| WO | WO 2009/005676 | 1/2009 |
| WO | WO 2009/010804 A1 | 1/2009 |
| WO | WO 2009/055335 A2 | 4/2009 |
| WO | WO 2009/064975 A1 | 5/2009 |
| WO | WO 2009/070692 A1 | 6/2009 |
| WO | WO 2009/073719 A1 | 6/2009 |
| WO | WO 2009/079353 A1 | 6/2009 |
| WO | WO 2009/082697 A1 | 7/2009 |
| WO | WO 2009/094443 A1 | 7/2009 |
| WO | WO 2009/108507 A1 | 9/2009 |
| WO | WO 2009/117594 A1 | 9/2009 |
| WO | WO 2009/134624 A1 | 11/2009 |
| WO | WO 2009/134987 A1 | 11/2009 |
| WO | WO 2010/011566 A1 | 1/2010 |
| WO | WO 2010/021717 A2 | 2/2010 |
| WO | WO 2010/030359 A2 | 3/2010 |
| WO | WO 2010/033466 A1 | 3/2010 |
| WO | WO 2010/036551 A1 | 4/2010 |
| WO | WO 2010/036896 A1 | 4/2010 |
| WO | WO 2010/045266 A1 | 4/2010 |
| WO | WO 2010/048468 A1 | 4/2010 |
| WO | WO 2010/065577 A1 | 6/2010 |
| WO | WO 2010/068761 A2 | 6/2010 |
| WO | WO 2010/080389 A1 | 7/2010 |
| WO | WO 2010/132163 A1 | 11/2010 |
| WO | WO 2010/135748 A1 | 11/2010 |
| WO | WO 2011/014487 A1 | 2/2011 |
| WO | WO 2011/038293 A1 | 3/2011 |
| WO | WO 2011/041551 A1 | 4/2011 |
| WO | WO 2011/049908 A2 | 4/2011 |
| WO | WO 2011/112558 A2 | 9/2011 |
| WO | WO 2011/156337 A1 | 12/2011 |
| WO | WO 2012/019299 A1 | 2/2012 |
| WO | WO 2012/037259 A1 | 3/2012 |
| WO | WO 2012/040040 A1 | 3/2012 |
| WO | WO 2012/040167 A1 | 3/2012 |
| WO | WO 2012/040242 A1 | 3/2012 |
| WO | WO 2012/047764 A1 | 4/2012 |
| WO | WO 2012/054874 A1 | 4/2012 |
| WO | WO 2012/061248 A2 | 5/2012 |
| WO | WO 2012/092409 A2 | 7/2012 |
| WO | WO 2012/092411 A2 | 7/2012 |
| WO | WO 2012/171332 A1 | 12/2012 |
| WO | WO 2012/173983 A1 | 12/2012 |
| WO | WO 2012/176149 A1 | 12/2012 |
| WO | WO 2013/028465 A1 | 2/2013 |
| WO | WO 2013/066753 A1 | 5/2013 |
| WO | WO 2013/074386 A2 | 5/2013 |
| WO | WO 2013/106506 A1 | 7/2013 |
| WO | WO 2014/008285 | 1/2014 |

OTHER PUBLICATIONS

Duan, et al., "Discovery of Novel P3-oxo Inhibitor of Hepatitis C Virus NS3/4A Serine Protease," *Bioorganic & Medicinal Chemistry Letters*, doi: 10.1016/j.bmcl.2012.02.039 (2012).

Flores, et al., "HCV-NS3 Inhibitors: Determination of their Kinetic Parameters and Mechanism," *Biochimica et Biophysica Acta*, 1794: 1441-1448 (2009).

Foster, et al., "Telaprevir Alone or with Peginterferon and Ribavirin Reduces HCV RNA in Patients with Chronic Genotype 2 but Not Genotype 3 Infections," *Gastroenterology*, 141: 881-889 (2011).

Fusco, et al., "New Protease Inhibitors for HCVC—Help is on the way," *Journal of Hepatology*, 54: 1087-1089 (2011).

Gallo, et al., "Structural Characterization of the Hepatitis C Virus NS3 Protease from Genotype 3a: The Basis of the Genotype 1b vs. 3a Inhibitor Potency Shift," *Virology*, 405: 424-438 (2010).

Gottwein, et al., "Differential Efficacy of Protease Inhibitors Against HCV Genotypes 2a, 3a, 5a, and 6a NS3/4A Protease Recombinant Viruses," *Gastroenterology*, 141: 1067-1079 (2011).

Halfon, et al., "Hepatitis C Virus Resistance to Protease Inhibitors," *Journal of Hepatology*, 55: 192-206 (2011).

Harper, et al., "Discovery of MK-5172, a Macrocyclic Hepatitis C Virus NS3/4a Protease Inhibitor," *ACS Medicinal Chemistry Letters*, dx.doi.org/10.1021/ml300017p (2012).

Harper, et al., "Inhibitors of the Hepatitis C Virus NS3 Protease with Basic Amine Functionality at the P3-Amino Acid N-Terminus:

(56) References Cited

OTHER PUBLICATIONS

Discovery and Optimization of a New Series of P2-P4 Macrocycles," *J. Med. Chem.*, 52: 4820-4837 (2009).
Hinrichsen, et al., "Short-term Antiviral Efficacy of BILN 2061, a Hepatitis C Virus Serine Protease Inhibitor, in Hepatitis C Genotype 1 Patients," *Gastroenterology*, 127: 1347-1355 (2004).
Huang, et al., "Discovery of Hepatitis C Virus NS3-NS4A Complex Inhibitors," *Hepatitis C Antiviral Drug Discovery and Development*, edited by Seng-Lai Tan and Yupeng He, Caister Academic Press, Chapter 11, 215-235 (2011).
Imhof, et al., "Genotype Differences in Susceptibility and Resistance Development of Hepatitis C Virus to Protease Inhibitors Telaprevir (VX-950) and Danoprevir (ITMN-191)," *Hepatology*, 53: 1090-1099 (2011).
International Search Report and Written Opinion dated Nov. 5, 2013 from PCT/US2013/049119.
Lallos, et al., "In Vitro Resistance and Cross-Resistance Profiles of IDX320, a Potent Macrocyclic HCV Protease Inhibitor," 5th International Workshop on Hepatitis C—Resistance and New Compounds, Boston, Jun. 24-25, 2010.
Lenz, et al., "In Vitro Resistance Profile of the Hepatitis C Virus NS3/4A Protease Inhibitor TMC435," *Antimicrobial Agents and Chemotherapy*, 54(5): 1878-1887 (2010).
Lin, et al., "In Vitro Resistance Studies of Hepatitis C Virus Serine Protease Inhibitors, VX-950 and BILN 2061," *The Journal of Biological Chemistry*, 279(17): 17508-17514 (2004).
Lin, et al., "VX-950, a Novel Hepatitis C Virus (HCV) NS3-4A Protease Inhibitor, Exhibits Potent Antiviral Activities in HCV Replicon Cells," *Antimicrobial Agents and Chemotherapy*, 50(5): 1813-1822 (2006).
Liu-Young, et al., "Hepatitis C Protease and Polymerase Inhibitors in Development," *AIDS Patient Care and STDs*, 22(6): 449-457 (2008).
Liverton, et al., "MK-7009, a Potent and Selective Inhibitor of Hepatitis C Virus NS3/4A Protease," *Antimicrobial Agents and Chemotherapy*, 54(1): 305-311 (2010).
Liverton, et al, "Molecular Modeling Based Approach to Potent P2-P4 Macrocyclic Inhibitors of Hepatitis C NS3/4A Protease," *J. Am. Chem. Soc.* 130: 4607-4609 (2008).
Lu, et al., "Drug-target Residence Time: Critical Information for Lead Optimization," *Current Opinion in Chemical Biology*, 14: 467-474 (2010).
McCauley, et al., "Bismacrocyclic Inhibitors of Hepatitis C NS3/4a Protease," *Angew. Chem. Int. Ed.*, 47: 9104-9107 (2008).
McCauley, et al., "Discovery of Vaniprevir (MK-7009), a Macrocyclic Hepatitis C Virus NS3/4a Protease Inhibitor" J. Med. Chem., 53: 2443-2463 (2010).
Monteagudo, et al., "The Metabolism and Disposition of a Potent Inhibitor of Hepatitis C Virus NS3/4A Protease," *Xenobiotica*, 40(12): 826-839.
Moreau, et al., "Discovery of Hepatitis C Virus N53-4A Protease Inhibitors with Improved Barrier to Resistance and Favorable Liver Distribution," *Journal of Medicinal Chemistry*, dx.doi.org/10.1021/jm400121t (2013).
Nature Outlook Hepatitis C, 474(7350): S1-S21, Jun. 9, 2011.
Örtqvist, et al., "Structure-activity Relationships of HCV NS3 Protease Inhibitors Evaluated on the Drug-Resistant Variants A156T and D168V," *Antiviral Therapy*, 15: 841-852 (2010).
Paolucci, et al., "Naturally Occurring Mutations to HCV Protease Inhibitors in Treatment-naïve Patients," *Virology Journal*, 9(245): 1-8 (2012).

Paulson, et al., "Comparison of HCV NS3 Protease and NS5B Polymerase Inhibitor Activity in 1a, 1b and 2a Replicons and 2a Infectious Virus," *Antiviral Research*, 83: 135-142 (2009).
Pompei, et al., "Novel P2-P4 Macrocyclic Inhibitors of HCV NS3/4A Protease by P3 Succinamide Fragment Depeptidization Strategy," *Bioorganic & Medicinal Chemistry Letters*, 20: 168-174 (2010).
Raboisson, et al., "Structure-activity Relationship Study on a Novel Series of Cyclopentane-containing Macrocyclic Inhibitors of the Hepatitis C Virus NS3/4A Protease Leading to the Discovery of TMC435350," *Bioorganic & Medicinal Chemistry Letters*, 18, 4853-4858 (2008).
Reiser, et al., "Antiviral Efficacy of NS3-Serine Protease Inhibitor BILN-2061 in Patients with Chronic Genotype 2 and 3 Hepatitis C," *Hepatology*, 41(4): 832-835 (2005).
Rieger, et al., "Pharmacokinetic Analysis and Liver Concentrations of a Series of Macrocyclic Peptidomimetic Inhibitors of HCV NS3/4A Protease: Identification of ITMN-191, a Potent NS3/4A Protease Inhibitor with High Liver Exposure Across Multiple Species," Poster T1795, Digestive Disease Week, May 20-25, 2006, Los Angeles, CA.
Rönn, et al., "Exploration of Acyl Sulfonamides as Carboxylic Acid Replacements in Protease Inhibitors of the Hepatitis C Virus Full-length N53," *Bioorganic & Medicinal Chemistry*, 14: 544-559 (2006).
Rönn, et al., "Evaluation of a Diverse Set of Potential $P_1$ Carboxylic Acid Bioisosteres in Hepatitis C Virus NS3 Protease Inhibitors," *Bioorganic & Medicinal Chemistry*, 15: 4057-4068 (2007).
Rudd, et al., "Discovery of MK-1220: A Macrocyclic Inhibitor of Hepatitis C Virus NS3/4A Protease with Improved Preclinical Plasma Exposure," *ACS Med. Chem. Lett*, 2: 207-212 (2011).
Sarrazin, et al., "Antiviral Strategies in Hepatitis C Virus Infection," *Journal of Hepatology*, S88-S100 (2012).
Seiwert, et al., "Preclinical Characteristics of ITMN-191, an Orally Active Inhibitor of the HCV NS3/4A Protease Nominated for Preclinical Development," Poster #T1793, *Digestive Disease Week*, May 20-25, 2006, Los Angeles, CA.
Soriano, et al., "Directly Acting Antivirals Against Hepatitis C Virus," *J. Antimicrob. Chemother.*, 66: 1673-1686 (2011).
Summa, et al., "MK-5172, a Selective Inhibitor of Hepatitis C Virus NS3/4a Protease with Broad Activity across Genotypes and Resistant Variants," *Antimicrobial Agents and Chemotherapy*, 56(8): 4161-4167 (2012).
Tong, et al., "Impact of Naturally Occurring Variants of HCV Protease on the Binding of Different Classes of Protease Inhibitors," *Biochemistry*, 45(5): 1353-1361 (2006).
Tong, et al., "Preclinical Characterization of the Antiviral Activity of SCH 900518 (Narlaprevir), a Novel Mechanism-Based Inhibitor of Hepatitis C Virus NS3 Protease," *Antimicrobial Agents and Chemotherapy*, 54(6) 2365-2370 (2010).
Venkatraman, et al, "Macrocyclic Inhibitors of HCV NS3 Protease," Expert Opin. Ther. Patents, 19(9), 1277-1303 (2009).
Xue, et al., "Molecular Modeling Study on the Resistance Mechanism of HCV NS3/4A Serine Protease Mutants R155K, A156V and D168A to TMC435," *Antiviral Research*, 93: 126-137 (2012).
Zeng, et al., "Epimerization Reaction of a Substituted Vinylcyclopropane Catalyzed by Ruthenium Carbenes: Mechanistic Analysis," *J. Org. Chem.*, 71: 8864-8875 (2006).
International Search Report and Written Opinion dated Sep. 2, 2014 for PCT/US2014/029765, 13 pages.
International Preliminary Report on Patentability dated Sep. 24, 2015 for PCT/US2014/029765, 8 pages.

\* cited by examiner

INHIBITORS OF HEPATITIS C VIRUS

CROSS REFERENCE TO RELATED APPLICATIONS

This application claims the benefit under 35 U.S.C. §119 (e) to U.S. Provisional Application No. 61/798,961, filed on Mar. 15, 2013, the entirety of which is incorporated herein by reference.

FIELD

Novel small molecule inhibitors of viral replication are disclosed, compositions containing such compounds, and therapeutic methods comprising the administration of such compounds are also disclosed.

BACKGROUND

The hepatitis C virus (HCV), a member of the hepacivirus genera within the Flaviviridae family, is the leading cause of chronic liver disease worldwide (Boyer, N. et al. *J Hepatol.* 2000, 32, 98-112). Consequently, a significant focus of current antiviral research is directed toward the development of improved methods for the treatment of chronic HCV infections in humans (Ciesek, S., von Hahn T., and Manns, M P., *Clin. Liver Dis.*, 2011, 15, 597-609; Soriano, V. et al, *J. Antimicrob. Chemother.*, 2011, 66, 1573-1686; Brody, H., *Nature Outlook*, 2011, 474, S1-S7; Gordon, C. P., et al., *J. Med. Chem.* 2005, 48, 1-20; Maradpour, D., et al., *Nat. Rev. Micro.* 2007, 5, 453-463).

Virologic cures of patients with chronic HCV infection are difficult to achieve because of the prodigious amount of daily virus production in chronically infected patients and the high spontaneous mutability of HCV (Neumann, et al., *Science* 1998, 282, 103-7; Fukimoto, et al., *Hepatology*, 1996, 24, 1351-4; Domingo, et al., *Gene* 1985, 40, 1-8; Martell, et al., *J. Virol.* 1992, 66, 3225-9). HCV treatment is further complicated by the fact that HCV is genetically diverse and expressed as several different genotypes and numerous subtypes. For example, HCV is currently classified into six major genotypes (designated 1-6), many subtypes (designated a, b, c, and so on), and about 100 different strains (numbered 1, 2, 3, and so on). HCV is distributed worldwide with genotypes 1, 2, and 3 predominate within the United States, Europe, Australia, and East Asia (Japan, Taiwan, Thailand, and China). Genotype 4 is largely found in the Middle East, Egypt and central Africa while genotype 5 and 6 are found predominantly in South Africa and South East Asia respectively (Simmonds, P. et al. *J Virol.* 84: 4597-4610, 2010).

The combination of ribavirin, a nucleoside analog, and interferon-alpha (α) (IFN), is utilized for the treatment of multiple genotypes of chronic HCV infections in humans. However, the variable clinical response observed within patients and the toxicity of this regimen have limited its usefulness. Addition of a HCV protease inhibitor (telaprevir or boceprevir) to the ribavirin and IFN regimen improves 12-week post-treatment virological response (SVR12) rates substantially. However, the regimen is currently only approved for genotype 1 patients and toxicity and other side effects remain. The use of directing acting antivirals to treat multiple genotypes of HCV infection has proven challenging due to the variable activity of antivirals against the different gentoypes. HCV protease inhibitors frequently have compromised in vitro activity against HCV genotypes 2 and 3 compared to genotype 1 (See, e.g., Table 1 of Summa, V. et al., *Antimicrobial Agents and Chemotherapy*, 2012, 56, 4161-4167; Gottwein, J. et al, *Gastroenterology*, 2011, 141, 1067-1079). Correspondingly, clinical efficacy has also proven highly variable across HCV genotypes. For example, therapies that are highly effective against HCV genotype 1 and 2 may have limited or no clinical efficacy against genotype 3. (Moreno, C. et al., Poster 895, 61st AASLD Meeting, Boston, Mass., USA, Oct. 29-Nov. 2, 2010; Graham, F., et al, Gastroenterology, 2011, 141, 881-889; Foster, G. R. et al., EASL 45th Annual Meeting, Apr. 14-18, 2010, Vienna, Austria.) In some cases, antiviral agents have good clinical efficacy against genotype 1, but lower and more variable against genotypes 2 and 3. (Reiser, M. et al., *Hepatology*, 2005, 41, 832-835.) To overcome the reduced efficacy in genotype 3 patients, substantially higher doses of antiviral agents may be required to achieve substantial viral load reductions (Fraser, I P et al., Abstract #48, HEP DART 2011, Koloa, Hi., December 2011.)

Antiviral agents that are less susceptible to viral resistance are also needed. For example, resistance mutations at positions 155 and 168 in the HCV protease frequently cause a substantial decrease in antiviral efficacy of HCV protease inhibitors (Mani, N. *Ann Forum Collab HIV Res.*, 2012, 14, 1-8; Romano, K P et al, *PNAS*, 2010, 107, 20986-20991; Lenz O, *Antimicrobial agents and chemotherapy*, 2010, 54, 1878-1887.)

In view of the limitations of current HCV therapy, there is a need to develop more effective anti-HCV therapies. It would also be useful to provide therapies that are effective against multiple HCV genotypes and subtypes.

SUMMARY

Novel compounds that inhibit the hepatitis C virus (HCV) NS3 protease are disclosed. In certain embodiments, the compounds disclosed inhibit multiple genotypes of the hepatitis C virus. These compounds are useful for the treatment of HCV infection and the related symptoms.

In one embodiment, there is provided a compound of formula (I):

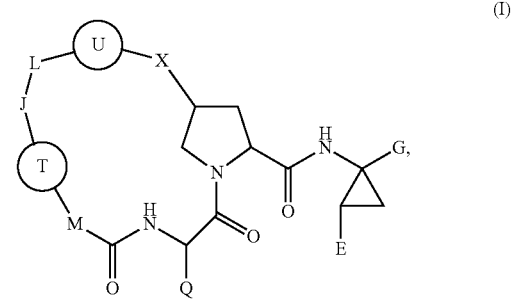

or a pharmaceutically acceptable salt thereof. In certain embodiments:

is $T^1$, $T^2$, $T^3$, $T^4$, $T^5$, or $T^6$;

L is $L^1$, $L^2$, $L^3$, $L^4$, $L^5$, $L^6$, $L^7$, $L^8$, $L^9$, $L^{10}$, $L^{11}$ or $L^{12}$;

X is —O—, —CH$_2$—, —OC(O)—, —C(O)O—, —C(O)—, —SO$_2$—, —S(O)—, —N(R$^{16}$)—, —S—, =N—O— or a bond;

M is a bond, $C_1$-$C_6$ alkylene, —O—, or —N($R^{16}$)—;
Q is $Q^1$, $Q^2$, $Q^3$, $Q^4$, $Q^5$, $Q^6$ or $Q^7$;
E is $E^1$, $E^2$, $E^3$, $E^4$, $E^5$, or $E^6$;

$$\bigcirc\!\!\!\!\!\text{U}$$

is heteroaryl or heterocyclic group wherein $$\bigcirc\!\!\!\!\!\text{U}$$

is optionally substituted with 1-4 W groups;

J is —O—, —$CH_2$—, —$CF_2$—, —C(O)—, —N($R^{16}$)—, or a direct bond;

G is —$CO_2H$, —$CONHSO_2Z^2$, tetrazolyl, —CONHP(O)($R^{16}$)$_2$, —P(O)(OH)($R^{16}$), or —P(O)($R^{16}$)$_2$;

$T^1$ is $C_5$-$C_{12}$ spiro bicyclic carbocyclene that is attached to J and M through two adjacent carbons, wherein said spiro bicyclic carbocyclene is optionally substituted with 1-4 $Z^1$ groups;

$T^2$ is $C_5$-$C_{12}$ fused bicyclic carbocyclene that is attached to J and M through two adjacent carbons, wherein said fused bicyclic carbocyclene is optionally substituted with 1-4 $Z^1$ groups;

$T^3$ is $C_5$-$C_{12}$ bridged bicyclic carbocyclene that is attached to J and M through two adjacent carbons, wherein said bridged bicyclic carbocyclene is optionally substituted with 1-4 $Z^1$ groups;

$T^4$ is $C_5$-$C_{12}$ spiro bicyclic heterocyclene that is attached to J and M through two adjacent atoms, wherein said spiro bicyclic heterocyclene is optionally substituted with 1-4 $Z^1$ groups;

$T^5$ is $C_5$-$C_{12}$ fused bicyclic heterocyclene that is attached to J and M through two adjacent atoms, wherein said fused bicyclic heterocyclene is optionally substituted with 1-4 $Z^1$ groups;

$T^6$ is $C_5$-$C_{12}$ bridged bicyclic heterocyclene that is attached to J and M through two adjacent atoms, wherein said bridged bicyclic heterocyclene is optionally substituted with 1-4 $Z^1$ groups;

$L^1$ is $C_1$-$C_8$ alkylene or $C_2$-$C_8$ alkenylene;

$L^2$ is $C_1$-$C_8$ alkylene or $C_2$-$C_8$ alkenylene wherein said $C_1$-$C_8$ alkylene or said $C_2$-$C_8$ alkenylene is substituted with 1-4 halogen atoms;

$L^3$ is $C_1$-$C_8$ alkylene or $C_2$-$C_8$ alkenylene wherein said $C_1$-$C_8$ alkylene or said $C_2$-$C_8$ alkenylene is substituted with 1-4 $Z^3$ groups and wherein said $C_1$-$C_8$ alkylene or $C_2$-$C_8$ alkenylene is optionally substituted with 1-4 halogen atoms;

$L^4$ is $C_1$-$C_8$ alkylene or $C_2$-$C_8$ alkenylene substituted with two geminal $C_1$-$C_4$ alkyl groups that come together to form a spiro $C_3$-$C_8$ carbocyclyl group, wherein $L^4$ is optionally substituted with 1-4 $Z^1$ groups;

$L^5$ is $C_1$-$C_8$ alkylene or $C_2$-$C_8$ alkenylene substituted with two geminal $Z^1$ groups that come together to form a spiro 4-8 membered heterocyclyl group,
wherein $L^5$ is optionally substituted with 1-4 additional $Z^1$ groups;

$L^6$ is 2-8 membered heteroalkylene or 4-8 membered heteroalkenylene;

$L^7$ is 2-8 membered heteroalkylene or 4-8 membered heteroalkenylene, wherein the carbon atoms of said heteroalkylene or heteroalkenylene is substituted with 1-4 halogen atoms;

$L^8$ is 2-8 membered heteroalkylene or 4-8 membered heteroalkenylene, wherein said heteroalkylene or heteroalkenylene is substituted with 1-4 $Z^3$ groups and said heteroalkylene or heteroalkenylene is optionally substituted with 1-4 halogen atoms;

$L^9$ is 2-8 membered heteroalkylene or 4-8 membered heteroalkenylene substituted with two geminal $C_1$-$C_4$ alkyl groups that come together to form a spiro $C_3$-$C_8$ carbocyclyl, wherein said $L^9$ is optionally substituted with 1-4 $Z^1$ groups;

$L^{10}$ is 2-8 membered heteroalkylene or 4-8 membered heteroalkenylene substituted with two geminal $Z^1$ groups that come together to form a spiro 4-8 membered heterocyclyl group, wherein $L^{10}$ is optionally substituted with 1-4 additional $Z^1$ groups;

$L^{11}$ is $L^{11A}$-$L^{11B}$-$L^{11C}$ wherein $L^{11A}$ and $L^{11C}$ are each independently selected from $C_1$-$C_6$ alkylene, $C_1$-$C_6$ heteroalkylene, $C_2$-$C_6$ alkenylene or a bond and $L^{11B}$ is a 3- to 6-membered saturated or unsaturated ring containing 0 to 3 heteroatoms selected from N, O, or S, wherein $L^{11A}$ and $L^{11C}$ connect to $L^{11B}$ at two different ring atoms and $L^{11}$ is optionally substituted with 1-4 $Z^1$ groups;

$L^{12}$ is $C_3$-$C_8$ alkynylene that is optionally substituted with 1-4 $Z^1$ groups;

$Q^1$ is H, $C_1$-$C_8$ alkyl, $C_3$-$C_8$ carbocyclyl, $C_6$-$C_{10}$ aryl, 5-6 membered heteroaryl, or 5-6 membered heterocyclyl, wherein when $Q^1$ is not H, said $Q^1$ is optionally substituted with 1-3 substituents independently selected from halogen, —$OR^6$, —$SR^6$, —N($R^6$)$_2$, $C_6$-$C_{10}$ aryl, $C_1$-$C_6$ alkyl, $C_1$-$C_6$ haloalkyl, $C_1$-$C_6$ haloalkoxy, —CN, —$SO_2(C_1$-$C_6$ alkyl), —S(O)($C_1$-$C_6$ alkyl), —$NR^6SO_2Z^2$, —$SO_2NR^{17}R^{18}$, —$NHCOOR^{16}$, —$NHCOZ^2$, —$NHCONHR^{16}$, —$CO_2R^6$, —C(O)$R^6$, or —CON($R^6$)$_2$;

$Q^2$ is $C_5$-$C_{10}$ spiro bicyclic carbocyclyl that is optionally substituted with 1-4 $Z^1$ groups;

$Q^3$ is $C_5$-$C_{10}$ fused bicyclic carbocyclyl that is optionally substituted with 1-4 $Z^1$ groups;

$Q^4$ is $C_5$-$C_{10}$ bridged bicyclic carbocyclyl that is optionally substituted with 1-4 $Z^1$ groups;

$Q^5$ is 4-8 membered heterocyclyl having 1 heteroatom selected from N, O or S wherein $Q^5$ is optionally substituted with 1-4 $Z^1$ groups;

$Q^6$ is $C_1$-$C_8$ alkyl, $C_3$-$C_8$ carbocyclyl, $C_6$-$C_{10}$ aryl, 5-6 membered heteroaryl, or 5-6 membered heterocyclyl, wherein $Q^6$ is substituted with 1 oxo group and optionally substituted with 1 to 3 substituents independently selected from halogen, —$OR^6$, —$SR^6$, —N($R^6$)$_2$, $C_6$-$C_{10}$ aryl, $C_1$-$C_6$ alkyl, $C_1$-$C_6$ haloalkyl, $C_1$-$C_6$ haloalkoxy, —$NO_2$, —CN, —$CF_3$, —$SO_2(C_1$-$C_6$ alkyl), —S(O)($C_1$-$C_6$ alkyl), —$NR^6SO_2Z^2$, —$SO_2NR^{17}R^{18}$, —$NHCOOR^{16}$, —$NHCOZ^2$, —$NHCONHR^{16}$, —$CO_2R^6$, —C(O)$R^6$, and —CON($R^6$)$_2$;

$Q^7$ is selected from $C_3$-$C_8$ carbocyclyl, wherein $Q^7$ is substituted with 4-8 F atoms and each carbon of $Q^7$ is substituted with 0-2 F atoms;

$E^1$ is $C_2$-$C_6$ alkenyl;
$E^2$ is $C_1$-$C_6$ alkyl;
$E^3$ is $C_1$-$C_6$ haloalkyl;
$E^4$ is $C_2$-$C_6$ haloalkenyl;
$E^5$ is $C_3$-$C_6$ carbocyclyl;
$E^6$ is $C_1$-$C_6$ alkyl substituted with —$OCH_3$, —$OCD_3$, —$OCF_3$, or —$OCF_2H$;

W is independently $W^1$, $W^2$, $W^3$, $W^4$, $W^5$, $W^6$ or $W^7$;

$W^1$ is oxo, halogen, —$OR^6$, $C_1$-$C_6$ alkyl, —CN, —$CF_3$, —$SR^6$, —C(O)$_2R^6$, —C(O)N($R^6$)$_2$, —C(O)$R^6$, —N($R^6$)C(O)$R^6$, —$SO_2(C_1$-$C_6$ alkyl), —S(O)($C_1$-$C_6$ alkyl), $C_3$-$C_8$ carbocyclyl, $C_3$-$C_8$ cycloalkoxy, $C_1$-$C_6$ haloalkyl, —N($R^6$)$_2$, —$NR^6(C_1$-$C_6$ alkyl)O($C_1$-$C_6$ alkyl), halo($C_1$-$C_6$ alkoxy), —NR$^6$SO$_2$R$^6$, —SO$_2$N(R$^6$)$_2$, —NHCOOR$^6$, —NHCONHR$^6$, C$_6$-C$_{10}$ aryl, 5-14 membered heteroaryl, 4-10 membered heterocyclyl or —O(4-10 membered heterocyclyl), wherein said C$_1$-C$_6$ alkyl, C$_3$-C$_8$ carbocyclyl, C$_3$-C$_8$ cycloalkoxy, C$_1$-C$_6$ haloalkyl, halo(C$_1$-C$_6$ alkoxy), C$_6$-C$_{10}$ aryl, 5-14 membered heteroaryl, or 4-10 membered heterocyclyl is optionally substituted with 1-4 Z$^{1c}$ groups;

W$^2$ is C$_1$-C$_6$ alkoxy substituted with a 5-14 membered heteroaryl or C$_6$-C$_{10}$ aryl; wherein said heteroaryl or aryl is substituted with 1-4 Z$^{1c}$ groups;

W$^3$ is C$_2$-C$_6$ alkynyl substituted with an C$_6$-C$_{10}$ aryl, C$_3$-C$_8$ carbocyclyl, C$_1$-C$_8$ alkyl, C$_1$-C$_6$ haloalkyl, 4-10 membered heterocyclyl, or 5-14 membered heteroaryl; wherein said aryl, carbocyclyl, alkyl, haloalkyl, heterocyclyl, or heteroaryl is optionally substituted with 1-4 Z$^1$ groups;

W$^4$ is —SF$_5$;

W$^5$ is —O(C$_2$-C$_6$ alkyl)OR$^{22}$ wherein R$^{22}$ is an C$_6$-C$_{10}$ aryl, 5-14 membered heteroaryl or 4-10 membered heterocyclyl that is optionally substituted with 1-4 Z$^1$ groups;

W$^6$ is —O(C$_2$-C$_6$ alkyl)NR$^{16}$R$^{22}$ wherein R$^{22}$ is an C$_6$-C$_{10}$ aryl, 5-14 membered heteroaryl or 4-10 membered heterocyclyl that is optionally substituted with 1-4 Z$^1$ groups;

W$^7$ is —O(5-14 membered heteroaryl); wherein said —O(5-14 membered heteroaryl) is optionally substituted with 1-4 Z$^1$ groups and 2 adjacent substituents of said —O(5-14 membered heteroaryl) may be taken together to form a 3- to 6-membered cyclic ring containing 0 to 3 heteroatoms independently selected from N, O, or S;

R$^6$ is H, C$_1$-C$_6$ alkyl or C$_6$-C$_{10}$ aryl, wherein said C$_6$-C$_{10}$ aryl or C$_1$-C$_6$ alkyl is optionally substituted with 1 to 4 substituents independently selected from halogen, C$_1$-C$_6$ alkyl, C$_6$-C$_{10}$ aryl, C$_3$-C$_8$ carbocyclyl, 5-14 membered heteroaryl, 4-10 membered heterocyclyl, halo(C$_1$-C$_6$ alkoxy), —OH, —O(C$_1$-C$_6$ alkyl), —SH, —S(C$_1$-C$_6$ alkyl), —NH$_2$, —NH(C$_1$-C$_6$ alkyl), —N(C$_1$-C$_6$ alkyl)$_2$, —C(O)(C$_1$-C$_6$ alkyl), —SO$_2$N(C$_1$-C$_6$ alkyl)$_2$, —NHCOO(C$_1$-C$_6$ alkyl), —NHCO(C$_1$-C$_6$ alkyl), —NHCONH(C$_1$-C$_6$ alkyl), —CO$_2$(C$_1$-C$_6$ alkyl), and —C(O)N(C$_1$-C$_6$ alkyl)$_2$, wherein said 4-10 membered heterocyclyl is optionally substituted with 1-4 Z$^c$ groups;

R$^{16}$ is H, C$_1$-C$_8$ alkyl, C$_2$-C$_8$ alkenyl, C$_2$-C$_8$ alkynyl, C$_3$-C$_8$ carbocyclyl, C$_5$-C$_{10}$ bicyclic carbocyclyl, C$_6$-C$_{10}$ aryl, 5-14 membered heteroaryl or 4-10 membered heterocyclyl, wherein said C$_1$-C$_8$ alkyl, C$_2$-C$_8$ alkenyl, C$_2$-C$_8$ alkynyl, C$_3$-C$_8$ carbocyclyl, C$_6$-C$_{10}$ aryl, 5-14 membered heteroaryl or 4-10 membered heterocyclyl of R$^{16}$ is optionally substituted with 1-4 Z$^{1c}$ groups;

R$^{17}$ and R$^{18}$ are each independently selected from H, C$_1$-C$_8$ alkyl, C$_2$-C$_8$ alkenyl, C$_2$-C$_8$ alkynyl, C$_3$-C$_8$ carbocyclyl, C$_5$-C$_{10}$ bicyclic carbocyclyl, —C(O)R$^{16}$, —C(O)OR$^{16}$, C$_6$-C$_{10}$ aryl, 5-14 membered heteroaryl or 4-10 membered heterocyclyl, wherein said alkyl, alkenyl, alkynyl, carbocyclyl, aryl, heteroaryl or heterocyclyl of R$^{17}$ or R$^{18}$ is optionally substituted with 1-4 Z$^{1c}$ groups, or R$^{17}$ and R$^{18}$ together with the nitrogen to which they are attached form a 4-7 membered heterocyclyl group, wherein said 4-7 membered heterocyclyl group is optionally substituted with 1-4 Z$^{1c}$ groups;

each Z$^1$ is independently oxo, halogen, C$_1$-C$_8$ alkyl, C$_2$-C$_8$ alkenyl, C$_2$-C$_8$ alkynyl, C$_3$-C$_8$ carbocyclyl, C$_5$-C$_{10}$ bicyclic carbocyclyl, C$_1$-C$_8$ haloalkyl, C$_6$-C$_{10}$ aryl, 5-14 membered heteroaryl, 4-10 membered heterocyclyl, —CN, —C(O)R$^{16}$, —C(O)OR$^{16}$, —C(O)NR$^{17}$R$^{18}$, —NR$^{17}$R$^{18}$, —NR$^{16}$C(O)R$^{16}$, —NR$^{16}$C(O)NR$^{17}$R$^{18}$, —NR$^{16}$S(O)$_2$R$^{16}$, —NR$^{16}$S(O)$_2$NR$^{17}$R$^{18}$, —NR$^{16}$S(O)$_2$OR$^{16}$, —OR$^{16}$, —OC(O)R$^{16}$, —OC(O)NR$^{17}$R$^{18}$, —SR$^{16}$, —S(O)R$^{16}$, —S(O)$_2$R$^{16}$ or —S(O)$_2$NR$^{17}$R$^{18}$ wherein said alkyl, alkenyl, alkynyl, carbocyclyl, bicyclic carbocyclyl, aryl, heteroaryl or heterocyclyl of Z$^1$ is optionally substituted with 1-4 Z$^{1a}$ groups;

each Z$^{1a}$ is independently oxo, halogen, C$_2$-C$_8$ alkenyl, C$_2$-C$_8$ alkynyl, C$_3$-C$_8$ carbocyclyl, C$_5$-C$_{10}$ bicyclic carbocyclyl, C$_1$-C$_8$ haloalkyl, C$_6$-C$_{10}$ aryl, 5-14 membered heteroaryl, 4-10 membered heterocyclyl, —CN, —C(O)R$^{16}$, —C(O)OR$^{16}$, —C(O)NR$^{17}$R$^{18}$, —NR$^{17}$R$^{18}$, —NR$^{16}$C(O)R$^{16}$, —NR$^{16}$C(O)OR$^{16}$, —NR$^{16}$C(O)NR$^{17}$R$^{18}$, —NR$^{16}$S(O)$_2$R$^{16}$, —NR$^{16}$S(O)$_2$NR$^{17}$R$^{18}$, —NR$^{16}$S(O)$_2$OR$^{16}$, —OR$^{16}$, —OC(O)R$^{16}$, —OC(O)NR$^{17}$R$^{18}$, —SR$^{16}$, —S(O)R$^{16}$, —S(O)$_2$R$^{16}$ or —S(O)$_2$NR$^{17}$R$^{18}$ wherein said alkenyl, alkynyl, carbocyclyl, bicyclic carbocyclyl, aryl, heteroaryl or heterocyclyl of Z$^{1a}$ is optionally substituted with 1-4 Z$^{1c}$ groups;

each Z$^{1c}$ is independently oxo, halogen, C$_1$-C$_8$ alkyl, C$_3$-C$_8$ carbocyclyl, C$_5$-C$_{10}$ bicyclic carbocyclyl, C$_1$-C$_8$ haloalkyl, C$_6$-C$_{10}$ aryl, 5-14 membered heteroaryl, 4-10 membered heterocyclyl, —CN, —C(O)(C$_1$-C$_8$ alkyl), —C(O)O(C$_1$-C$_8$ alkyl), —C(O)N(C$_1$-C$_8$ alkyl)$_2$, —NH$_2$, —NH(C$_1$-C$_8$ alkyl), —N(C$_1$-C$_8$ alkyl)$_2$, —NHC(O)O(C$_1$-C$_8$ alkyl), —NHC(O)(C$_1$-C$_8$ alkyl), —NHC(O)NH(C$_1$-C$_8$ alkyl), —OH, —O(C$_1$-C$_8$ alkyl), C$_3$-C$_8$ cycloalkoxy, C$_5$-C$_{10}$ bicyclic carbocyclyloxy, —S(C$_1$-C$_8$ alkyl) or —S(O)$_2$N(C$_1$-C$_8$ alkyl)$_2$ wherein said alkyl, carbocyclyl, bicyclic carbocyclyl, aryl, heteroaryl, heterocyclyl or cycloalkoxy portion of Z$^{1c}$ is optionally substituted with 1-4 halogen atoms, C$_1$-C$_6$ alkoxy, —S(O)$_2$C$_1$-C$_6$alkyl, or C$_1$-C$_6$ haloalkoxy;

each Z$^2$ is independently C$_1$-C$_8$ alkyl, C$_3$-C$_8$ carbocyclyl, C$_5$-C$_{10}$ bicyclic carbocyclyl, C$_6$-C$_{10}$ aryl, 5-14 membered heteroaryl, 4-10 membered heterocyclyl, —NR$^{17}$R$^{18}$ or —OR$^{16}$ wherein any alkyl, carbocyclyl, bicyclic carbocyclyl, aryl, heteroaryl or heterocyclyl portion of Z$^2$ is optionally substituted with 1-4 Z$^{2a}$ groups;

each Z$^{2a}$ is independently hydrogen, oxo, halogen, C$_1$-C$_8$ alkyl, C$_2$-C$_8$ alkynyl, C$_3$-C$_8$ carbocyclyl, C$_5$-C$_{10}$ bicyclic carbocyclyl, C$_1$-C$_8$ haloalkyl, C$_6$-C$_{10}$ aryl, 5-14 membered heteroaryl, 4-10 membered heterocyclyl, —(C$_2$-C$_8$ alkynyl)aryl, —(C$_2$-C$_8$ alkynyl)heteroaryl, —CN, —C(O)(C$_1$-C$_6$ alkyl), —O(O)O(C$_1$-C$_6$ alkyl), —C(O)N(C$_1$-C$_6$ alkyl)$_2$, —NH$_2$, —NH(C$_1$-C$_6$ alkyl), —N(C$_1$-C$_6$ alkyl)$_2$, —NHC(O)O(C$_1$-C$_6$ alkyl), —NHC(O)(C$_1$-C$_6$ alkyl), —NHC(O)NH(C$_1$-C$_6$ alkyl), —OH, —O(C$_1$-C$_6$ alkyl), halo(C$_1$-C$_6$ alkoxy), C$_3$-C$_8$ cycloalkoxy, —S(C$_1$-C$_6$ alkyl), or —SO$_2$N(C$_1$-C$_6$ alkyl)$_2$; wherein any alkyl, alkynyl, carbocyclyl, cycloalkoxy, bicyclic carbocyclyl, aryl, heteroaryl or heterocyclyl portions of Z$^{2a}$ is optionally substituted with 1-4 halogen or C$_1$-C$_6$ alkoxy groups;

each Z$^3$ is independently oxo, C$_2$-C$_8$ alkenyl, C$_2$-C$_8$ alkynyl, C$_3$-C$_8$ carbocyclyl, C$_5$-C$_{10}$ bicyclic carbocyclyl, C$_1$-C$_8$ haloalkyl, C$_6$-C$_{10}$ aryl, 5-14 membered heteroaryl, 4-10 membered heterocyclyl, —CN, —C(O)OR$^{16}$, —C(O)NR$^{17}$R$^{18}$, —NR$^{17}$R$^{18}$, —NR$^{16}$C(O)NR$^{17}$R$^{18}$, —OR$^{16}$, —SR$^{16}$ or —SO$_2$R$^{16}$, wherein any alkenyl, alkynyl, carbocyclyl, aryl, heteroaryl or heterocyclyl portion of Z$^3$ is optionally substituted with 1-4 halogen.

In another embodiment, there is provided a compound of formula (II):

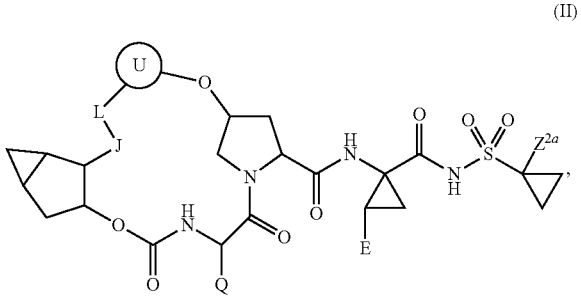

(II)

or a pharmaceutically acceptable salt thereof. In certain embodiments, in the compound of formula II:

L is $L^1$, $L^2$, $L^3$, $L^4$, $L^5$, $L^6$, $L^7$, $L^8$, $L^9$, $L^{10}$, $L^{11}$ or $L^{12}$;
Q is $Q^1$, $Q^2$, $Q^3$, $Q^4$, $Q^5$, $Q^6$ or $Q^7$;
E is $E^1$, $E^2$, $E^3$, $E^4$, E $E^5$, or $E^6$;
J is —$CH_2$— or —$CF_2$—;

is $U^1$, $U^2$, $U^3$, $U^4$, $U^5$, $U^6$, $U^7$ or $U^8$;

$L^1$ is $C_1$-$C_8$ alkylene or $C_2$-$C_8$ alkenylene;

$L^2$ is $C_1$-$C_8$ alkylene or $C_2$-$C_8$ alkenylene wherein said $C_1$-$C_8$ alkylene or said $C_2$-$C_8$ alkenylene is substituted with 1-4 halogen atoms;

$L^3$ is $C_1$-$C_8$ alkylene or $C_2$-$C_8$ alkenylene wherein said $C_1$-$C_8$ alkylene or said $C_2$-$C_8$ alkenylene is substituted with 1-4 $Z^3$ groups and wherein said $C_1$-$C_8$ alkylene or $C_2$-$C_8$ alkenylene is optionally substituted with 1-4 halogen atoms;

$L^4$ is $C_1$-$C_8$ alkylene or $C_2$-$C_8$ alkenylene substituted with two geminal $C_1$-$C_4$ alkyl groups that come together to form a spiro $C_3$-$C_8$ carbocyclyl group, wherein $L^4$ is optionally substituted with 1-4 $Z^1$ groups;

$L^5$ is $C_1$-$C_8$ alkylene or $C_2$-$C_8$ alkenylene substituted with two geminal $Z^1$ groups that come together to form a spiro 4-8 membered heterocyclyl group, wherein $L^5$ is optionally substituted with 1-4 additional $Z^1$ groups;

$L^6$ is 2-8 membered heteroalkylene or 4-8 membered heteroalkenylene;

$L^7$ is 2-8 membered heteroalkylene or 4-8 membered heteroalkenylene, wherein the carbon atoms of said heteroalkylene or heteroalkenylene is substituted with 1-4 halogen atoms;

$L^8$ is 2-8 membered heteroalkylene or 4-8 membered heteroalkenylene, wherein said heteroalkylene or heteroalkenylene is substituted with 1-4 $Z^3$ groups and said heteroalkylene or heteroalkenylene is optionally substituted with 1-4 halogen atoms;

$L^9$ is 2-8 membered heteroalkylene or 4-8 membered heteroalkenylene substituted with two geminal $C_1$-$C_4$ alkyl groups that come together to form a spiro $C_3$-$C_8$ carbocyclyl group, wherein said $L^9$ is optionally substituted with 1-4 $Z^1$ groups;

$L^{10}$ is 2-8 membered heteroalkylene or 4-8 membered heteroalkenylene substituted with two geminal $Z^1$ groups that come together to form a spiro 4-8 membered heterocyclyl group, wherein $L^{10}$ is optionally substituted with 1-4 additional $Z^1$ groups;

$L^{11}$ is $L^{11A}$-$L^{11B}$-$L^{11C}$ wherein $L^{11A}$ and $L^{11C}$ are each independently selected from $C_1$-$C_6$ alkylene, $C_1$-$C_6$ heteroalkylene, $C_2$-$C_6$ alkenylene or a bond and $L^{11B}$ is a 3- to 6-membered saturated or unsaturated ring containing 0 to 3 heteroatoms selected from N, O, or S, wherein $L^{11A}$ and $L^{11C}$ connect to $L^{11B}$ at two different ring atoms and $L^{11}$ is optionally substituted with 1-4 $Z^1$ groups;

$L^{12}$ is $C_3$-$C_8$ alkynylene that is optionally substituted with 1-4 $Z^1$ groups;

$Q^1$ is H, $C_1$-$C_8$ alkyl, $C_3$-$C_8$ carbocyclyl, $C_6$-$C_{10}$ aryl, 5-6 membered heteroaryl, or 5-6 membered heterocyclyl, wherein when $Q^1$ is not H, said $Q^1$ is optionally substituted with 1-3 substituents independently selected from halogen, —$OR^6$, —$SR^6$, —$N(R^6)_2$, $C_6$-$C_{10}$ aryl, $C_1$-$C_6$ alkyl, $C_1$-$C_6$ haloalkyl, $C_1$-$C_6$ haloalkoxy, —CN, —$SO_2$($C_1$-$C_6$ alkyl), —S(O)($C_1$-$C_6$ alkyl), —$NR^6SO_2Z^2$, —$SO_2NR^{17}R^{18}$, —$NHCOOR^{16}$, —$NHCOZ^2$, —$NHCONHR^{16}$, —$CO_2R^6$, —C(O)$R^6$, or —CON($R^6)_2$;

$Q^2$ is $C_5$-$C_{10}$ spiro bicyclic carbocyclyl that is optionally substituted with 1-4 $Z^1$ groups;

$Q^3$ is $C_5$-$C_{10}$ fused bicyclic carbocyclyl that is optionally substituted with 1-4 $Z^1$ groups;

$Q^4$ is $C_5$-$C_{10}$ bridged bicyclic carbocyclyl that is optionally substituted with 1-4 $Z^1$ groups;

$Q^5$ is 4-8 membered heterocyclyl having 1 heteroatom selected from N, O or S wherein $Q^5$ is optionally substituted with 1-4 $Z^1$ groups;

$Q^6$ is selected from $C_1$-$C_8$ alkyl, $C_3$-$C_8$ carbocyclyl, $C_6$-$C_{10}$ aryl, 5-6 membered heteroaryl, or 5-6 membered heterocyclyl, wherein $Q^6$ is substituted with 1 oxo group and with 0 to 3 substituents independently selected from halogen, —$OR^6$, —$SR^6$, —$N(R^6)_2$, $C_6$-$C_{10}$ aryl, $C_1$-$C_6$ alkyl, $C_1$-$C_6$ haloalkyl, $C_1$-$C_6$ haloalkoxy, —$NO_2$, —CN, —$CF_3$, —$SO_2$($C_1$-$C_6$ alkyl), —S(O)($C_1$-$C_6$ alkyl), —$NR^6SO_2Z^2$, —$SO_2NR^{17}R^{18}$, —$NHCOOR^{16}$, —$NHCOZ^2$, —$NHCONHR^{16}$, —$CO_2R^6$, —C(O)$R^6$, or —CON($R^6)_2$;

$Q^7$ is $C_3$-$C_8$ carbocyclyl, wherein $Q^7$ is substituted with 4-8 F atoms and each carbon of $Q^7$ is substituted with 0-2 F atoms;

$E^1$ is $C_2$-$C_6$ alkenyl;
$E^2$ is $C_1$-$C_6$ alkyl;
$E^3$ is $C_1$-$C_6$ haloalkyl;
$E^4$ is $C_2$-$C_6$ haloalkenyl;
$E^5$ is $C_3$-$C_6$ carbocyclyl;
$E^6$ is $C_1$-$C_6$ alkyl substituted with —$OCH_3$, —$OCD_3$, —$OCF_3$, or —$OCF_2H$;

$U^1$ is

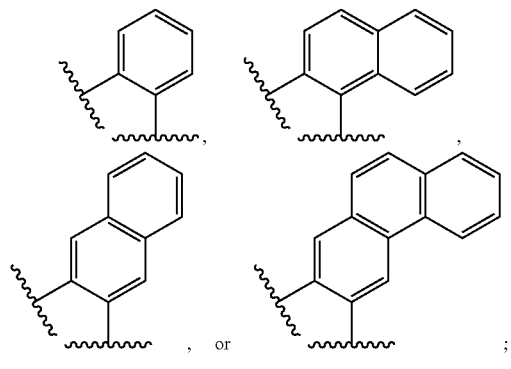

, or ;

wherein each U[1] is optionally substituted with 1-2 W groups;
U[2] is
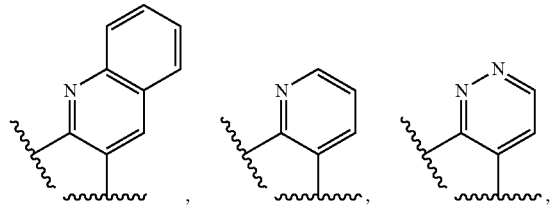
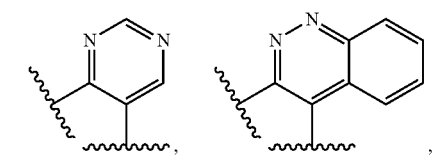
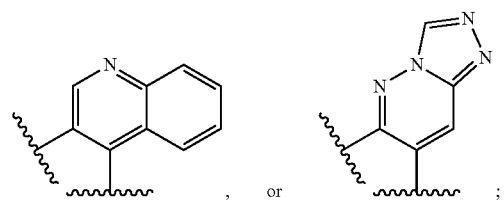
wherein each U[2] is optionally substituted with 1-2 W groups;
U[3] is
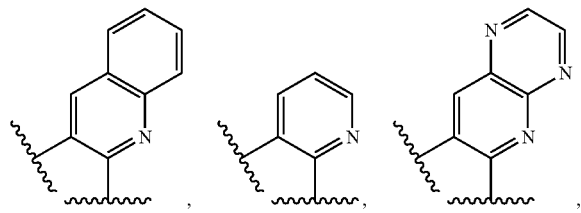
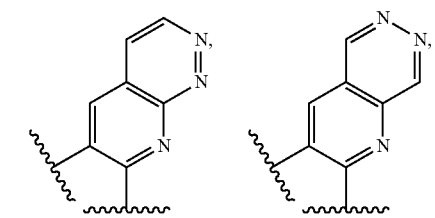
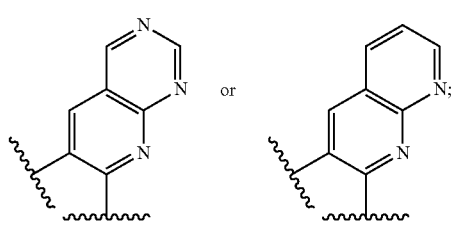
wherein each U[3] is optionally substituted with 1-2 W groups;
U[4] is
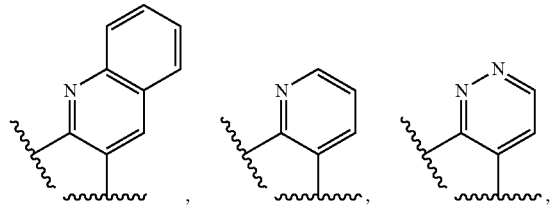
wherein each U[4] is optionally substituted with 1-2 W groups;
U[5] is
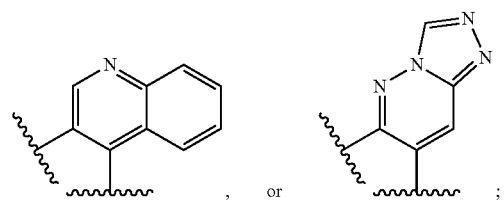
wherein each U[5] is optionally substituted with 1-2 W groups;
U[6] is
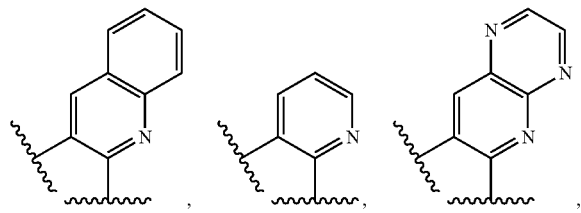

-continued

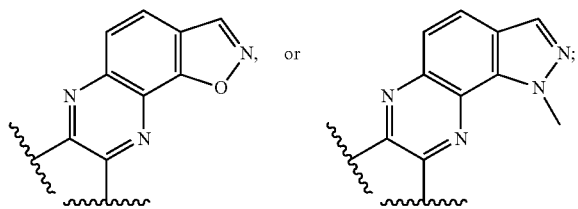

wherein each U⁶ is optionally substituted with 1-2 W groups;
U⁷ is

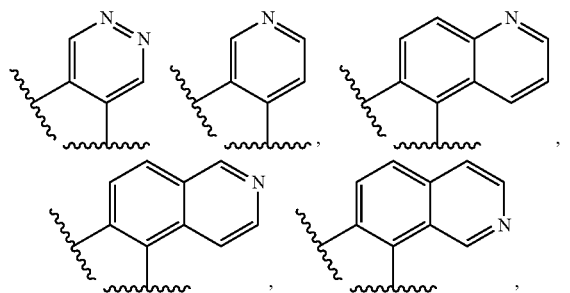

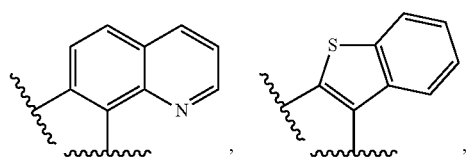

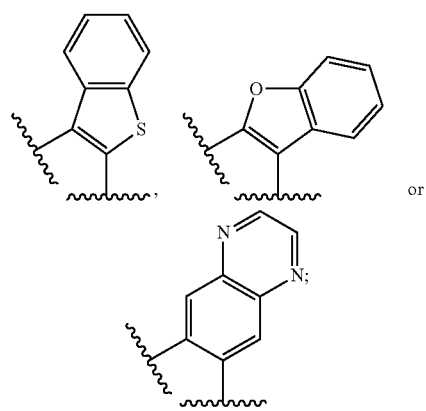

wherein each U⁷ is optionally substituted with 1-2 W groups;
U⁸ is

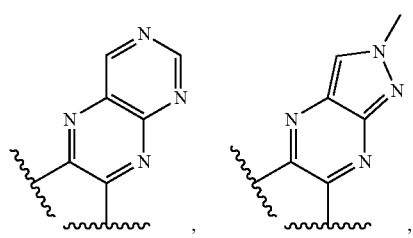

-continued

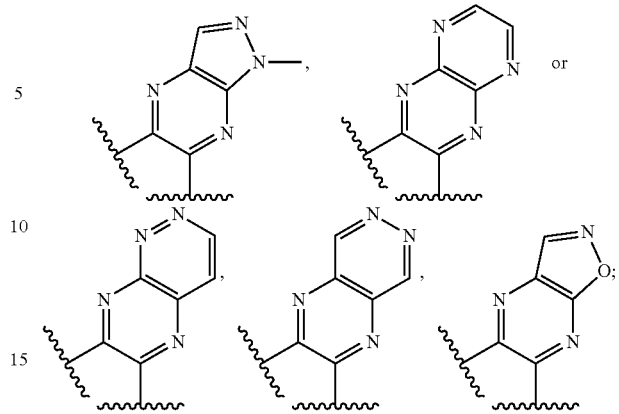

wherein each U⁸ is optionally substituted with 1-2 W groups;
each W is independently W¹, W², W³, W⁴, W⁵, W⁶ or W⁷;
each W¹ is oxo, halogen, —OR⁶, C₁-C₆ alkyl, —CN, —CF₃, —SR⁶, —C(O)₂R⁶, —C(O)N(R⁶)₂, —C(O)R⁶, —N(R⁶)C(O)R⁶, —SO₂(C₁-C₆ alkyl), —S(O)(C₁-C₆ alkyl), C₃-C₈ carbocyclyl, C₃-C₈ cycloalkoxy, C₁-C₆ haloalkyl, —N(R⁶)₂, —NR⁶(C₁-C₆ alkyl)O(C₁-C₆ alkyl), halo(C₁-C₆ alkoxy), —NR⁶SO₂R⁶, —SO₂N(R⁶)₂, —NHCOOR⁶, —NHCONHR⁶, C₆-C₁₀ aryl, 5-14 membered heteroaryl, 4-10 membered heterocyclyl or —O(4-10 membered heterocyclyl), wherein said W¹ alkyl, carbocyclyl, cycloalkoxy, haloalkyl, haloalkoxy, aryl, heteroaryl, or heterocyclyl is optionally substituted with 1-4 Z¹ᶜ groups;
each W² is C₁-C₆ alkoxy substituted with a 5-14 membered heteroaryl or C₆-C₁₀ aryl; wherein said heteroaryl or aryl is substituted with 1-4 Z¹ᶜ groups;
each W³ is C₂-C₆ alkynyl substituted with an C₆-C₁₀ aryl, C₃-C₈ carbocyclyl, C₁-C₈ alkyl, C₁-C₆ haloalkyl, 4-10 membered heterocyclyl, or 5-14 membered heteroaryl; wherein said aryl, carbocyclyl, alkyl, haloalkyl, heterocyclyl, or heteroaryl is optionally substituted with 1-4 Z¹ groups;
each W⁴ is —SF₅;
each W⁵ is —O(C₂-C₆ alkyl)OR²² wherein R²² is an C₆-C₁₀ aryl, 5-14 membered heteroaryl or 4-10 membered heterocyclyl that is optionally substituted with 1-4 Z¹ groups;
each W⁶ is —O(C₂-C₆ alkyl)NR¹⁶R²² wherein R²² is an C₆-C₁₀ aryl, 5-14 membered heteroaryl or 4-10 membered heterocyclyl that is optionally substituted with 1-4 Z¹ groups;
each W⁷ is —O(5-14 membered heteroaryl); wherein said —O(5-14 membered heteroaryl) is optionally substituted with 1-4 Z¹ groups and 2 adjacent substituents of said —O(5-14 membered heteroaryl) may be taken together to form a 3- to 6-membered cyclic ring containing 0 to 3 heteroatoms independently selected from N, O, or S;
each R⁶ is independently selected from H, C₁-C₆ alkyl or C₆-C₁₀ aryl, wherein said aryl or alkyl is optionally substituted with 1 to 4 substituents independently selected from halogen atoms, C₁-C₆ alkyl, C₆-C₁₀ aryl, C₃-C₈ carbocyclyl, 5-14 membered heteroaryl, 4-10 membered heterocyclyl, halo(C₁-C₆ alkoxy), —OH, —O(C₁-C₆ alkyl), —SH, —S(C₁-C₆ alkyl), —NH₂, —NH(C₁-C₆ alkyl), —N(C₁-C₆ alkyl)₂, —C(O)(C₁-C₆ alkyl), —SO₂N(C₁-C₆ alkyl)₂, —NHCOO(C₁-C₆ alkyl), —NHCO(C₁-C₆ alkyl), —NHCONH(C₁-C₆ alkyl), —CO₂(C₁-C₆ alkyl), or —C(O)N(C₁-C₆ alkyl)₂, wherein said 4-10 membered heterocyclyl is optionally substituted with 1-4 Zᶜ groups;

each $R^{16}$ is independently selected from H, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, $C_6$-$C_{10}$ aryl, 5-14 membered heteroaryl or 4-10 membered heterocyclyl, wherein any alkyl, alkenyl, alkynyl, carbocyclyl, aryl, heteroaryl or heterocyclyl of $R^{16}$ is optionally substituted with 1-4 $Z^{1c}$ groups;

$R^{17}$ and $R^{18}$ are each independently selected from H, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, —C(O)$R^{16}$, —C(O)O$R^{16}$, $C_6$-$C_{10}$ aryl, 5-14 membered heteroaryl or 4-10 membered heterocyclyl, wherein any alkyl, alkenyl, alkynyl, carbocyclyl, aryl, heteroaryl or heterocyclyl of $R^{17}$ or $R^{18}$ is optionally substituted with 1-4 $Z^{1c}$ groups, or $R^{17}$ and $R^{18}$ together with the nitrogen to which they are attached form a 4-7 membered heterocyclyl group, wherein said 4-7 membered heterocyclyl group is optionally substituted with 1-4 $Z^{1c}$ groups;

each $Z^1$ is independently selected from oxo, halogen, $C_1$-$C_8$ alkyl, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)$R^{16}$, —C(O)O$R^{16}$, —C(O)N$R^{17}R^{18}$, —N$R^{17}R^{18}$, —N$R^{16}$C(O)$R^{16}$, —N$R^{16}$C(O)N$R^{17}R^{18}$, —N$R^{16}$S(O)$_2$$R^{16}$, —N$R^{16}$S(O)$_2$N$R^{17}R^{18}$, —N$R^{16}$S(O)$_2$O$R^{16}$, —O$R^{16}$, —OC(O)$R^{16}$, —OC(O)N$R^{17}R^{18}$, —S$R^{16}$, —S(O)$R^{16}$, —S(O)$_2$$R^{16}$ or —S(O)$_2$N$R^{17}R^{18}$ wherein any alkyl, alkenyl, alkynyl, carbocyclyl, bicyclic carbocyclyl, aryl, heteroaryl or heterocyclyl of $Z^1$ is optionally substituted with 1-4 $Z^{1a}$ groups;

each $Z^{1a}$ is independently selected from oxo, halogen, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)$R^{16}$, —C(O)O$R^{16}$, —C(O)N$R^{17}R^{18}$, —N$R^{17}R^{18}$, —N$R^{16}$C(O)$R^{16}$, —N$R^{16}$C(O)O$R^{16}$, —N$R^{16}$C(O)N$R^{17}R^{18}$, —N$R^{16}$S(O)$_2$$R^{16}$, —N$R^{16}$S(O)$_2$N$R^{17}R^{18}$, —N$R^{16}$S(O)$_2$O$R^{16}$, —O$R^{16}$, —OC(O)$R^{16}$, —OC(O)N$R^{17}R^{18}$, —S$R^{16}$, —S(O)$R^{16}$, —S(O)$_2$$R^{16}$ or —S(O)$_2$N$R^{17}R^{18}$ wherein any alkenyl, alkynyl, carbocyclyl, bicyclic carbocyclyl, aryl, heteroaryl or heterocyclyl of $Z^{1a}$ is optionally substituted with 1-4 $Z^{1c}$ groups;

each $Z^{1c}$ is independently selected from oxo, halogen, $C_1$-$C_8$ alkyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)($C_1$-$C_8$ alkyl), —C(O)O($C_1$-$C_8$ alkyl), —C(O)N($C_1$-$C_8$ alkyl)$_2$, —NH$_2$, —NH($C_1$-$C_8$ alkyl), —N($C_1$-$C_8$ alkyl)$_2$, —NHC(O)O($C_1$-$C_8$ alkyl), —NHC(O)($C_1$-$C_8$ alkyl), —NHC(O)NH($C_1$-$C_8$ alkyl), —OH, —O($C_1$-$C_8$ alkyl), $C_3$-$C_8$ cycloalkoxy, $C_5$-$C_{10}$ bicyclic carbocyclyloxy, —S($C_1$-$C_8$ alkyl) or —S(O)$_2$ N($C_1$-$C_8$ alkyl)$_2$ wherein any alkyl, carbocyclyl, bicyclic carbocyclyl, aryl, heteroaryl, heterocyclyl or cycloalkoxy portion of $Z^{1c}$ is optionally substituted with 1-4 halogen atoms, $C_1$-$C_6$ alkoxy, —S(O)$_2$$C_1$-$C_6$alkyl, or $C_1$-$C_6$ haloalkoxy;

each $Z^2$ is independently selected from $C_1$-$C_8$ alkyl, $C_3$-$C_8$ carbocyclyl, $C_5$-$C_{10}$ bicyclic carbocyclyl, $C_6$-$C_{10}$ aryl, 5-14 membered heteroaryl, 4-10 membered heterocyclyl, —N$R^{17}R^{18}$ or —O$R^{16}$ wherein any alkyl, carbocyclyl, bicyclic carbocyclyl, aryl, heteroaryl or heterocyclyl portion of $Z^2$ is optionally substituted with 1-4 $Z^{2a}$ groups;

each $Z^{2a}$ is independently selected from hydrogen, oxo, halogen, $C_1$-$C_8$ alkyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —($C_2$-$C_8$ alkynyl)aryl, —($C_2$-$C_8$ alkynyl)heteroaryl, —CN, —C(O)($C_1$-$C_6$ alkyl), —C(O)O($C_1$-$C_6$ alkyl), —C(O)N($C_1$-$C_6$ alkyl)$_2$, —NH$_2$, —NH($C_1$-$C_6$ alkyl), —N($C_1$-$C_6$ alkyl)$_2$, —NHC(O)O($C_1$-$C_6$ alkyl), —NHC(O)($C_1$-$C_6$ alkyl), —NHC(O)NH($C_1$-$C_6$ alkyl), —OH, —O($C_1$-$C_6$ alkyl), halo ($C_1$-$C_6$ alkoxy), $C_3$-$C_8$ cycloalkoxy, —S($C_1$-$C_6$ alkyl), or —SO$_2$N($C_1$-$C_6$ alkyl)$_2$; wherein any alkyl, alkynyl, carbocyclyl, cycloalkoxy, bicyclic carbocyclyl, aryl, heteroaryl or heterocyclyl portions of $Z^{2a}$ is optionally substituted with 1-4 halogen or $C_1$-$C_6$ alkoxy groups;

each $Z^3$ is independently selected from oxo, $C_2$-$C_8$ alkenyl, $C_2$-$C_8$ alkynyl, $C_3$-$C_8$ carbocyclyl, $C_5$-$C_{10}$ bicyclic carbocyclyl, $C_1$-$C_8$ haloalkyl, $C_6$-$C_{10}$ aryl, 5-14 membered heteroaryl, 4-10 membered heterocyclyl, —CN, —C(O)O$R^{16}$, —C(O)N$R^{17}R^{18}$, —N$R^{17}R^{18}$, —N$R^{16}$C(O)N$R^{17}R^{18}$, —O$R^{16}$, —S$R^{16}$ or —SO$_2$$R^{16}$, wherein any alkenyl, alkynyl, carbocyclyl, aryl, heteroaryl or heterocyclyl portion of $Z^3$ is optionally substituted with 1-4 halogen.

In another embodiment, there is provided a compound of formula (III):

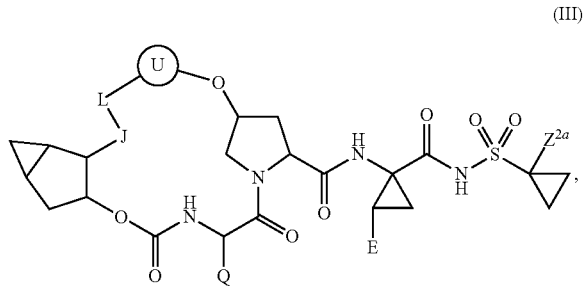

(III)

or a pharmaceutically acceptable salt thereof. In certain embodiments:

L is $C_1$-$C_8$ alkylene or $C_2$-$C_8$ alkenylene wherein said $C_1$-$C_8$ alkylene or said $C_2$-$C_8$ alkenylene is optionally substituted with one or more $R^{25}$, wherein each $R^{25}$ is independently selected from halogen, $C_1$-$C_4$ alkyl, $C_1$-$C_4$ haloalkyl, $C_3$-$C_6$ carbocyclyl, 3 to 6 membered heteroalkyl, —OH, or —O—(C1-C4 alkyl), or oxo;

Q is H, $C_1$-$C_8$ alkyl, 4-8 membered heterocyclyl, or $C_3$-$C_8$ carbocyclyl;

E is $C_1$-$C_4$ alkyl, $C_2$-$C_4$ alkenyl, $C_3$-$C_6$ carbocyclyl, wherein E is optionally substituted with or more halogen atoms;

J is —CH$_2$— or —CF$_2$—;

☺ is a bicyclic or tricyclic heteroaryl or heterocyclyl, optionally substituted with 1-2 W groups;

each W is independently halogen, —O$R^6$, $C_1$-$C_6$ alkyl, —CN, —CF$_3$, or $C_1$-$C_6$ haloalkyl;

each $R^6$ is independently selected from H, or $C_1$-$C_4$ alkyl; and $Z^{2a}$ is hydrogen or $C_1$-$C_4$ alkyl.

One embodiment provides a pharmaceutical composition comprising a compound of Formula I, II, or III, or a pharmaceutically acceptable salt thereof, and a pharmaceutically acceptable carrier.

One embodiment provides a method for treating a Flaviviridae viral infection (e.g., an HCV viral infection) in a patient in need thereof (e.g., mammal such as a human). The method includes administering a compound of Formula I, II or III, or a pharmaceutically acceptable salt thereof, to the patient.

One embodiment provides a method for inhibiting the proliferation of the HCV virus, treating HCV or delaying the onset of HCV symptoms in a patient in need thereof (e.g., mammal such as a human). The method includes administering a compound of Formula I, II, or III or a pharmaceutically acceptable salt thereof, to the patient.

One embodiment provides a compound of Formula I, II, or III or a pharmaceutically acceptable salt thereof for use in medical therapy (e.g., for use in treating a Flaviviridae viral infection such as an HCV viral infection or in treating the proliferation of the HCV virus or delaying the onset of HCV symptoms in a patient in need thereof (e.g., mammal such as a human)).

One embodiment provides a compound of Formula I, II, or III or a pharmaceutically acceptable salt thereof for use in the manufacture of a medicament for treating a Flaviviridae viral infection (e.g., an HCV viral infection) or the proliferation of the HCV virus or delaying the onset of HCV symptoms in a patient in need thereof (e.g., mammal such as a human).

One embodiment provides a compound of Formula I, II, or III, or a pharmaceutically acceptable salt thereof, for use in the prophylactic or therapeutic treatment of the proliferation of a Flaviviridae virus, an HCV virus or for use in the therapeutic treatment of delaying the onset of HCV symptoms.

One embodiment provides a compound of Formula I, II, or III or a pharmaceutically acceptable salt thereof, for use in the prophylactic or therapeutic treatment of a Flaviviridae virus infection (e.g., an HCV virus infection).

One embodiment provides the use of a compound of Formula I, II, or III, or a pharmaceutically acceptable salt thereof, for the manufacture of a medicament for a Flaviviridae virus infection (e.g., an HCV virus infection) in a patient in need thereof (e.g., mammal such as a human). One embodiment provides processes and intermediates disclosed herein that are useful for preparing compounds of Formula I, II, or III or salts thereof.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

ABBREVIATIONS

The following abbreviations are used throughout the specification, and have the following meanings:

| | |
|---|---|
| ° C. | degrees Celsius |
| Å | Angstrom |
| Ac | acetyl |
| AcOH | acetic acid |
| aq | aqueous |
| Ar | argon |
| atm | atmosphere |
| BEP | 2-bromo-1-ethyl pyridinium tetrafluoroborate |
| | Bis(diphenylphosphino)ferrocene)palladium(II) dichloride |
| BHT | Tert-butylhydroxytoluene |
| Bn | benzyl |
| Boc | tert-butoxy carbonyl |
| Boc$_2$O | di-tert-butyl dicarbonate |
| bp | Boiling point |
| Bs | 4-bromophenylsulfonyl |
| Bu | butyl |
| Calcd | calculated |
| CBS | Corey-Bakshi-Shibata |
| CBZ; Cbz | carboxybenzyl |
| CDI | 1,1'-carbonyldiimidazole |
| CHAPS | 3-[(3-cholamidopropyl)dimethylammonio]-1-propanesulfonate |
| COMU | (1-cyano-2-ethoxy-2-oxoethylidenaminooxy)dimethylamino-morpholino-carbenium hexafluorophosphate |
| DABCO | 1,4-diazabicyclo[2.2.2]octane |
| DAST | (diethylamino)sulfur trifluoride |
| DBU | 1,8-diazabicycloundec-7-ene |
| DCE | 1,2-dichloroethane |
| DCM | Dichloromethane |
| DDQ | 2,3-dichloro-5,6-dicyano-1,4-benzoquinone |
| DIAD | Diisopropyl azodicarboxylate |
| Dioxane | 1,4-dioxane |
| DIPEA | N, N-diisopropyl-N-ethylamine |
| DMF | N,N-dimethylformamide |
| DMAP | 4-dimethylaminopyridine |
| DMEM | Eagle's medium |
| DMPU | 1,3-dimethyl-3,4,5,6-tetrahydro-2(1H)-pyrimidinone |
| DMSO | dimethysulfoxide |
| dppf | 1,1'-bis(diphenylphosphino)ferrocene |
| DSC | N,N'-disuccinimidyl carbonate |
| DTT | dithiothreitol |
| EA; EtOAc | ethyl acetate |
| EC$_{50}$ | half maximal effective concentration |
| EDC | N-(3-d imethylaminopropyl)-N'-ethylcarbodiimide |
| Et | ethyl |
| Et$_2$O | diethyl ether |
| Et$_3$N | triethylamine |
| EtOH | ethanol |
| equiv | equivalent |
| FBS | fetal bovine serum |
| F-NMR | Fluorine nuclear magnetic resonance spectroscopy |
| g | gram |
| h | hour |
| HATU | 0-(7-azabenzotriazol-1 -yl)-N,N,N',N'-tetramethyluronium hexafluorophosphate |
| HCV | hepatitis C virus |
| Hex; hex | hexanes |
| HMDS | hexamethyldisilazane(azide) |
| HMPA | hexamethylphosphoramide |
| $^1$H-NMR | proton nuclear magnetic resonance spectroscopy |
| HOAC | acetic acid |
| HPLC | high pressure liquid chromatography |
| i | iso |
| IPA | isopropyl alcohol |
| iPr$_2$NEt | diisopropylethyl amine |
| KHMDS | potassium bis(trimethylsilyl)amide |
| L | liter |
| LCMS-ESI$^+$ | liquid chromatography mass spectrometer (electrospray ionization) |
| LDA | lithium diisopropylamide |
| LiHMDS | lithium bis(trimethylsilyl)amide |
| M | molar concentration (mol/L) |
| mCPBA | meta-chloroperoxybenzoic acid |
| Me | methyl |
| MeCN | acetonitrile |

| | |
|---|---|
| MeOH | methanol |
| MeTHF | 2-methyltetrahydrofuran |
| mg | milligram |
| MHz | mega Hertz |
| mL | milliliter |
| mmol | millimole |
| min | minute |
| MTBE | methyl tert-butylether |
| Ms | methanesulfonyl |
| MsCl | methanesulfonyl chloride |
| MS | molecular sieves |
| n | normal |
| N | normal concentration |
| NaHDMS | Sodium bis(trimethylsilyl)amide |
| NCS | N-chlorosuccinimide |
| NMO | N-methylmorpholine-N-oxide |
| NMP | N-methylpyrrolidinone |
| o/n | overnight |
| Pf | 9-phenyl-9H-fluoren-9-yl |
| PG | protecting group |
| PE | petroleum ether |
| Ph | phenyl |
| PhMe | toluene |
| Piv-Cl | pivaloyl chloride |
| pM | picomolar |
| PMB | 4-methoxybenzyl |
| PMSF | phenylmethanesulfonyl fluoride |
| Pr | propyl |
| Pd(dppf)Cl$_2$; PdCl$_2$(dppf) | [1,1'-Bis(diphenylphosphino)ferrocene] |
| PdCl$_2$dppf | dichloropalladium(II) |
| PPh$_3$ | triphenylphosphine |
| RetTime | retention time |
| rt | room temperature |
| sat; sat. | saturated |
| sec | secondary |
| S$_N$1 | nucleophilic substitution unimolecular |
| S$_N$2 | nucleophilic substitution bimolecular |
| S$_N$Ar | nucleophilic substitution aromatic |
| t; tert | tertiary |
| TBAF | tetra-n-butylammonium fluoride |
| TBS; TBDMS | tert-Butyldimethylsilyl |
| TBTU | O-(benzotriazol-1-yl)-N,N,N',N'-tetramethyluronium tetrafluoroborate |
| TEA | triethylamine |
| temp | temperature |
| TEMPO | (2,2,6,6-Tetramethylpiperidin-1-yl)oxyl |
| Tf | trifluoromethanesulfonyl |
| TFA | trifluoroacetic acid |
| THF | tetrahydrofuran |
| TIPS | triisoproylsilyl |
| TLC | thin layer chromatography |
| TMS | trimethylsilyl |
| TMSCl | chlorotrimethylsilane |
| TMSOTf | trimethylsilyl trifluoromethanesulfonate |
| TPAP | tetrapropylammonium perruthenate |
| Tr | triphenylmethyl |
| Ts | para-toluenesulfonyl |
| w/w | weight/weight ratio |

DEFINITIONS

Unless stated otherwise, the following terms and phrases as used herein are intended to have the following meanings:

When a cyclic group (e.g. cycloalkyl, carbocycle, bicyclic carbocyclyl, heteroaryl, heterocyclyl) is limited by a number or range of numbers, the number or numbers refer to the number of atoms making up the cyclic group, including any heteroatoms. Therefore, for example, a 4-8 membered heterocyclyl group has 4, 5, 6, 7 or 8 ring atoms.

"Alkenyl" refers to a straight or branched chain hydrocarbyl with at least one site of unsaturation, e.g., a (sp$^2$) carbon-(sp$^2$)carbon double bond. For example, an alkenyl group can have 2 to 8 carbon atoms (i.e., C$_2$-C$_8$ alkenyl), or 2 to 6 carbon atoms (i.e., C$_2$-C$_6$ alkenyl). Examples of suitable alkenyl groups include, but are not limited to, ethylene or vinyl (—CH═CH$_2$) and allyl (—CH$_2$CH═CH$_2$).

"Alkenylene" refers to an alkene having two monovalent radical centers derived by the removal of two hydrogen atoms from the same or two different carbon atoms of a parent alkene. Exemplary alkenylene radicals include, but are not limited to, 1,2-ethenylene (—CH═CH—) or prop-1-enylene (—CH$_2$CH═CH—).

"Alkoxy" is RO— where R is alkyl, as defined herein. Non-limiting examples of alkoxy groups include methoxy, ethoxy and propoxy.

"Alkyl" refers to a saturated, straight or branched chain hydrocarbyl radical. For example, an alkyl group can have 1 to 8 carbon atoms (i.e., (C$_1$-C$_8$) alkyl) or 1 to 6 carbon atoms (i.e., (C$_1$-C$_6$ alkyl) or 1 to 4 carbon atoms. Examples of alkyl groups include, but are not limited to, methyl, ethyl, propyl, isopropyl, butyl, isobutyl, t-butyl, pentyl, hexyl, heptyl, octyl, nonyl and decyl.

"Alkylene" refers to an alkyl having two monovalent radical centers derived by the removal of two hydrogen atoms from the same or two different carbon atoms of a parent alkane. Examples of alkylene radicals include, but are not limited to, methylene (—CH$_2$—), ethylene (—CH$_2$CH$_2$—), propylene (—CH$_2$CH$_2$CH$_2$—) and butylene (—CH$_2$CH$_2$CH$_2$CH$_2$—).

"Alkynyl" refers to a straight or branched chain hydrocarbon with at least one site of unsaturation, e.g., a (sp) carbon-(sp)carbon triple bond. For example, an alkynyl group can have 2 to 8 carbon atoms (i.e., C$_2$-C$_8$ alkynyl) or 2 to 6 carbon atoms (i.e., C$_2$-C$_6$ alkynyl). Examples of alkynyl groups include, but are not limited to, acetylenyl (—C≡CH) and propargyl (—CH$_2$C≡CH) groups.

"Alkynylene" refers to an alkynyl having two monovalent radical centers derived by the removal of two hydrogen atoms from the same or two different carbon atoms of a parent alkyne. Typical alkynylene radicals include, but are not limited to, acetylene (—C≡C—), propargylene (—CH$_2$C≡C—), and 1-pentynylene (—CH$_2$CH$_2$CH$_2$C≡C—).

"Aryl" refers to a single all carbon aromatic ring or a multiple condensed all carbon ring system (e.g., a fused muticyclic ring system) wherein at least one of the rings is aromatic. For example, an aryl group can have 6 to 20 carbon atoms, 6 to 14 carbon atoms, or 6 to 12 carbon atoms. It is to be understood that the point of attachment of a multiple condensed ring system, as defined above, can be at any position of the ring system including an aromatic or a carbocycle portion of the ring. Examples of aryl groups include, but are not limited to, phenyl, naphthyl, tetrahydronaphthyl and indanyl.

"Arylene" refers to an aryl as defined herein having two monovalent radical centers derived by the removal of two hydrogen atoms from two different carbon atoms of a parent aryl. Typical arylene radicals include, but are not limited to, phenylene, e.g.,

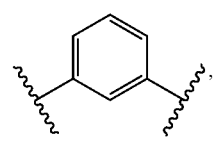 [SMILES: *c1cccc(*)c1]

and naphthylene, e.g.,

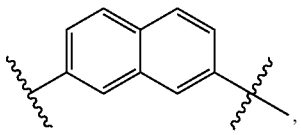 [SMILES: *c1ccc2ccc(*)cc2c1]

"Bicyclic carbocyclyl" refers to a 5-14 membered saturated or partially unsaturated bicyclic fused, bridged, or spiro ring hydrocarbon attached via a ring carbon. In a spiro bicyclic carbocycle, the two rings share a single common carbon atom. In a fused bicyclic carbocycle, the two rings share two common and adjacent carbon atoms. In a bridged bicyclic carbocycle, the two rings share three or more common, non-adjacent carbon atoms. Examples of bicyclic carbocyclyl groups include, but are not limited to spiro bicyclic carbocyclyl groups

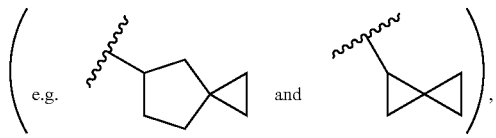

fused bicyclic carbocyclyl groups

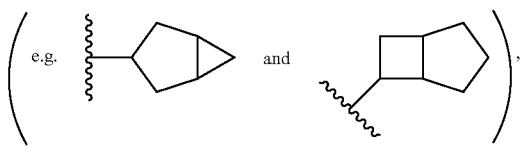

and bridged bicyclic carbocyclyl groups

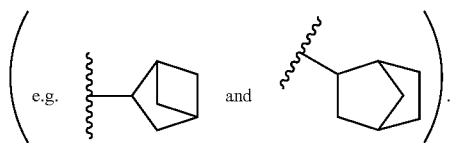

"Bicyclic carbocyclene" refers to a bicyclic carbocyclyl, as defined above, having two monovalent radical centers derived from the removal of two hydrogen atoms from the same or two different carbon atom of a parent bicyclic carbocyclyl. Examples of bicyclic carbocyclene groups include, but are not limited to, spiro bicyclic carbocyclene groups

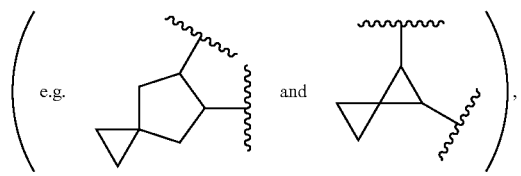

fused bicyclic carbocyclene groups

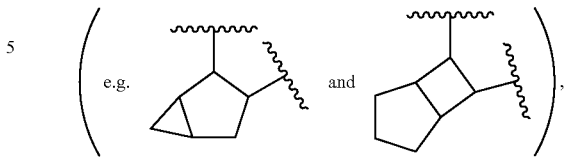

and bridged bicyclic carbocyclene groups

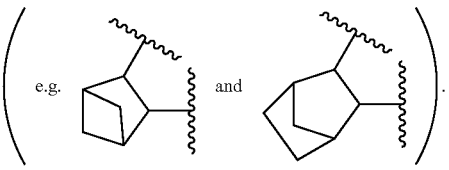

"Bicyclic carbocyclyloxy" is RO— where R is bicyclic carbocyclyl, as defined herein.

"Carbocyclyl (or "carbocycle") refers to a hydrocarbyl group containing one saturated or partially unsaturated ring structure, attached via a ring carbon. In various embodiments, carbocyclyl refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl.

"Carbocyclylene" refers to a carbocyclyl, as defined herein, having two monovalent radical centers derived by the removal of two hydrogen atoms from the same or two different carbon atoms of a parent carbocyclyl. Examples of carbocyclene include, but are not limited to, cyclopropylene, cyclobutylene, cyclopentylene and cyclohexylene.

"Carbocyclylalkyl" refers to a hydrocarbyl group containing one saturated or partially unsaturated ring structure attached to an alkyl group, attached via a ring carbon or an alkyl carbon. In various embodiments, carbocyclylalkyl refers to a saturated or a partially unsaturated $C_r$-$C_{12}$ carbocyclylalkyl moiety, examples of which include cyclopropylalkyl, cyclobutylalkyl, cyclopropylethyl, and cyclopropylpropyl.

"Carbocyclylalkylene" refers to a carbocyclylalkyl, as defined herein, having two monovalent radical centers derived by the removal of two hydrogen atoms from the same or two different carbon atoms of a parent cycloalkylalkyl. Examples of cycloalkylene include, but are not limited to, cyclopropylmethylene and cyclopropyl methylene.

"Cycloalkyl" refers to a hydrocarbyl group containing one saturated ring structure, attached via a ring carbon. In various embodiments, cycloalkyl refers to a saturated $C_3$-$C_{12}$ cyclic moiety, examples of which include cyclopropyl, cyclobutyl, cyclopentyl, cyclohexyl, cycloheptyl and cyclooctyl.

"Cycloalkoxy" is RO— where R is cycloalkyl, as defined herein.

"Halo" or "halogen" refers to chloro (—Cl), bromo (—Br), fluoro (—F) or iodo (—I).

"Haloalkenyl" refers to alkenyl group, as defined herein, substituted with one or more halogen atoms.

"Haloalkoxy" refers to alkoxy, as defined herein, substituted with one or more halogen atoms.

"Haloalkyl" refers to an alkyl group, in which one or more hydrogen atoms of the alkyl group is replaced with a halogen atom. Examples of haloalkyl groups include, but are not limited to, —CF$_3$, —CHF$_2$, —CFH$_2$ and —CH$_2$CF$_3$.

"Haloalkylene" refers to alkylene group, as defined herein, substituted with one or more halogen atoms.

"Heteroalkyl" refers to an alkyl group, as defined herein, in which one or more carbon atoms is replaced with an oxygen, sulfur, or nitrogen atom.

"Heteroalkylene" refers to an alkylene group, as defined herein, in which one or more carbon atoms is replaced with an oxygen, sulfur, or nitrogenatom.

"Heteroalkenyl" refers to an alkenyl group, as defined herein, in which one or more carbon atoms is replaced with an oxygen, sulfur, or nitrogenatom.

"Heteroalkenylene" refers to heteroalkenyl group, as defined above, having two monovalent radical centers derived by the removal of two hydrogen atoms from the same or two different atoms of a parent heteroalkenyl group.

"Heteroaryl" refers to a single aromatic ring that has at least one atom other than carbon in the ring, wherein the atom is selected from the group consisting of oxygen, nitrogen and sulfur; the term also includes multiple condensed ring systems that have at least one such aromatic ring. For example, heteroaryl includes monocyclic, bicyclic or tricyclic ring having up to 6 atoms in each ring, wherein at least one ring is aromatic and contains from 1 to 4 heteroatoms in the ring selected from the group consisting of oxygen, nitrogen and sulfur. The rings of the multiple condensed ring system can be connected to each other via fused, spiro and bridged bonds when allowed by valency requirements. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, quinoxalinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl.

"Heteroarylene" refers to a heteroaryl, as defined above, having two monovalent radical centers derived by the removal of two hydrogen atoms from the same or two different carbon atoms or the removal of a hydrogen from one carbon atom and the removal of a hydrogen atom from one nitrogen atom of a parent heteroaryl group. Non-limiting examples of heteroarylene groups are:

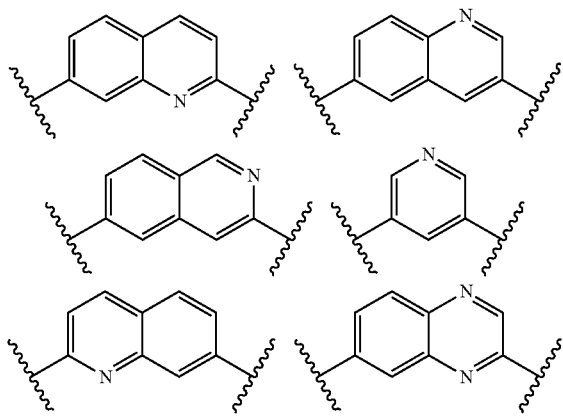

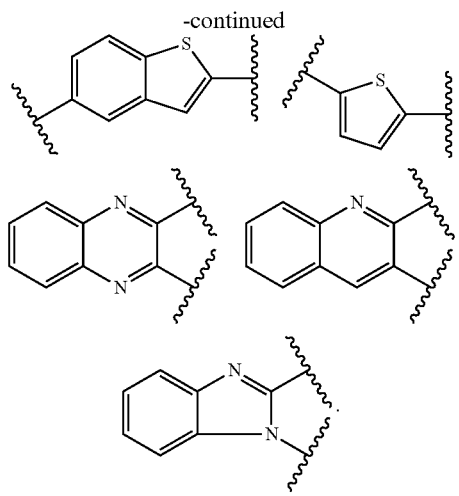

"Heterocyclyl" refers to a saturated or partially unsaturated monocyclic, bicyclic or tricyclic group of 2 to 14 ring-carbon atoms and, in addition to ring-carbon atoms, 1 to 4 heteroatoms selected from nitrogen, oxygen and sulfer. Bi- or tricyclic heterocyclyl groups may have fused, bridged, or spiro ring connectivity. In various embodiments the heterocyclic group is attached to another moiety through carbon or through a heteroatom, and is optionally substituted on carbon or a heteroatom. Examples of heterocyclyl include without limitation azetidinyl, oxazolinyl, isoxazolinyl, oxetanyl, tetrahydropyranyl, tetrahydrothiopyranyl, tetrahydroisoquinolinyl, 1,4-dioxanyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, chromanyl, dihydropyranoquinoxalinyl, tetrahydroquinoxalinyl, tetrahydroquinolinyl, dihydropyranoquinolinyl and tetrahydrothienyl and N-oxides thereof.

"Heterocyclene" refers to a heterocyclyl, as defined herein, having two monovalent radical centers derived from the removal of two hydrogen atoms from the same or two different carbon atoms, through a carbon and a heteroatom, or through two heteroatoms of a parent heterocycle.

The term "oxo" or "oxo group" refers to an oxygen atom (e.g. an oxygen double bonded to a carbon, an —OH group bonded to a carbon, etc).

"Prodrug" refers to any compound that when administered to a biological system generates the drug substance, or active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound. Non-limiting examples of prodrugs include ester moieties, quaternary ammonium moieties, glycol moieties, and the like.

The term "optionally substituted" refers to a moiety wherein all substituents are hydrogen or wherein one or more of the hydrogens of the moiety are replaced by non-hydrogen substituents; that is to say the moiety that is optionally substituted is either substituted or unsubstituted.

"Leaving group" (LG) refers to a moiety of a compound that is active towards displacement or substitution in a chemical reaction. Examples of in which such as displacement or substitution occur include, but are not limited to, nucleophilic substitution bimolecular ($S_N2$), nucleophilic substitution unimolecular ($S_N1$), nucleophilic aromatic substitution ($S_NAr$), and transition metal catalyzed cross-couplings. Examples of leaving groups include, but are not limited to, a halogen atom (e.g. —Cl, —Br, —I) and sulfonates (e.g. mesylate (—OMs), tosylate (—OTs) or triflate (—OTf)). The skilled artisan will be aware of various chemical leaving groups and strategies for activation and will appreciate the appropriate moiety that will act as leaving groups, based on the particular chemical reaction, the functionality that the group is attached to, and the chemical reagents used to affect the displacement or substitution reaction. As a non-limiting example, in some situations, a halogen atom (e.g. —Cl, —Br, or —I) serves as a leaving group in a reaction catalyzed by a transition metal (e.g. Pd catalyzed Suzuki coupling between an aryl halide and aryl boronic acid) and another reagents such as a base.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their mirror image partner.

"Isomers" are different compounds that have the same molecular formula. Isomers include stereoisomers, enantiomers and diastereomers.

"Diastereoisomers" are stereoisomers that have at least two asymmetric atoms, but which are not mirror-images of each other.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

The term "stereoisomers" refers to compounds which have identical chemical constitution, but differ with regard to the arrangement of the atoms or groups in space. The term "atropisomers" refers to stereoisomers having hindered rotation about a single bond.

The compounds disclosed herein may have chiral centers, e.g., chiral carbon atoms. Such compounds thus include racemic mixtures of all stereoisomers, including enantiomers, diastereomers, and atropisomers. In addition, the compounds disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

Tautomers

The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Isotopes

It is understood by one skilled in the art that this invention also includes any compound claimed that may be enriched at any or all atoms above naturally occurring isotopic ratios with one or more isotopes such as, but not limited to, deuterium ($^2H$ or D). As a non-limiting example, a —$CH_3$ group may be replaced by —$CD_3$.

Specific values listed below for radicals, substituents, and ranges are for illustration only; they do not exclude other defined values or other values within defined ranges for the radicals and substituents.

Protecting Groups

In certain embodiments, protecting groups include prodrug moieties and chemical protecting groups. Protecting groups may be represented by the abbreviation "PG."

"Protecting group" ("PG") refers to a moiety of a compound that masks or alters the properties of a functional group or the properties of the compound as a whole. Chemical protecting groups and strategies for protection/deprotection are well known in the art. See e.g. Peter G. M. Wuts and Theodora W. Greene, *Protective Groups in Organic Synthesis*, 4th edition; John Wiley & Sons, Inc.: New Jersey, 2007. Protecting groups are often utilized to mask the reactivity of certain functional groups, to assist in the efficiency of desired chemical reactions, e.g., making and breaking chemical bonds in an ordered and planned fashion.

Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

In certain embodiments, protecting groups are optionally employed to prevent side reactions with the protected group during synthetic procedures. Selection of the appropriate groups to protect, when to do so, and the nature of the chemical protecting group "PG" is dependent upon the chemistry of the reaction to be protected against (e.g., acidic, basic, oxidative, reductive or other conditions) and the intended direction of the synthesis. PGs do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free deprotected groups is dependent upon the intended direction of the synthesis and the reaction conditions to be encountered, and may occur in any order as determined by the artisan.

Salts and Hydrates

Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein each X is independently selected from H or a $C_1$-$C_4$ alkyl group).

For therapeutic use, salts of active ingredients of the compounds disclosed herein will typically be pharmaceutically acceptable, i.e., they will be salts derived from a physiologically acceptable acid or base. However, salts of acids or bases which are not pharmaceutically acceptable may also find use, for example, in the preparation or purification of a compound of formula I or another compound disclosed herein. All salts, whether or not derived from a physiologically acceptable acid or base, are within the scope of the present invention.

Metal salts typically are prepared by reacting the metal hydroxide with a compound disclosed herein. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, such as amines. Finally, it is to be understood that the compositions herein comprise compounds disclosed herein in their un-ionized, as well as zwitterionic form, and combinations with stoichiometric amounts of water as in hydrates.

Embodiments

In certain embodiments, M is —O— or a bond. In certain other embodiments of Formula 1, M is —O—.

In certain embodiments, X is —OC(O)—, —O—, or a direct bond. In certain other embodiments of Formula 1, X is —O—.

In certain embodiments, G is —$CO_2H$ or —$CONHSO_2Z^2$. In certain embodiments of Formula 1, G is:

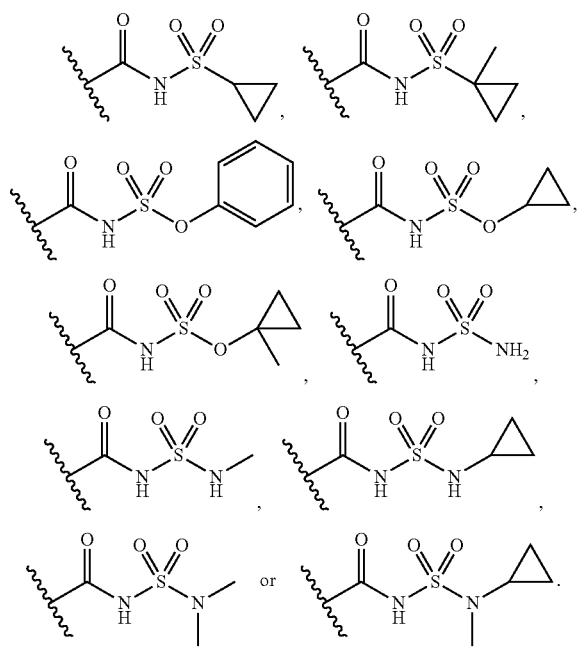

In certain embodiments, $Z^{2a}$ is hydrogen or $C_1$-$C_2$ alkyl. In certain embodiments, $Z^{2a}$ is hydrogen or methyl. In other embodiments, $Z^{2a}$ is hydrogen. In further embodiments, $Z^{2a}$ is methyl.

In certain embodiments,

is $T^1$, $T^2$, or $T^3$, optionally substituted with 1-4 $Z^1$ groups which are the same or different. In certain embodiments where

optionally substituted with 1-4 $Z^1$ groups and where is $T^1$, $T^2$, or $T^3$, $T^1$ is:

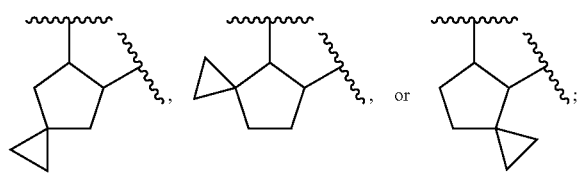 [SMILES: *C1CC2(CC2)CC1* ; *C1CCC2(CC2)C1* ; *C1CCC2(CC2)C1*]

T² is:

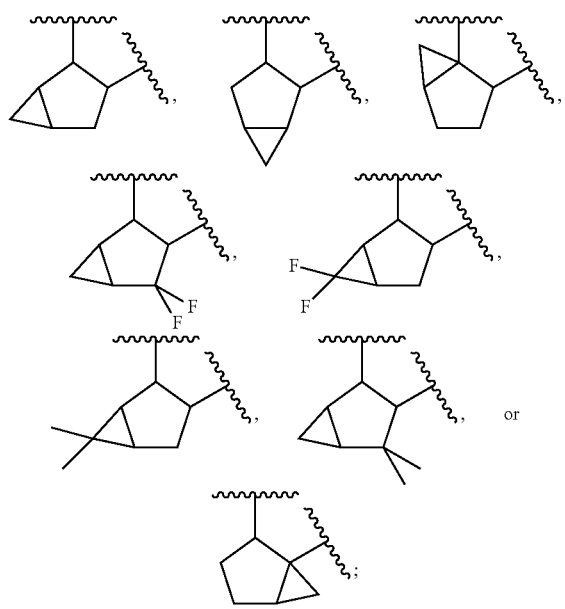

and
T³ is:

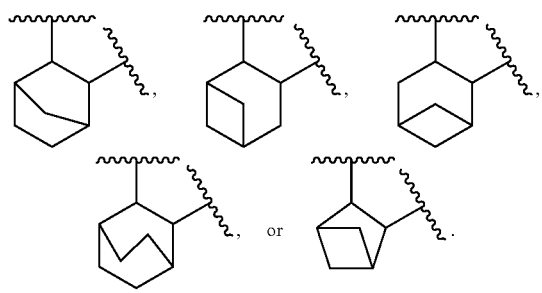

In certain embodiments,

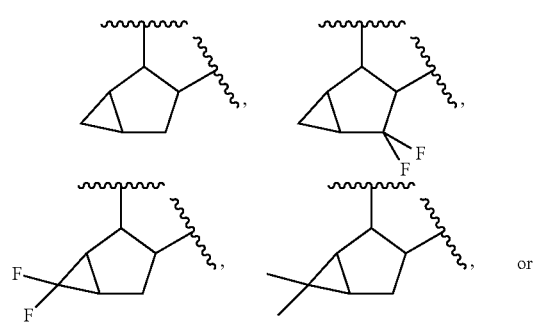

is T², which is optionally substituted with 1-4 Z¹ groups, which are the same or different.

In certain embodiments, T² is:

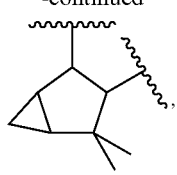

In certain embodiments,

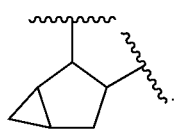 [SMILES: *C1CC2CC2C1*]

T² is:

In certain embodiments,

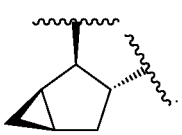 [SMILES: *[C@@H]1[C@@H]2C[C@@H]2C[C@H]1*]

T² is:

In certain embodiments,

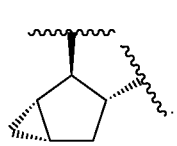 [SMILES: *[C@@H]1[C@H]2C[C@H]2C[C@H]1*]

T² is:

In certain embodiments, J is —O—, —CH$_2$—, —CF$_2$—, —C(O)—, —N(R$^{16}$)—, or a bond. In certain embodiments, J is —O— or —CH$_2$—. In certain other embodiments, J is —O—. In further embodiments, J is —CH$_2$—, —CF$_2$—, —C(O)—, —N(R$^{16}$)—, or a bond. In still more embodiments, J is —CH$_2$— or —CF$_2$—. In further other embodiments, J is —CH$_2$—.

In certain embodiments, J is C$_1$-C$_3$ alkylene optionally substituted with 1-2 halogen atoms. In certain other embodiments, J is optionally substituted with 1-2 halogen atoms connected to the same carbon atom. In certain embodiments, J is optionally substituted with one or more fluoro or chloro atoms. In certain embodiments, J is optionally substituted with one or two fluoro or chloro atoms connected to the same carbon atom. In still further embodiments, J is —CH$_2$— or —CF$_2$—.

In certain embodiments, L is L¹, L², L³, L⁴, L⁵, L⁶, L⁷, L⁸, L⁹, L¹⁰, L¹¹ or L¹². In certain embodiments, L is L¹ or L².

In certain embodiments, $L^1$ is:
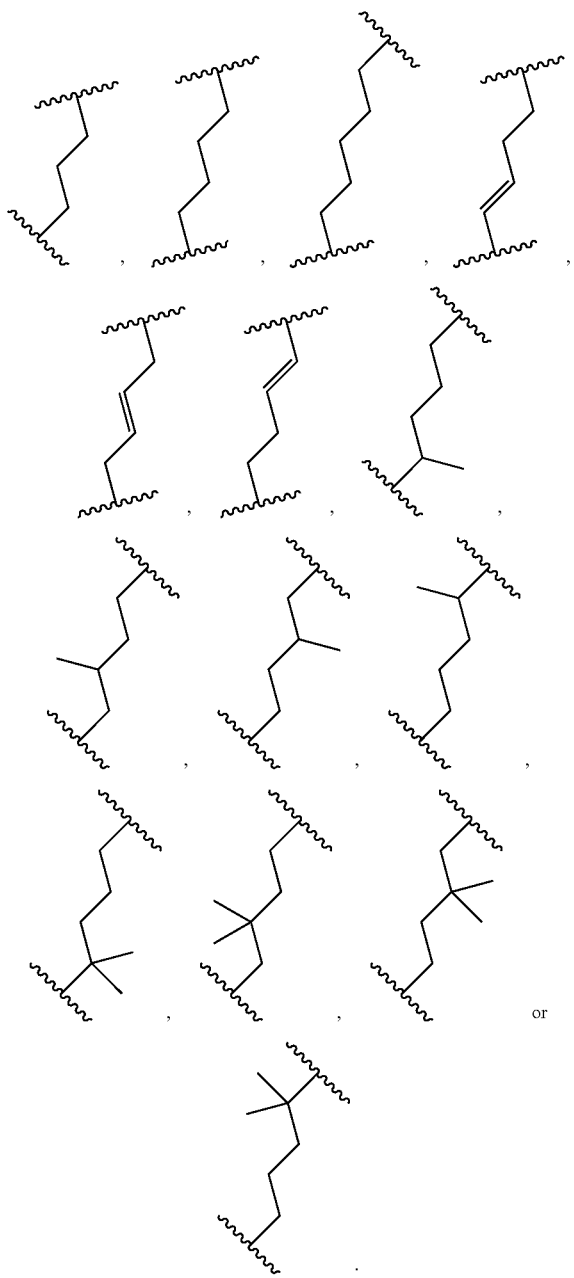
In certain embodiments $L^2$ is:
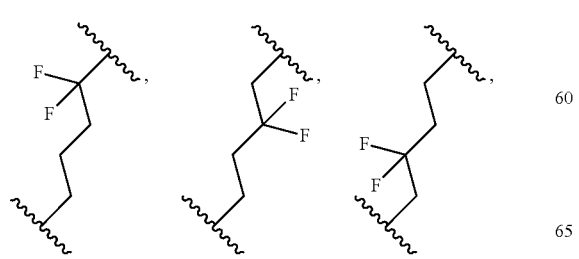
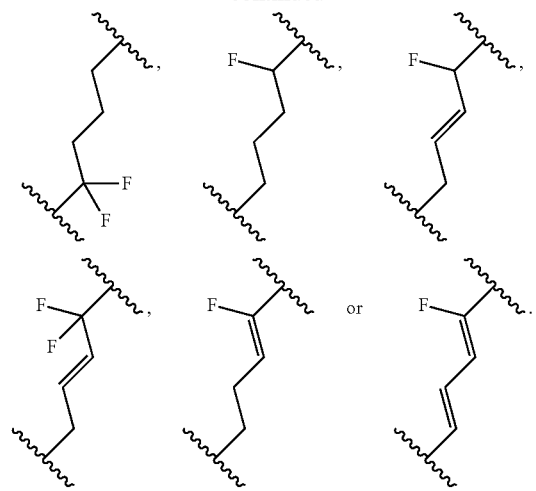
In certain embodiments $L^3$ is:
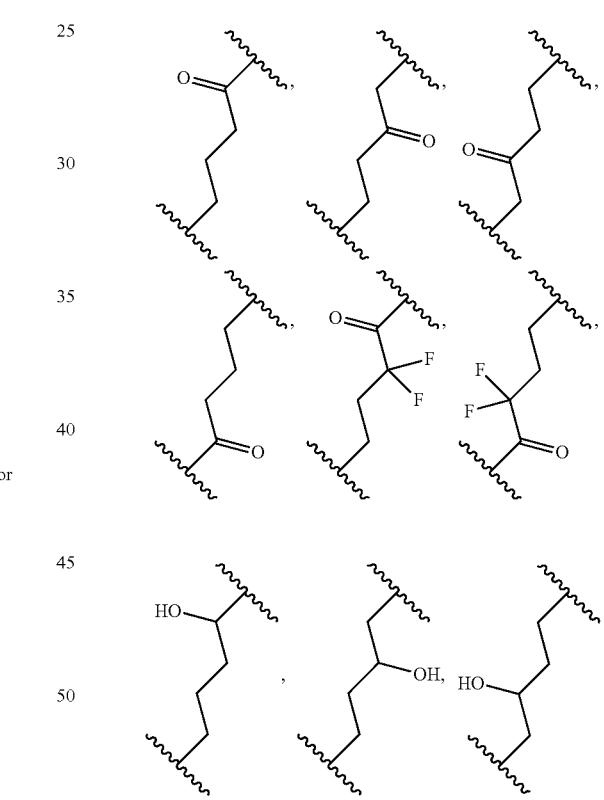
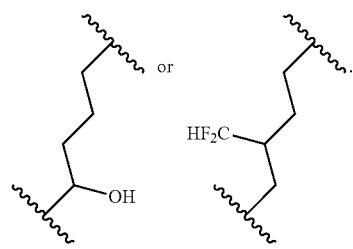

In certain embodiments, $L^4$ is:
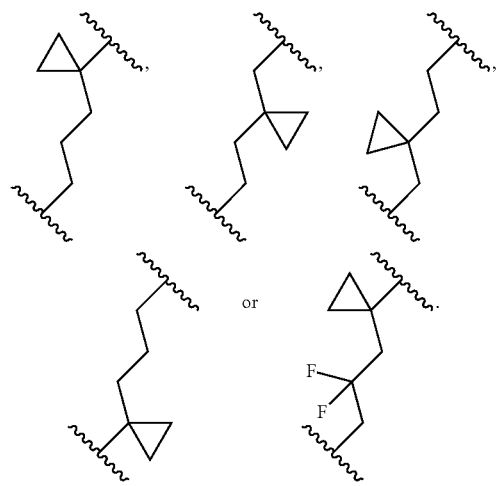
In certain embodiments, $L^5$ is:
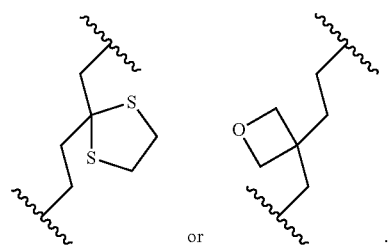 [SMILES: *CCC1(C*)SCCS1 ; *CCC1(C*)COC1]
In certain embodiments, $L^6$ is:
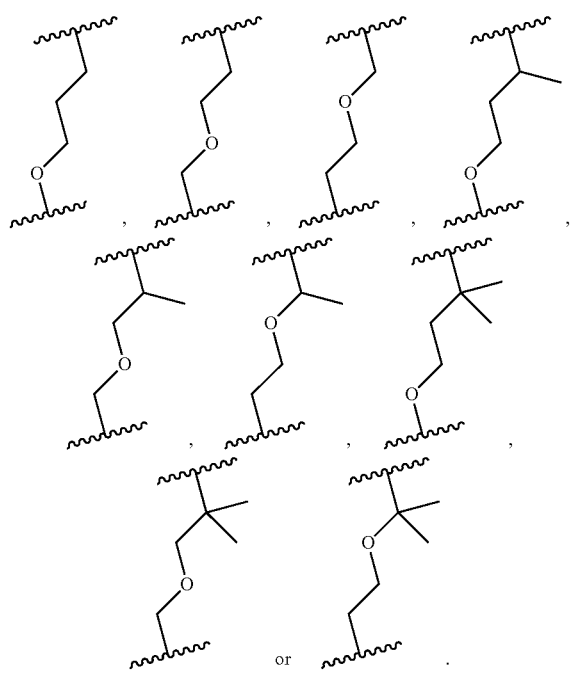
In certain embodiments, $L^7$ is:
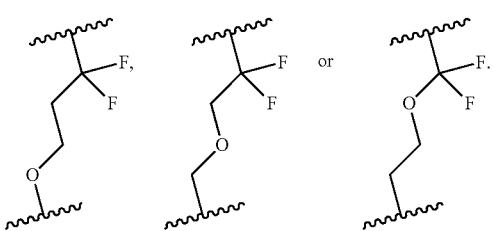 [SMILES: *OCCC(*)(F)F ; *COCC(*)(F)F ; "or" ; *CCOC(*)(F)F]
In certain embodiments, $L^8$ is:
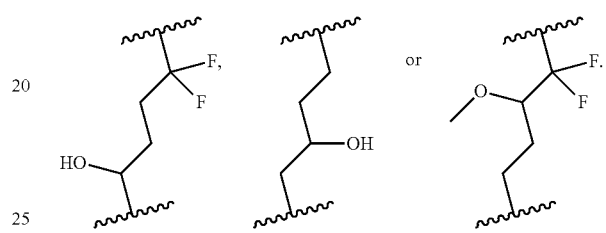
In certain embodiments, $L^9$ is:
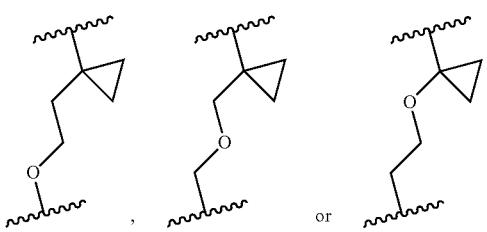
In certain embodiments, $L^{10}$ is:
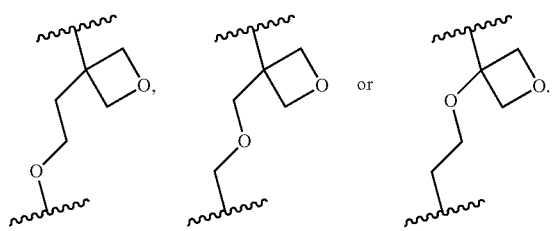 [SMILES: *OCCC1(*)COC1 ; *COCC1(*)COC1 ; "or" ; *CCOC1(*)COC1]
In certain embodiments, $L^{11}$ is:
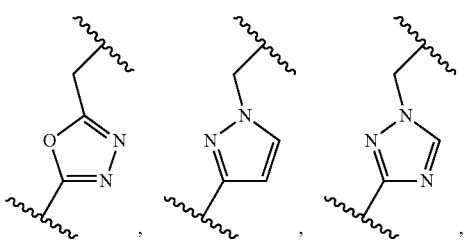

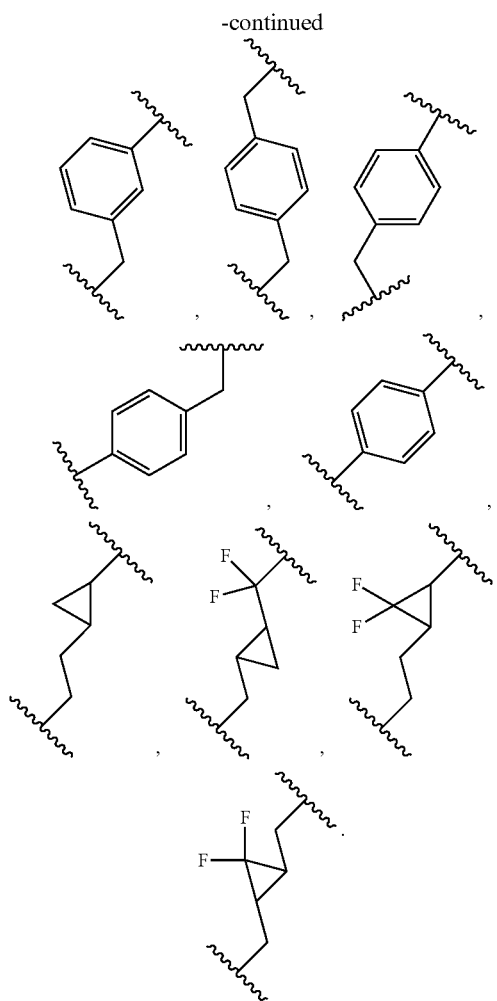
In certain embodiments, $L^{12}$ is:
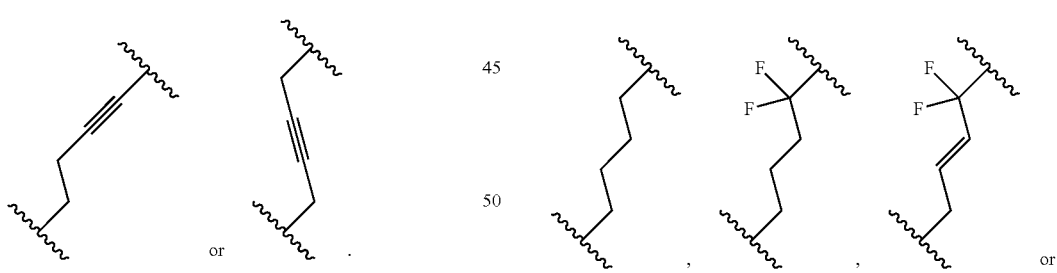
In certain other embodiments, L is:
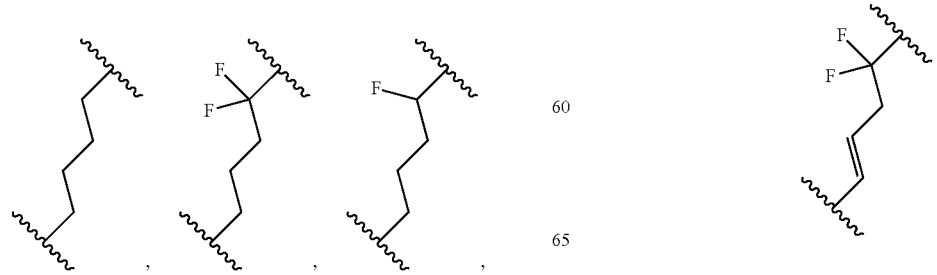
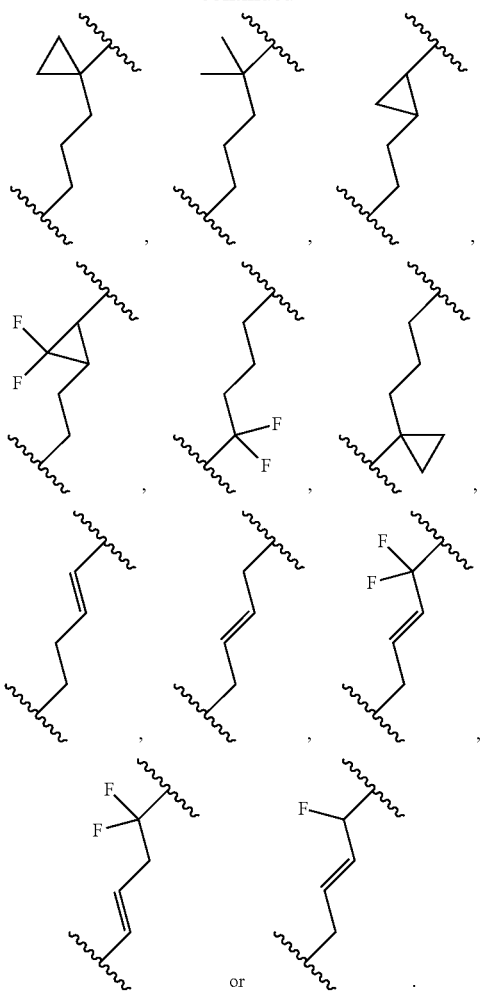
In further embodiments, L is:

In still other embodiments, L is

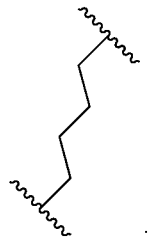 [SMILES: *CCCC*]

In additional embodiments, L is

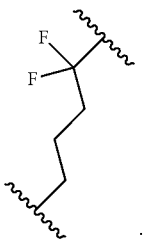 [SMILES: *CCCC(*)(F)F]

In certain embodiments, L is

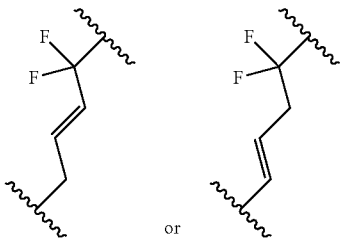

or

In certain embodiments, L is

In certain embodiments, L is $C_1$-$C_8$ alkylene or $C_2$-$C_8$ alkenylene wherein said $C_1$-$C_8$ alkylene or said $C_2$-$C_8$ alkenylene is optionally substituted with one or more $R^{25}$. In certain other embodiments, L is $C_3$-$C_6$ alkylene or $C_3$-$C_6$ alkenylene wherein said $C_3$-$C_6$ alkylene or $C_3$-$C_6$ alkenylene is optionally substituted with one or more $R^{25}$. In further embodiments, L is $C_4$ alkylene or $C_4$ alkenylene wherein said $C_4$ alkylene or $C_4$ alkenylene is optionally substituted with one or more $R^{25}$.

In certain embodiments, each $R^{25}$ is independently halogen, $C_1$-$C_4$ alkyl, $C_1$-$C_4$ haloalkyl, $C_3$-$C_6$ carbocyclyl, $C_3$-$C_6$ cycloalkyl, 3 to 6 membered heteroalkyl, —OH, or —O—($C_1$-$C_4$ alkyl), or oxo. In certain other embodiments, each $R^{25}$ is independently halogen, $C_1$-$C_4$ alkyl, $C_1$-$C_4$ haloalkyl, or —OH. In further embodiments, each $R^{25}$ is independently halogen.

In certain embodiments, L is $C_3$-$C_8$ alkyl or $C_3$-$C_8$ alkylene, wherein L is optionally substituted with up to two halogen atoms. In some embodiments, L is $C_3$-$C_8$ alkylene, $C_4$-$C_8$ carbocyclylalkylene or $C_3$-$C_8$ alkenylene, wherein L is optionally substituted with up to two halogen atoms.

In certain other embodiments, L is $C_3$-$C_6$ alkyl or $C_3$-$C_6$ alkylene, wherein L is optionally substituted with up to two halogen atoms. In certain other embodiments, L is $C_4$ alkyl or $C_4$ alkylene, wherein L is optionally substituted with up to two halogen atoms. In certain embodiments, when L is optionally substituted with up to two halogen atoms, the halogen atoms are connected to the same carbon atom.

In certain embodiments, L is:

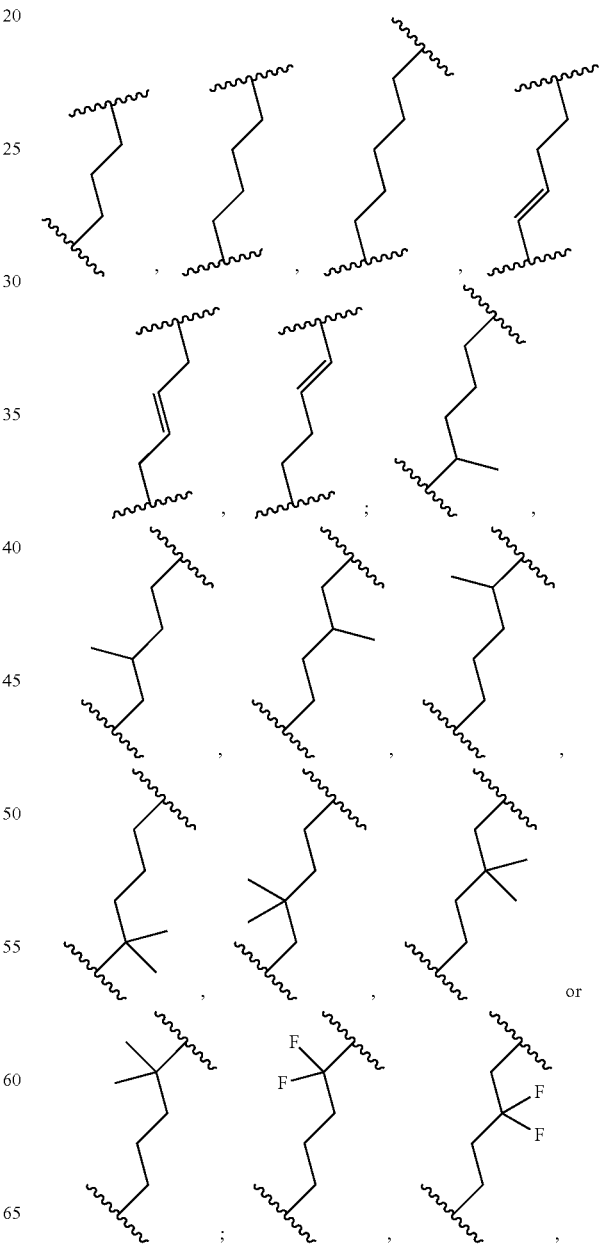

or

-continued
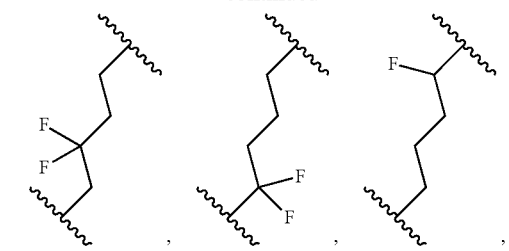
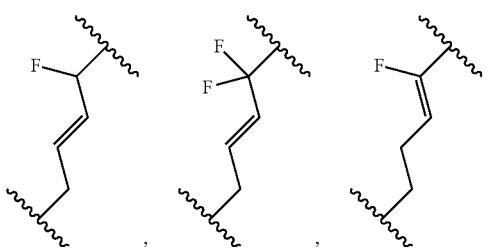
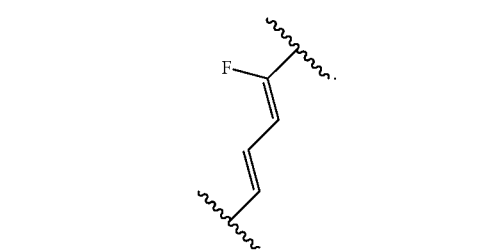 [SMILES: */C=C/C=C(/*)F]
In certain embodiments, L is
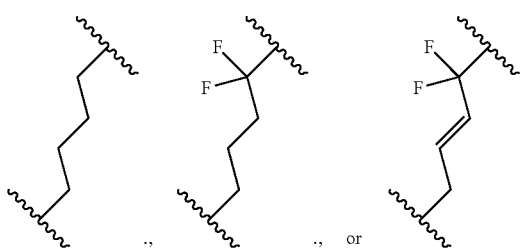
In certain embodiments, L is
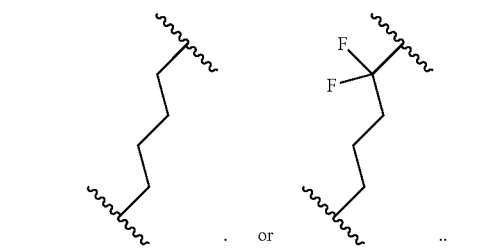 [SMILES: *CCCC* ; *CCCC(*)(F)F]
In certain embodiments, L is
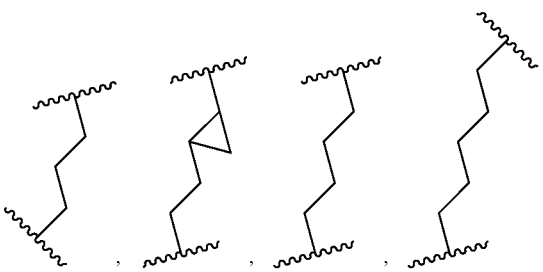
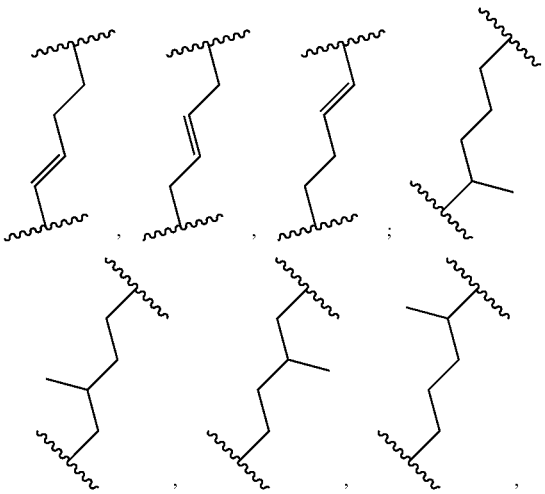
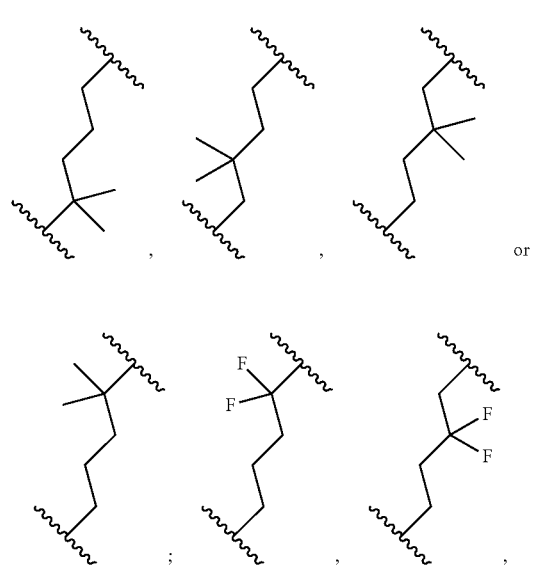
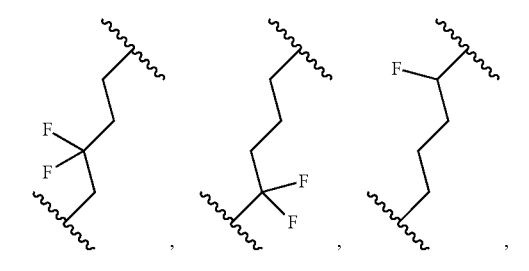

-continued

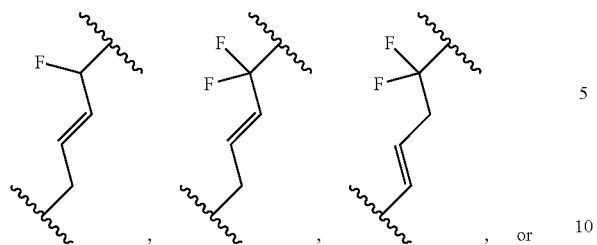
, , , or

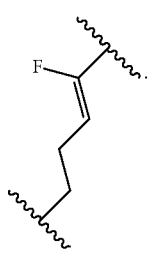 [SMILES: *CC/C=C(/*)F]
.

In certain embodiments, Q is $Q^1$, $Q^2$, $Q^3$, $Q^4$, $Q^5$ or $Q^7$. In certain embodiments, Q is $Q^1$.

In certain embodiments, Q is $C_1$-$C_6$ alkyl, $C_3$-$C_6$ carbocyclyl, or $C_3$-$C_8$ cycloalkyl. In certain embodiments, Q is $C_1$-$C_6$ alkyl, or $C_3$-$C_8$ carbocyclyl. In certain embodiments, Q is $C_1$-$C_6$ alkyl or $C_3$-$C_8$ cycloalkyl. In certain other embodiments, Q is $C_1$-$C_4$ alkyl. In further embodiments, Q is t-butyl. In some embodiments, Q is t-butyl or $C_5$-$C_6$ cycloalkyl.

In certain embodiments, $Q^1$ is

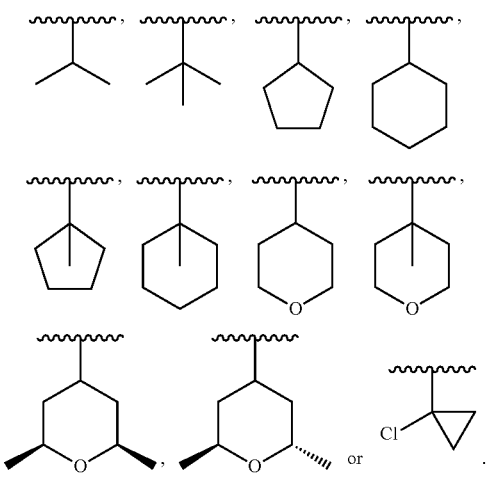

In certain embodiments, $Q^2$ is

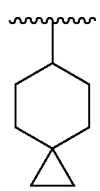
.

In certain embodiments, $Q^3$ is

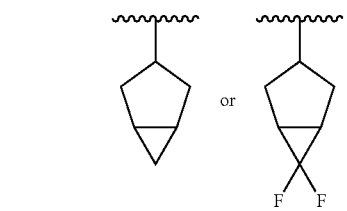

In certain embodiments, $Q^4$ is:

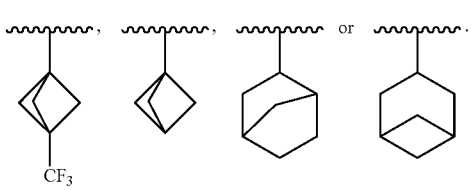

In certain embodiments, $Q^5$ is

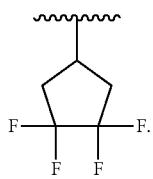

In certain embodiments, $Q^7$ is

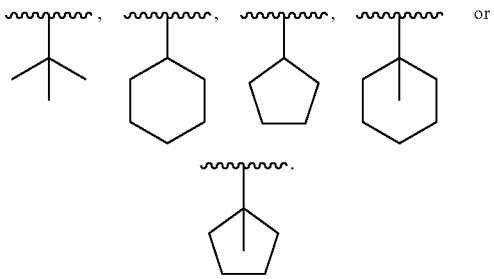

In certain embodiments, Q is:

In certain embodiments, Q is

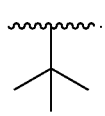
.

In certain embodiments, E is E¹, E², E³, or E⁴. In certain embodiments of Formula II, E is E¹, E² or E³. In other embodiments of Formula II, E is E² or E³. In certain embodiments, E is E³.

In certain other embodiments, E¹ is

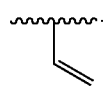 [SMILES: *C=C]

In certain embodiments, E² is:

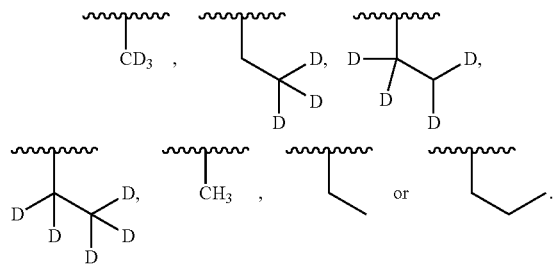

In certain embodiments, E³ is:

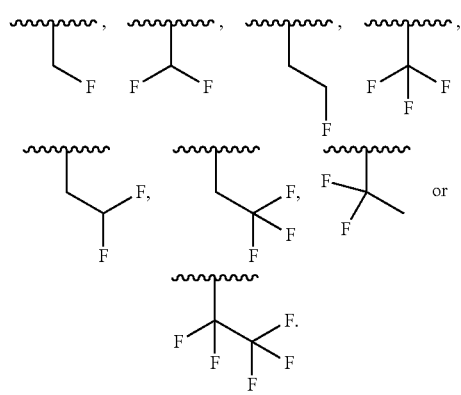

In certain embodiments E⁴ is:

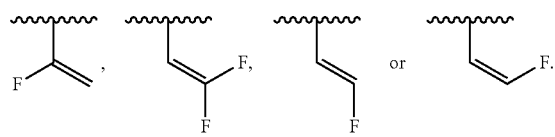

In some embodiments, E is

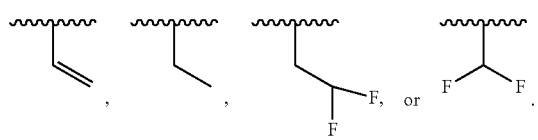

In other embodiments, E is

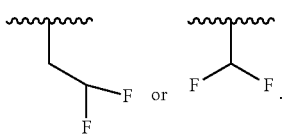

In certain embodiments, E is

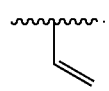

In other embodiments, E is

In further embodiments, E is

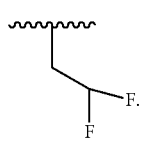 [SMILES: *CC(F)F]

In still more embodiments, E is

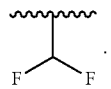

In certain embodiments, E is $C_1$-$C_4$ alkyl or $C_2$-$C_4$ alkenyl. In certain embodiments, E is $C_1$-$C_4$ alkyl.

In certain embodiments, E is optionally substituted with one, one or two, or one to three halogen atoms. In certain embodiments, E is optionally substituted with 1-2 halogen atoms connected to the same carbon atom. In certain embodiments, E is optionally substituted with two halogen atoms connected to the same carbon atom.

In certain embodiments, E is optionally substituted with one or more fluoro or chloro atoms. In certain embodiments, E is optionally substituted with 1-2 fluoro or chloro atoms connected to the same carbon atom. In certain embodiments, E is optionally substituted with two fluoro or chloro atoms connected to the same carbon atom.

In certain embodiments, when E is $C_1$-$C_4$ alkyl or $C_2$-$C_4$ alkenyl, E is optionally substituted with one or more fluoro (F) atoms. In certain other embodiments, when E is $C_1$-$C_4$ alkyl, E is optionally substituted with one or more fluoro (F) atoms.

In certain embodiments, E is —CHF₂ or —CH₂CHF₂.

In certain embodiments,

is bicyclic heteroaryl, optionally substituted with 1-4 W groups which are the same or different.

In certain other embodiments,

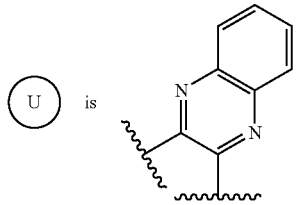

optionally substituted with 1-4 W groups, which are the same or different.

In certain embodiments,

is substituted with one W group.

In certain embodiments,

is optionally substituted with one or two W at any substitutable position.

In certain embodiments,

is

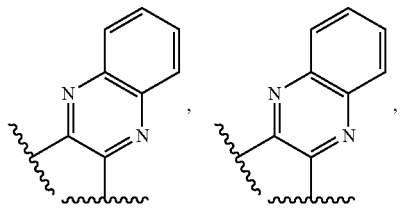

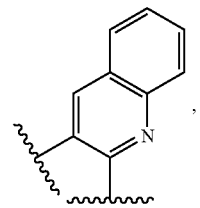

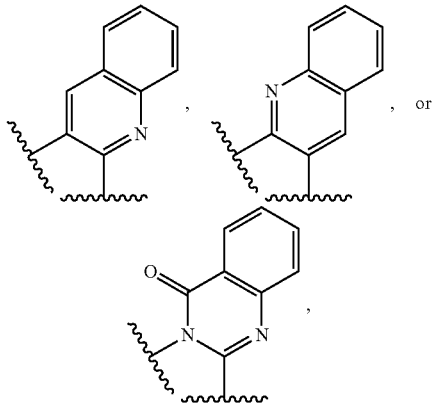

and

is optionally substituted with 1-2 W at any substitutable position.

In certain embodiments,

is optionally substituted with one or two W at any substitutable position, wherein

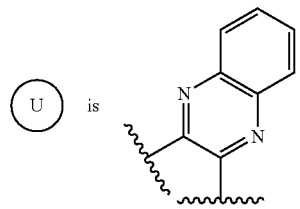

In certain embodiments,

is optionally substituted with one W at any substitutable position wherein

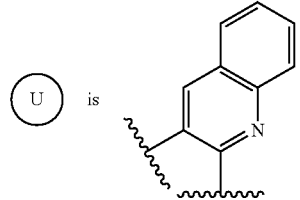

In certain embodiments,

is optionally substituted with one W at any substitutable position, wherein

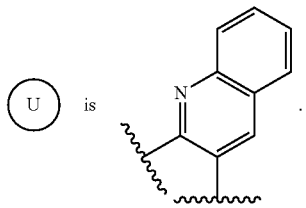

In certain embodiments,

is optionally substituted with one W at any substitutable position, wherein

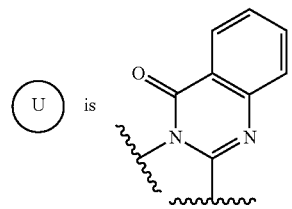

In certain embodiments,

is 8-12 membered bicyclic heteroaryl, 8-12 membered tricyclic heteroaryl, 8-12 membered bicyclic heterocyclyl, 8-12 membered tricyclic heterocyclyl, optionally substituted with 1-2 W groups.

In certain embodiments,

is 8-12 membered bicyclic heteroaryl, wherein the 8-12 membered bicyclic heteroaryl, has 4-10 carbon atoms and 1-5 heteroatoms in the ring system, and wherein any 8-12 membered bicyclic heteroaryl of

is optionally substituted with 1-2 W groups.

In certain embodiments,

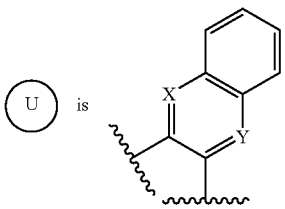

optionally substituted with 1-2 W groups, wherein X and Y are both H, or when one of X or Y is N, the other of X or Y is H.

In certain embodiments,

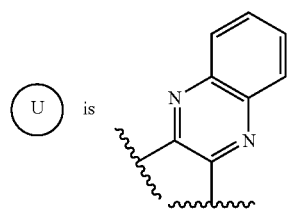

is optionally substituted with 1-2 W groups.

In certain embodiments,

is optionally substituted with one W at any substitutable position.

In certain embodiments, each W is independently $W^1$, $W^2$, $W^3$, $W^5$, $W^6$ or $W^7$. In certain other embodiments, each W is $W^1$.

In certain embodiments, each W is, independently, Cl, F, —OCH$_3$, —OCHF$_2$, or —CN. In certain embodiments, each W is, independently, F or —OCH$_3$.

In certain embodiments, each W is independently halogen or $C_1$-$C_4$ alkoxy.

In certain embodiments, $W^1$ is:

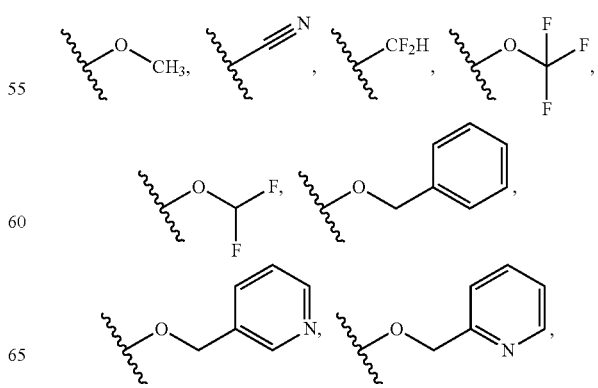

-continued
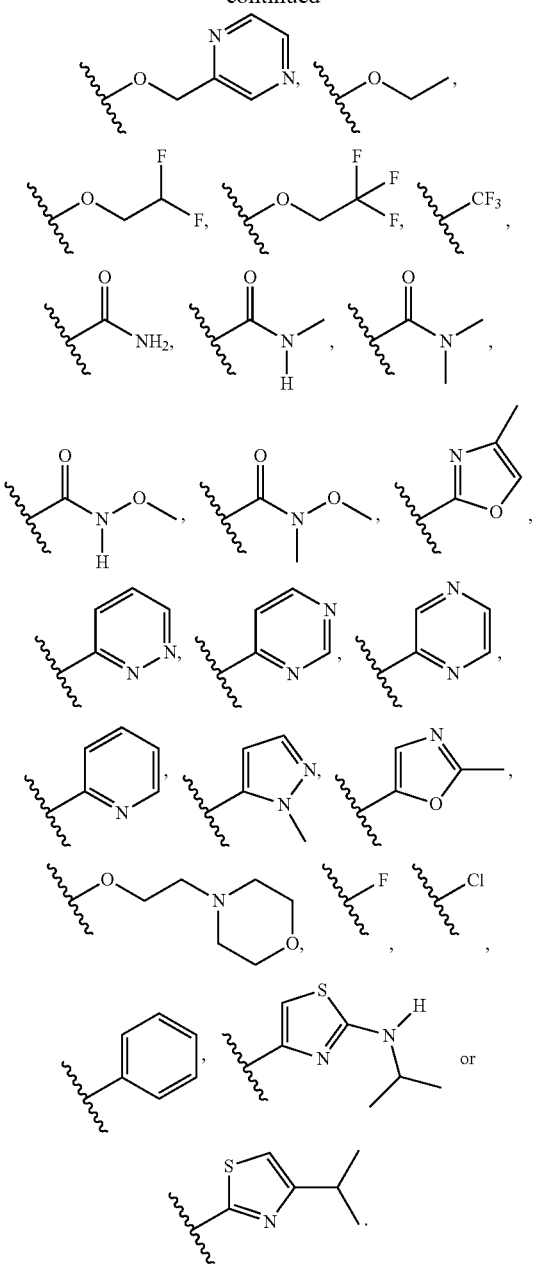
In certain embodiments, W² is
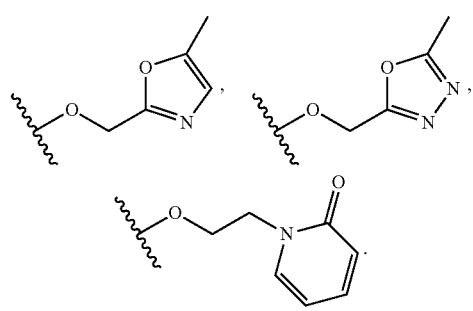
In certain embodiments, W³ is:
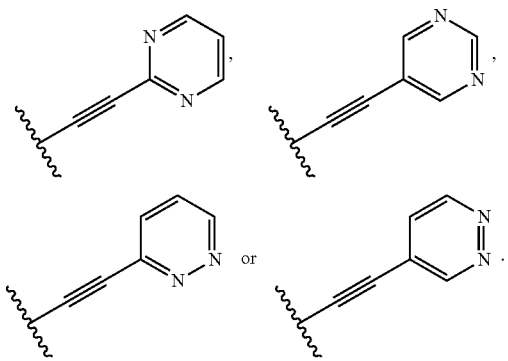
In certain embodiments, W⁵ is
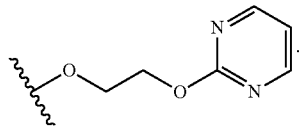 [SMILES: *OCCOc1ncccn1]
In certain embodiments, W⁶ is
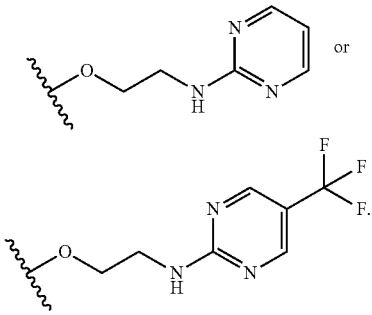
In certain embodiments, W⁷ is:
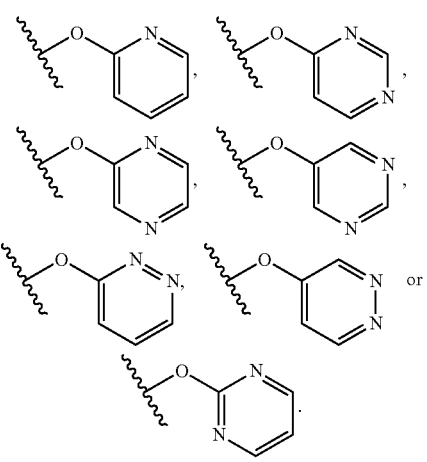

In certain embodiments, W is:

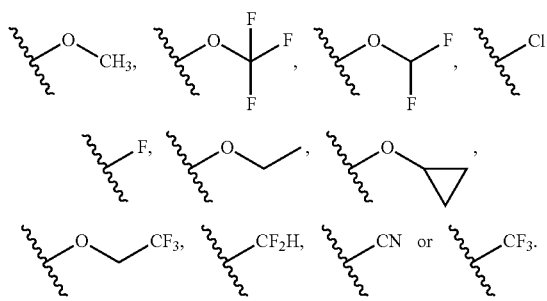

In certain embodiments, W is

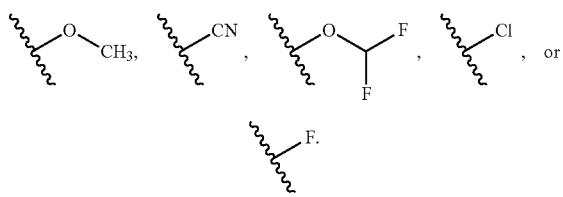

A specific group of compounds of Formula II are compounds of Formula IIa:

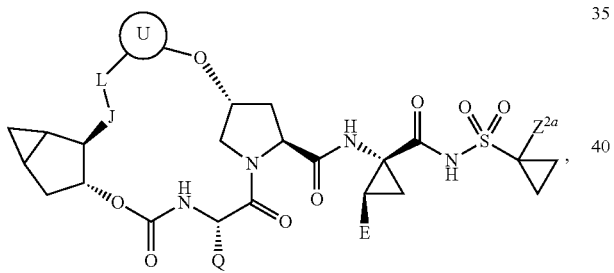

or a pharmaceutically acceptable salt thereof.

Another specific group of compounds of Formula II are compounds of Formula IIb:

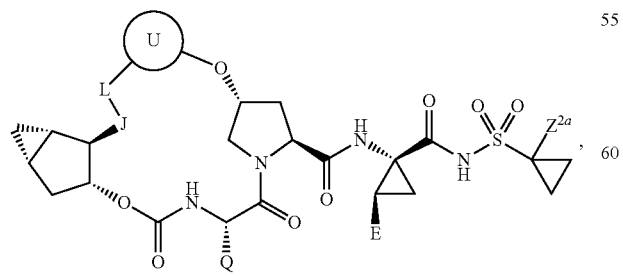

or a pharmaceutically acceptable salt thereof.

A specific group of compounds of Formula III are compounds of formula IIIa:

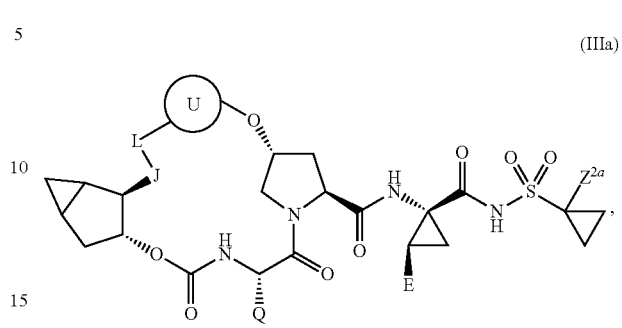

or a pharmaceutically acceptable salt thereof.

Another specific group of compounds of Formula III are compounds of formula IIIb:

or a pharmaceutically acceptable salt thereof.

One embodiment provides any one of the following compounds:

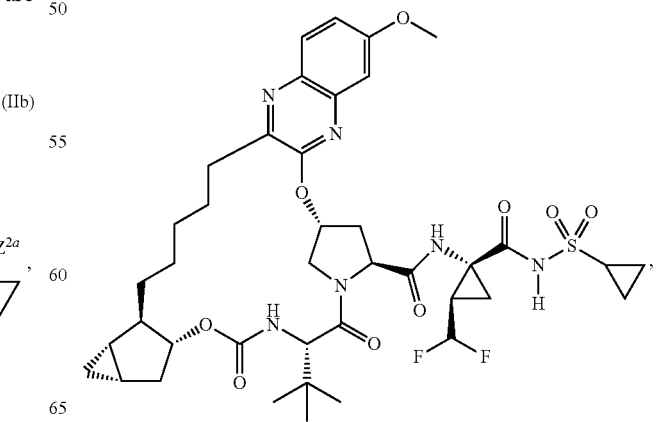

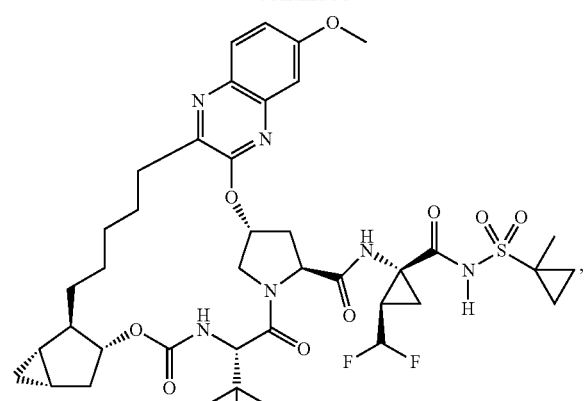
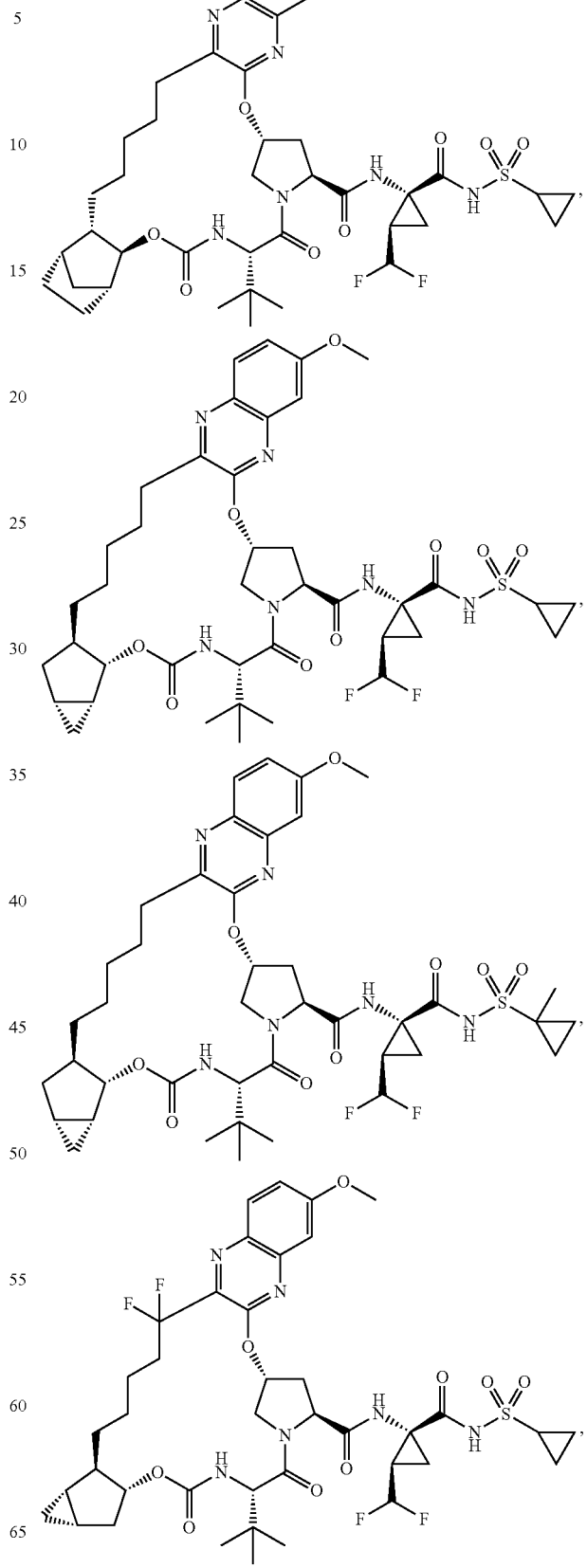

53
-continued
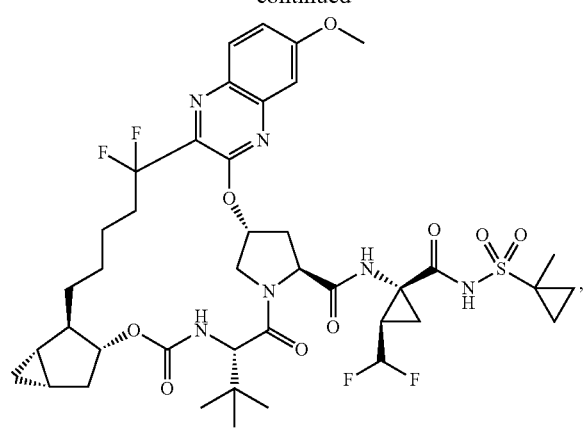
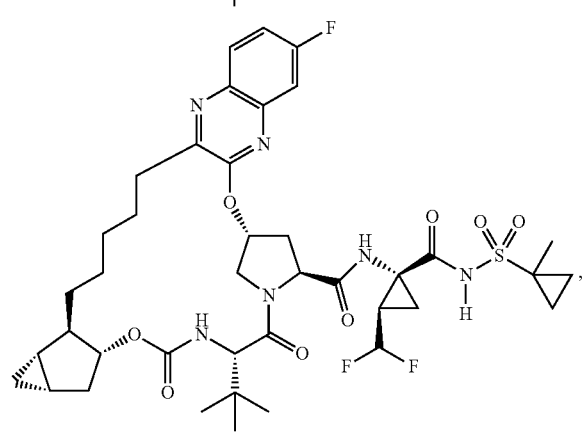
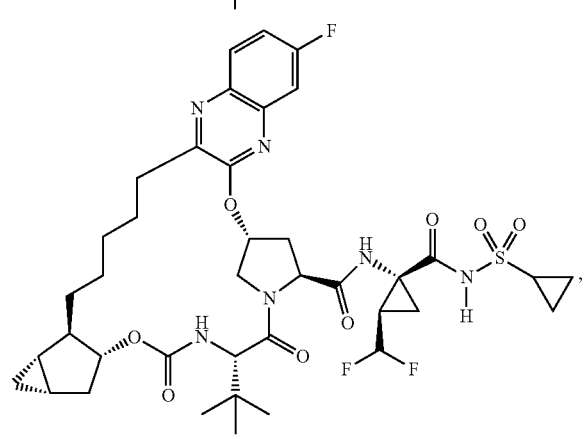
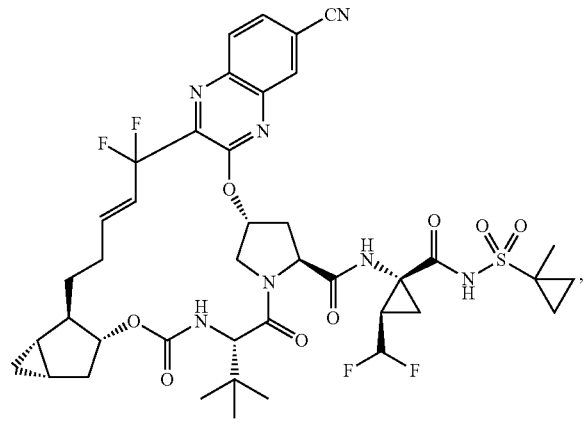
54
-continued
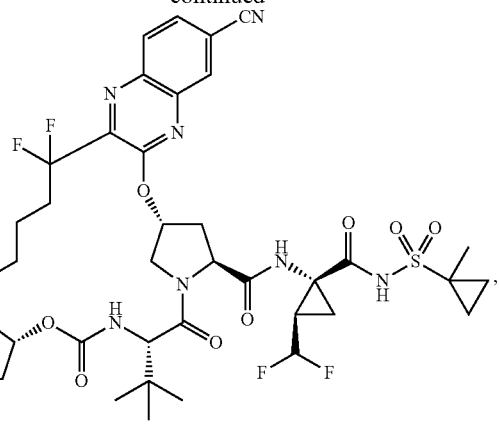
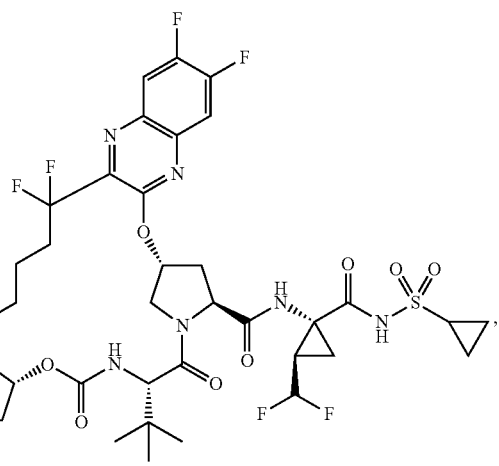
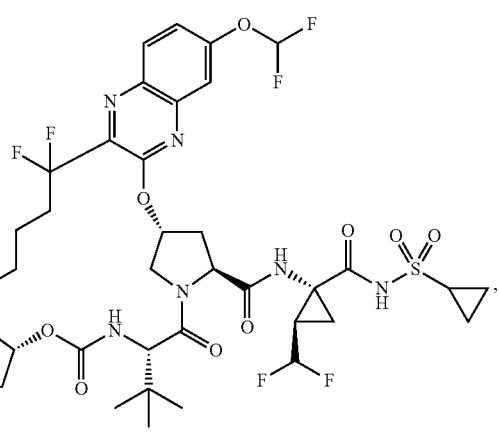

55
-continued
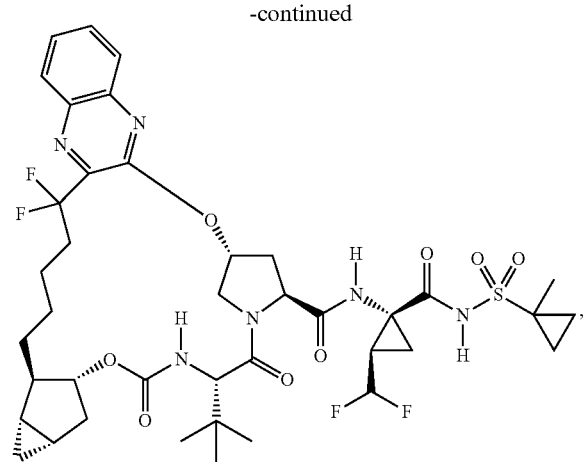
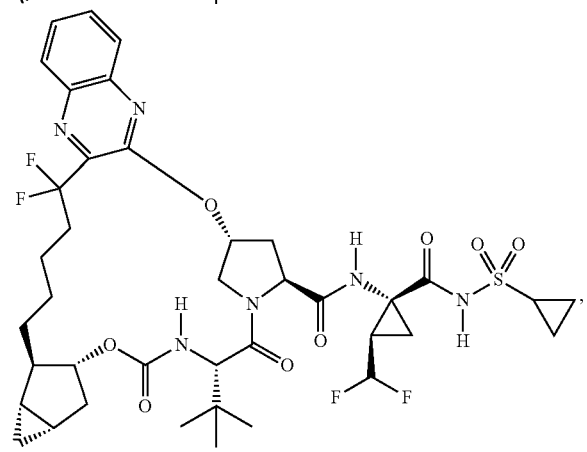
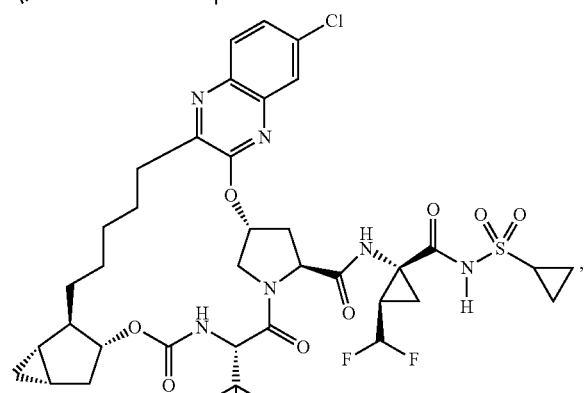
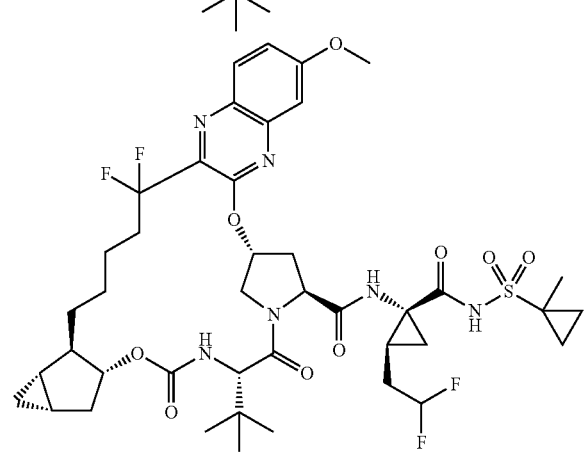
56
-continued
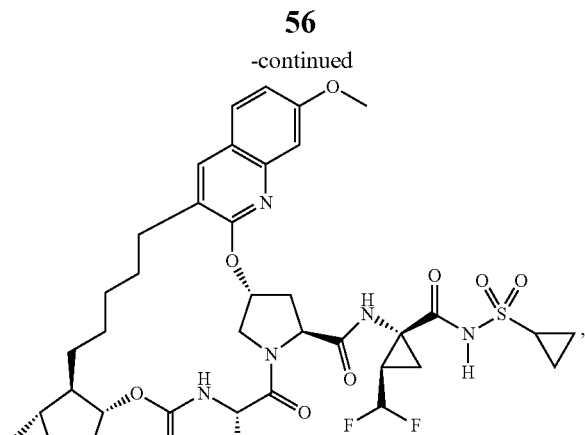
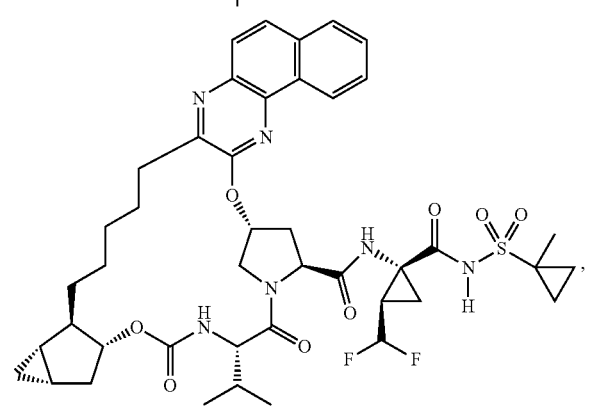
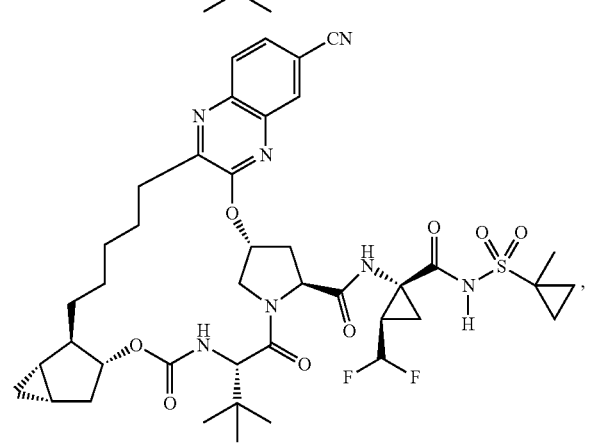
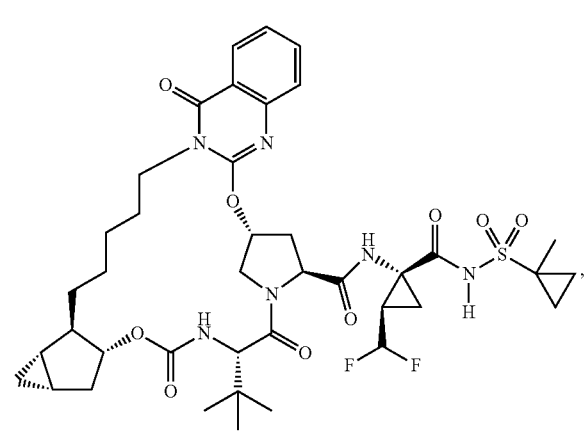

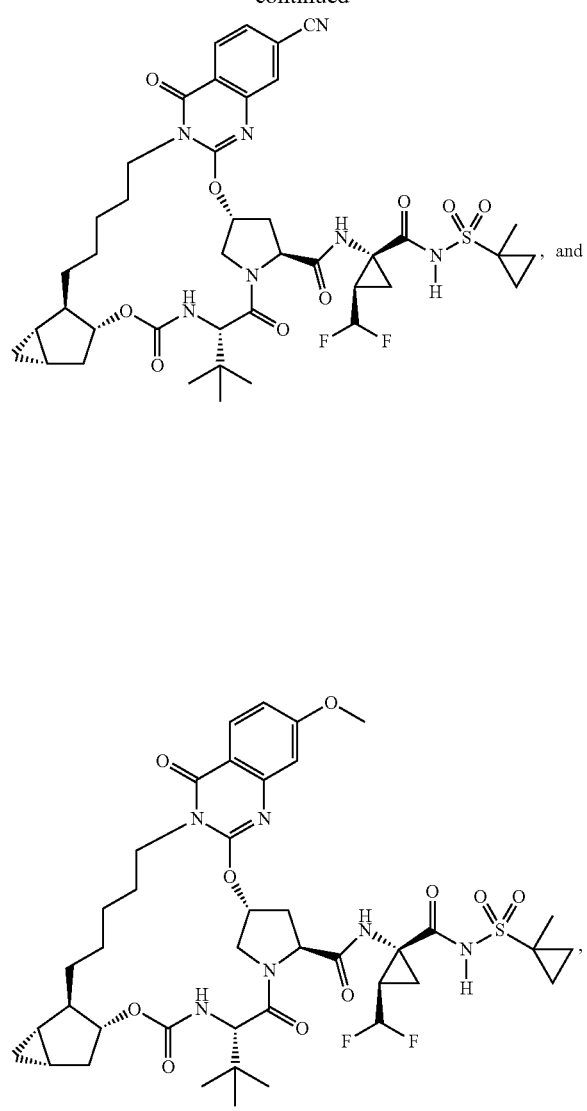

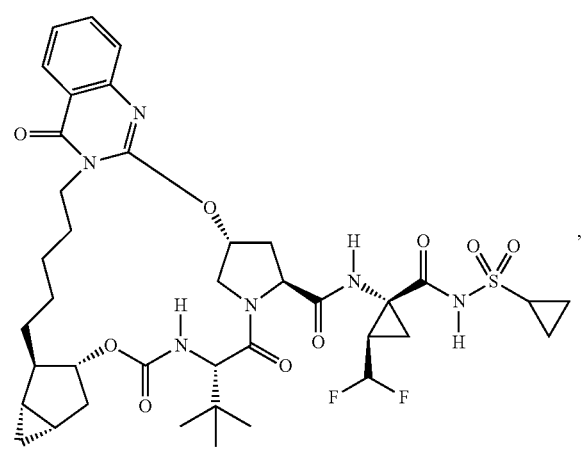

or a pharmaceutically acceptable salt thereof.
One embodiment provides for the following compounds:

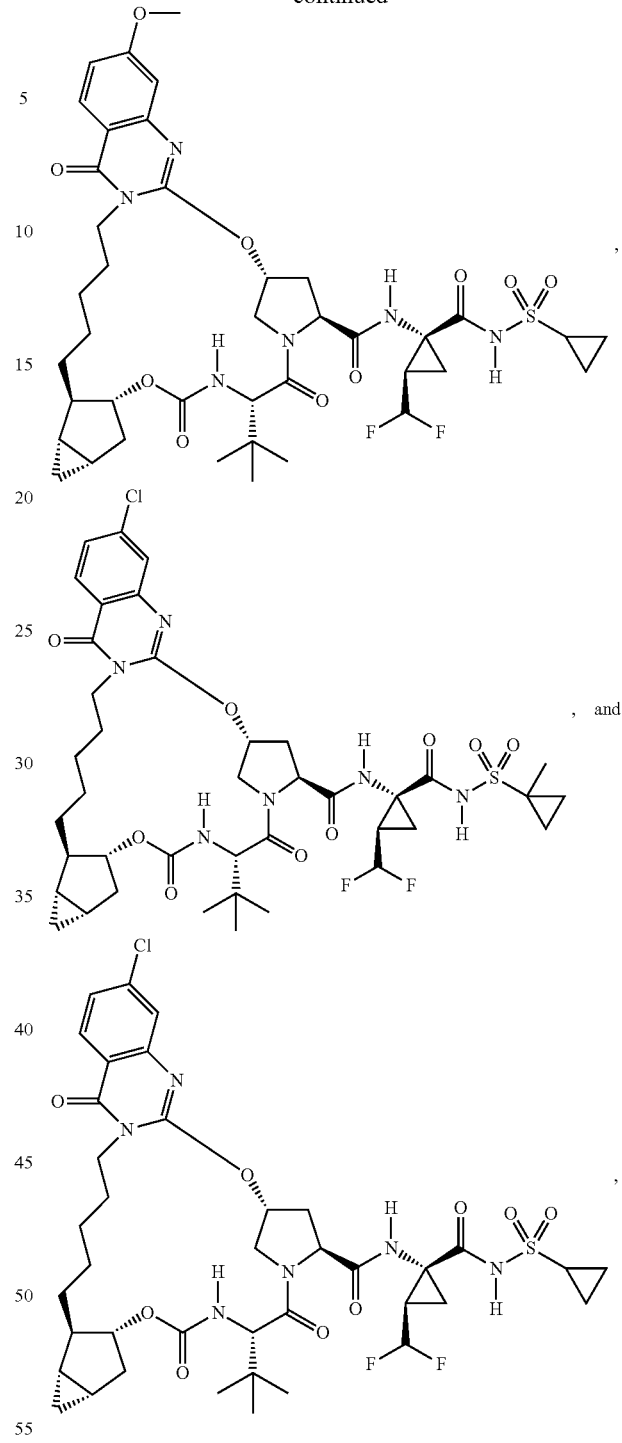

or a pharmaceutically acceptable salt thereof.

Methods of Treatment

One embodiment provides a method for treating a Flaviviridae viral infection (e.g., an HCV viral infection) in a patient in need thereof (e.g., a mammal such as a human). The method includes administering a compound of Formula I, II or III, or a pharmaceutically acceptable salt thereof, to the patient.

One embodiment provides a method for inhibiting the proliferation of the HCV virus, treating HCV infection or delaying the onset of HCV symptoms in a patient in need thereof (e.g., a mammal such as a human). The method includes administering a compound of Formula I, II, or III, or a pharmaceutically acceptable salt thereof, to the patient.

One embodiment provides a compound of Formula I, II, or III or a pharmaceutically acceptable salt thereof for use in medical therapy (e.g., for use in treating a Flaviviridae viral infection (e.g., an HCV viral infection) or the proliferation of the HCV virus or delaying the onset of HCV symptoms in a patoent (e.g., a mammal such as a human).

One embodiment provides a compound of Formula I, II, III or a pharmaceutically acceptable salt thereof for use in the manufacture of a medicament for treating a Flaviviridae viral infection (e.g., an HCV viral infection) or the proliferation of the HCV virus or delaying the onset of HCV symptoms in a patient in need thereof (e.g., mammal such as a human).

One embodiment provides a compound of Formula I, II, or III, or a pharmaceutically acceptable salt thereof, for use in the prophylactic or therapeutic treatment of the proliferation of a Flaviviridae virus, an HCV virus or for use in the therapeutic treatment of delaying the onset of HCV symptoms.

One embodiment provides a compound of Formula I, II or III or a pharmaceutically acceptable salt thereof, for use in the prophylactic or therapeutic treatment of a Flaviviridae virus infection (e.g., an HCV virus infection).

One embodiment provides the use of a compound of Formula I, II, or III, or a pharmaceutically acceptable salt thereof, for the manufacture of a medicament for a Flaviviridae virus infection (e.g., an HCV virus infection) in a mammal (e.g., a human).

In certain embodiments, a method of treating chronic hepatitis C infection is provided. The method includes administering to a patient in need thereof, a compound of Formula I, II or III, or a pharmaceutically acceptable salt thereof, to the patient.

In certain embodiments, a method of treating hepatitis C infection in treatment-naïve patients is provided. The method includes administering to a treatment-naïve patient, a compound of Formula I, II or III, or a pharmaceutically acceptable salt thereof.

In certain embodiments, a method of treating hepatitis C infection in treatment-experienced patients is provided. The method includes administering to a treatment-experienced patient, a compound of Formula I, II or III, or a pharmaceutically acceptable salt thereof.

In certain embodiments, a method of treating hepatitis C infection in an interferon ineligible or an interferon intolerant patient is provided. The method includes administering, a compound of Formula I, II or III, or a pharmaceutically acceptable salt thereof, to the patient.

In certain embodiments, the methods of treatment described herein include administering the compound of Formula I, II or III, or a pharmaceutically acceptable salt thereof, to the patient for a fixed period of duration. In some embodiments, the fixed period of duration is 4 weeks, 6 weeks, 8 weeks, 10 weeks or 12 weeks. In other embodiments, the fixed period of duration is not more than 12 weeks.

In some embodiments, the compound is administered for about 12 weeks. In further embodiments, the compound is administered for about 12 weeks or less, for about 10 weeks or less, for about 8 weeks or less, for about 6 weeks or less, or for about 4 weeks or less.

In certain embodiments, the methods of treatment described herein includes administering a compound of Formula I, II or III, or a pharmaceutically acceptable salt thereof, to is infected with HCV genotype (GT) 1, 2, 3, 4, 5, or 6 (i.e., a method for treating a GT 1, 2, 3, 4, 5, or 6 HCV infection).

One embodiment provides a method for treating an HCV infection in a patient in need thereof (e.g., a mammal such as a human), wherein the patient is infected with HCV genotype 1. The method includes administering a compound of Formula I, II or III, or a pharmaceutically acceptable salt thereof, to the patient.

One embodiment provides a method for treating an HCV infection in a patient in need thereof (e.g., a mammal such as a human), wherein the patient is infected with HCV genotype 2. The method includes administering a compound of Formula I, II or III, or a pharmaceutically acceptable salt thereof, to the patient.

One embodiment provides a method for treating an HCV infection in a patient in need thereof (e.g., a mammal such as a human), wherein the patient is infected with HCV genotype 3. The method includes administering a compound of Formula I, II or III, or a pharmaceutically acceptable salt thereof, to the patient.

One embodiment provides a method for treating an HCV infection in a patient in need thereof (e.g., a mammal such as a human), wherein the patient is infected with HCV genotype 4. The method includes administering a compound of Formula I, II or III, or a pharmaceutically acceptable salt thereof, to the patient.

One embodiment provides a method for treating an HCV infection in a patient in need thereof (e.g., a mammal such as a human), wherein the patient is infected with HCV genotype 5. The method includes administering a compound of Formula I, II or III, or a pharmaceutically acceptable salt thereof, to the patient.

One embodiment provides a method for treating an HCV infection in a patient in need thereof (e.g., a mammal such as a human), wherein the patient is infected with HCV genotype 6. The method includes administering a compound of Formula I, II or III, or a pharmaceutically acceptable salt thereof, to the patient.

In the methods of treatment described herein, the administering step includes administering a therapeutically effective amount of a compound of Formula I, II or III, or a pharmaceutically acceptable salt thereof, to the patient in need of treatment.

In certain embodiments, methods of inhibiting the activity of HCV are provided. Such methods include the step of treating a sample suspected of containing HCV with a compound or composition disclosed herein.

In one embodiment, compounds disclosed herein act as inhibitors of HCV, as intermediates for such inhibitors or have other utilities as described below.

In certain embodiments, compounds binding in the liver may bind with varying degrees of reversibility.

In one embodiment, a method for treating HCV includes adding a compound disclosed herein to the sample. The addition step comprises any method of administration as described above.

If desired, the activity of HCV after application of the compound can be observed by any method including direct and indirect methods of detecting HCV activity. Quantitative, qualitative, and semiquantitative methods of determining HCV activity are all contemplated. Typically one of the screening methods described above are applied, however, any other method such as observation of the physiological properties of a living organism are also applicable.

Many organisms contain HCV. The compounds of this invention are useful in the treatment or prophylaxis of conditions associated with HCV activation in animals or in humans.

Pharmaceutical Formulations

"Pharmaceutically-acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

"Pharmaceutically-acceptable carrier" refers to a diluent, adjuvant, excipient, or carrier, or other ingredient which is pharmaceutically-acceptable and with which a compound of the invention is administered.

The compounds of this invention are formulated with conventional carriers (e.g., inactive ingredient or excipient material), which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as ethylenediaminetetraacetic acid, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipient, etc.) which constitutes one or more accessory ingredients. In general the formulations are prepared by uniformly and intimately bringing into association the active ingredient with liquid carriers or finely divided solid carriers or both, and then, if necessary, shaping the product.

In certain embodiments, formulations suitable for oral administration are presented as discrete units such as capsules, cachets or tablets each containing a predetermined amount of the active ingredient.

In certain embodiments, the pharmaceutical formulations include one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight:weight). In some embodiments, the pharmaceutical compositions described herein contain about 1 to 800 mg, 1 to 600 mg, 1 to 400 mg, 1 to 200 mg, 1 to 100 mg or 1 to 50 mg of the compound of Formula I, II, or III. In some embodiments, the pharmaceutical compositions described herein contain not more than about 400 mg of the compound of Formula I, II, or III. In some embodiments, the pharmaceutical compositions described herein contain about 100 mg of the compound of Formula I, II, or III.

It should be understood that in addition to the ingredients particularly mentioned above the formulations disclosed herein may include other agents conventional in the art having regard to the type of formulation in question, for example those suitable for oral administration may include flavoring agents.

Veterinary compositions comprising at least one active ingredient as above defined together with a veterinary carrier are further provided.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds of Formula I, II, or III (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally. Accordingly, in one embodiment, the pharmaceutical compositions described herein are oral dosage forms. In certain embodiments, the pharmaceutical compositions described herein are oral solid dosage forms.

One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

Combination Therapy

In yet another embodiment, the present application discloses pharmaceutical compositions comprising a compound of Formulas I, II, or III, or a pharmaceutically acceptable salt thereof, in combination with at least one additional therapeutic agent (i.e., active ingredient), and a pharmaceutically acceptable carrier or excipient. In certain embodiments, additional therapeutic agents include additional antiviral agents.

The additional therapeutic agent used in combination with the compounds described herein includes, without limitation, any agent having a therapeutic effect when used in combination with the compound of the present invention. Such combinations are selected based on the condition to be treated, cross-reactivities of ingredients and pharmaco-properties of the combination. For example, in certain embodiments, the therapeutic agent used in combination with the compounds of Formulas I, II, or III include, without limitation, one of more of the following: interferons, ribavirin analogs, NS3 protease inhibitors, NS5a inhibitors, NS5b inhibitors, alpha-glucosidase 1 inhibitors, hepatoprotectants, non-nucleoside inhibitors of HCV, nucleoside analogues, and other drugs for treating HCV infection. In some embodiments, the additional therapeutic agents include, without limitation, NS3 protease inhibitors, NS5a inhibitors, and/or NS5b inhibitors. In some embodiments, a pharmaceutical composition including a compound of Formulas I, II, or III, or a pharmaceutically acceptable salt thereof and one or more of an NS3 protease inhibitor, an NS5a inhibitor, and/or an NS5b inhibitor is provided. In some embodiments, a pharmaceutical composition including a compound of Formulas I, II, or III, or a pharmaceutically acceptable salt thereof and one or more of an NS5a inhibitor and/or an NS5b inhibitor is provided. In certain embodiments, pharmaceutical compositions is provided which includes a compound of Formulas I, II, or III and one or more additional antiviral agents, wherein the additional antiviral agent is not an interferon, ribavirin, or a ribavirin analogue. In further embodiments, pharmaceutical compositions is provided which includes a compound of Formulas I, II, or III, and one or more additional antiviral agents, wherein the additional antiviral agent is not ribavirin or a ribavirin analogue.

In certain embodiments, the compounds disclosed herein are combined with one or more other active ingredients (e.g., one or more additional antiviral agents) in a unitary dosage form for simultaneous or sequential administration to a patient. The combination therapy may be administered as a simultaneous or sequential regimen. When administered sequentially, the combination is administered in two or more administrations. In certain embodiments, the active ingredients are: (1) co-formulated and administered or delivered simultaneously in a combined pharmaceutical composition; (2) delivered by alternation or in parallel as separate pharmaceutical composition; or (3) by some other regimen. When delivered in alternation therapy, the active ingredients are administered or delivered sequentially, e.g., in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together.

Exemplary inferferons include, without limitation, pegylated rIFN-alpha 2b (PEG-Intron), pegylated rIFN-alpha 2a (Pegasys), rIFN-alpha 2b (Intron A), rIFN-alpha 2a (Roferon-A), interferon alpha (MOR-22, OPC-18, Alfaferone, Alfanative, Multiferon, subalin), interferon alfacon-1 (Infergen), interferon alpha-n1 (Wellferon), interferon alpha-n3 (Alferon), interferon-beta (Avonex, DL-8234), interferon-omega (omega DUROS, Biomed 510), albinterferon alpha-2b (Albuferon), IFN alpha XL, BLX-883 (Locteron), DA-3021, glycosylated interferon alpha-2b (AVI-005), PEG-Infergen, PEGylated interferon lambda (PEGylated IL-29), or belerofon, IFN alpha-2b XL, rIFN-alpha 2a, consensus IFN alpha, infergen, rebif, pegylated IFN-beta, oral interferon alpha, feron, reaferon, intermax alpha, r-IFN-beta, and infergen+actimmune.

Exemplary ribavarin analogs include, without limitation, ribavirin (Rebetol, Copegus), levovirin VX-497, and taribavirin (Viramidine).

Exemplary NS5A inhibitors include, without limitation, ledipasvir (GS-5885), GS-5816, JNJ-47910382, daclatasvir (BMS-790052), ABT-267, MK-8742, EDP-239, IDX-719, PPI-668, GSK-2336805, ACH-3102, A-831, A-689, AZD-2836 (A-831), AZD-7295 (A-689), and BMS-790052.

Exemplary NS5B inhibitors include, without limitation, polymerase inhibitor is sofosbuvir (GS-7977), tegobuvir (GS-9190), GS-9669, TMC647055, ABT-333, ABT-072, setrobuvir (ANA-598), filibuvir (PF-868554), VX-222, IDX-375, IDX-184, IDX-102, BI-207127, valopicitabine (NM-283), R1626, PSI-6130 (R1656), PSI-7851, BCX-4678, nesbuvir (HCV-796), BILB 1941, MK-0608, NM-107, R7128, VCH-759, GSK625433, XTL-2125, VCH-916, JTK-652, MK-3281, VBY-708, A848837, GL59728, A-63890, A-48773, A-48547, BC-2329, BMS-791325, and BILB-1941.

Exemplary NS3 protease inhibitors include, without limitation, GS-9451, GS-9256, simeprevir (TMC-435), ABT-450, boceprevir (SCH-503034), narlaprevir (SCH-900518), vaniprevir (MK-7009), MK-5172, danoprevir (ITMN-191), sovaprevir (ACH-1625), neceprevir (ACH-2684), Telaprevir (VX-950), VX-813, VX-500, faldaprevir (BI-201335), asunaprevir (BMS-650032), BMS-605339, VBY-376, PHX-1766, YH5531, BILN-2065, and BILN-2061.

Exemplary alpha-glucosidase 1 inhibitors include, without limitation, celgosivir (MX-3253), Miglitol, and UT-231B.

Exemplary hepatoprotectants include, without limitation, IDN-6556, ME 3738, MitoQ, and LB-84451.

Exemplary non-nucleoside inhibitors of HCV include, without limitation, benzimidazole derivatives, benzo-1,2,4-thiadiazine derivatives, and phenylalanine derivatives.

Exemplary nucleoside analogues include, without limitation, ribavirin, viramidine, levovirin, a L-nucleoside, or isatoribine and said interferon is α-interferon or pegylated interferon.

Exemplary other drugs for treating HCV infection include, without limitation, imiquimod, 852A, GS-9524, ANA-773, ANA-975, AZD-8848 (DSP-3025), PF-04878691, and SM-360320, cyclophillin inhibitors (e.g., DEBIO-025, SCY-635, or NIM811) or HCV IRES inhibitors (e.g., MCI-067); emericasan (IDN-6556), ME-3738, GS-9450 (LB-84451), silibilin, or MitoQ. BAS-100, SPI-452, PF-4194477, TMC-41629, GS-9350, GS-9585, and roxythromycin.

Additional exemplary other drugs for treating HCV infection include, without limitation, zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975 (isatoribine), XTL-6865, ANA 971, NOV-205, tarvacin, EHC-18, and NIM811.

Still further exemplary other drugs for treating HCV infection include, without limitation, thymosin alpha 1 (Zadaxin), nitazoxanide (Alinea, NTZ), BIVN-401 (virostat), PYN-17 (altirex), KPE02003002, actilon (CPG-10101), GS-9525, KRN-7000, civacir, GI-5005, XTL-6865, BIT225, PTX-111, ITX2865, TT-033i, ANA 971, NOV-205, tarvacin, EHC-18, VGX-410C, EMZ-702, AVI 4065, BMS-650032, Bavituximab, MDX-1106 (ONO-4538), Oglufanide, FK-788, VX-497 (merimepodib), DEBIO-025, ANA-975 (isatoribine), XTL-6865, or NIM811.

General Synthetic Procedures

The schemes, procedures, and examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

The following schemes describe methods that are useful for preparing compounds disclosed herein.

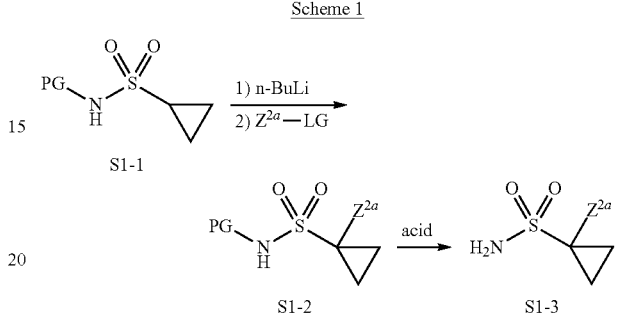

Scheme 1

Where:
Lg = halogen, —OTf, etc.

Scheme 1 shows a general synthesis of sulfonamide intermediate S1-3 which is useful for preparing compounds described herein. Cyclopropylsulfonamide S1-1 includes protecting group PG. A nonlimiting example of protecting group PG is Boc. Protected cyclopropylsulfonamide S1-1 is deprotonated (e.g. n-butyl lithium) and treated with an electrophile containing an appropriate leaving group, LG to give the substituted sulfonamide S1-2. Reagents useful for deprotonation include, without limitation, n-butyl lithium. Exemplary eletrophiles include, without limitation, alkyl halides. Deprotection with acid (e.g. 4 N HCl in dioxane) provides intermediate S1-3.

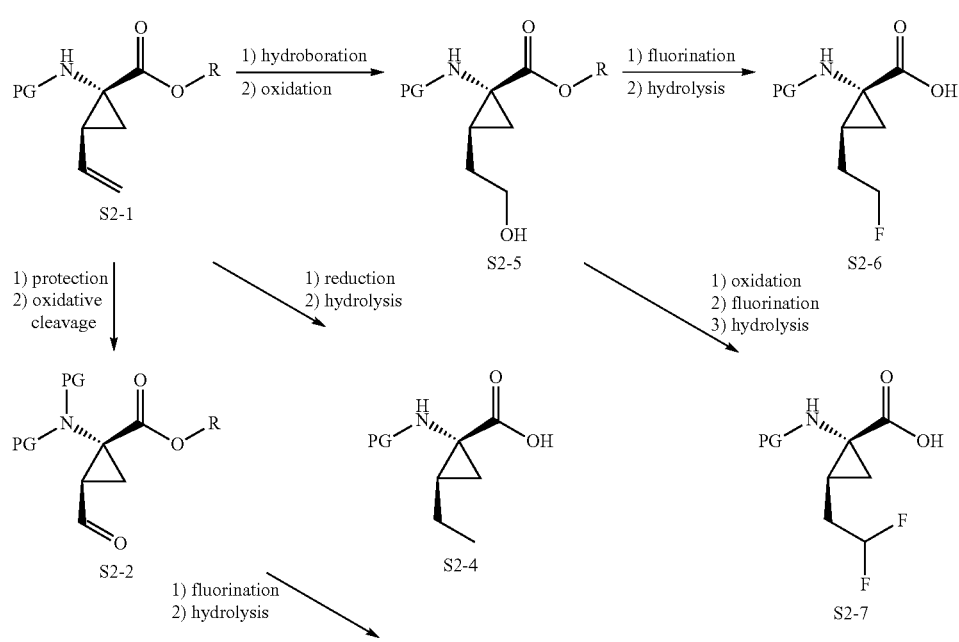

Scheme 2

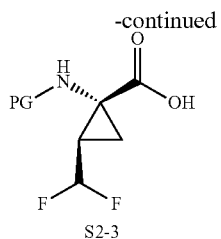

S2-3

Where:
PG = Boc, Cbz, etc.
R = alkyl

Scheme 2 summarizes methods to prepare intermediates S2-3, S2-4, S2-6, and S2-7, which are useful for preparing compounds described herein. Starting material S2-1 includes protecting group PG. Nonlimiting examples of protecting groups PG are Boc and Cbz. R in starting material S2-1 is alkyl, which is cleaved during hydrolysis to yield the carboxylic acid of S2-3, S2-4, S2-6, and S2-7. Exemplary appropriate R groups include, without limitation, -methyl, -ethyl, and -benzyl. An additional protection of the amine in S2-1 (e.g. Boc$_2$O) followed by subjection to oxidative cleavage (e.g. OSO$_4$) provides intermediate aldehyde S2-2, which is then fluorinated (e.g. DAST) followed by hydrolysis of the ester (e.g. LiOH) to provide difluoromethyl intermediate S2-3. Intermediate S2-4 is achieved directly by reduction of the olefin moiety of S2-1, followed by hydrolysis of the ester (e.g. H$_2$, Rh/Al$_2$O$_3$, then LiOH). Alternatively, S2-1 undergoes a hydroboration and oxidation (e.g. BH$_3$.THF, then NaBO$_3$) to give alcohol S2-5. Fluorination of S2-5 followed by hydrolysis (e.g. DAST, followed by LiOH) affords monofluoroethyl species S2-6. Intermediate S2-5 is also oxidized to an aldehyde (e.g. Dess-Martin periodinane), fluorinated (e.g. DAST or Deoxofluor) and finally hydrolyzed (e.g. LiOH) to provide difluoroethyl S2-7.

Scheme 3

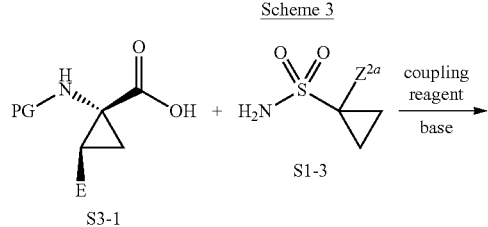

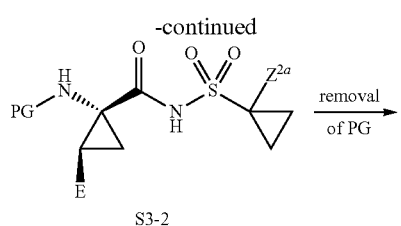

S3-2

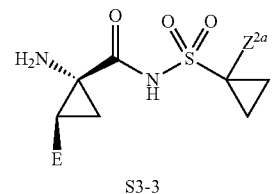

S3-3

Where:
PG = Boc, Cbz, etc.

Scheme 3 shows a general route to intermediate S3-3 which is useful for preparing certain compounds described herein. Protected amino acid S1-3 is prepared as demonstrated in Scheme 2, where is E is as defined herein. As shown in Scheme 2, specific examples of S1-3 include, without limitation, S2-3, S2-4, S2-6, and S2-7. Accordingly, exemplary E groups for S3-1 include, without limitation, ethyl, 1-fluoroethyl, 1-difluoroethyl, and difluoro methyl. Sulfonamide S1-3 is coupled to a protected amino acid S3-1 via a coupling agent in the presence of an appropriate base (e.g. CU with DBU) to produce peptide S3-2. The amino protecting group is removed by treatment with an appropriate reagent (e.g. 4 N HCl in dioxane when PG is Boc) to provide intermediate S3-3.

Scheme 4

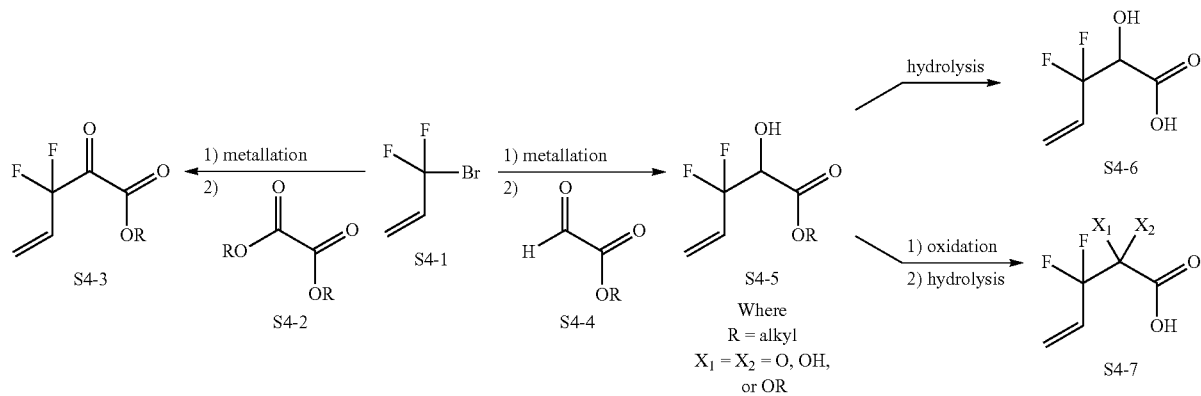

Scheme 4 shows some general methods for obtaining fluorinated intermediates useful for preparing certain compounds described herein. Metallation of allyl bromide S4-1 (e.g. n-BuLi) followed by treatment with an oxalate S4-2 (e.g. diethyl oxalate) provides keto ester S4-3. Alternate metallation of S4-1 (e.g. indium), followed by treatment with glyoxylate S4-4 provides α-hydroxy ester S4-5. Hydrolysis (e.g. LiOH) of S4-5 provides intermediate α-hydroxy acid S4-6. Treatment of S4-5 with oxidative conditions (e.g TEMPO/bleach), followed by hydrolysis (e.g. LiOH), provides keto-acid S4-7, which may be isolated in α-keto ($X_1=X_2=O$), hydrated ($X_1=X_2=$—OH), or hemi-acetal form ($X_1=$—OH, $X_2=$—OR, where R is -methyl, -ethyl, and benzyl, depending on workup conditions.

Scheme 5

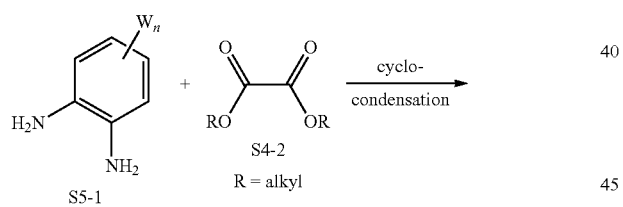

Scheme 5 shows a general method for synthesis of dichloroquinoxaline S5-3 which is useful for preparing certain compounds described herein. Treatment of diamine S5-1 with diethyl oxalate S4-2 provides quinoxaline S5-2. Dehydrohalogenation (e.g. POCl$_3$) of this intermediate provides the dichloroquinoxaline intermediate S5-3.

Scheme 6

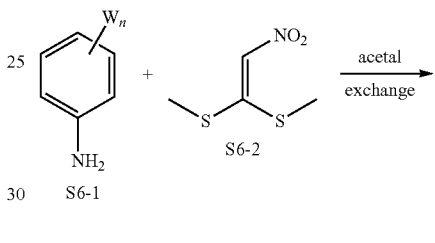

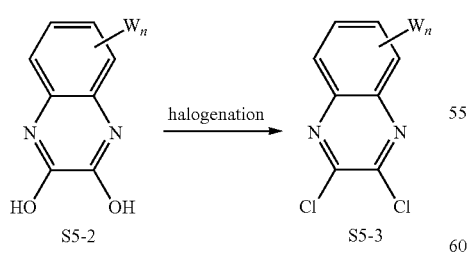

Scheme 6 shows a general route to intermediate S6-5 which is useful for preparing certain compounds described herein. Acetal exchange between S6-1 and S6-2 provides mixed acetal intermediate S6-3. Condensation of S6-4 with concomitant halogenation (e.g. POCl$_3$) provides thio ether S6-4. Sulfide oxidation (e.g. m-CPBA) of S6-4 provides sulfone S6-5.

Scheme 7

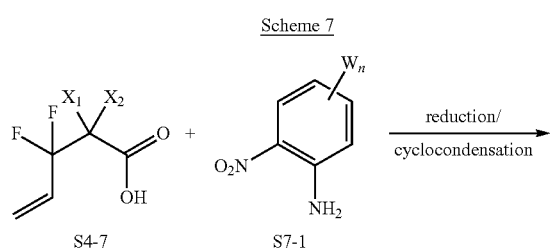

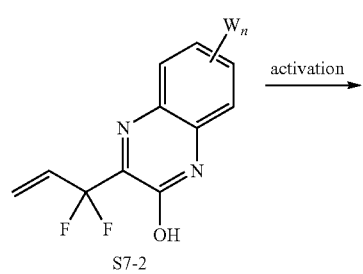

Where:
$X_1 = X_2 = O$, OH, or OR;
R = alkyl;
LG = halogen or pseudohalogen

Scheme 7 demonstrates a general route to intermediate S7-3 which is useful for preparing certain compounds described herein, where $W_n$ is as defined herein. In general Scheme 7, an α-keto acid S4-7, or the hydrate of such compound, is combined with nitro-aniline S7-1 under reductive cyclization conditions (e.g. Fe, AcOH) to produce S7-2. Activation (e.g. dehydrohalogenation with $POCl_3$ or $Tf_2O$/DIPEA) of the alcohol of hydroxyquinoxaline S7-2 to an appropriate leaving group (LG) provides intermediate S7-3. Exemplary leaving groups include, without limitation, —Cl, —F, —Br, —I, —$SO_2$Me, and —OTf.

Scheme 8

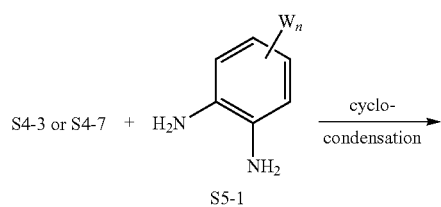

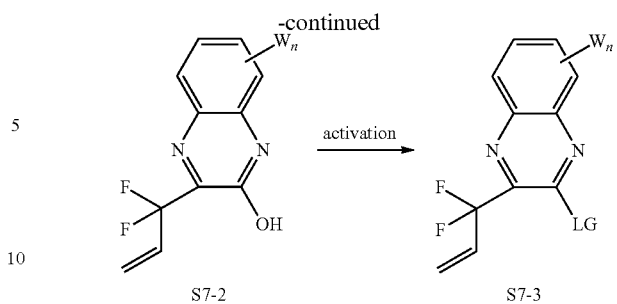

Where:
$X_1 = X_2 = O$, OH, or OR;
R = alkyl or H
LG = halogen or pseudohalogen

Scheme 8 demonstrates an alternative general route to intermediate S7-3 which is useful for preparing certain compounds described herein, where $W_n$ is as defined herein. In general Scheme 8, keto acid S4-7 or keto ester S4-3, or the hydrate of such compounds, is heated with diamine S5-1 (e.g. when R=alkyl) or in the presence of a coupling reagent (e.g. HATU when R=H) and base (e.g. DIPEA) to provide an alternate route to intermediate S7-2. Activation (e.g. dehydrohalogenation with $POCl_3$ or $Tf_2O$/DIPEA) of the alcohol of hydroxyquinoxaline S7-2 to an appropriate leaving group (LG) provides intermediate S7-3. Exemplary leaving groups LG include, without limitation, —Cl, —F, —Br, —I, —$SO_2$Me, and —OTf.

Scheme 9

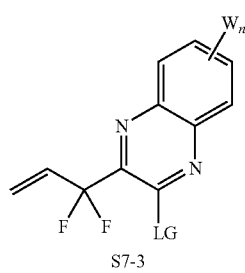

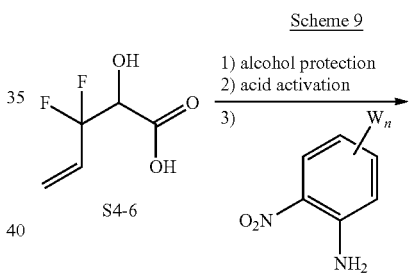

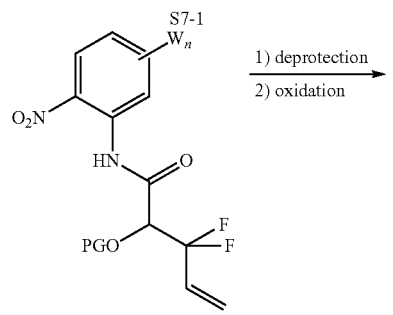

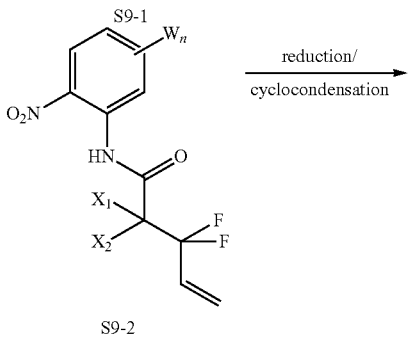

-continued

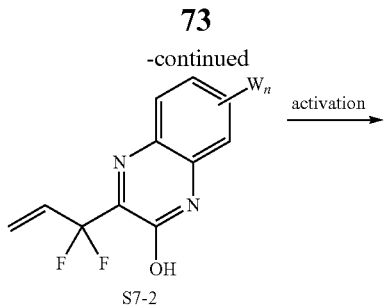

S7-2

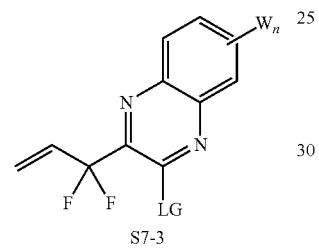

S7-3

Where:
$X_1 = X_2 = $ O, OH, or OR
PG = protecting group
R = alkyl
LG = halogen or pseudohalogen Scheme 9 demonstrates a further alternative general route to intermediate S7-3 which is useful for preparing certain compounds described herein, where $W_n$ is as defined herein. In general Scheme 9, α-hydroxy acid S4-6 is protected as an ether (e.g. TMSCl), followed by activation of the acid (e.g. HATU), and coupling to aniline S7-1, to arrive at intermediate S9-1, where PG is an appropriate protecting group. Deprotection of product S9-1 (e.g. HCl, MeOH), followed by oxidation (e.g. TEMPO, NCS) provides compound S9-2, which is isolated as a mixture of hydrate and hemi-acetal. Subsequent reduction (e.g. Fe, AcOH) of the aromatic nitro functionality leads to in-situ cyclocondensation to afford hydroxyquinoxoline S7-2. Activation (e.g. dehydrohalogenation with POCl₃ or Tf₂O/DIPEA) of the alcohol of hydroxyquinoxaline S7-2 to an appropriate leaving group (LG) provides intermediate S7-3. Exemplary leaving groups LG include, without limitation, —Cl, —F, —Br, —I, —SO₂Me, and —OTf.

Scheme 10

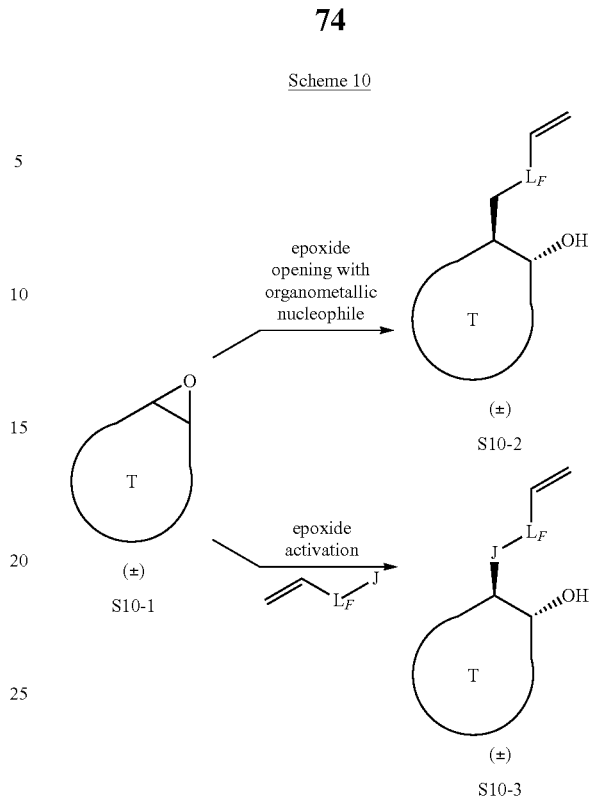

Scheme 10 summarizes two different methods for preparing a (T)

group, as defined herein, with a trans-1,2 relationship of M (when M=—O—) and J groups attached to adjacent atoms of the (T)

group from a common epoxide starting material. As depicted in Scheme 10, (T),

M, J and $L_F$ are as defined elsewhere herein. An epoxide of a (T)

group precursor S10-1 can be opened to alcohol S10-2 with an organometallic nucleophile (e.g. Grignard or organocuprate reagent). Epoxide S10-1 can also be activated (e.g.

Lewis Acid) and opened with a J-L$_F$ group fragment (e.g. 1-hydroxy-γ-alkenyl) to provide intermediate S10-3.

L$_F$ is a "linker fragment," (that is to say, a precursor to L) wherein an attached unsaturated carbon-carbon bond (e.g. alkene or alkyne) at the portion of L$_F$ distal to

facilitates, as a non-limiting example, a metal catalyzed reaction that results in the connection of L$_F$ to U to form an L group. Non-limiting examples of metal catalyzed reactions that result in such a connection include Ru catalyzed ring closing metathesis or a Pd catalyzed cross coupling reaction (e.g. Negishi, Heck, or Sonagashira couplings).

group are illustrated. As depicted in Scheme 10, and

and L$_F$ are as defined elsewhere herein. Beginning with common ketone S11-1, an enolate is formed via treatment with an appropriate base (e.g. LDA or LiHMDS) which after

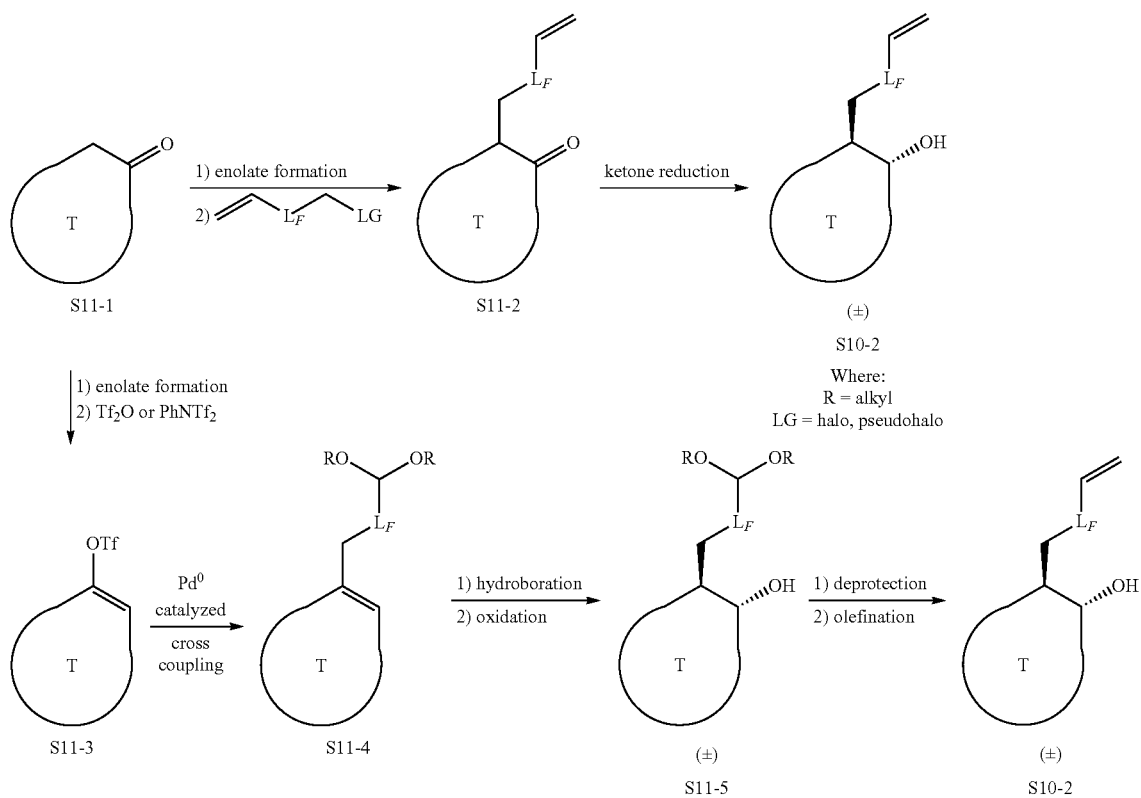

Scheme 11

In general scheme 11, two additional methods for preparing a

group with a trans-1,2 relationship of M (when M=—O—) and J groups attached to adjacent atoms of the treatment with an appropriate electrophile (e.g. alkyl bromide) produces a functionalized ketone S11-2 following work up. This ketone is reduced (e.g. NaBH$_4$) to provide a racemic mixture of intermediate fragment S10-2 following separation from cis diastereomers via chromatography or recrystallization. Alternatively, the enolate generated from ketone S11-1 is trapped (e.g. LDA, then Tf$_2$O) to form vinyl triflate S11-3. This undergoes a palladium catalyzed cross coupling (e.g. Suzuki or Heck coupling) to install the L$_F$ group in intermediate S11-4. Hydroboration of the olefin followed by oxidation (e.g. BH$_3$.DMS, then NaOH/H$_2$O$_2$) affords S11-5. Hydrolysis of the acetal (e.g. aqueous HCl), followed by olefination (e.g. Wittig or Tebbe reagent) affords a racemic mixture of intermediate olefin S10-2.

Scheme 12

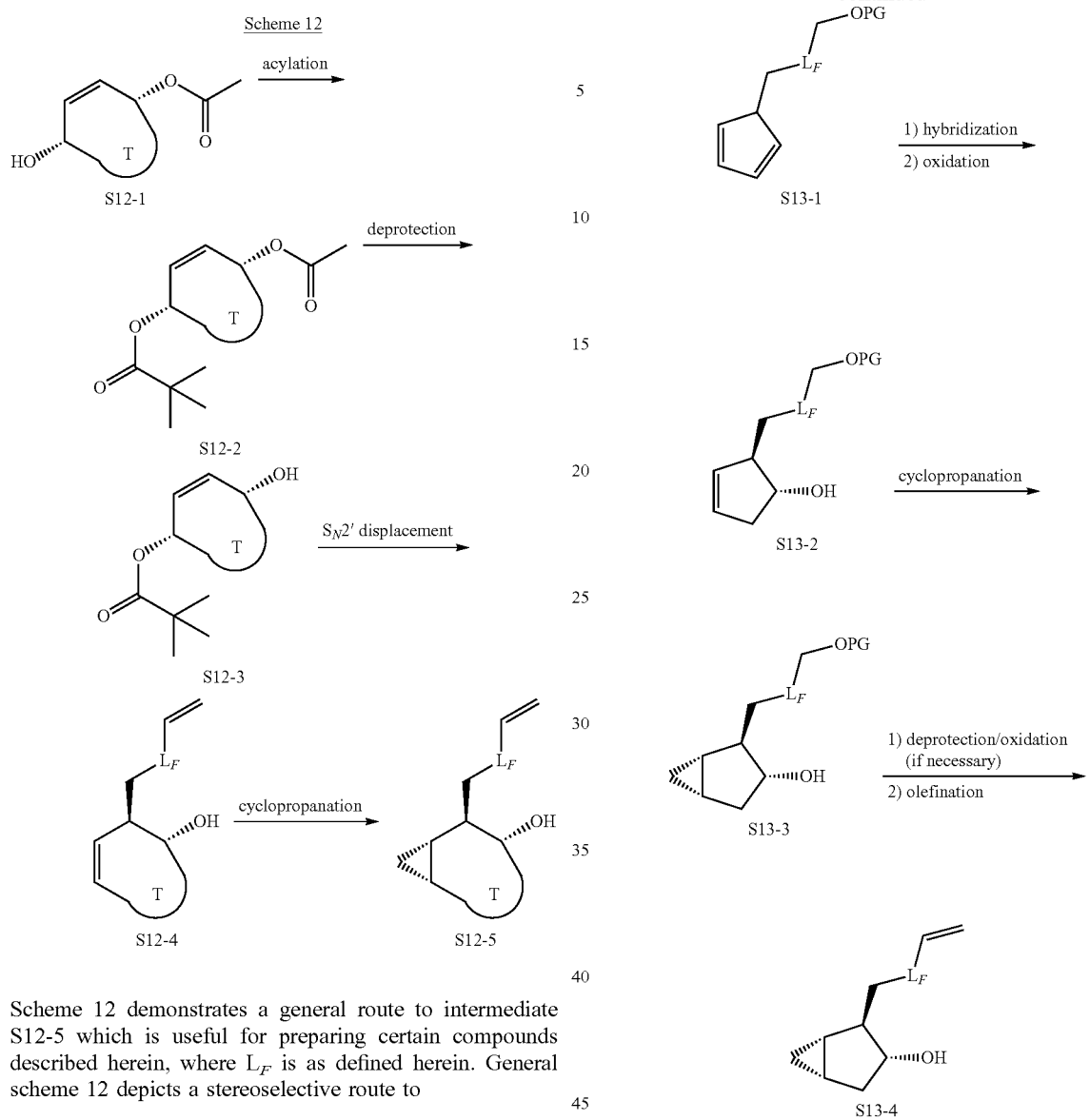

Scheme 12 demonstrates a general route to intermediate S12-5 which is useful for preparing certain compounds described herein, where $L_F$ is as defined herein. General scheme 12 depicts a stereoselective route to groups such as S12-5. Allylic alcohol S12-1 can be protected (e.g. Piv-Cl) to produce mixed di-acetate S12-2. The acetyl group can be selectively hydrolysed under mild conditions (e.g. $K_2CO_3$, MeOH) to provide allylic alcohol S12-3. This intermediate then undergoes $S_N2'$ displacement (e.g. organocuprate reagent) to afford allylic alcohol S12-4. Cyclopropanation (e.g. Simmons-Smith conditions) provide fused bicyclic intermediate S12-5.

Scheme 13

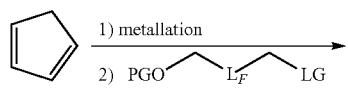

Where:
PG = protecting group
LG = halo, pseudohalo

Scheme 13 demonstrates a general route to intermediate S13-4 which is useful for preparing certain compounds described herein, where $L_F$ is as defined herein. In Scheme 13, cyclopenta-1,3-diene is metallated (e.g. Na) and then treated with a linker fragment containing a protected oxygen functionality (PG, e.g. a silyl ether or a dialkyl acetal) and a leaving group (LG, e.g. a halogen or pseudohalogen leaving group) to provide intermediate S13-1. Subsequent hydroboration-oxidation (e.g. $BH_3$.DMS, $NaOH/H_2O_2$) provides alcohol S13-2, which undergoes stereoselective cycloaddition (e.g. Simmons-Smith cyclopropanation) to yield fused [3.1.0]bicycle S13-3. Deprotection of the protected oxygen functionality of $L_F$ (e.g. aqueous acid for an acetal or TBAF for a silyl ether) is followed by an oxidation to the aldehyde oxidation state (e.g. Dess-Martin periodinane) if required. Finally, olefination (e.g. methyl triphenylphosphonium bromide, NaHMDS) provides intermediate S13-4.

Scheme 14

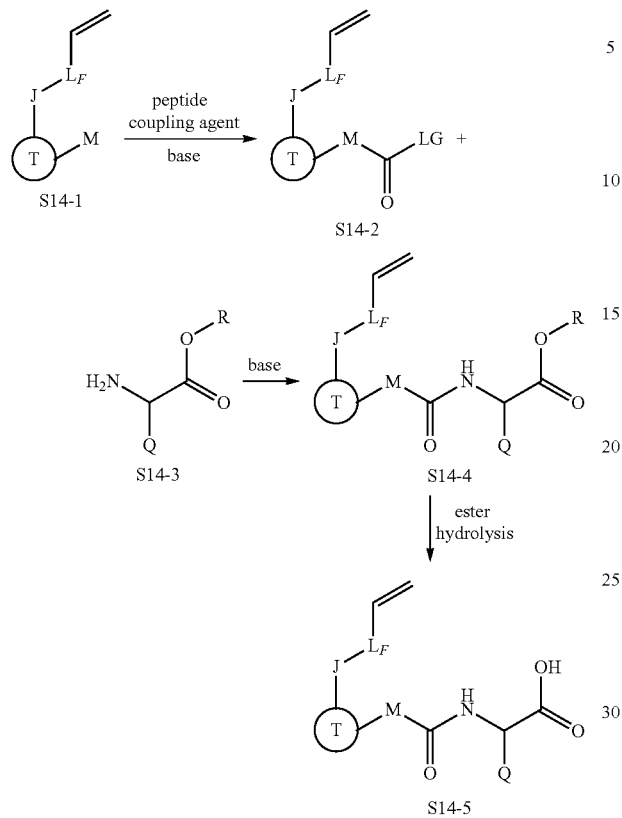

Where:
R = alkyl
LG = imidazole, N—OH succinimide, etc.

Scheme 14 demonstrates a general route to intermediate S14-5 which is useful for preparing certain compounds described herein, where J, $L_F$ and T are as defined herein. In Scheme 14, alkene S14-1 is treated with a coupling reagent (e.g. DSC) and base (e.g. pyridine) to yield activated intermediate S14-2, wherein LG is a suitable leaving group. Exemplary leaving groups LG include, without limitation, imidazole and N—OH succinimide. Intermediate S14-2 is subsequently treated with an amino ester S14-3 in the presence of base (e.g. $K_3PO_4$) to yield intermediate S14-4. Hydrolysis (e.g. LiOH) of the ester provides amino acid S14-5.

Scheme 15

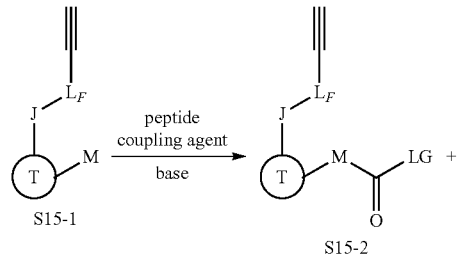

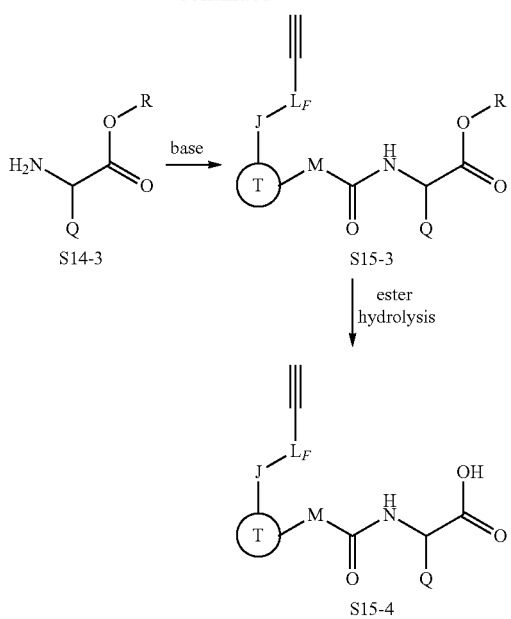

Where:
R = alkyl
LG = imidazole, N—OH succinimide, etc.

Scheme 15 demonstrates a general route to intermediate S15-4 which is useful for preparing certain compounds described herein, where J, $L_F$, T and Q are as defined herein. In Scheme 15, alkyne S15-1 is treated with a coupling reagent (e.g. DSC) and base (e.g. pyridine) to yield activated intermediate S15-2, where LG is an appropriate leaving groups. Exemplary leaving groups include, without limitation, imidazole and N—OH succinimide. Intermediate S15-2 is subsequently treated with an amino ester S14-3 in the presence of base (e.g. $K_3PO_4$) to yield intermediate S15-3. Hydrolysis (e.g. LiOH) of the ester provides amino acid S15-4.

Scheme 16

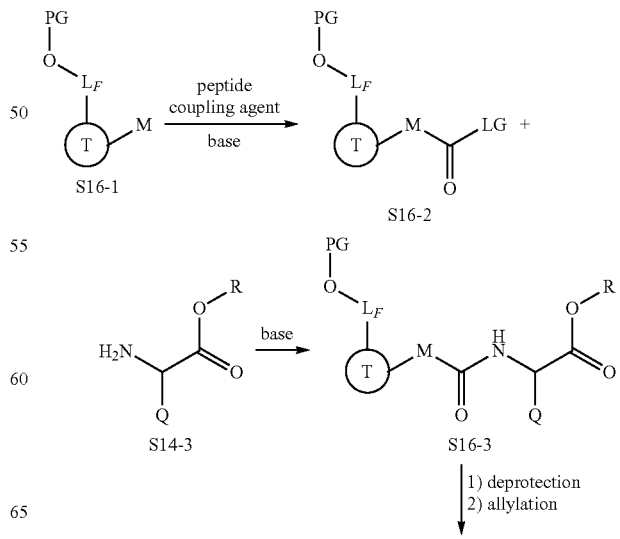

1) deprotection
2) allylation

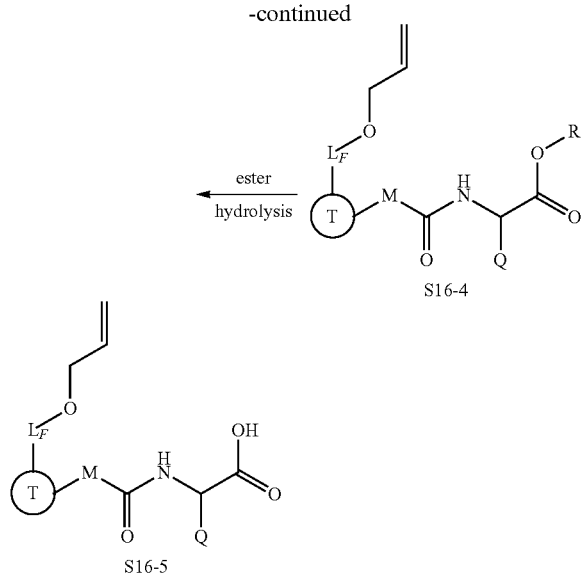

Where:
R = alkyl
PG = protecting group
LG = imidazole, N—OH succinimide, etc.

Scheme 16 demonstrates a general route to intermediate S16-5 which is useful for preparing certain compounds described herein, where $L_F$, T, M and Q are as defined herein. Alcohol S16-1 includes a protecting group, PG. Examples of suitable protecting groups include, without limitation, -TBS, -TIPS, -Bn, -PMB, and -Ac. Scheme 16 begins with the treatment of protected alcohol S16-1 with a coupling reagent (e.g. DSC) and base (e.g. pyridine) to yield activated intermediate S16-2. This intermediate is then coupled with an amino ester S14-3 in the presence of base (e.g. $K_3PO_4$) to yield intermediate S16-3. Deprotection of the alcohol (e.g. TBAF when PG is a silicon protecting group) followed by treatment with an appropriate alkyl or alkenyl bromide (e.g. allyl bromide) yields alkene S16-4. Ester hydrolysis (e.g. LiOH) of S16-4 provides acid S16-5.

Scheme 17

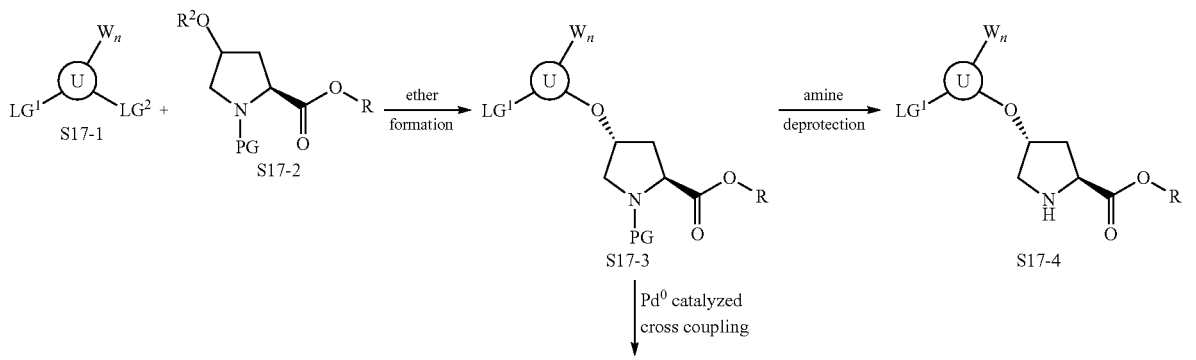

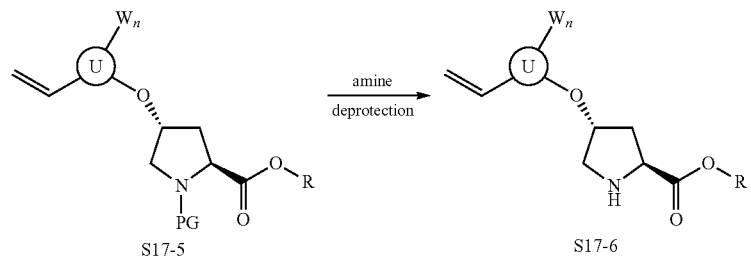

Where:
R = alkyl;
$R^2$ = H or Bs;
PG = protecting group;
$LG^1$ = leaving group;
$LG^2$ = leaving group or —OH Scheme 17 demonstrates a general route to intermediates S17-4 and S17-6 which is useful for preparing certain compounds described herein, where U and $W_n$ are as defined herein. In Scheme 17, protected proline species S17-2 includes two leaving groups, $LG^1$ and $LG^2$, which may be the same or different. Exemplary leaving groups $LG^1$ and $LG^2$ include, without limitation, chloro or OH. S17-2 undergoes an etherification reaction via reaction conditions such as $S_NAr$ (e.g. $R^2$=H, $Cs_2CO_3$ treated with S17-1 where LG=—Cl), $S_N2$ displacement of a prolinol brosylate (S17-2 where $R^2$=Bs) by S17-1 where LG=—OH, or Mitsunobu reaction (e.g. DIAD and triphenylphosphine treatment of an appropriate prolinol (e.g. S17-2 where $R^2$=H) followed by addition of S17-1 where LG=—OH to produce proline ether S17-3, where PG is a suitable protecting group. Removal of the protecting group (e.g. TFA when PG=Boc) yields S17-4. Alternatively, intermediate S17-3 undergoes metal catalyzed cross-coupling (e.g. Suzuki with potassium vinyltrifluoroborate) to provide vinylated species S17-5, wherein subsequent removal of the protecting group (e.g. TFA when PG=Boc) yields S17-6.

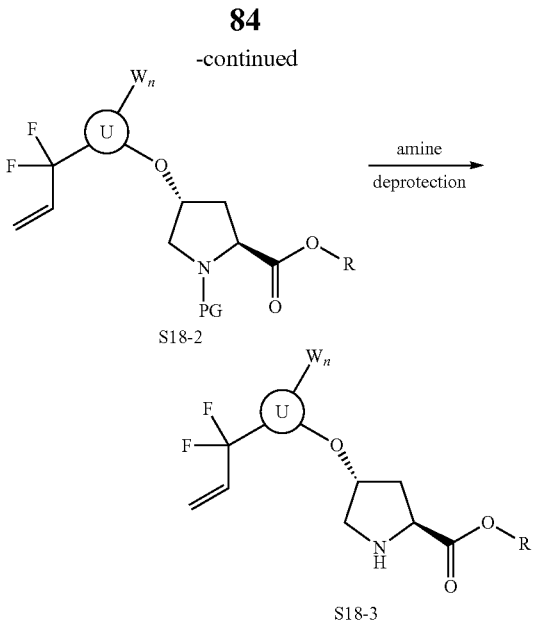

Where:
R = alkyl;
$R^2$ = H or Bs;
PG = protecting group;
LG = leaving group or —OH Scheme 18 demonstrates a general route to intermediate S18-3 which is useful for preparing certain compounds described herein, where U and $W_n$ are as defined herein. In Scheme 18, S18-1 includes a leaving group, LG. Exemplary leaving groups LG include, without limitation, chloro or OH. Protected proline species S17-2 (where PG is a suitable protecting group) undergoes an etherification reaction via reaction conditions such as $S_NAr$ (e.g. $R^2$=H, $Cs_2CO_3$ treated with S18-1 where LG=—Cl), $S_N2$ displacement of a prolinol brosylate (S17-2 where $R^2$=Bs) by S18-1 where LG=—OH, or Mitsunobu reaction (e.g. DIAD and triphenylphosphine treatment of an appropriate prolinol (e.g. S17-2 where $R^2$=H) followed by addition of S18-1 where LG=—OH to produce proline ether S18-2. Removal of the protecting group (e.g. TFA when PG=Boc) yields S18-3.

Scheme 18

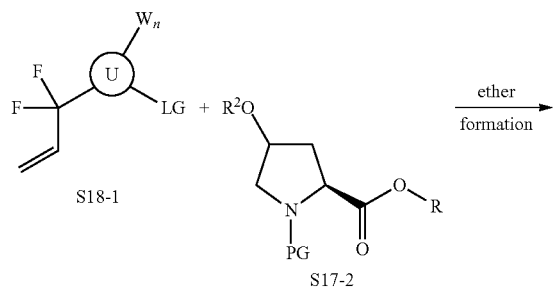

Scheme 19

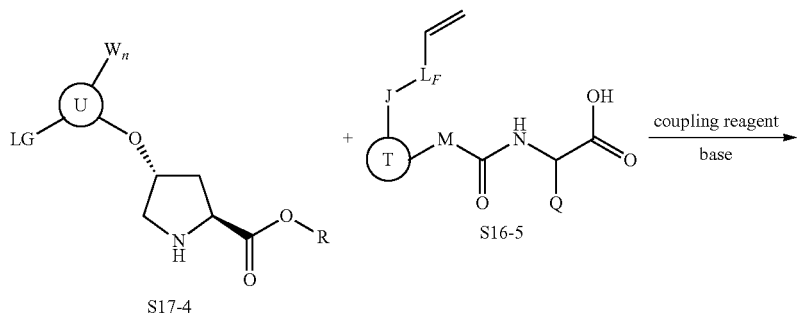

-continued

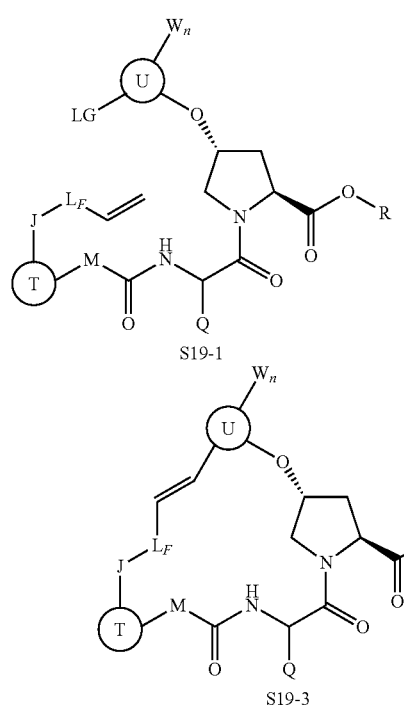
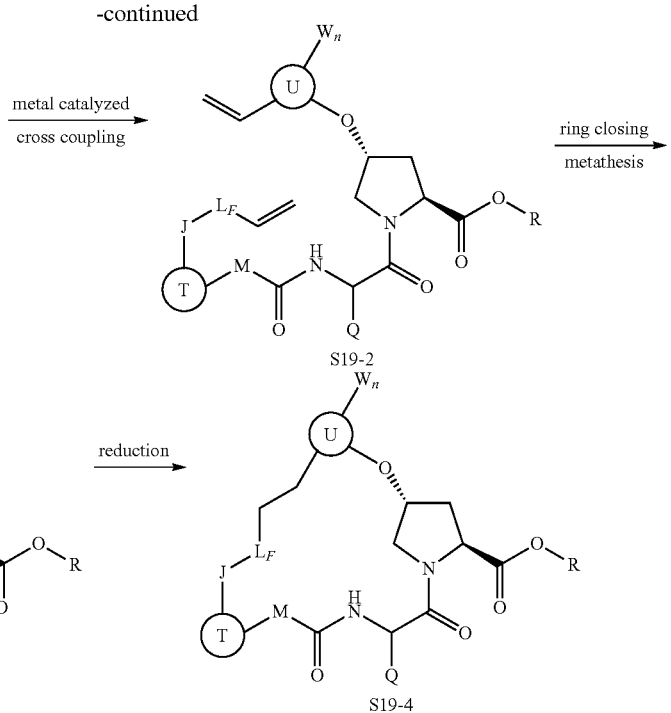

Where:
R = alkyl
LG = halogen or —OTf

Scheme 19 demonstrates a general route to intermediate S19-4 which is useful for preparing certain compounds described herein, where J, $L_F$, T, U, $W_n$ and Q are as defined herein. In scheme 19, proline S17-4 (LG is an appropriate leaving group) and acid S16-5 are coupled in the presence of a coupling agent (e.g. HATU) and base (e.g. DIPEA) to provide intermediate S19-1. Metal catalyzed cross-coupling (e.g. Suzuki with potassium vinyltrifluoroborate) produces vinylated species S19-2. Subsequent ring closing metathesis (e.g. Zhan 1B) produces macrocycle intermediate S19-3. Reduction of the macrocyclic double bond (e.g. $H_2$, Pd/C or Rh/$Al_2O_3$) yields S19-4.

Scheme 20

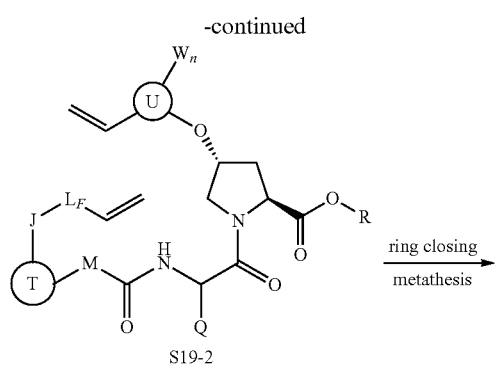

-continued

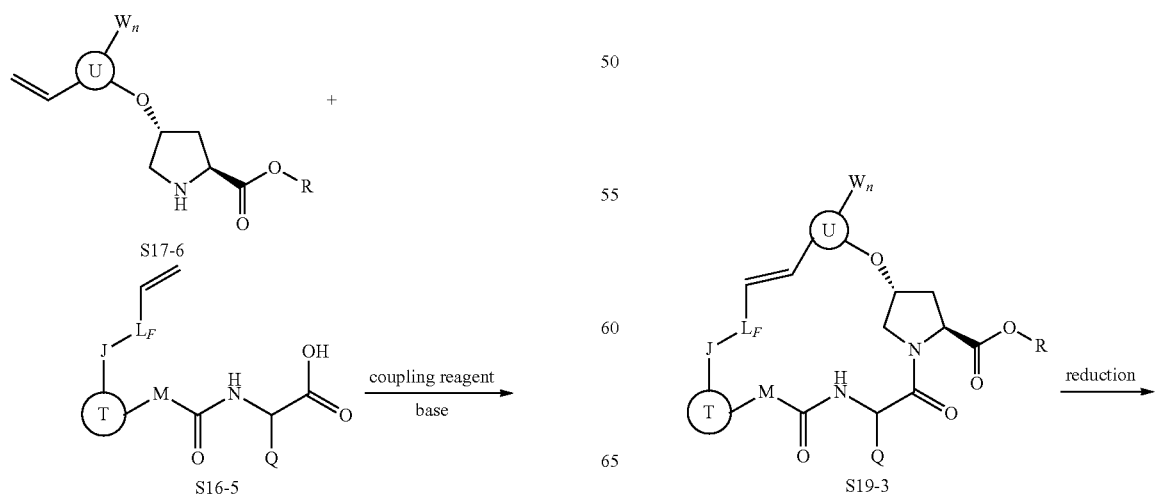

-continued

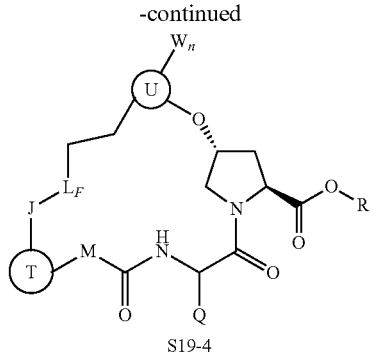
S19-4

Where:
R = alkyl

Scheme 20 demonstrates another general route to intermediate S19-4 which is useful for preparing certain compounds described herein, where J, $L_F$, T, U, $W_n$ and Q are as defined herein. Scheme 20 begins with the coupling of proline S17-6 and acid S16-5 in the presence of a coupling agent (e.g. HATU) and base (e.g. DIPEA) to provide intermediate S19-2. Subsequent ring closing metathesis (e.g. Zhan 1B) produces macrocycle intermediate S19-3. Reduction of the macrocyclic double bond (e.g. $H_2$, Pd/C or Rh/$Al_2O_3$) yields S19-4.

Scheme 21

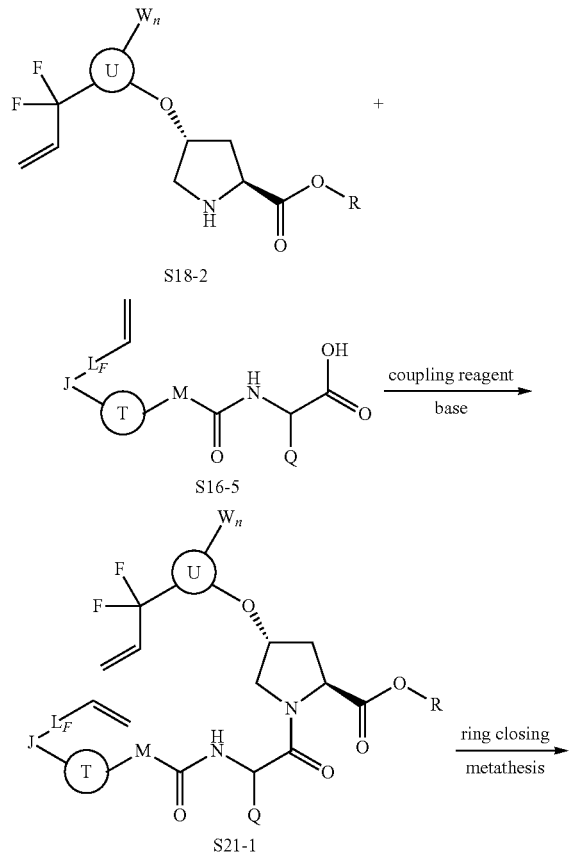

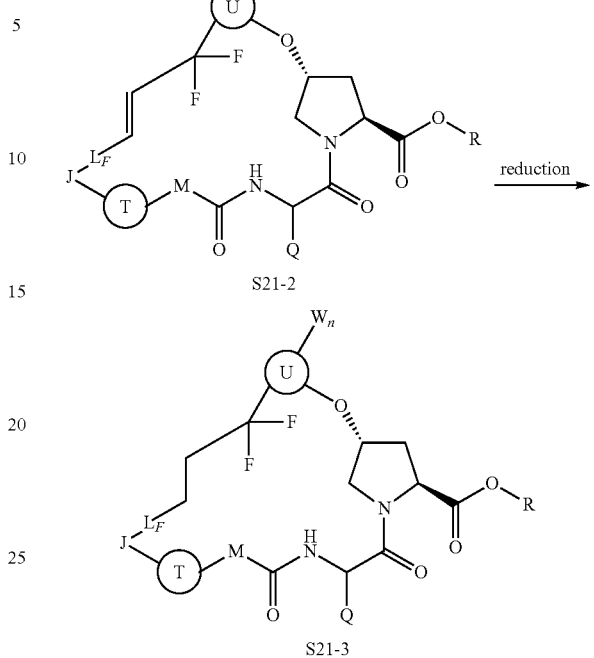

Where:
R = alkyl

Scheme 21 demonstrates a general route to intermediate S21-3 which is useful for preparing certain compounds described herein, where J, $L_F$, T, U, $W_n$ and Q are as defined herein. Scheme 21 begins with the coupling of proline S18-2 and acid S16-5 in the presence of a coupling agent (e.g. HATU) and base (e.g. DIPEA) to provide intermediate S21-1. Subsequent ring closing metathesis (e.g. Zhan 1B) produces macrocycle intermediate S21-2. Reduction of the macrocyclic double bond (e.g. $H_2$, Pd/C or Rh/$Al_2O_3$) yields S21-3.

Scheme 22

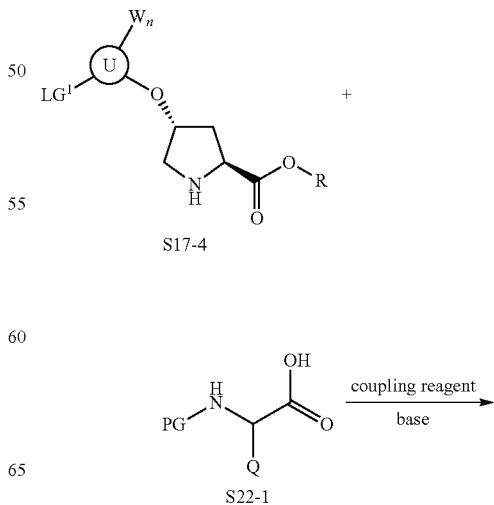

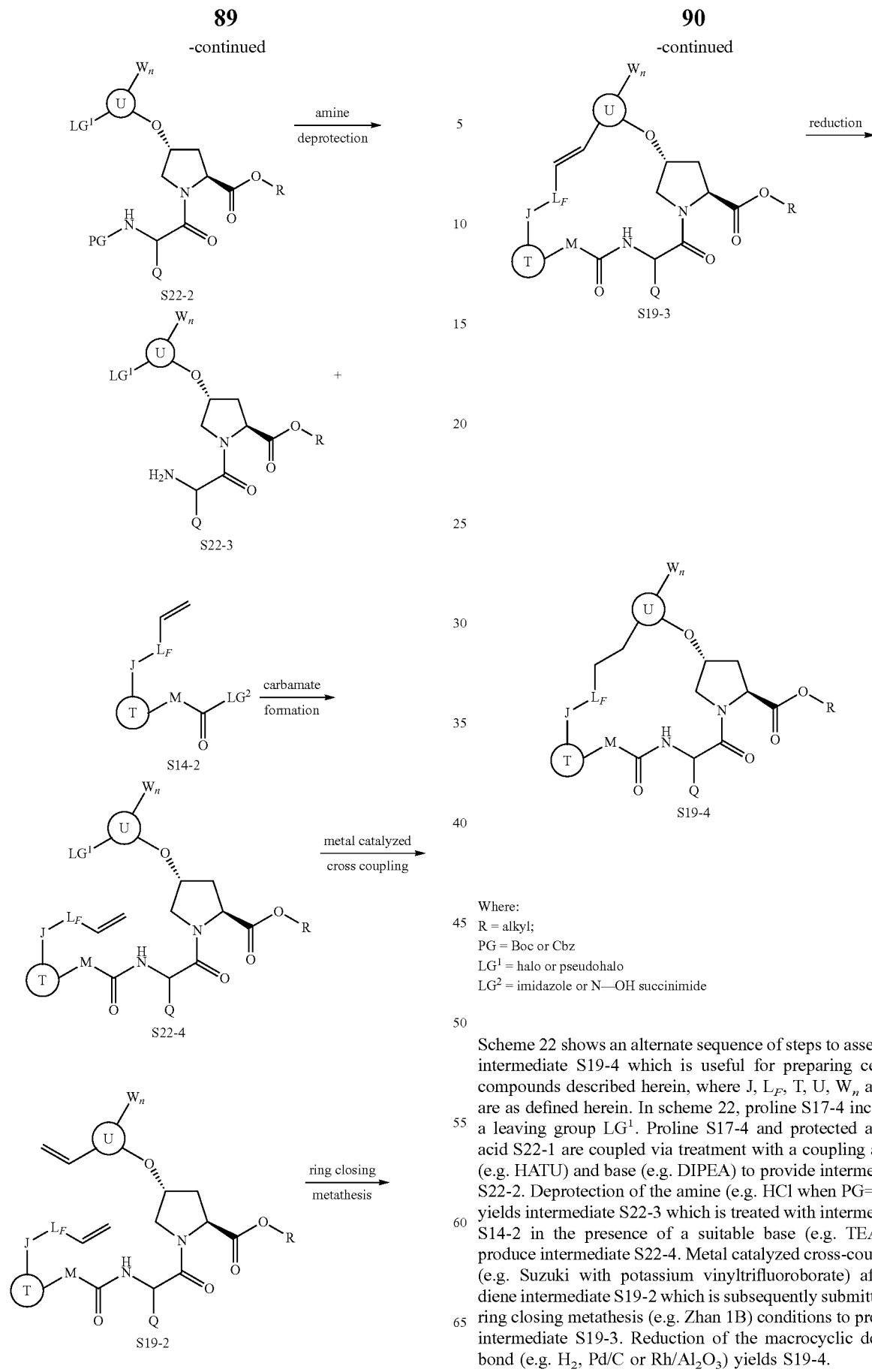

Where:
R = alkyl;
PG = Boc or Cbz
LG¹ = halo or pseudohalo
LG² = imidazole or N—OH succinimide Scheme 22 shows an alternate sequence of steps to assemble intermediate S19-4 which is useful for preparing certain compounds described herein, where J, $L_F$, T, U, $W_n$ and Q are as defined herein. In scheme 22, proline S17-4 includes a leaving group LG¹. Proline S17-4 and protected amino acid S22-1 are coupled via treatment with a coupling agent (e.g. HATU) and base (e.g. DIPEA) to provide intermediate S22-2. Deprotection of the amine (e.g. HCl when PG=Boc) yields intermediate S22-3 which is treated with intermediate S14-2 in the presence of a suitable base (e.g. TEA) to produce intermediate S22-4. Metal catalyzed cross-coupling (e.g. Suzuki with potassium vinyltrifluoroborate) affords diene intermediate S19-2 which is subsequently submitted to ring closing metathesis (e.g. Zhan 1B) conditions to provide intermediate S19-3. Reduction of the macrocyclic double bond (e.g. $H_2$, Pd/C or Rh/$Al_2O_3$) yields S19-4.

Scheme 23

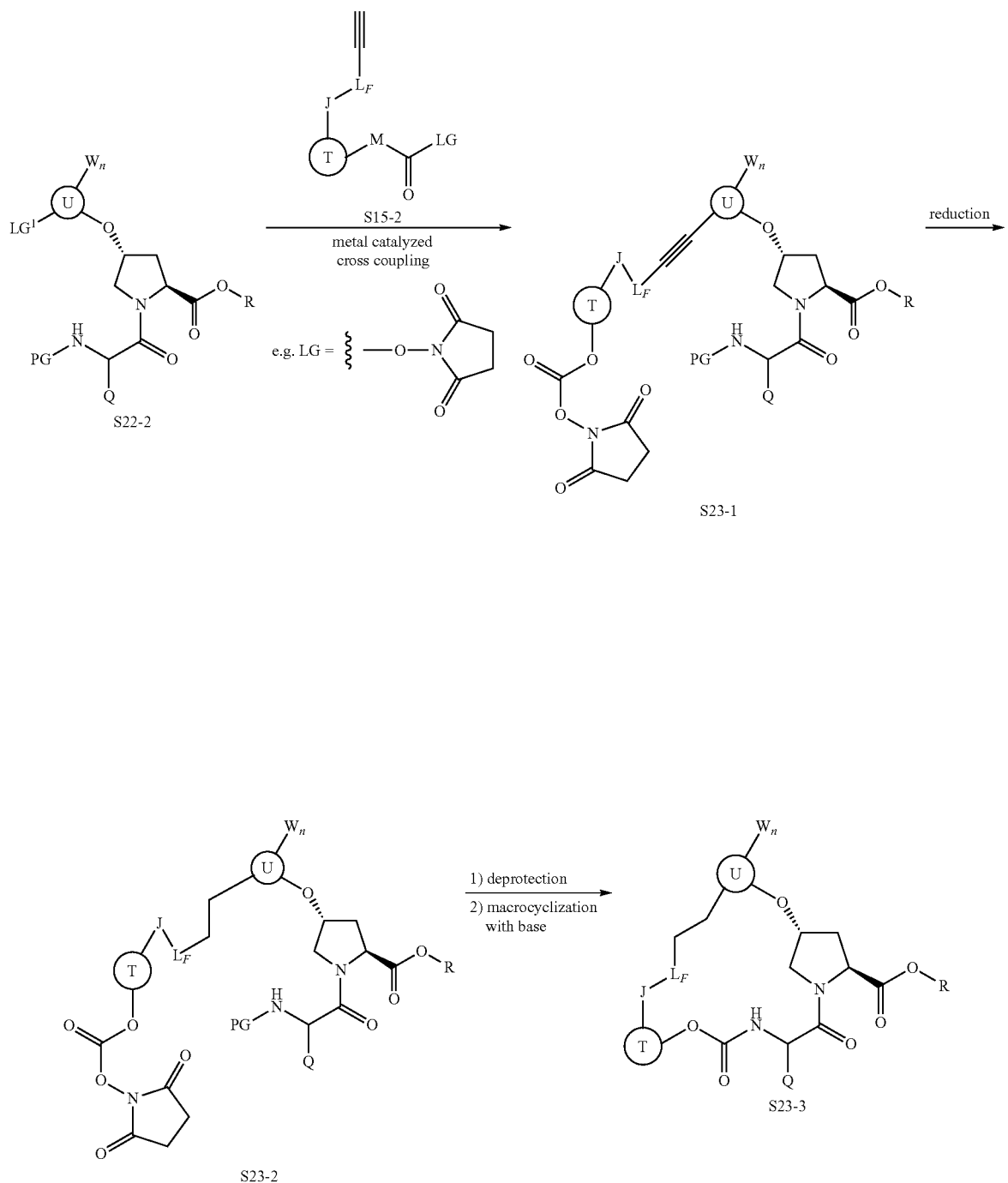

Where:
R - alkyl;
PG = Boc or Cbz
LG¹ = halo or pseudohalo

Scheme 23 shows a general synthesis of intermediate S19-4 which is useful for preparing certain compounds described herein, where J, $L_F$, T, U, $W_n$ and Q are as defined herein. In scheme 23, intermediate S22-2 includes protecting group PG and leaving group LG¹. Intermediate S22-2 undergoes a metal catalyzed cross coupling (e.g. Sonagashira) with an activated alkynyl linker fragment S15-2 to give intermediate S23-1. Reduction of the alkyne (e.g. $H_2$, Pd/C or Rh/$Al_2O_3$) provides intermediate S23-2. Deprotection of the amine (e.g. HCl when PG=Boc) followed by macrocyclization via carbamate formation in the presence of base (e.g. TEA) gives S23-3.

Scheme 24

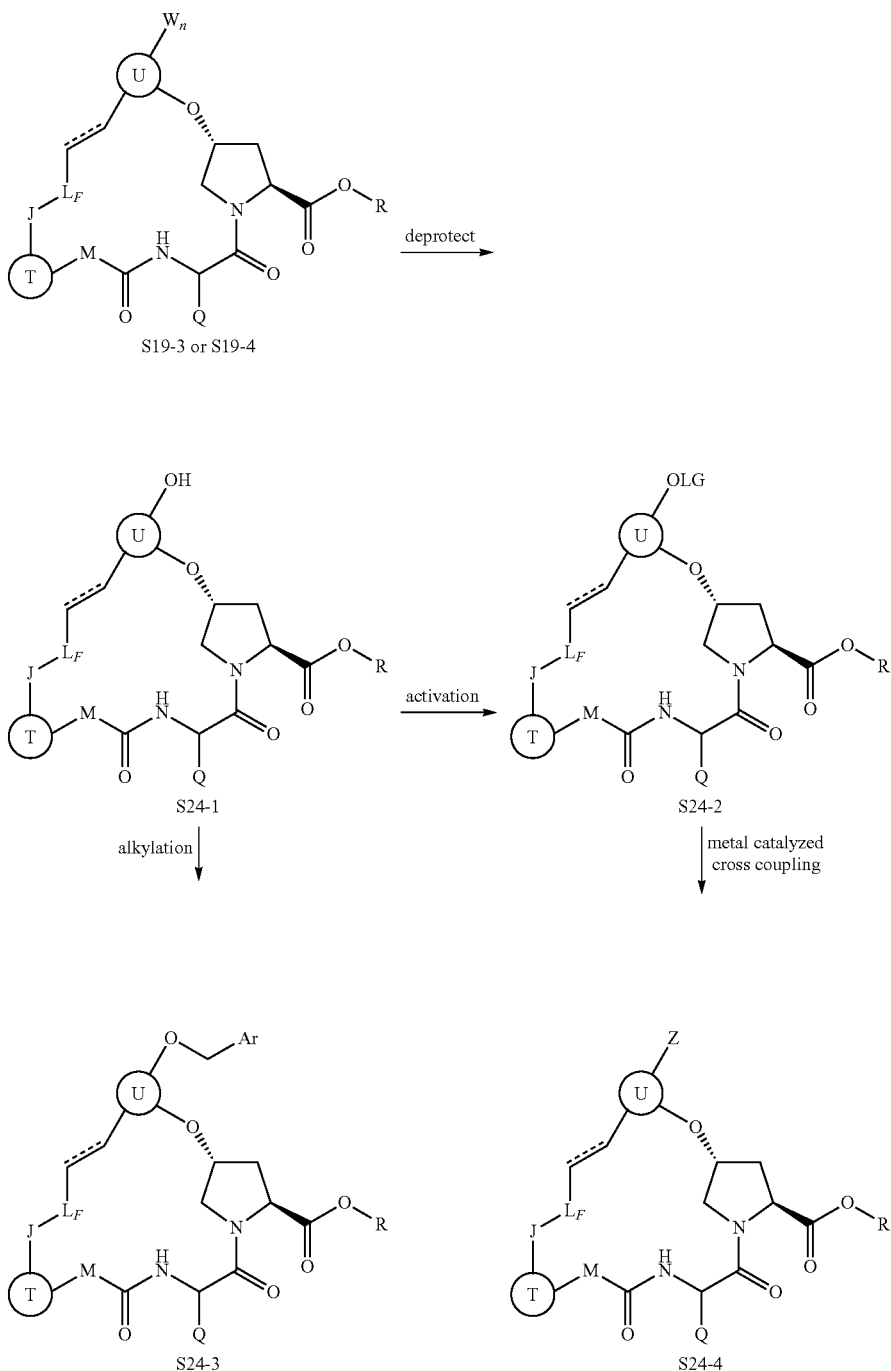

Where:
$W_n$ = OPG
R = alkyl;
Ar = aryl or heteroaryl
LG = pseudohalo

Scheme 24 shows a general synthesis of intermediates S24-3 and S24-4 which are useful for preparing certain compounds described herein, where J, $L_F$, T, U, $W_n$ and Q are as defined herein. In scheme 24, deprotection of S19-3 or S19-4 to remove $W_n$ (e.g. $H_2$, Pd/C when PG=benzyl) yields intermediate heteroaryl alcohol S24-1. Activation of the resulting alcohol (e.g. $Tf_2O$) to a suitable leaving group (LG) such as triflate produces intermediate S24-2. Subsequent metal catalyzed cross coupling (e.g. Suzuki) provides intermediate S24-4. Intermediate S24-1 can also be alternatively be alkylated (e.g. alkyl halide) to give intermediate S24-3.

Scheme 25

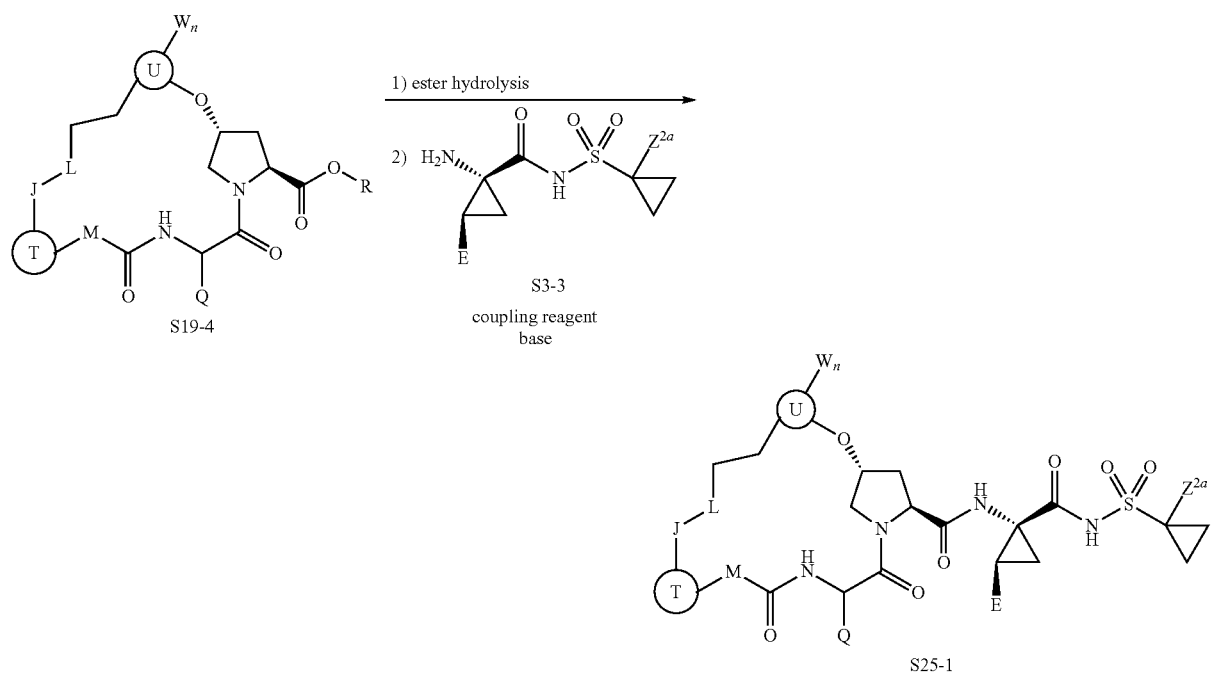

Scheme 25 demonstrates a general route to S25-1, where J, $L_F$, T, U, $W_n$ and Q are as defined herein. In Scheme 25, proline ester intermediate S19-4 is hydrolyzed to its corresponding carboxylic acid and subsequently coupled with intermediate S3-3 in the presence of a coupling agent (e.g. HATU) and base (e.g. DIPEA) to provide compounds of the general type S25-1.

The following non-limiting Preparations and Examples illustrate the preparation of various embodiments disclosed herein.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The following abbreviations have been used for common solvents used in nuclear magnetic resonance experiments: $CDCl_3$, deuterochloroform; $CD_3OD$, perdeuteromethanol; $CD_3CN$, perdeuteroacetonitrile; $d_6$-DMSO, perdeuterodimethylsulfoxide. Mass spectra were obtained using Thermo Scientific or Agilent Technologies mass spectrometers equipped with electrospray ionization (ESI). Masses are reported as ratios of mass to charge (m/z). Analytical HPLC measurements were performed on Agilent Technologies Series 1100 HPLC using Phenomenex Kinetex C18, 2.6 um 100 Å, 4.6×100 mm column with an elution program of 2% Solvent B for 0.55 min, gradient to 98% solvent B over 8 min which is maintained at 98% solvent B for 0.40 min before returning to 2% solvent B over 0.02 min and maintaining at 2% solvent B for 2.03 min at a flow rate of 1.5 mL/min (Solvent A=MiliQ filtered $H_2O$+0.1% TFA, Solvent B=MeCN+0.1% TFA). The term "thin layer chromatography (TLC)" refers to silica gel chromatography using silica gel 60 $F_{254}$ plates. The retention factor ("$R_f$") of a compound is the distance travelled by a compound divided by the distance travelled by the solvent front on a TLC plate. Terms such as "early eluting" and "late eluting" refer to the order in which a compound elutes or is recovered from a solid stationary phase/liquid solvent mobile phase based chromatography method (e.g. normal phase silica gel chromatography or reverse phase high pressure liquid chromatography (HPLC)).

EXAMPLES

Preparation of Selected Intermediates

Intermediate Group A

Preparation of Intermediate A1

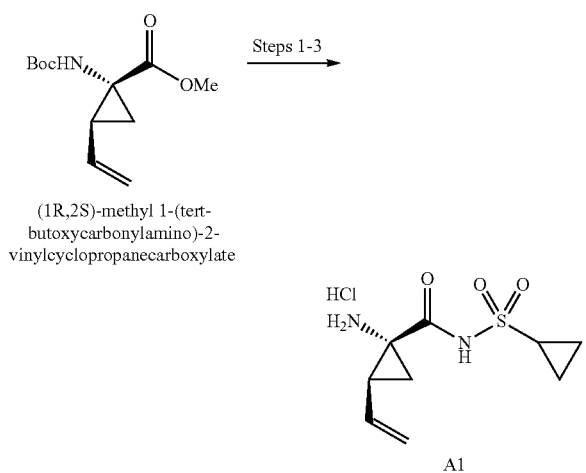

(1R,2S)-methyl 1-(tert-butoxycarbonylamino)-2-vinylcyclopropanecarboxylate

A1

Steps 1-3. Preparation of Intermediate A1: Intermediate A1 was prepared by following the procedure detailed in Example 2.12 of International Patent Publication No. WO 2008/064066 (p. 75-76) substituting (1R,2S)-methyl 1-(tert-butoxycarbonylamino)-2-vinylcyclopropane-carboxylate (prepared according to Beaulieu, P. L., et al., *J. Org. Chem.* 2005, 70, 5869) for (1R,2S)-ethyl 1-(tert-butoxycarbonylamino)-2-vinylcyclopropane-carboxylate.

Preparation of Intermediate A2

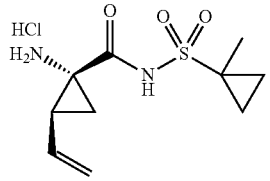

Intermediate A2 was prepared similarly to Intermediate A1, substituting 1-methylcyclopropane-1-sulfonamide (prepared according to Example 1.2 of International Patent Publication No. WO 2008/064066, p. 47) for cyclopropanesulfonamide.

Preparation of Intermediate A3

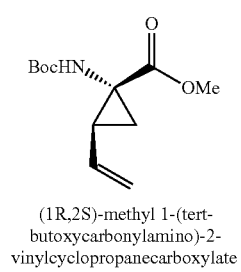

(1R,2S)-methyl 1-(tert-butoxycarbonylamino)-2-vinylcyclopropanecarboxylate

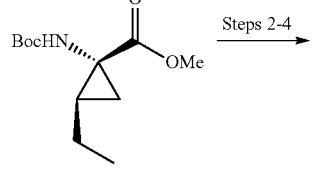

A3-1

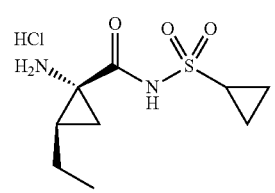

A3

Step 1. Preparation of A3-1: Cyclopropane ester A3-1 was prepared from (1R,2S)-methyl 1-(tert-butoxycarbonylamino)-2-vinylcyclopropanecarboxylate (prepared according to Beaulieu, P. L., et al., *J. Org. Chem.* 2005, 70, 5869) using the procedure detailed in Example 26 of International Patent Publication No. WO2009005677 (p. 176).

Steps 2-4. Preparation of Intermediate A3: Intermediate A3 was prepared similarly to (1R,2S)-1-amino-N-(cyclopropylsulfonyl)-2-vinylcyclopropanecarbox-amide hydrochloride of Example 2.12 of International Patent Publication No. WO 2008/064066 (p. 75-76) substituting A3-1 for (1R,2S)-ethyl 1-(tert-butoxycarbonylamino)-2-vinylcyclopropane-carboxylate.

Preparation of Intermediate A4

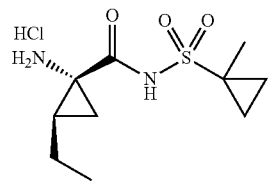

Intermediate A4 was prepared similarly to Intermediate A3, substituting 1-methylcyclopropane-1-sulfonamide (prepared according to Example 1.2 of International Patent Publication No. WO 2008/064066, p. 47) for cyclopropanesulfonamide.

Preparation of Intermediate A5

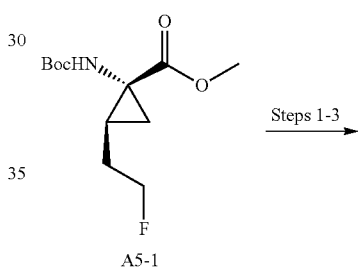

A5-1

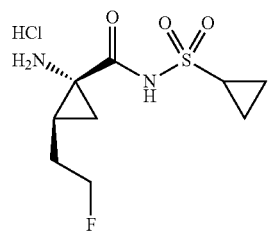

A5

Steps 1-3. Preparation of Intermediate A5: Intermediate A5 was prepared similarly to (1R,2S)-1-amino-N-(cyclopropylsulfonyl)-2-vinylcyclopropane-carboxamide hydrochloride of Example 2.12 of International Patent Publication No. WO 2008/064066 (p. 75-76) substituting A5-1 (prepared according to Example 104 of International Patent Publication No. WO 2009/005677, p. 265) for (1R,2S)-ethyl 1-(tert-butoxycarbonylamino)-2-vinylcyclopropanecarboxylate.

Preparation of Intermediate A6

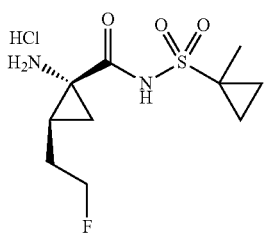

Intermediate A6 was prepared similarly to Intermediate A5, substituting 1-methylcyclopropane-1-sulfonamide (prepared according to Example 1.2 of International Patent Publication No. WO 2008/064066, p. 47) for cyclopropanesulfonamide.

Preparation of Intermediate A7

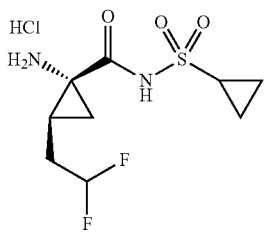

Intermediate A7 was prepared according to Example 97.1.6 of U.S. Patent Publication No. 2009/274652, p. 72-73.

Preparation of Intermediate A8

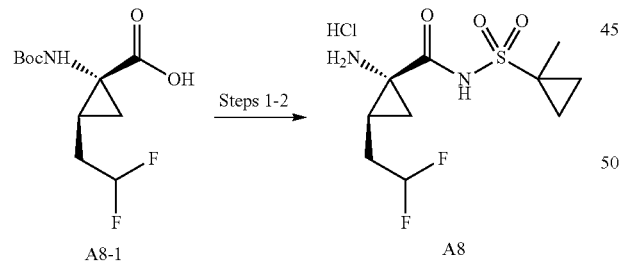

Steps 1-2. Preparation of Intermediate A8: Intermediate A8 was prepared similarly to (1R,2S)-1-amino-N-(cyclopropylsulfonyl)-2-vinylcyclopropane-carboxamide hydrochloride of Example 2.12 of International Patent Publication No. WO 2008/064066 (p. 75-76) substituting A8-1 (prepared according to the procedure detailed in Example 97.1.4 of U.S. Patent Publication No. 2009/274652, p. 72-3) for (1R,2S)-1-(tert-butoxycarbonylamino)-2-vinylcyclo-propanecarboxylic acid and substituting 1-methylcyclopropane-1-sulfonamide (prepared according to Example 1.2 of International Patent Publication No. WO 2008/064066, p. 47) for cyclopropanesulfonamide.

Preparation of Intermediate A9

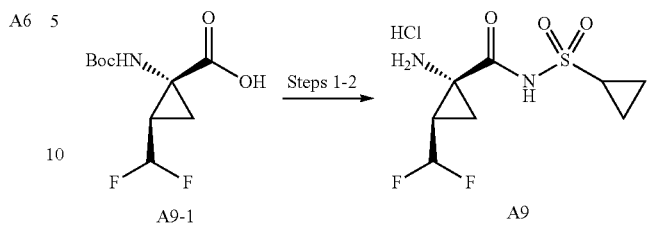

Step 1-2. Preparation of Intermediate A9: Intermediate A9 was prepared similarly to (1R,2S)-1-amino-N-(cyclopropylsulfonyl)-2-vinylcyclopropane-carboxamide hydrochloride of Example 2.12 of International Patent Publication No. WO 2008/064066 (p. 75-76) substituting A9-1 (prepared according to Example 1, Steps 1L-1O of International Patent Publication No. WO 2009/134987, p. 75-77) for (1R,2S)-1-(tert-butoxycarbonylamino)-2-vinylcyclopropanecarboxylic acid.

Preparation of Intermediate A10

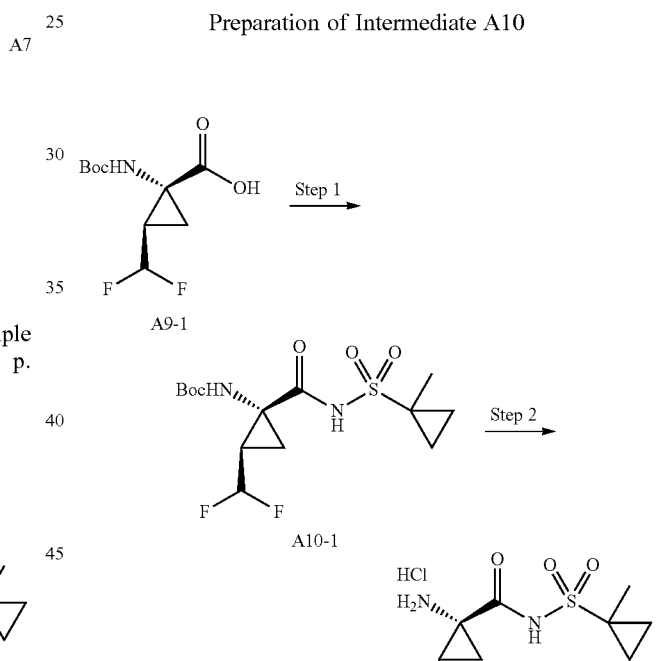

Step 1. Preparation of A10-1: A solution of A9-1 (25 g, 100 mmol) and 1-methylcyclopropane-1-sulfonamide (prepared according to Example 1.2 of International Patent Publication No. WO 2008/064066, p. 47; 15 g, 110 mmol) in DCM (330 mL) was treated with DMAP (24.4 g, 200 mmol) followed by slow addition of EDC (38.3 g, 200 mmol) at 0° C. After addition was completed, the mixture stirred vigorously at 0° C. and allowed to warm rt over 36 h. The reaction was diluted with EtOAc (300 mL). The organic layer was washed with 10% citric acid (3×30 mL) and sat. NaHCO$_3$(2×20 mL). The combined aqueous washes were extracted once with EtOAc. The combined organic layers were washed with brine (2×25 mL), dried over anhydrous Na$_2$SO$_4$, filtered and concentrated in vacuo. After trituration with hexane/EtOAc (10/1), acyl sulfonamide A10-1 (31 g) was obtained as a white solid.

Step 2. Preparation of Intermediate A10. To a suspension of acyl sulfonamide A10-1 (18.5 g, 50 mmol) in DCM (300 mL) was slowly added 4 M HCl in dioxane (150 mL, 600 mmol). After addition was completed, the mixture was stirred vigorously at rt for 4 h. The reaction was then concentrated in vacuo and the residue triturated with Et$_2$O to provide Intermediate A10 (14.7 g) as an amorphous white solid. $^1$H-NMR (400 MHz, CD$_3$OD) δ 5.94 (m, 1H), 2.26 (m, 2H), 1.76 (m, 1H), 1.62 (m, 1H), 1.60 (m, 1H), 1.53 (S, 3H), 0.93 (m, 2H).

Intermediate Group B

Preparation of Intermediate Mixture B1 and B2

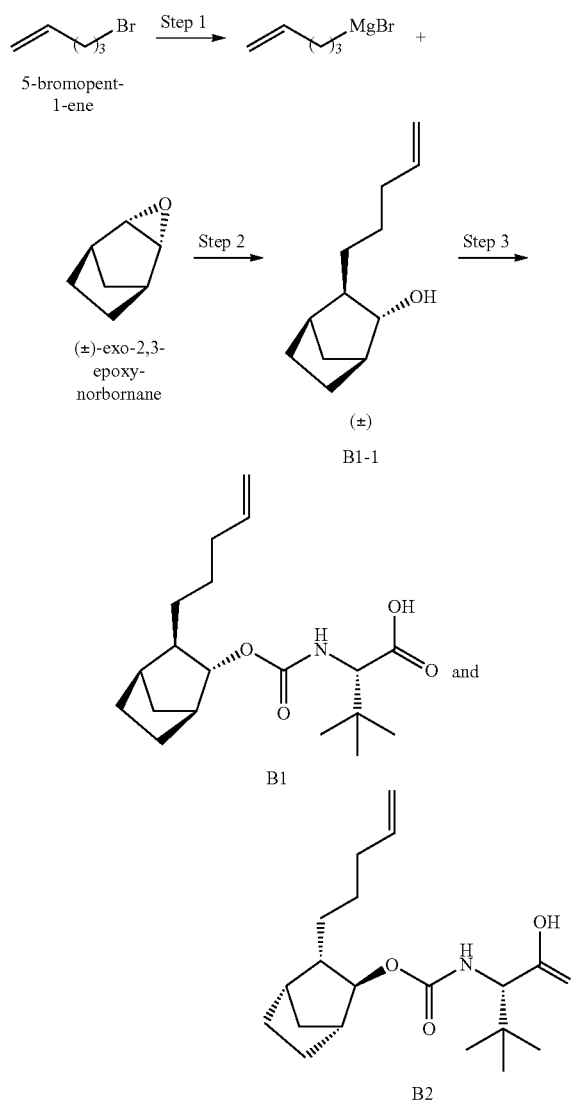

B1-1

B1

B2

Steps 1 and 2: Preparation of racemate B1-1: Magnesium metal (1.32 g, 54.3 mmol) was added to a 2-neck flask fitted with a reflux condenser and the vessel was flushed with Ar. THF (42 mL) was added followed by iodine (ca. 5 mg). The stirred suspension was heated to 45° C. and 5-bromopent-1-ene was added (1.2 g, 8.1 mmol) in one portion. After stirring several minutes, additional 5-bromopent-1-ene (5.5 g, 37 mmol) was added at a rate sufficient to maintain gentle reflux. The resulting mixture was stirred at 50° C. for 15 min and was then cooled to ambient temperature and used immediately in the following step. A suspension of CuI (630 mg, 3.3 mmol) in THF (24 mL) under Ar was cooled to −5° C. An aliquot of pent-4-enylmagnesium bromide (ca. 0.95 M, 20 mL, 19 mmol) prepared in step 1 was added over 5 min, and the resulting mixture was stirred for an additional 15 min. The reaction mixture was then cooled to −20° C., and (±)-exo-2,3-epoxynorbornane (1.5 g, 14 mmol) was added as a solution in THF (5 mL) over 1 min. Two additional portions of THF (2.5 mL each) were used to ensure complete transfer, and the resulting mixture was stirred for 20 min. The reaction was then removed from the cold bath and warmed to rt. After stirring an additional 1.75 h, the reaction was quenched with saturated aqueous NH$_4$Cl (5 mL) and was filtered with EtOAc (100 mL) and H$_2$O (100 mL) through Celite. The phases were separated, and the organic phase was dried over anhydrous Na$_2$SO$_4$, filtered, and concentrated in vacuo to afford (±)-B1-1. $^1$H-NMR (300 MHz, CDCl$_3$) δ 5.90-5.67 (m, 1H), 5.04-4.86 (m, 2H), 3.12 (s, 1H), 2.20-1.92 (m, 5H), 1.69-1.57 (m, 1H), 1.55-1.12 (m, 9H), 1.03-0.84 (m, 1H).

Step 3. Preparation of diastereomeric Intermediate mixture B1 and B2: Alcohol mixture (±)-B1-1 (813 mg, 4.51 mmol) was dissolved in DMF (4.5 mL). Pyridine (370 µL, 4.5 mmol) was added followed by DSC (1.5 g, 5.8 mmol). The reaction mixture was heated to 45° C. and was stirred for 4 h. The reaction mixture was then cooled to 0° C. and water (4.5 mL) was added dropwise over 2 min. The reaction mixture was stirred for 5 min and was removed from the cold bath. After an additional 5 min, the reaction mixture was cooled to 0° C. and L-tert-leucine (835 mg, 6.37 mmol) and K$_3$PO$_4$ (2.70 g, 12.7 mmol) were added. The mixture was stirred for 10 min and was removed from the cold bath. After stirring an additional 24 h, the mixture was diluted with EtOAc (30 mL), acidified with 1 M aqueous HCl (15 mL), and diluted with 0.2 M aqueous HCl (15 mL). The phases were separated, and the organic phase was washed with 0.2 M aqueous HCl (2×20 mL), dried over anhydrous Na$_2$SO$_4$, filtered, and concentrated in vacuo to afford diastereomeric Intermediate mixture B1 and B2 (1.64 g). LCMS-ESI$^-$ (m/z): [M−H]$^-$ calc'd for C$_{19}$H$_{30}$NO$_4$: 336.2. found: 336.0.

Preparation of Intermediate Mixture B3 and B4

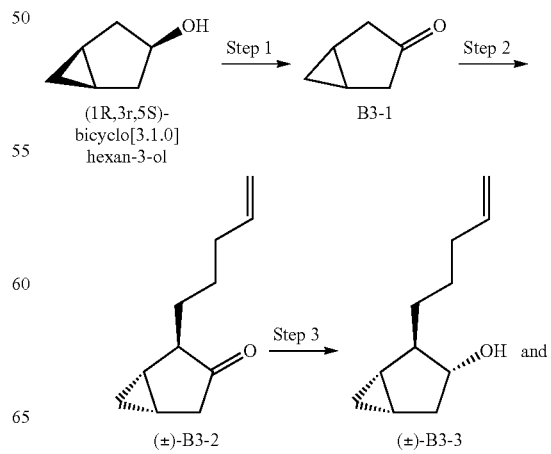

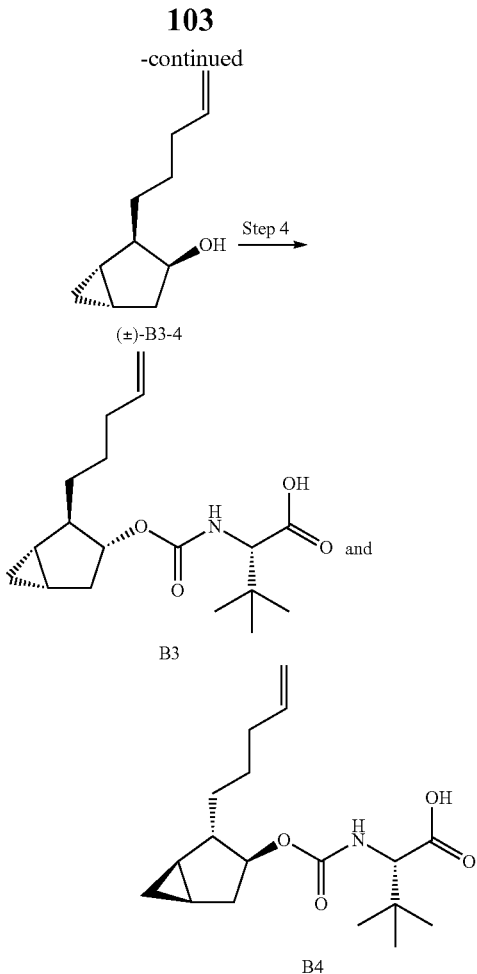

Step 1: Preparation of B3-1: To a solution of $K_2Cr_2O_7$ (121 g, 0.41 mol) in $H_2O$ (1.5 L) was added dropwise $H_2SO_4$ (143 g, 1.46 mol) at rt and the mixture was stirred for 1 h. The mixture was then cooled to 0° C. and (1R,3r,5S)-bicyclo[3.1.0]hexan-3-ol (80 g, 0.814 mol; prepared according to Section A, Intermediate 1 of U.S. Pat. No. 8,178,491 B2, p 192) in MTBE (1.5 L) was added dropwise. The reaction mixture was stirred at rt for 2 h. The aqueous phase was extracted with MTBE (3×500 mL), dried over anhydrous $MgSO_4$, filtered, and concentrated in vacuo. The crude product was purified by distillation (20 mmHg, bp: 60-62° C.) to provide B3-1. $^1$H-NMR (400 MHz, $CDCl_3$) δ 2.57-2.63 (m, 2H), 2.14-2.19 (d, J=20 Hz, 2H), 1.52-1.57 (m, 2H), 0.89-0.94 (m, 1H), −0.05--0.02 (m, 1H).

Step 2: Preparation of (±)-B3-2: Under Ar, a mixture of THF (4.4 mL) and HMPA (1.8 mL) was cooled to −78° C. A 1 M solution of LiHMDS in THF (2.2 mL, 2.2 mmol) was added. Ketone B3-1 (202 mg, 2.10 mmol) was added as a solution in THF (2 mL) over 1 min, washing with additional THF (2×1 mL) to ensure complete transfer. After 25 min, 5-iodopent-1-ene (prepared according to Jin, J. et. al. *J. Org. Chem.* 2007, 72, 5098-5103) (880 mg, 4.5 mmol) was added over 30 s by syringe. After 10 min, the reaction was placed in a cold bath at −45° C. and was warmed to −30° C. over 1.5 h. The reaction was quenched with saturated aqueous $NH_4Cl$ (15 mL) and was diluted with EtOAc (30 mL) and $H_2O$ (15 mL). The phases were separated, and the aqueous phase was extracted with EtOAc (30 mL). The combined organics were dried over anhydrous $Na_2SO_4$, filtered, and concentrated in vacuo to afford a crude residue that was purified by silica gel chromatography (0% to 15% EtOAc in hexanes) to provide (±)-B3-2. $^1$H-NMR (400 MHz, $CDCl_3$) δ 5.82-5.67 (m, 1H), 5.03-4.87 (m, 2H), 2.61-2.51 (m, 1H), 2.11 (d, J=19.1 Hz, 1H), 2.08-1.99 (m, 3H), 1.61-1.40 (m, 5H), 1.36-1.28 (m, 1H), 0.92-0.81 (m, 1H), −0.03--0.11 (m, 1H).

Step 3: Preparation of (±)-B3-3 and (±)-B3-4: A solution of (±)-B3-2 (142 mg, 0.865 mmol) in THF (4 mL) was cooled to −78° C. A 1 M THF solution of $LiBHEt_3$ (1.3 mL, 1.3 mmol) was added dropwise over 30 s. The reaction was stirred 15 min and was removed from the cold bath. After warming to rt (15 min), the reaction was quenched with saturated aqueous $NH_4Cl$ (1 mL). The resulting mixture was diluted with $Et_2O$ (20 mL) and $H_2O$ (20 mL). The phases were separated, and the aqueous phase was extracted with $Et_2O$ (20 mL). The combined organics were dried over anhydrous $MgSO_4$, filtered, and concentrated in vacuo. Purification by silica gel chromatography (0% to 10% EtOAc in hexanes) provided 133 mg of a mixture of diastereomers (±)-B3-3 and (±)-B3-4. The combined material from two experiments (253 mg) was further purified by silica gel chromatography (0% to 15% EtOAc in hexanes) to provide (±)-B3-3 (150 mg) and (±)-B3-4 (58 mg). $^1$H-NMR for (±)-B3-3 (300 MHz, $CDCl_3$) δ 5.91-5.69 (m, 1H), 5.07-4.88 (m, 2H), 3.97 (d, J=6.7 Hz, 1H), 2.19-1.99 (m, 3H), 1.84-1.73 (m, 1H), 1.62 (d, J=14.1 Hz, 1H), 1.54-1.40 (m, 2H), 1.32-1.17 (m, 3H), 1.16-1.06 (m, 1H), 0.60-0.43 (m, 2H). $^1$H-NMR for (±)-B3-4 (300 MHz, $CDCl_3$) δ 5.95-5.73 (m, 1H), 5.09-4.88 (m, 2H), 4.05-3.86 (m, 1H), 2.17-1.84 (m, 4H), 1.72-1.34 (m, 5H), 1.28-1.08 (m, 3H), 0.49-0.36 (m, 1H), 0.21-0.11 (m, 1H).

Step 4: Preparation of diastereomeric Intermediate mixture B3 and B4: A mixture of (±)-B3-3 (150 mg, 0.90 mmol) was dissolved in DMF (1.0 mL). Pyridine (75 μL, 0.92 mmol) and DSC (302 mg, 1.18 mmol) were added, and the reaction was stirred at 45° C. for 21.5 h. The reaction was then placed in an ice water bath and $H_2O$ (1.0 mL) was added dropwise via syringe over 1 min. The mixture was removed from the cold bath and allowed to stir 5 min. The mixture was re-cooled in an ice water bath and L-tert-leucine (154 mg, 1.17 mmol) was added followed by $K_3PO_4$ (502 mg, 2.36 mmol). The reaction mixture was removed from the cold bath and allowed to stir at rt for 24 h. The mixture was then diluted with EtOAc (40 mL) and 1 M aqueous HCl (20 mL). The phases were separated, and the aqueous phase was extracted with EtOAc (30 mL). The combined organic phase was washed with 0.2 M aqueous HCl (2×20 mL), dried over anhydrous $MgSO_4$, filtered, and concentrated in vacuo to afford diastereomeric Intermediate mixture B3 and B4. LCMS-ESI⁻ (m/z): [M−H]⁻ calcd for $C_{18}H_{28}NO_4$: 322.2. found: 322.0).

Preparation of Intermediate B3

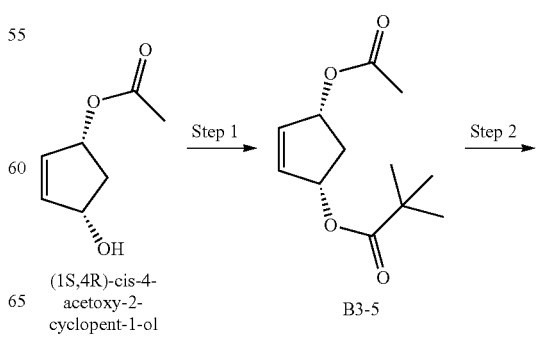

(1S,4R)-cis-4-acetoxy-2-cyclopent-1-ol

B3-5

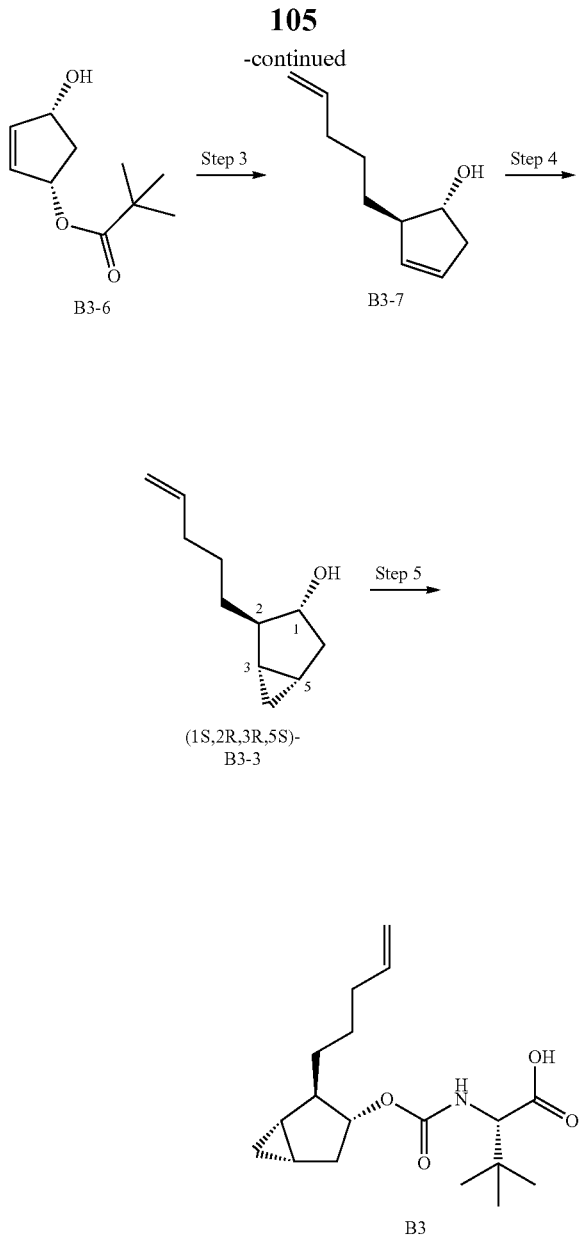

Step 1: Preparation of B3-5: To a solution of (1S,4R)-cis-4-acetoxy-2-cyclopent-1-ol (Aldrich, 10 g, 70.4 mmol), triethylamine (48.8 mL, 350 mmol), and DMAP (4.29 g, 35.2 mmol) in dichloromethane (352 mL) was added pivaloyl chloride (10.8 mL, 87.75 mmol) dropwise via syringe at 0° C. under an Ar atmosphere. After 2 h, the reaction mixture was diluted with saturated aqueous sodium bicarbonate solution (500 mL), and extracted with dichloromethane (2×500 mL). The combined organic extracts were dried over anhydrous $Na_2SO_4$ and were concentrated in vacuo to afford B3-5. $^1$H-NMR (300 MHz, $CDCl_3$) δ 6.08 (br s, 2H), 5.54 (td, J=8.0, 4.1 Hz, 2H), 2.88 (dt, J=14.9, 7.5 Hz, 1H), 2.07 (s, 3H), 1.69 (dt, J=14.7, 4.1 Hz, 1H), 1.20 (s, 9H).

Step 2: Preparation of B3-6: To a solution of B3-5 (15.0 g, 70.4 mmol) in methanol (352 mL) was added potassium carbonate (9.73 g, 70.4 mmol) at rt under an argon atmosphere. After 5 h, the reaction mixture was filtered and concentrated in vacuo. The residue was dissolved into ethyl acetate (500 mL) and the resulting mixture was washed with water (500 mL) and brine (500 mL), dried over anhydrous $Na_2SO_4$, and concentrated in vacuo. The crude residue was purified by silica gel chromatography (0-100% ethyl acetate/hexanes) to afford B3-6. $^1$H-NMR (300 MHz, $CDCl_3$) δ 6.11 (br d, J=5.5 Hz, 1H), 5.97 (br d, J=5.6 Hz, 1H), 5.48 (br s, 1H), 4.73 (br s, 1H), 2.82 (dt, J=14.6, 7.3 Hz, 1H), 1.67 (s, 1H), 1.61 (dt, J=14.5, 4.0 Hz, 1H), 1.20 (s, J=3.8 Hz, 9H).

Step 3: Preparation of B3-7: To a solution of copper(I) cyanide (5.10 g, 57.0 mmol) in diethyl ether (95 mL) was added pent-4-enylmagnesium bromide (Novel Chemical Solutions, 0.5 M in THF, 114 mL, 57.0 mmol) dropwise via cannula over a 30 min period at 0° C. under an argon atmosphere. After 10 min, a solution of B3-6 (3.50 g, 19.0 mmol) in diethyl ether (10 mL) was added slowly via cannula. The reaction mixture was then allowed to slowly warm to rt. After 16 h, the resulting mixture was quenched with saturated aqueous ammonium chloride solution (400 mL) and the resulting mixture was extracted into ethyl acetate (2×400 mL). The combined organic phases were washed with brine (400 mL), dried over anhydrous $Na_2SO_4$, and concentrated in vacuo. The crude residue was purified by silica gel chromatography (0-100% ethyl acetate/hexanes) to afford B3-7. $^1$H-NMR (400 MHz, $CDCl_3$) δ 5.80 (ddt, J=16.9, 10.2, 6.7 Hz, 1H), 5.69 (dd, J=5.8, 1.7 Hz, 1H), 5.65 (d, J=7.2 Hz, 1H), 5.00 (dd, J=17.1, 1.3 Hz, 1H), 4.94 (d, J=10.2 Hz, 1H), 4.12-4.05 (m, 1H), 2.69 (ddd, J=17.2, 6.4, 1.5 Hz, 1H), 2.54-2.45 (m, 1H), 2.24 (d, J=17.2 Hz, 1H), 1.69 (br s, 1H), 1.52-1.19 (m, 6H).

Step 4: Preparation of (1S,2R,3R,5S)—B3-3: To a solution of B3-7 (20 mg, 0.13 mmol), and diethyl zinc (1 M in hexanes, 132 μL, 0.132 mmol) in diethyl ether (0.66 mL) was added diiodomethane (21 μL, 0.26 mmol) at rt under an argon atmosphere. After 2 h, the reaction mixture was quenched with 1 N aqueous HCl solution (0.66 mL). After 5 min, the resulting yellow mixture was diluted with saturated aqueous sodium bicarbonate solution (5 mL) and the resulting mixture was extracted with dichloromethane (3×5 mL). The combined organic extracts were dried over anhydrous $Na_2SO_4$, and were concentrated in vacuo. The crude residue was purified by silica gel chromatography (0-100% ethyl acetate/hexanes) to afford (1S,2R,3R,5S)—B3-3. $^1$H-NMR (400 MHz, $CDCl_3$) δ 5.83 (ddt, J=16.9, 10.2, 6.7 Hz, 1H), 5.02 (d, J=17.2 Hz, 1H), 4.96 (d, J=11.3 Hz, 1H), 4.00 (d, J=6.7 Hz, 1H), 2.19-2.02 (m, 3H), 1.82 (t, J=7.2 Hz, 1H), 1.64 (d, J=14.2 Hz, 1H), 1.55-1.42 (m, 2H), 1.38-1.20 (m, 4H), 1.19-1.08 (m, 1H), 0.62-0.47 (m, 2H).

Step 5: Preparation of Intermediate B3: Alcohol (1S,2R,3R,5S)—B3-3 (0.450 g, 2.7 mmol) was taken up in DMF (2.7 mL) and treated subsequently with DSC (0.92 g, 3.52 mmol) and pyridine (0.22 mL, 2.8 mmol). The reaction was then heated to 50° C. overnight. The reaction was then cooled to 0° C. and water (5.5 mL) was added dropwise over 1 min. The resulting opaque suspension was stirred at rt for 10 min before recooling to 0° C. The reaction was then treated subsequently with L-tert-leucine (0.462 g, 3.5 mmol) and $K_3PO_4$ (1.5 g, 7.0 mmol) and allowed to warm to rt overnight with vigorous stirring. The resulting opaque suspension was diluted with EtOAc and 1 M aqueous HCl. Additional HCl (12 M) was added dropwise to adjust the pH ~3. The aqueous layer was extracted with EtOAc and the combined organics were washed with brine and dried over anhydrous $MgSO_4$. Following concentration in vacuo, Intermediate B3 was obtained that was contaminated with small amounts of DMF and EtOAc. The material was used in subsequent reactions without further purification. LCMS-ESI$^+$ (m/z): [M+H]$^+$ calcd for $C_{18}H_{30}NO_4$: 324.2; found 324.7.

Preparation of Intermediate B5

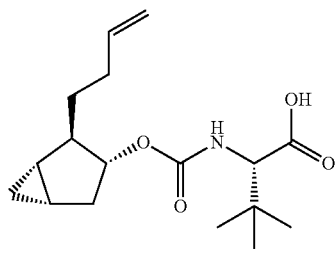

Intermediate B5 was prepared in a similar fashion to the preparation of Intermediate B3, substituting but-3-enylmagnesium bromide for pent-4-enyl magnesium bromide in Step 3. LCMS-ESI$^+$ (m/z): [M+H]$^+$ calcd for $C_{17}H_{28}NO_4$: 310.2; found 310.8.

Preparation of Intermediate mixture B6 and B7

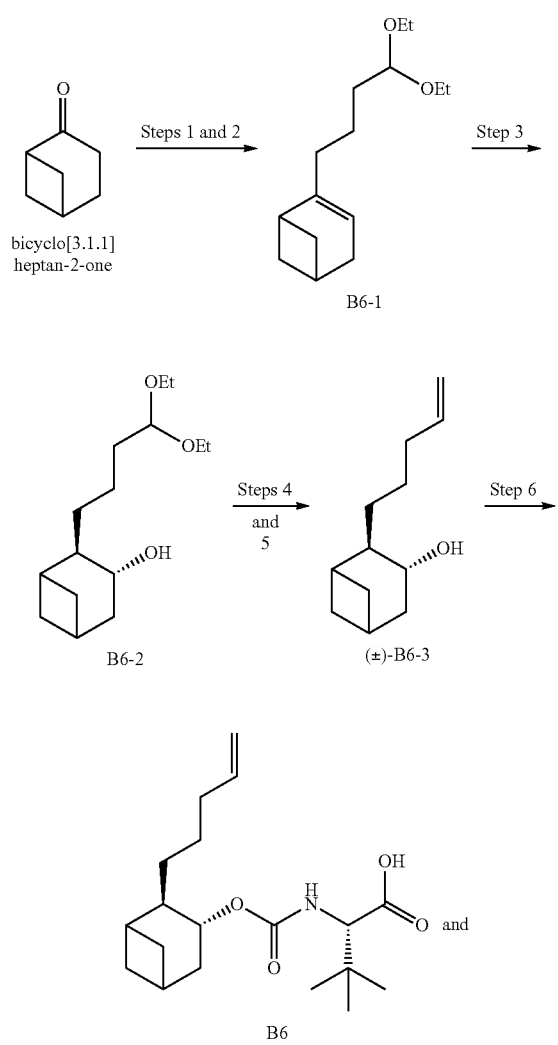

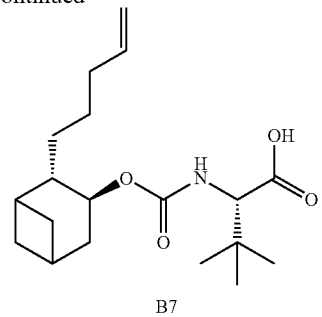

Step 1: Preparation of B6-1: A 1.0 M THF solution of KHMDS (10 mL, 10 mmol) was diluted with THF (10 mL) under Ar and the resulting solution was cooled to −78° C. Bicyclo[3.1.1]heptan-2-one (1.0 g, 9.1 mmol, prepared according to Yin, et al. *J. Org. Chem.* 1985, 50, 531) was added as a solution in THF (5 mL) over 2 min, washing with additional THF (2×2.5 mL) to ensure complete transfer. The resulting mixture was stirred for 30 min, and N-(5-chloro-2-pyridyl)bis(trifluoromethanesulfonimide) (3.8 g, 9.7 mmol) was added as a solution in THF (10 mL) over 2 min, washing with additional THF (2×2.5 mL). The resulting mixture was stirred for 5 min and removed from the cold bath. After stirring an additional 30 min, the reaction was diluted with Et$_2$O (70 mL) and 1 M aqueous HCl (50 mL). The phases were separated, and the organic phase was washed with 1 M aqueous NaOH (2×30 mL). The combined organic phase was dried over anhydrous MgSO$_4$, filtered and concentrated in vacuo. The resulting residue was filtered through a plug of silica with 30% EtOAc in hexanes to afford a crude residue that was used directly in the following step.

Step 2: Preparation of B6-1: To a solution of 3-butenal diethyl acetal (1.4 mL, 8.3 mmol) under Ar at 0° C. was added a 0.5 M THF solution of 9-borabicyclo[3.3.1]nonane (15.9 mL, 7.95 mmol) over 3 min. The reaction was allowed to warm to rt with stirring for 20 h. A 3 M aqueous solution of NaOH (2.9 mL, 8.7 mmol) was then added. After stirring 20 min, the resulting solution was transferred to a flask containing the vinyl triflate (ca. 5.16 mmol) described above and PdCl$_2$(dppf).CH$_2$Cl$_2$ (420 mg, 0.51 mmol). The resulting mixture was stirred at 60° C. for 14 h, allowed to cool to rt, and diluted with Et$_2$O (50 mL) and H$_2$O (50 mL). The phases were separated, and the organic phase was dried over anhydrous MgSO$_4$, filtered, and concentrated in vacuo. Purification by silica gel chromatography (0% to 10% EtOAc in hexanes following pre-equilibration with 1% Et$_3$N in EtOAc) provided intermediate B6-1. $^1$H-NMR (300 MHz, CDCl$_3$) δ 5.36-5.28 (m, 1H), 4.59 (t, J=5.6 Hz, 1H), 3.73-3.58 (m, 2H), 3.54-3.39 (m, 2H), 2.72-2.60 (m, 1H), 2.45-2.34 (m, 3H), 2.23-2.08 (m, 4H), 1.89-1.76 (m, 2H), 1.67 (dt, J=16.1, 6.9 Hz, 2H), 1.58-1.47 (m, 2H), 1.23 (t, J=7.0 Hz, 6H).

Step 3: Preparation of B6-2: A solution of olefin B6-1 (660 mg, 2.77 mmol) in THF (25 mL) at 0° C. was treated with BH$_3$.SMe$_2$ as a 1 M solution in CH$_2$Cl$_2$ (2.9 mL, 2.9 mmol) over 1 min. The resulting solution was stirred for 2 h at 0° C. and allowed to warm to rt. After stirring an additional 3 h, the reaction mixture was re-cooled to 0° C. and was diluted with 2 M aqueous NaOH (7 mL) followed by 30% aqueous H$_2$O$_2$ (7 mL). The resulting mixture was allowed to warm to rt with stirring over additional 16 h. The mixture was partitioned between Et$_2$O (100 mL) and H$_2$O (50 mL). The phases were separated, and the organic phase was washed with 0.5 M aqueous NaOH (50 mL). The organic phase was dried over anhydrous MgSO$_4$, filtered, and concentrated in vacuo to afford a crude residue that was purified by silica gel chromatography (15% to 40% EtOAc in hexanes) to afford the desired compound. $^1$H-NMR (300 MHz, CDCl$_3$) δ 4.60 (t, J=5.6 Hz, 1H), 3.76-3.60 (m, 3H), 3.58-3.42 (m, 2H), 2.39-2.05 (m, 4H), 1.91-1.48 (m, 9H), 1.43-1.35 (m, 1H), 1.25 (t, J=7.0 Hz, 6H), 1.06-0.98 (m, 1H).

Steps 4 and 5: Preparation of (±)-B6-3: Acetal B6-2 (360 mg, 1.4 mmol) was dissolved in THF (8 mL) and H$_2$O (2 mL). para-Toluenesulfonic acid monohydrate (40 mg, 0.2 mmol) was added and the resulting solution was stirred 16 h at rt. The reaction was diluted with Et$_2$O (50 mL) and H$_2$O (30 mL) and the phases were separated. The aqueous phase was extracted with Et$_2$O (30 mL) and the combined organic phase was washed with saturated aqueous NaHCO$_3$ (15 mL). The organic phase was dried over anhydrous MgSO$_4$, filtered, and concentrated in vacuo to afford a crude residue that was used immediately in the following step. Methyl triphenylphosphonium bromide (1.66 g, 4.6 mmol) was suspended in THF (40 mL) under Ar and was cooled to −78° C. A 1 M solution of NaHMDS in THF (4.2 mL, 4.2 mmol) was added in dropwise fashion and the resulting yellow suspension was stirred for 5 min. The mixture was removed from the cold bath and stirring continued an additional 30 min. The mixture was then re-cooled to −78° C. and the crude residue from the previous step (ca. 1.4 mmol) was added as a solution in THF (5 mL) over 5 min, washing with additional THF (2×2.5 mL) to ensure complete transfer. The resulting mixture was stirred for 5 min and was then placed in an ice water bath and stirred an additional 1 h. The reaction was quenched with saturated aqueous NH$_4$Cl (20 mL) and was diluted with Et$_2$O (30 mL) and H$_2$O (20 mL). The phases were separated and the organic phase was dried over anhydrous MgSO$_4$, filtered, and adsorbed onto 5 g silica gel. Purification by silica gel chromatography (10% to 30% EtOAc in hexanes) provided (±)-B6-3. $^1$H-NMR (300 MHz, CDCl$_3$) 6.01-5.81 (m, 1H), 5.22-5.05 (m, 2H), 3.79-3.66 (m, 1H), 2.43-2.25 (m, 2H), 2.24-2.04 (m, 4H), 1.83-1.16 (m, 10H).

Step 6: Preparation of Intermediate mixture B6 and B7. Alcohol (±)-B6-3 (270 mg, 1.5 mmol) was dissolved in DMF (2.0 mL). Pyridine (125 µL, 1.5 mmol) and DSC (500 mg, 1.9 mmol) were added, and the reaction was stirred at 45° C. for 15 h. The reaction was then placed in an ice water bath and H$_2$O (2.0 mL) was added dropwise via syringe over 30 s. The mixture was removed from the cold bath and allowed to stir 10 min. The mixture was re-cooled in an ice water bath and L-tert-leucine (259 mg, 1.97 mmol) was added followed by K$_3$PO$_4$ (835 mg, 3.93 mmol). The reaction mixture was removed from the cold bath and allowed to stir at rt for 5.25 h. The mixture was then diluted with EtOAc (40 mL) and 1 M aqueous HCl (20 mL), and H$_2$O (15 mL). The phases were separated, and the aqueous phase was extracted with EtOAc (30 mL). The combined organic phase was washed with 0.2 M aqueous HCl (2×25 mL), dried over anhydrous Na$_2$SO$_4$, filtered, and concentrated in vacuo to afford Intermediate mixture B6 and B7. LCMS-ESI$^+$ (m/z): [M+H]$^+$ calcd for C$_{19}$H$_{32}$NO$_4$: 338.2. found: 337.8.

Preparation of Intermediate B8

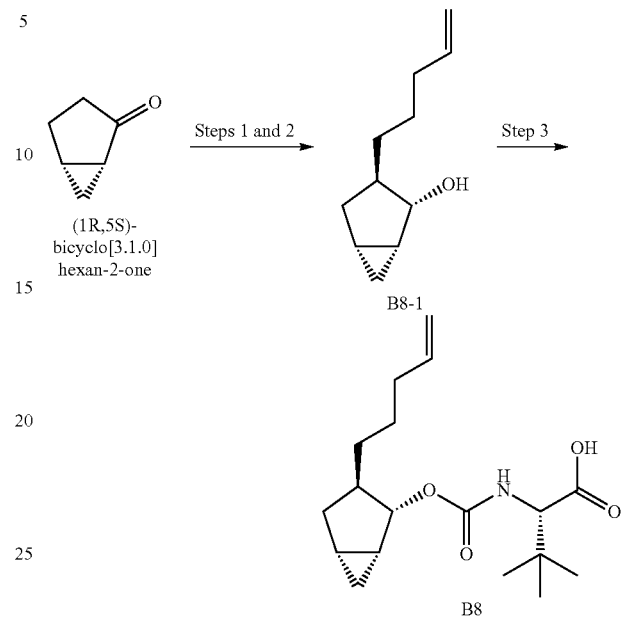

Steps 1 and 2: Preparation of B8-1: To a solution of HMPA (1.8 mL) in THF (4.4 mL) under Ar cooled to −78° C. was added a 1 M solution of LiHMDS (2.2 mL, 2.2 mmol). (1R,5S)—Bicyclo[3.1.0]hexan-2-one (200 mg, 2.08 mmol, prepared according to Hodgson, D. M. et al. *Synthesis*, 2005, 2264) was added as a solution in THF (2 mL) over 1 min, washing with additional THF (2×1 mL) to ensure complete transfer. After 50 min, 5-iodopent-1-ene (870 mg, 4.4 mmol, prepared as described in: Jin, J. et. al. *J. Org. Chem.* 2007, 72, 5098) was added over 30 s. The reaction was stirred for 1 h and was warmed to −50° C. After 2 h, the bath temperature had reached −35° C. and was re-cooled to −50° C. After an additional 2 h, the bath temperature had reached 0° C. The reaction was then poured into saturated aqueous NH$_4$Cl (50 mL) and diluted with EtOAc. The phases were separated, and the organic phase was dried over anhydrous Na$_2$SO$_4$, filtered and concentrated in vacuo. Purification by silica gel chromatography (0% to 15% EtOAc in hexanes) provided a colorless oil (245 mg). The aforementioned residue (200 mg, 1.22 mmol) was dissolved in MeOH (5 mL) and was cooled to −50° C. bath. NaBH$_4$ (188 mg, 4.97 mmol) was added in one portion and the resulting mixture was stirred for 30 min and was removed from the cold bath. After an additional 30 min, the reaction was quenched with saturated aqueous NH$_4$Cl (15 mL) and was diluted with EtOAc (25 mL) and H$_2$O (20 mL). The phases were separated and the organic phase was extracted with EtOAc (30 mL). The combined organic phase was dried over anhydrous Na$_2$SO$_4$, filtered, and concentrated in vacuo. Purification by silica gel chromatography (10% to 30% EtOAc in hexanes) provided B8-1. $^1$H-NMR (300 MHz, CDCl$_3$) δ 5.88-5.71 (m, 1H), 5.04-4.88 (m, 2H), 4.01 (dd, J=7.4, 4.8 Hz, 1H), 2.08-1.99 (m, 2H), 1.93 (dd, J=12.3, 6.9 Hz, 1H), 1.67-1.09 (m, 9H), 0.60-0.52 (m, 1H), 0.41-0.31 (m, 1H) ppm.

Step 3: Preparation of Intermediate B8: Alcohol B8-1 (180 mg, 1.08 mmol) was dissolved in DMF (1.5 mL). Pyridine (90 µL, 1.1 mmol) and DSC (349 mg, 1.36 mmol)

were added, and the reaction was stirred at 45° C. for 50 min. Additional DSC (115 mg, 0.449 mmol) was added and the reaction was stirred an additional 15 h. The reaction was then placed in an ice water bath and H$_2$O (1.5 mL) was added dropwise via syringe over 30 s. Additional DMF (2.5 mL) was added to facilitate stirring. L-tert-leucine (174 mg, 1.33 mmol) was added followed by K$_3$PO$_4$ (550 mg, 2.6 mmol). The reaction mixture was removed from the cold bath and allowed to stir at rt for 2 h. Additional L-tert-leucine (50 mg, 0.38 mmol) and K$_3$PO$_4$ (162 mg, 0.76 mmol) were added and the reaction mixture was stirred an additional 2 h. The mixture was then diluted with EtOAc (30 mL) and H$_2$O (30 mL) and the aqueous phase was acidified with 3 M aqueous HCl to pH~3. The phases were separated, and the organic phase was washed with 0.2 M aqueous HCl (3×20 mL) and dried over anhydrous Na$_2$SO$_4$, filtered and concentrated in vacuo. The resulting crude residue of Intermediate B8 was used subsequently without further purification.

Intermediate Group C

Preparation of Intermediate C1

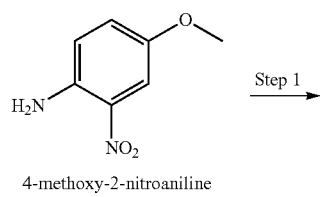

4-methoxy-2-nitroaniline

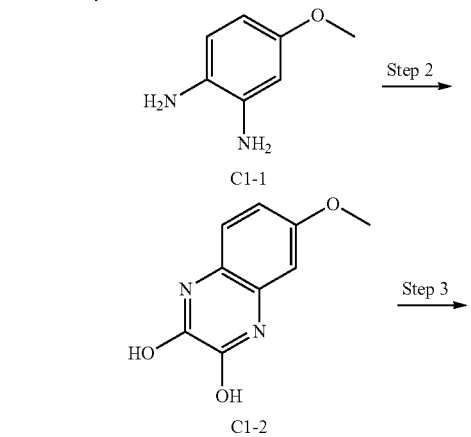

Step 1: Preparation of C1-1: 10% Palladium on activated carbon (10.0 g, 0.300 mol) was added at rt to a stirred solution of 4-methoxy-2-nitroaniline (46.0 g, 275 mmol) in methanol (1 L). The mixture was stirred under 50 PSI H$_2$ atmosphere for 17 h, then filtered through Celite. Solvent was removed in vacuo to afford C1-1. $^1$H-NMR (DMSO-d$_6$, 400 MHz): δ 6.42 (d, J=8.4 Hz, 1H), 6.16 (d, J=2.8 Hz, 1H), 5.97 (dd, J=8.4, 2.8 Hz, 1H), 4.45 (s, 2H), 3.94 (s, 2H), 3.57 (s, 3H).

Step 2: Preparation of C1-2: A suspension of C1-1 in diethyl oxalate (235 g) was treated with Et$_3$N (54.6 g) and heated at 155° C. for 2 h. The mixture was allowed to cool to rt and filtered. The collected solid was washed with H$_2$O and EtOH, then dried to give C1-2. $^1$H-NMR (DMSO-d$_6$, 400 MHz): δ 11.81 (d, J=18 Hz, 2H), 7.04 (d, J=8.8 Hz, 1H), 6.72 (dd, J=8.8, 2.8 Hz, 1H), 6.68 (d, J=2.8 Hz, 1H), 3.72 (s, 3H).

Step 3: Preparation of Intermediate C1: In a dry flask under a dry N$_2$ atmosphere was placed 41.0 g (213 mmol) of C1-2, 200 mL of POCl$_3$, and 41 mL tri-n-propylamine (41 mL, 217 mmol). The exothermic reaction mixture was then allowed to stir at rt for 1 h and thereafter was refluxed overnight. The mixture was cooled again to rt and poured slowly over ice/water. The resulting aqueous mixture was stirred at rt for 20 min, then filtered. The recovered precipitate was washed with water and dissolved in chloroform. The chloroform solution was filtered to remove insoluble material and the filtrate was successively washed with water, saturated sodium bicarbonate solution and brine. Concentration of the washed solution in vacuo was followed by recrystallization of the residue from ethanol. The product was purified via silica gel chromatography to produce Intermediate C1. $^1$H-NMR (DMSO-d$_6$, 400 MHz): δ 7.99 (d, J=9.2 Hz, 1H), 7.59 (dd, J=9.2, 2.8 Hz, 1H), 7.50 (d, J=2.8 Hz, 1H), 3.96 (s, 1H).

Preparation of Intermediate C2

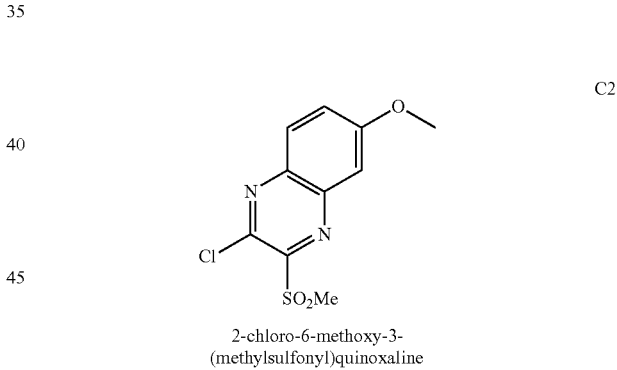

2-chloro-6-methoxy-3-(methylsulfonyl)quinoxaline

Intermediate C2 (2-chloro-6-methoxy-3-(methylsulfonyl)quinoxaline) was prepared according to Mahata, P. K., et al. *Org. Lett.* 2005, 7, 2169.

Preparation of Intermediate C3

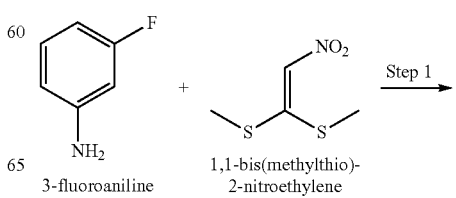

3-fluoroaniline 1,1-bis(methylthio)-2-nitroethylene

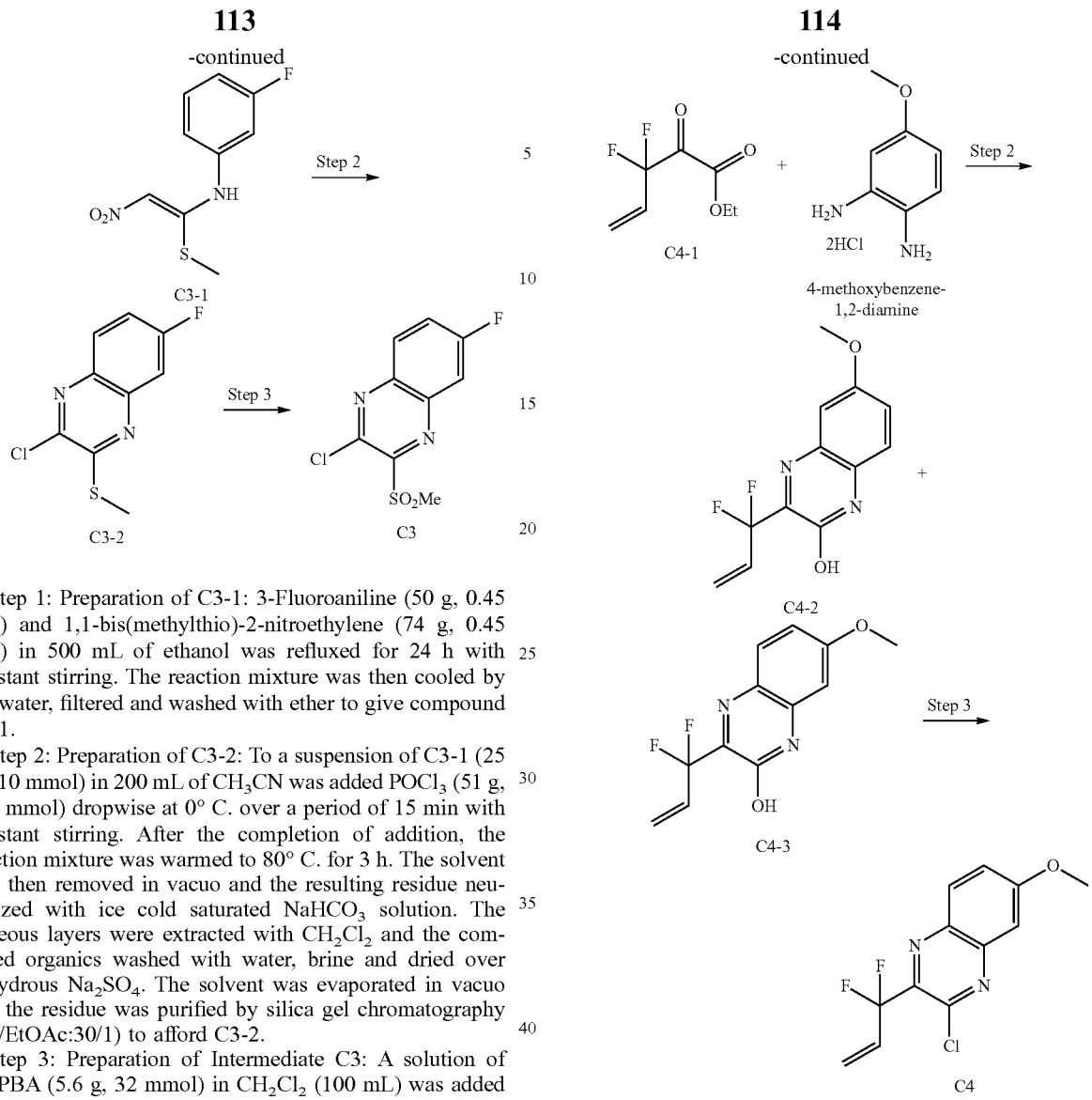

Step 1: Preparation of C3-1: 3-Fluoroaniline (50 g, 0.45 mol) and 1,1-bis(methylthio)-2-nitroethylene (74 g, 0.45 mol) in 500 mL of ethanol was refluxed for 24 h with constant stirring. The reaction mixture was then cooled by ice-water, filtered and washed with ether to give compound C3-1.

Step 2: Preparation of C3-2: To a suspension of C3-1 (25 g, 110 mmol) in 200 mL of $CH_3CN$ was added $POCl_3$ (51 g, 330 mmol) dropwise at 0° C. over a period of 15 min with constant stirring. After the completion of addition, the reaction mixture was warmed to 80° C. for 3 h. The solvent was then removed in vacuo and the resulting residue neutralized with ice cold saturated $NaHCO_3$ solution. The aqueous layers were extracted with $CH_2Cl_2$ and the combined organics washed with water, brine and dried over anhydrous $Na_2SO_4$. The solvent was evaporated in vacuo and the residue was purified by silica gel chromatography (PE/EtOAc:30/1) to afford C3-2.

Step 3: Preparation of Intermediate C3: A solution of mCPBA (5.6 g, 32 mmol) in $CH_2Cl_2$ (100 mL) was added dropwise to a stirred solution of C3-2 (3.0 g, 13 mmol) in $CH_2Cl_2$ (100 mL) at 0° C. over a period of 30 min and then allowed to warm to rt with stirring overnight. It was then washed with 1 N aqueous NaOH (3×100 mL), water (100 mL) and brine (100 mL) and then dried over anhydrous $Na_2SO_4$. The solvent was evaporated in vacuo and the residue purified by silica gel chromatography (PE/EtOAc=10/1) to afford Intermediate C3. $^1$H-NMR (400 MHz, $CDCl_3$) δ 3.55 (s, 3H), 7.73-7.82 (m, 2H), 8.15 (dd, J=9.2, 5.6 Hz, 1H).

Preparation of Intermediate C4

Method A:

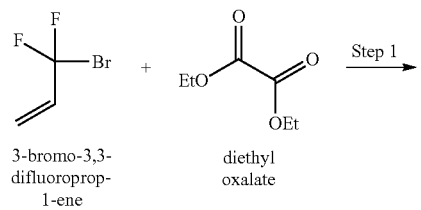

Step 1. Preparation of C4-1: To a solution of 3-bromo-3,3-difluoroprop-1-ene (25.0 g, 159 mmol) and diethyl oxalate (21.6 mL, 159 mmol) in THF (380 mL), diethyl ether (90 mL) and n-pentane (90 mL) at −100° C. was added dropwise n-butyllithium (2.5 M in hexane, 67 mL, 167.6 mmol) over 30 min. The reaction mixture was stirred at −95° C. for 1 h and −78° C. for 2 h, and quenched with aq. $NH_4Cl$ (11 g in 150 mL of water). The mixture was extracted with ether (three times). The organic layers were washed with 1 N aqueous HCl, brine, and dried over anhydrous $Na_2SO_4$, and concentrated in vacuo to give the crude residue, which was purified by silica gel chromatography (EtOAc in hexanes: 0% to 40%) to give C4-1. $^1$H-NMR (300 MHz, $CDCl_3$) δ 5.98-6.18 (m, 1H), 5.78 (dd, J=0.9 Hz, 13 Hz, 1H), 5.60 (dd, J=0.9 Hz, 11 Hz, 1H), 4.38 (q, J=6.9 Hz, 2H), 1.37 (t, J=7.2 Hz, 3H).

Step 2. Preparation of C4-2 and C4-3: To a solution of C4-1 (14.0 g, 78.6 mmol) and 4-methoxybenzene-1,2-diamine dihydrochloride (15.08 g, 71.4 mmol) in EtOH (360 mL) at rt was added triethylamine (19.9 mL, 142.8 mmol). The reaction mixture was stirred at rt overnight. The mixture was concentrated in vacuo. Slurrying in dichloromethane (30 mL) and filtering gave some separation of regioisomers with C4-2 as the precipitating species. $^1$H-NMR (400 MHz, CDCl$_3$) δ 11.940 (br s, 1H), 7.850 (d, J=9 Hz, 1H), 6.985 (dd, J=3 Hz, 9 Hz, 1H), 6.754 (d, J=2 Hz, 1H), 6.625-6.498 (m, 1H), 5.907 (dt, J=17, 2 Hz, 1H), 5.601 (d, J=11 Hz, 1H), 3.938 (s, 3H). The mixture was slurried, filtered, and concentrated in vacuo once more, then was purified by silica gel chromatography (EtOAc in hexanes: 5% to 34%) to give C4-3 as the first eluting component. $^1$H-NMR (400 MHz, CDCl$_3$) δ 12.05 (br s, 1H), 7.850 (d, J=9 Hz, 1H), 6.986 (dd, J=3 Hz, 9 Hz, 1H), 6.761 (d, J=3 Hz, 1H), 6.597-6.526 (m, 1H), 5.91 (dt, J=17, 2 Hz, 1H), 5.601 (d, J=11 Hz, 1H), 3.939 (s, 3H).

Step 3. Preparation of Intermediate C4: A solution of C4-3 (2.07 g, 8.2 mmol in 1 mL DMF was treated with POCl$_3$ (0.8 mL) and heated at 65° C. for 2.5 h. The reaction was diluted with EtOAc and quenched by pouring into ice water. The organic phase was washed subsequently with saturated aqueous sodium bicarbonate and brine, dried over anhydrous Na$_2$SO$_4$ and concentrated in vacuo to give 2.1 g of Intermediate C4. $^1$H-NMR (400 MHz, CDCl$_3$) δ 8.028 (d, J=10 Hz, 1H), 7.46 (dd, J=3 Hz, 9 Hz, 1H), 7.32 (d, J=3 Hz, 1H), 6.549-6.478 (m, 1H), 5.86 (dt, J=17, 2 Hz, 1H), 5.67 (d, J=11 Hz, 1H), 3.981 (s, 3H).

Method B:

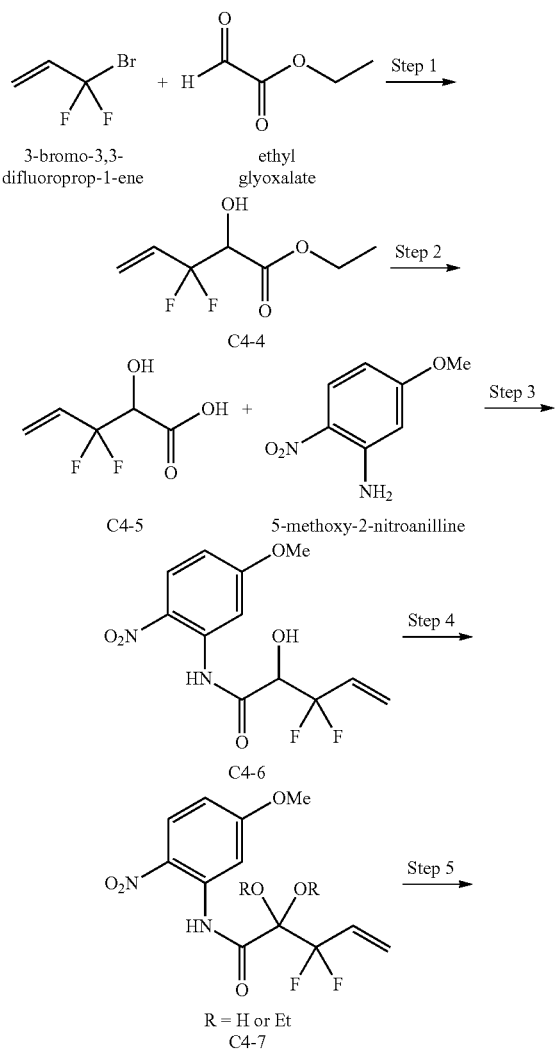

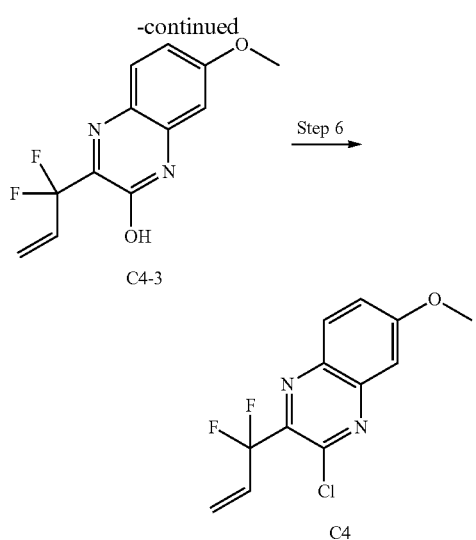

Step 1. Preparation of C4-4: A 1-L 3-necked round-bottom flask was charged with a solution of 3-bromo-3,3-difluoroprop-1-ene (25 g, 159.3 mmol) in DMF (360 mL) and water (90 mL). The resulting solution was treated with ethyl 2-oxoacetate (33 mL, 1 M in toluene), and In (25 g). The reaction mixture was stirred overnight at rt and then extracted with 3×300 mL of ether. The organic layers were combined, washed with 1×100 mL of saturated aqueous NH$_4$Cl and 1×100 mL of brine, dried over anhydrous Na$_2$SO$_4$ and concentrated in vacuo to afford 25 g of C4-4 that was used subsequently without additional purification.

Step 2. Preparation of C4-5: THF (20 mL) and water (4 mL) were added to C4-4 (2.0 g, 11.10 mmol) in a 250 mL round bottom flask. LiOH.H$_2$O (0.7 g, 16.7 mmol, 1.5 equiv) was added in one portion at 20-25° C. The reaction was stirred at rt until judged complete by TLC analysis. Upon completion, water (10 mL) and MTBE (10 mL) were added. The aqueous layer (pH>9) is separated and the organic layer extracted once with water (4 mL). The aqueous layers were combined and MTBE (10 mL) was added. The biphasic mixture was agitated while the pH was adjusted to 1 with 1 N HCl. The aqueous layer was extracted with MTBE (10 mL). The combined MTBE layers were washed once with 25% NaCl solution (4 mL), then dried with anhydrous Na$_2$SO$_4$ and concentrated in vacuo provide C4-5. $^1$H-NMR (400 MHz, CDCl$_3$) δ 5.97-6.07 (m, 1H), 5.76-5.82 (m, 1H), 5.60 (dd, J=0.6, 10.9 Hz, 1H), 4.4 (dd, J=8.0, 13.1 Hz, 1H).

Step 3. Preparation of C4-6: The hydroxy acid C4-5 (27.7 g, 182.1 mmol) was added to 1 L flask equipped with a temperature probe and overhead stirring. DCM (280 mL), DMAP (2.0 g, 16.5 mmol) and pyridine (29.4 mL, 364.1 mmol) were added to the substrate at 20-25° C. TMSCl (46.0 mL, 364.1 mmol) was added over 1 h at a rate to maintain the internal temperature between 18-28° C. The slurry was then stirred for 1.5 h at 20° C. The reaction was cooled to 0° and treated with DMF (0.1 mL) and (C001)$_2$ (15.6 mL, 182.1 mmol) that was added as a rate to maintain the internal temperature below 10° C. This slurry was stirred for 1 h at 0° C. and 30 min at 20° C. The internal temperature of the slurry was then decreased to 0° C. and pyridine (20.0 mL, 248.3 mmol) was added while keeping the internal temperature below 10° C. Upon addition of pyridine, large solids formed and increased agitation was necessary. 5-Methoxy-2-nitroaniline (27.8 g, 165.5 mmol) was added in portions, while keeping the internal temperature below 10° C. After the addition is complete the reaction temperature was raised to 20° C. Upon reaction completion (monitored by UPLC) the slurry was filtered and the solids were washed with DCM. The DCM solution was washed with 1 M HCl and then slurried with silica gel for 15 min. The slurry was filtered and washed with DCM. HCl in MeOH (prepared from MeOH and AcCl (1.3 equiv) at 0° C.) was added and the reaction monitored by UPLC until complete. The DCM solution was neutralized with saturated aqueous $NaHCO_3$. The aqueous layer was extracted with DCM and the combined DCM layers were concentrated to a foam. The foam was taken up in DCM and warmed to 35° C. Heptane was added slowly, seed was added and the slurry was agitated for 30 min. Heptane was added slowly over 1 h, the slurry was aged for 1 h and then cooled to 25° C. over 1 h. The slurry was agitated for 2 h, filtered and washed with DCM/Heptane (1:3 mix) to produce of C4-6.

$^1$H-NMR (400 MHz, $CDCl_3$): 11.64 (s, 1H), 8.36 (d, J=2.3 Hz, 1H), 8.20 (d, J=9.4 Hz, 1H), 6.69 (dd, J=9.4, 2.1 Hz, 1H), 6.19-5.95 (m, 1H), 5.78 (br-d, J=17.4 Hz, 1H), 5.58 (d, J=11.1 Hz, 1H), 4.53 (t, J=10.2 Hz, 1H), 3.90 (s, 3H)

Step 4. Preparation of C4-7: Nitroaniline C4-6 (10.96 g, 36.3 mmol) was diluted in DCM (75 mL) and treated with TEMPO (569 mg, 3.64 mmol) and $Bu_4NCl$ (1.0 g, 3.6 mmol) in a 500 mL 3-neck flask equipped with overhead stirring and an internal temperature probe. Buffer solution (0.5 M $NaHCO_3$, 0.05 M $Na_2CO_3$, 90 mL) was added and the mixture was stirred vigorously. NCS (5.85 g, 43.8 mmol) was added in one portion. After 2.25 h, EtOH (2.5 mL) was added to aid dissolution of solids. The aqueous layer was removed and extracted once with DCM. The combined DCM layers were washed with saturated sodium thiosulfate, water and then slurried with silica gel (15 g). The silica was filtered off and washed with DCM. Following concentration in vacuo, C4-7 was collected. This material was dissolved in 45 mL hot DCM. Heptane (25 mL) was added dropwise over 3 min and the resulting solution was seeded with 30 mg of hydrate product. The crystallization was stirred 5 min at ~45° C. and then cooled to rt. A mechanical stirrer was added to facilitate agitation. Additional heptane (35 mL) was added via syringe pump at a rate of 20 mL/min and the resulting suspension was stirred overnight. Solids were then vacuum filtered through a medium porosity fritted glass funnel and the filter cake washed with 4×9 mL 2:1 heptane:DCM. Drying afforded a mixture of hydrate and ethyl hemiketal forms. $^1$H-NMR (400 MHz, $d_6$-acetone): δ 8.41 (d, J=2.8 Hz, 1H), 8.30 (d, J=9.4 Hz, 1H), 6.90 (dd, J=9.4, 2.7 Hz, 1H), 6.34-6.16 (m, 1H), 5.75 (br-d, J=17.4 Hz, 1H), 5.62 (d, J=11.1 Hz, 1H), 3.97 (s, 3H) ppm. (note: the corresponding ethyl ketal/hemiketal species will also be observed to some extent along with the desired product. These byproducts will be apparent from peak doubling and multiplets in the 3.4-3.9 ppm and 0.9-1.3 ppm range. The listed values correspond to the major product.)

Step 5. Preparation of C4-3. Nitroaniline C4-6 (32.9 g, 103 mmol) was suspended in EtOH (460 mL) and HOAc (190 mL) in a 3-neck flask equipped with overhead stirring, temperature probe, and $N_2$ inlet. Iron powder (37.5 g, 672 mmol) was added and the vigorously stirred heterogeneous mixture was heated in a heat block pre-heated to 55° C. After 20 min, the internal reaction temperature was ~50° C., and was judged to be undergoing exotherm based on rate of temperature increase. Heating was removed, and the internal temperature continued to increase to 57° C. over 10 min. After the temperature began to drop, the heat source was re-applied. A relatively constant internal temperature of 51° C. was observed thereafter. After 3 h, the reaction was diluted with EtOAc (300 mL) and Celite (50 g) was added. The resulting thick reaction mixture was filtered through a short pad of Celite, washing with sufficient EtOAc to ensure elution of yellow/red color. The filtrate was concentrated in vacuo and partitioned between EtOAc (300 mL), 0.2 M aqueous HCl (250 mL), and brine (50 mL). The layers were separated and the organic phase was washed with 2×300 mL 15% saturated brine, 1×300 mL 1:1 $H_2O$:saturated aqueous $NaHCO_3$ and 200 mL brine. The organic phase was dried over anhydrous $Na_2SO_4$, filtered, and concentrated to 50 g of a golden solid residue. An additional 30 mL of EtOAc was added, and the heterogeneous mixture was heated in a 65° C. heat block. Hexane (500 mL) was added dropwise via addition funnel over 1 h, and the resulting suspension was cooled to ambient temperature and stirred an additional 5 h. Filtration through an medium porosity fritted glass funnel provided the desired product. $^1$H-NMR (400 MHz, $CDCl_3$): 12.43 (s, 1H), 7.83 (d, J=9.0 Hz, 1H), 6.98 (d, J=8.9 Hz, 1H), 6.81 (s, 1H), 6.64-6.42 (m, 1H), 5.90 (br-d, J=17.4 Hz, 1H), 5.59 (d, J=11.0 Hz, 1H), 3.93 (s, 3H) ppm.

Step 6. Preparation of Intermediate C4. Hydroxyquinoxaline (22.4 g, 88.8 mmol) was dissolved in DMF (45 mL) in a round-bottomed flask equipped with a temperature probe and $N_2$ inlet. $POCl_3$ (12.5 mL, 134 mmol, 1.5 equiv) was added via syringe at a rate to keep the internal temperature below 50° C. The dark red solution was then heated via heat block pre-heated to 75° C. (internal temperature ~74° C.). After 2.5 h, the reaction was then transferred via cannula to 370 mL of stirred $H_2O$ in a 3-neck flask equipped with temperature probe, overhead stirring, and vent to atmosphere. The rate of quench was controlled such that the internal temperature remained below 35° C. Three additional portions of DMF (3 mL each) were used to ensure complete transfer. Once the internal temperature decreased to 30° C., 3 M aqueous NaOH was added until a pH of ~6-7 was obtained (160 mL total). The brown heterogeneous mixture was then cooled to an internal temperature of 15° C. and was filtered through an M-grade frit. The filter cake was washed with $H_2O$ (2×30 mL) and 3:1 $H_2O$:MeCN (3×20 mL). The filter cake was suspended in $CH_2Cl_2$ (200 mL), and the mixture was dried with anhydrous $MgSO_4$ and filtered through a short pad of Celite. Concentration in vacuo provided 19 g of a dark red oil. This oil was dissolved in $CH_2Cl_2$ (100 mL) and was slurried with silica gel (40 g) for 20 min. The slurry was filtered through a short pad of fresh silica gel (20 g), washing with 6×40 mL $CH_2Cl_2$. The filtrate was concentrated to afford the desired product. This material was recrystallized from hot hexanes to afford 14.5 g of Intermediate C4 as yellow needles. $^1$H-NMR (400 MHz, $CDCl_3$): 8.02 (d, J=9.2 Hz, 1H), 7.45 (dd, J=9.3, 2.8 Hz, 1H), 7.32 (d, J=2.7 Hz, 1H), 6.59-6.43 (m, 1H), 5.86 (dt, J=17.3, 2.5 Hz, 1H), 5.67 (d, J=11.0 Hz, 1H), 3.98 (s, 3H) ppm.

Method C:

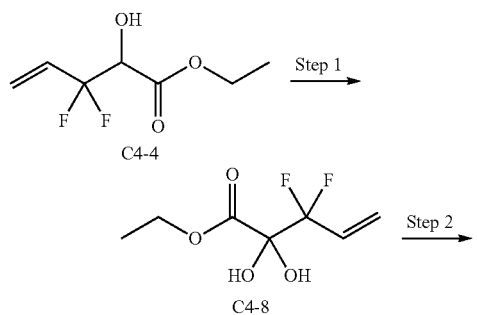

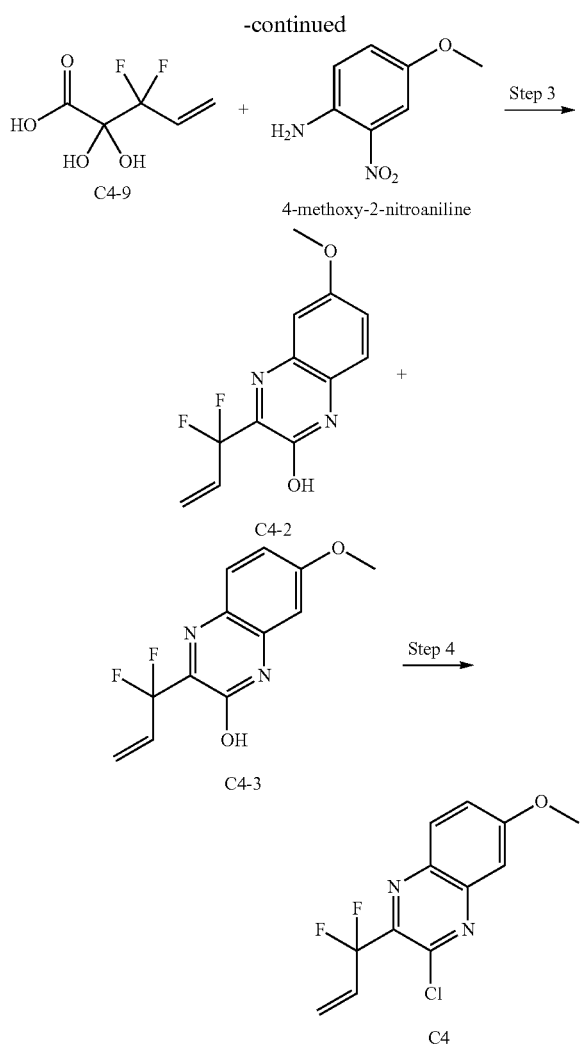

Step 1. Preparation of C4-8. To hydroxyester C4-4 (58.1 g, 323 mmol) was added DCM (700 mL) in a 2 L 3-neck flask equipped with overhead stirring and an internal temperature probe. Then TEMPO (5.4 g, 35 mmol), buffer solution (prepared by dissolving 4.2 g NaHCO$_3$ and 0.53 g Na$_2$CO$_3$ per 100 mL water, 700 mL, 7 v), and NaOCl (Clorox 6.15% wt, 422 mL, 395 mmol) were sequentially added to the flask at 20° C. After 2 h the organic layer was separated and the aqueous phase extracted with ethyl acetate (2×300 mL). The combined organic layers were dried over anhydrous Na$_2$SO$_4$ and concentrated in vacuo to afford C4-8. $^1$H-NMR (300 MHz, CDCl$_3$) δ 5.98-6.18 (m, 1H), 5.78 (dd, J=0.9 Hz, 13 Hz, 1H), 5.60 (dd, J=0.9 Hz, 11 Hz, 1H), 4.38 (q, J=6.9 Hz, 2H), 1.37 (t, J=7.2 Hz, 3H).

Step 2. Preparation of C4-9. To a solution of ethyl 3,3-difluoro-2,2-dihydroxypent-4-enoate C4-8 (57.4 g, 292 mmol) in THF (725 mL) and water (131 mL) was added LiOH.H$_2$O (22 g, 529 mmol) at 20° C. After 2.5 h, the reaction mixture was concentrated in vacuo. The solid residue was suspended in water (300 mL) and the resulting mixture was acidified to pH=1 with concentrated aqueous hydrochloric acid solution. The resulting mixture was stirred until all solids were dissolved (~1.5 h), and then sodium chloride was added until the solution was saturated. The resulting solution was extracted with MTBE (2×500 mL) and ethyl acetate (2×500 mL), and the combined organic layers were dried over anhydrous Na$_2$SO$_4$ and were concentrated in vacuo. The crude orange solid residue was suspended into DCM (100 mL) and was stirred until the solids were finely distributed before hexanes (75 mL) were slowly added via addition funnel. The resulting solids were collected by vacuum filtration through a medium fritted funnel and washed with 1:1 dichloromethane/hexanes (2×10 mL) to afford the desired product. $^1$H-NMR (400 MHz, DMSO-d$_6$) δ 13.17 (bs, 1H), 6.18-6.01 (m, 1H), 5.64-5.52 (m, 2H).

Step 3. Preparation of C4-2 and C4-3. 4-Methoxy-2-nitroaniline (10.0 g, 59.5 mmol), ketal-acid C4-9 (11.1 g, 74.4 mmol), and BHT (1.31 g, 5.95 mmol) were added to a 1 L 3-neck flask equipped with overhead stirring, temperature probe, and Ar inlet. Ethanol (200 mL) and acetic acid (100 mL) were sequentially added at 20° C. and the vessel was purged with Ar. Iron powder (16.6 g, 297 mmol) was added and the vigorously stirred heterogeneous mixture was heated in a heat block pre-heated to 65° C. After 10 min, the internal temperature reached a maximum temperature of 70° C., and was judged to be undergoing exotherm based on rate of temperature increase. Heating was removed, and the internal temperature dropped to 65° C. at which point the heat source was re-applied. After 30 min the reaction mixture contained brown solid precipitate and was allowed to cool to rt. The mixture was then diluted with ethyl acetate (1 L), and silica gel (200 mL) was added and stirred. The resulting slurry was filtered through a course fritted funnel, washing with sufficient ethyl acetate to ensure elution of desired product. The resulting clear light red/orange filtrate was concentrated in vacuo and the crude residue was partitioned between ethyl acetate (300 mL) and saturated aqueous sodium bicarbonate solution (300 mL). The phases were split and the organic phase was dried over anhydrous Na$_2$SO$_4$, was filtered, and was concentrated in vacuo to afford a ~4:1 ratio of regioisomers favoring C4-3. The solid residue was suspended into ethyl acetate (150 mL) and was stirred via magnetic stirring until the mixture was a finely dispersed suspension (~10 min). Hexanes (1.5 L) were slowly added over a ~10 min period and the resulting solids were collected from the slurry by vacuum filtration via a medium fritted funnel to afford the desired product as a tan powder after drying.

Step 4. Preparation of Intermediate C-4. Hydroxyquinoxaline mixture C4-2 and C4-3 (46.8 g, 97:3 regioisomeric mixture, 186 mmol) was dissolved in DMF (93 mL) in a 1 L 3-neck round-bottomed flask equipped with an overhead stirrer, temperature probe, and Ar inlet. POCl$_3$ (20.2 mL, 217 mmol) was added slowly via syringe at a rate to keep the internal temperature below 45° C. The dark red solution was then heated via heat block pre-heated to 65° C. After 4 h, the reaction mixture was allowed to cool to rt. The reaction was then transferred slowly via cannula to 1 L of vigorously stirred water. The rate of quench was controlled such that the internal temperature remained below 35° C. Brown solids formed upon quenching the reaction mixture. The resulting mixture was then basified to pH=8 via the slow addition of 50% wt aqueous KOH solution at a rate such that the internal temperature remained below 35° C. The solids were collected by vacuum filtration through a course fritted funnel to afford a solid. The solids were taken up into dichloromethane (500 mL, 10 v) and the resulting mixture was slurried with silica gel (50 g, 10 s). The slurry was filtered through a pad of silica gel (50 g, 10 s) on a course fritted funnel followed by washing with 3×10 mL dichloromethane. The filtrate was concentrated in vacuo to afford a solid that was recrystallized from hot hexanes (50 mL, 65° C.) to afford Intermediate C-4.

Preparation of Intermediate C5

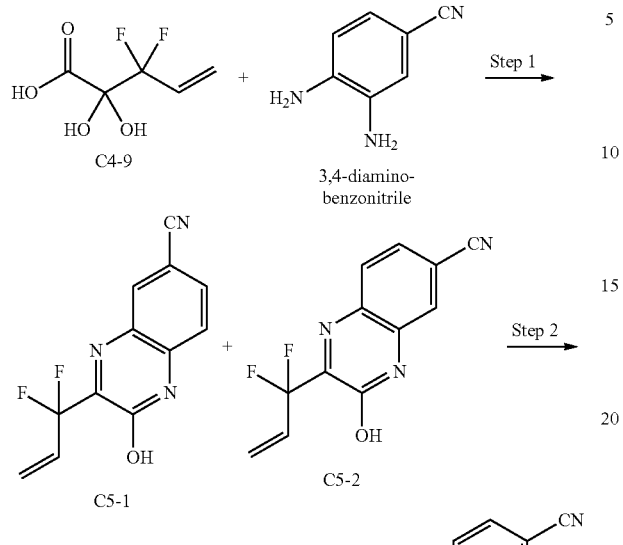

Step 1. Preparation of C5-1 and C5-2: A solution of C4-9 (0.5 g, 3.3 mmol) in EtOH (12 mL) was treated with 3,4-diaminobenzonitrile (0.47 g, 3.5 mmol). The reaction mixture was heated at 80° C. for 1 h, then concentrated in vacuo. The resulting residue was absorbed on silica gel, then purified by column chromatography to give C5-2 as the first eluting component. $^1$H-NMR (400 MHz, CD$_3$OD) δ 8.01 (d, 1H), 7.65 (dd, 2H), 6.49 (m, 1H), 5.80 (dt, 1H), 5.60 (d, 1H). C5-1 was recovered as the second eluting component. $^1$H-NMR (400 MHz, CD$_3$OD) δ 8.25 (d, 1H), 7.87 (dd, 1H), 7.41 (d, 1H), 6.49 (m, 1H), 5.80 (dt, 1H), 5.59 (d, 1H).

Step 2. Preparation of Intermediate C5: A solution of C5-2 (0.5 g, 2 mmol in 4.5 mL DMF was treated with POCl$_3$ (3 mL) and heated at 65° C. for 3 h. The reaction was diluted with EtOAc and quenched by pouring into ice water. The organic phase was washed subsequently with saturated aqueous NaHCO$_3$ and brine, dried over anhydrous Na$_2$SO$_4$ and concentrated in vacuo to give Intermediate C5.

Preparation of Intermediate C6

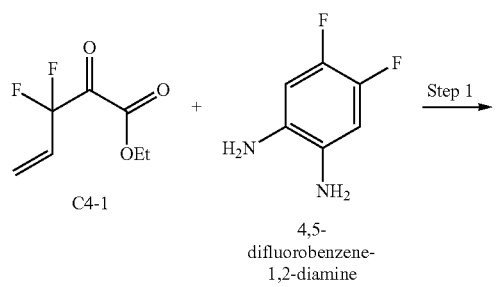

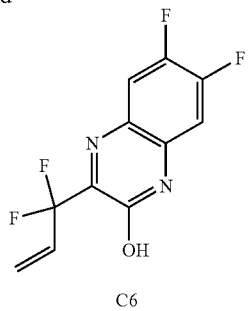

Step 1. Preparation of Intermediate C6: To a solution of C4-1 (2.1 g, 11.79 mmol) and 4,5-difluorobenzene-1,2-diamine (1.715 g, 11.9 mmol) in EtOH (50 mL) at rt was added triethylamine (3.0 mL, 21.5 mmol). The reaction mixture was refluxed for 2 h. Following concentration of the reaction mixture in vacuo, the residue was purified via silica gel chromatography to afford Intermediate C6. LCMS-ESI$^+$ (m/z): [M+H]$^+$ calcd for C$_{11}$H$_7$F$_4$N$_2$O: 259.0. found: 259.0.

Preparation of Intermediate C7

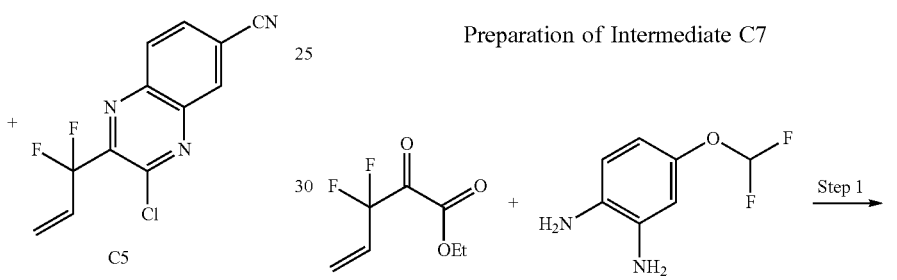

Step 1. Preparation of C7-1: To a solution of C4-1 (1.84 g, 10.93 mmol) and 4-(difluoromethoxy)benzene-1,2-diamine (1.90 g, 10.93 mmol, prepared according to Reference Example 30y of International Patent Publication No. WO 2003/035065, p. 511.) in DMF (40 mL) at rt was added DIPEA (9.5 mL, 54.65 mmol) and HATU (6.23 g, 16.4 mmol). The reaction mixture was stirred at room temperature for 24 h, diluted with ethyl acetate (100 mL), washed with water (100 mL) and brine (50 mL). The mixture was concentrated in vacuo. Purification via silica gel chromatography (EtOAc in hexanes: 20% to 60%) provided C7-1 as the later eluting fraction of two with the similar mass spectra. LCMS-ESI⁺ (m/z): [M+H]⁺ calcd for $C_{12}H_9F_4N_2O$: 289.2. found: 289.0.

Step 2: Preparation of Intermediate C7: Hydroxyquinoxaline C7-1 (800 mg, 2.8 mmol), POCl₃ (1.65 mL, 3.0 mmol) and DMF (10 mL) are combined at rt and then heated to 65° C. for 2.5 h at which time additional POCl₃ (0.2 mL, 0.36 mmol) was added. The reaction was heated an additional 3 h at 65° C. then cooled to rt. The reaction was quenched by addition of cold water (30 mL), and taken up into ethyl acetate (50 mL), washed with saturated aqueous Na₂CO₃ (100 mL) followed by brine (50 mL), and dried over anhydrous MgSO₄. The resulting solution was concentrated in vacuo to give Intermediate C7 which was used subsequently without further purification. LCMS-ESI⁺ (m/z): [M+H]⁺ calcd for $C_{12}H_8ClF_4N_2O$: 307.0. found: 307.0.

Preparation of Intermediate C8

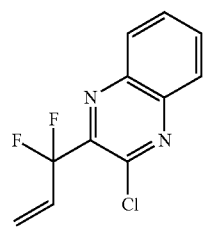

C8

Intermediate C8 was prepared in a similar fashion to Method A of preparing Intermediate C4, substituting 1,2-diaminobenzene for 4-methoxybenzene-1,2-diamine dihydrochloride in Step 2.

Preparation of Intermediate C9

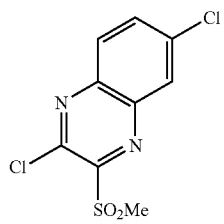

C9

Intermediate C9 was prepared according to Venkatesh, C., et al. *Org. Lett.* 2005, 7, 2169.

Preparation of Intermediate C10

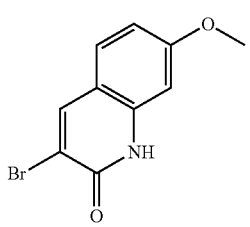

C10

Intermediate C10 was prepared according to the method described in Steps 1 and 2 of Intermediate C11 from U.S. Patent Publication No. 2010/0099695, p. 31.

Preparation of Intermediate C11

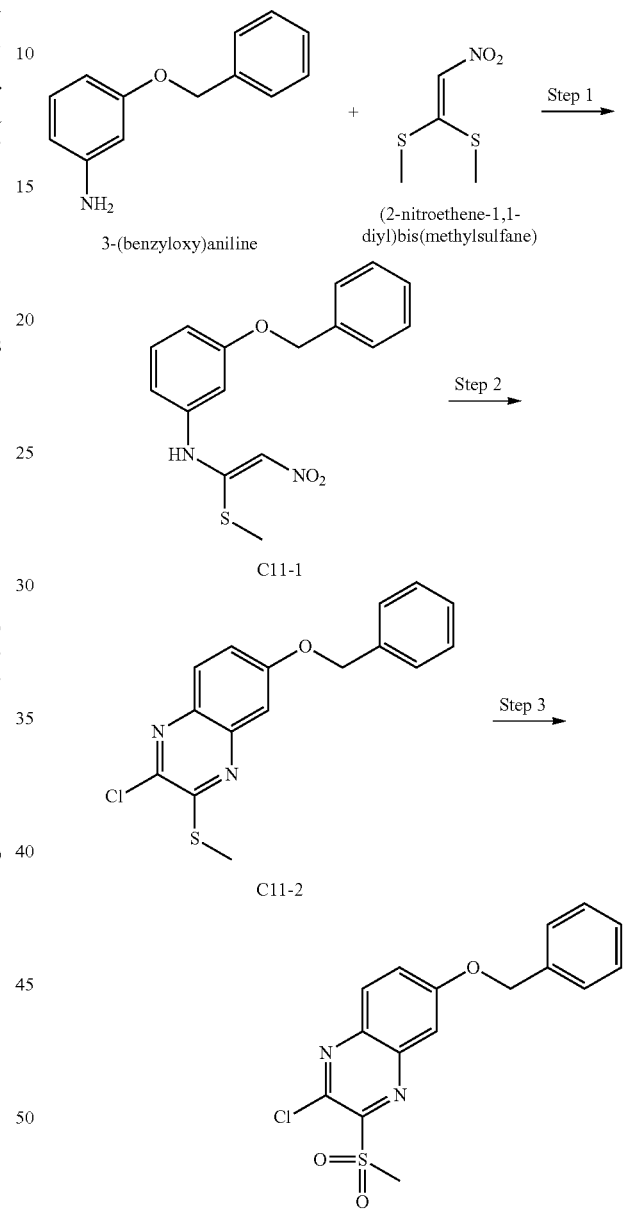

Step 1. Preparation of C11-1: In a round bottom flask, 3-(benzyloxy)aniline (4.025 g, 20.20 mmol) and 1,1-bis(methylthio)-2-nitroethylene (3.338 g, 20.20 mmol) in ethanol (40 mL) was refluxed for 24 h with constant stirring. The reaction mixture was then cooled in an ice bath and diluted with ether (150 mL). The mixture was filtered and washed with ether to afford C11-1 (3.32 g) as a yellow solid which was used directly in the following in step. LCMS-ESI⁺ (m/z): [M+H]⁺ calcd for $C_{16}H_{17}N_2O_3S$: 317.1. found: 317.1.

Step 2. Preparation of C11-2: To a suspension of C11-1 (3.32 g, 10.49 mmol) in 25 mL MeCN, POCl₃ (2.93 mL, 31.5 mmol) was added dropwise over 15 min with constant stirring. The reaction mixture was warmed to 80° C. and stirred for 5 h. The reaction was then cooled to ambient temperature and neutralized with ice cold saturated aqueous NaHCO$_3$ solution, extracted three times with CH$_2$Cl$_2$ (100 mL), washed with water, brine and dried over anhydrous Na$_2$SO$_4$. The solvent was removed under reduced pressure. The crude material was eluted through a plug of silica with CH$_2$Cl$_2$. The solvent was removed under reduced pressure and the solid was washed with MeCN to afford C11-2 (1.56 g) as an off white solid. LCMS-ESI$^+$ (m/z): [M+H]$^+$ calcd for C$_{16}$H$_{14}$ClN$_2$OS: 317.1. found: 317.3.

Step 3. Preparation of Intermediate C11. A solution of mCPBA (1.87 g, 10.83 mmol) in CH$_2$Cl$_2$ (40 mL) was added dropwise to a stirred solution of C11-2 (1.56 g, 4.92 mmol) in CH$_2$Cl$_2$ (40 mL) at 0° C. over a period of 30 min. The reaction mixture was further stirred at ambient temperature for 5 h. It was then poured into ice could saturated aqueous NaHCO$_3$ and partitioned with CH$_2$Cl$_2$. The organic layer was then washed subsequently with water, brine and dried over anhydrous Na$_2$SO$_4$. The solvent was removed under reduced pressure and the crude material was purified by normal phase chromatography with CH$_2$Cl$_2$ to provide the title compound Intermediate C11 as a pale yellow solid. LCMS-ESI$^+$ (m/z): [M+H]$^+$ calcd for C$_{16}$H$_{14}$ClN$_2$O$_3$S: 349.0. found: 349.0.

Preparation of Intermediate C12

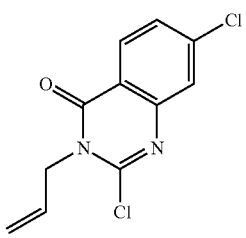

C12

2,7-dichloro-3-(prop-2-en-1-yl)quinazolin-4(3H)-one (Intermediate C12) was prepared according to Step 3 of Intermediate D5 of WO12040040 p 53-4.

Preparation of Intermediate C13

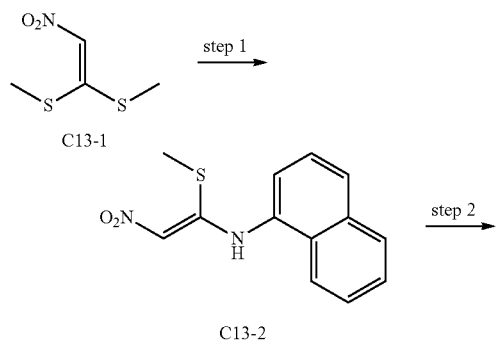

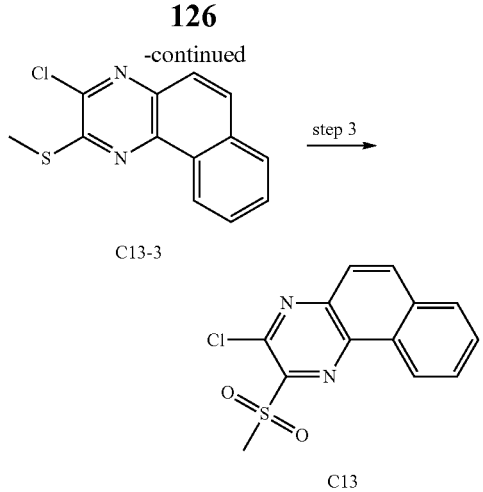

Step 1. Into a 1-L round-bottom flask purged and maintained with an inert atmosphere of nitrogen was placed naphthalen-1-amine (15 g, 104.76 mmol, 1.00 equiv), 1,1-bis(methylsulfanyl)-2-nitroethene C13-1 (17.3 g, 104.70 mmol, 1.00 equiv), and ethanol (520 mL). The resulting solution was stirred at 80° C. for 18 h. The solids were collected by filtration and washed with 1×100 mL of ether to afford 20 g (73%) of N—[(Z)-1-(methylsulfanyl)-2-nitroethenyl]naphthalen-1-amine C13-2 as a yellow solid.

(ES, m/z): 261 [M+H]$^+$

Step 2. Into a 250-mL 3-necked round-bottom flask purged and maintained with an inert atmosphere of nitrogen was placed N—[(Z)-1-(methylsulfanyl)-2-nitroethenyl]naphthalen-1-amine C13-2 (10 g, 38.42 mmol, 1.00 equiv), CH$_3$CN (92 mL), followed by the addition of phosphoroyl trichloride (10.8 mL, 3.00 equiv) dropwise with stirring at 0° C. The mixture was stirred at 0° C. for 15 min and at 80° C. for 4 h. The resulting mixture was concentrated under vacuum and the residue was diluted with 300 mL of DCM. The resulting mixture was washed with 2×200 mL of sodium bicarbonate (sat.) and 1×100 mL of brine, dried over anhydrous sodium sulfate and concentrated under vacuum. The residue was applied onto a silica gel column eluting with ethyl acetate:PE (1:20) to afford 5.5 g (27%) of 3-chloro-2-(methylsulfanyl)benzo[f]quinoxaline C13-3 as a yellow solid.

Step 3. Into a 1-L round-bottom flask purged and maintained with an inert atmosphere of nitrogen was placed a solution of 3-chloro-2-(methylsulfanyl)benzo[f]quinoxaline C13-3 (5.0 g, 19.18 mmol, 1.00 equiv) in dichloromethane (116 mL). To the mixture was added a solution of 3-chlorobenzene-1-carboperoxoic acid (16.6 g, 96.20 mmol, 5.00 equiv) in dichloromethane (263 mL) at 0° C. The mixture was stirred at 0° C. for 30 min and at room temperature for 3 h. The reaction was then quenched by the addition of 200 mL of water. The resulting mixture was washed with 2×300 mL of NaHCO$_3$ (10%), 2×200 mL of H$_2$O and 2×200 mL of brine, dried over anhydrous sodium sulfate and concentrated under vacuum. The residue was triturated with 30 mL of CH$_3$CN. The solids were collected by filtration to afford 5.0 g (89%) of 3-chloro-2-methanesulfonylbenzo[f]quinoxaline C13 as a yellow solid. (ES, m/z): 293 [M+H]$^+$ H-NMR: (CDCl$_3$, 300 MHz, ppm): 9.03-9.00 (m, 1H), 8.26 (d, J=2.7 Hz, 1H), 8.05-8.03 (m, 1H), 7.97 (d, J=9.3 Hz, 1H), 7.88-7.85 (m, 2H), 3.68 (s, 3H).

Intermediate Group D

Preparation of Intermediate D1

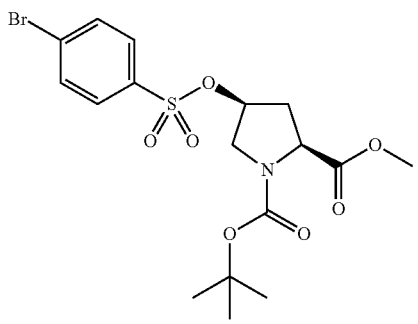

D1

Intermediate D1 was prepared according to the method described in Example 4A of International Patent Publication No. WO 2006/007700, p. 87.

PREPARATION OF EXAMPLES

Example 1

Preparation of (1aS,2aR,6S,9S,11R,23aR,23bS)-6-tert-butyl-N-[(1R,2R)-1-[(cyclopropylsulfonyl)carbamoyl]-2-(difluoromethyl)cyclopropyl]-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

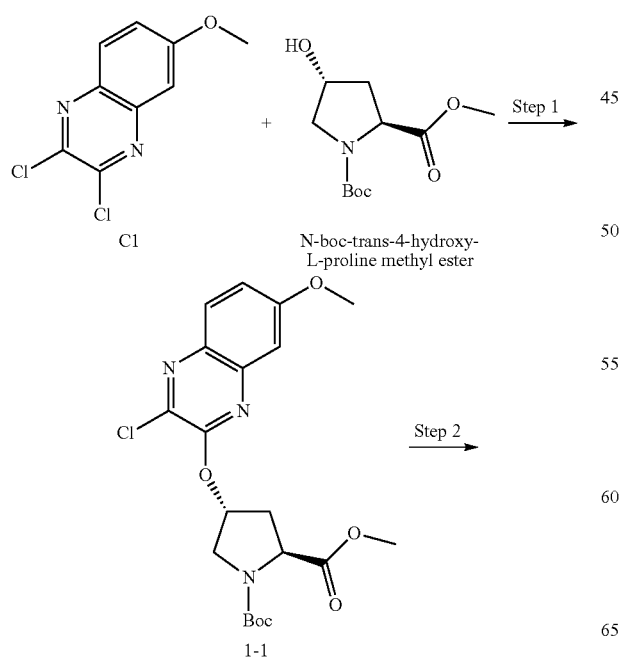

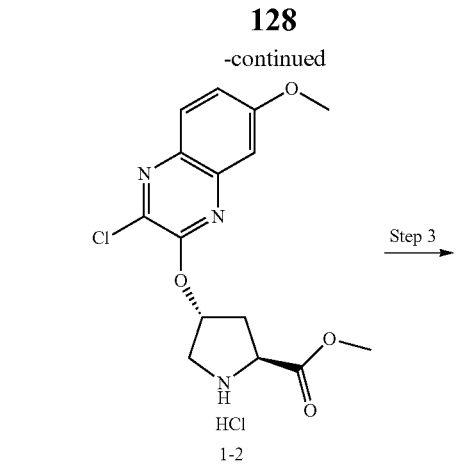

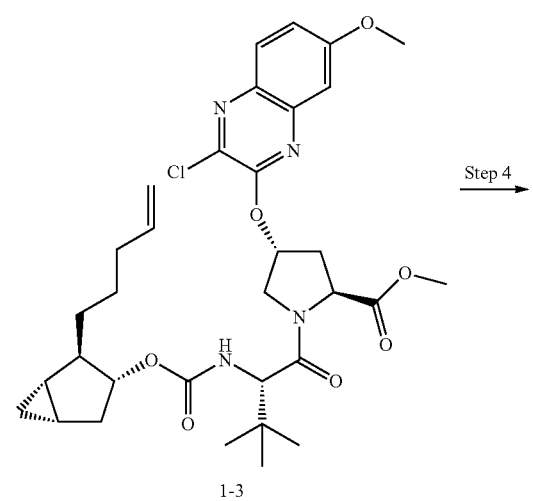

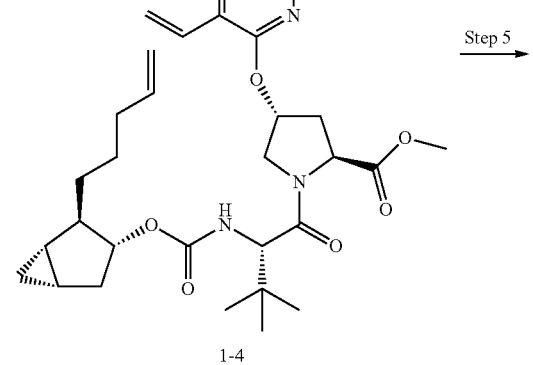

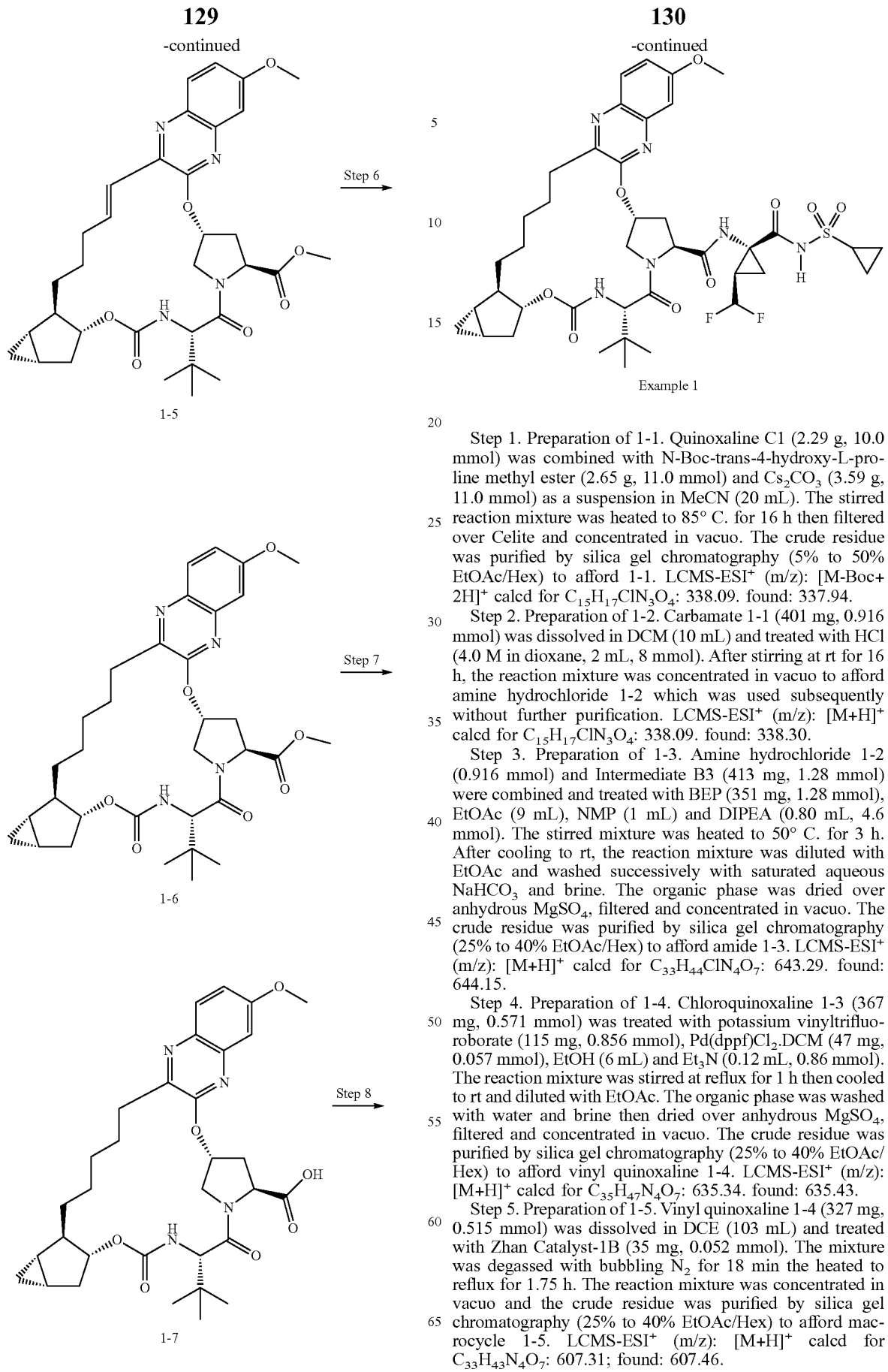

Step 1. Preparation of 1-1. Quinoxaline C1 (2.29 g, 10.0 mmol) was combined with N-Boc-trans-4-hydroxy-L-proline methyl ester (2.65 g, 11.0 mmol) and $Cs_2CO_3$ (3.59 g, 11.0 mmol) as a suspension in MeCN (20 mL). The stirred reaction mixture was heated to 85° C. for 16 h then filtered over Celite and concentrated in vacuo. The crude residue was purified by silica gel chromatography (5% to 50% EtOAc/Hex) to afford 1-1. LCMS-ESI$^+$ (m/z): [M-Boc+2H]$^+$ calcd for $C_{15}H_{17}ClN_3O_4$: 338.09. found: 337.94.

Step 2. Preparation of 1-2. Carbamate 1-1 (401 mg, 0.916 mmol) was dissolved in DCM (10 mL) and treated with HCl (4.0 M in dioxane, 2 mL, 8 mmol). After stirring at rt for 16 h, the reaction mixture was concentrated in vacuo to afford amine hydrochloride 1-2 which was used subsequently without further purification. LCMS-ESI$^+$ (m/z): [M+H]$^+$ calcd for $C_{15}H_{17}ClN_3O_4$: 338.09. found: 338.30.

Step 3. Preparation of 1-3. Amine hydrochloride 1-2 (0.916 mmol) and Intermediate B3 (413 mg, 1.28 mmol) were combined and treated with BEP (351 mg, 1.28 mmol), EtOAc (9 mL), NMP (1 mL) and DIPEA (0.80 mL, 4.6 mmol). The stirred mixture was heated to 50° C. for 3 h. After cooling to rt, the reaction mixture was diluted with EtOAc and washed successively with saturated aqueous $NaHCO_3$ and brine. The organic phase was dried over anhydrous $MgSO_4$, filtered and concentrated in vacuo. The crude residue was purified by silica gel chromatography (25% to 40% EtOAc/Hex) to afford amide 1-3. LCMS-ESI$^+$ (m/z): [M+H]$^+$ calcd for $C_{33}H_{44}ClN_4O_7$: 643.29. found: 644.15.

Step 4. Preparation of 1-4. Chloroquinoxaline 1-3 (367 mg, 0.571 mmol) was treated with potassium vinyltrifluoroborate (115 mg, 0.856 mmol), Pd(dppf)$Cl_2$.DCM (47 mg, 0.057 mmol), EtOH (6 mL) and $Et_3N$ (0.12 mL, 0.86 mmol). The reaction mixture was stirred at reflux for 1 h then cooled to rt and diluted with EtOAc. The organic phase was washed with water and brine then dried over anhydrous $MgSO_4$, filtered and concentrated in vacuo. The crude residue was purified by silica gel chromatography (25% to 40% EtOAc/Hex) to afford vinyl quinoxaline 1-4. LCMS-ESI$^+$ (m/z): [M+H]$^+$ calcd for $C_{35}H_{47}N_4O_7$: 635.34. found: 635.43.

Step 5. Preparation of 1-5. Vinyl quinoxaline 1-4 (327 mg, 0.515 mmol) was dissolved in DCE (103 mL) and treated with Zhan Catalyst-1B (35 mg, 0.052 mmol). The mixture was degassed with bubbling $N_2$ for 18 min the heated to reflux for 1.75 h. The reaction mixture was concentrated in vacuo and the crude residue was purified by silica gel chromatography (25% to 40% EtOAc/Hex) to afford macrocycle 1-5. LCMS-ESI$^+$ (m/z): [M+H]$^+$ calcd for $C_{33}H_{43}N_4O_7$: 607.31; found: 607.46.

Step 6. Preparation of 1-6. Macrocycle 1-5 (236 mg, 0.389 mmol) was dissolved in EtOH (20 mL) and EtOAc (5 mL). 10% Pd/C (56 mg) was added and $H_2$ was bubbled through the suspension for 4 min. The stirred reaction mixture was kept under 1 atm of $H_2$ for 50 min before being filtered over Celite and concentrated in vacuo to afford 1-6 which was carried on without further purification. LCMS-ESI$^+$ (m/z): [M+H]$^+$ calcd for $C_{33}H_{45}N_4O_7$: 609.33. found: 609.34.

Step 7. Preparation of 1-7. Compound 1-6 (ca. 0.389 mmol) was treated with THF (10 mL) and LiOH (1.0 M in $H_2O$, 10 mL, 10 mmol). The mixture was stirred for 15 h then poured into a separatory funnel containing 40 mL 10% aqueous HCl. The aqueous layer was extracted with DCM. The combined organics were dried over anhydrous $MgSO_4$, filtered and concentrated in vacuo to afford carboxylic acid 1-7 which was carried on without further purification. LCMS-ESI$^+$ (m/z): [M+H]$^+$ calcd for $C_{32}H_{43}N_4O_7$: 595.31. found: 595.38.

Step 8. Preparation of Example 1. Carboxylic acid 1-7 (95 mg, 0.160 mmol) was treated with Intermediate A9 (60 mg, 0.21 mmol), TBTU (62 mg, 0.19 mmol), DMAP (23 mg, 0.19 mmol), DCM (2 mL) and DIPEA (0.14 mL, 0.80 mmol). The reaction mixture was stirred for 1 h, then more Intermediate A9 (35 mg, 0.12 mmol), TBTU (20 mg, 0.062 mmol) and DIPEA (0.14 mL, 0.80 mmol) were added. After an additional 34 min at rt, the reaction mixture was concentrated in vacuo. The crude residue was purified by HPLC to afford Example 1 as a TFA salt. Analytical HPLC RetTime: 8.89 min. LCMS-ESI$^+$ (m/z): [M+H]$^+$ calcd for $C_{40}H_{53}F_2N_6O_9S$: 831.36. found: 831.58. $^1$H-NMR (400 MHz, CD$_3$OD) δ 9.36 (s, 1H), 7.79 (dd, J=7.7, 1.9 Hz, 1H), 7.27-7.18 (m, 2H), 6.09 (t, J=3.5 Hz, 1H), 5.90 (td, J=55.9, 6.7 Hz, 1H), 5.00 (d, J=7.5 Hz, 1H), 4.53-4.37 (m, 2H), 4.33 (s, 1H), 4.12 (dd, J=11.8, 3.8 Hz, 1H), 3.93 (s, 3H), 3.05-2.89 (m, 2H), 2.84-2.70 (m, 1H), 2.49 (dd, J=13.8, 6.2 Hz, 1H), 2.31-2.13 (m, 2H), 2.09-1.91 (m, 3H), 1.79 (dd, J=28.6, 9.7 Hz, 2H), 1.68-1.46 (m, 5H), 1.46-1.19 (m, 7H), 1.17-1.09 (m, 2H), 1.09-1.02 (m, 11H), 0.63-0.45 (m, 2H).

Example 2

Preparation of (1aS,2aR,6S,9S,11R,23aR,23bS)-6-tert-butyl-N-[(1R,2R)-2-(difluoromethyl)-1-{[(1-methylcyclopropyl)sulfonyl]carbamoyl}cyclopropyl]-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2'18,19][1,10,3,6]dioxadiazacyclononadecino[11,12-b]quinoxaline-9-carboxamide

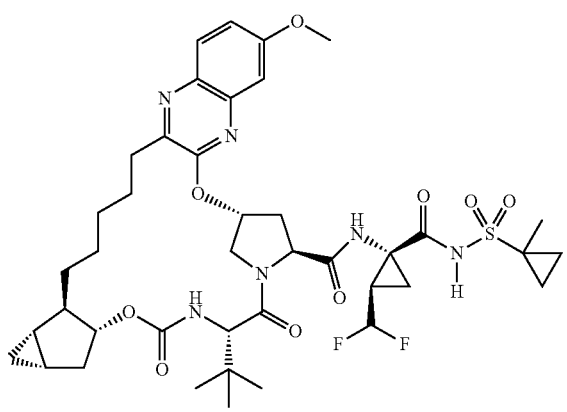

Example 2

Example 2 was prepared in a similar fashion to Example 1, substituting Intermediate A10 for Intermediate A9 in Step 8. Example 2 (107 mg) was isolated as a TFA salt. Analytical HPLC RetTime: 8.85 min. LCMS-ESI$^+$ (m/z): [M+H]$^+$ calcd for $C_{41}H_{55}F_2N_6O_9S$: 845.37. found: 845.67. $^1$H-NMR (400 MHz, CD$_3$OD) δ 9.31 (s, 1H), 7.78 (d, J=8.8 Hz, 1H), 7.20 (dt, J=3.9, 2.6 Hz, 2H), 6.06 (t, J=3.5 Hz, 1H), 5.87 (td, J=55.8, 6.7 Hz, 1H), 5.00 (d, J=7.5 Hz, 1H), 4.51-4.38 (m, 2H), 4.34 (s, 1H), 4.11 (dd, J=11.8, 3.8 Hz, 1H), 3.92 (s, 3H), 3.04-2.85 (m, 1H), 2.85-2.67 (m, 1H), 2.49 (dd, J=13.9, 6.4 Hz, 1H), 2.24 (ddd, J=20.1, 12.0, 6.2 Hz, 2H), 2.08-1.90 (m, 3H), 1.90-1.66 (m, 2H), 1.66-1.46 (m, 10H), 1.46-1.20 (m, 6H), 1.05 (s, 9H), 0.98-0.82 (m, 3H), 0.58 (q, J=4.1 Hz, 1H), 0.55-0.45 (m, 1H).

Example 3

Preparation of (1aS,2aR,6S,9S,11R,23aR,23bS)-6-tert-butyl-N-[(1R,2S)-1-[(cyclopropylsulfonyl)carbamoyl]-2-(2,2-difluoroethyl)cyclopropyl]-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

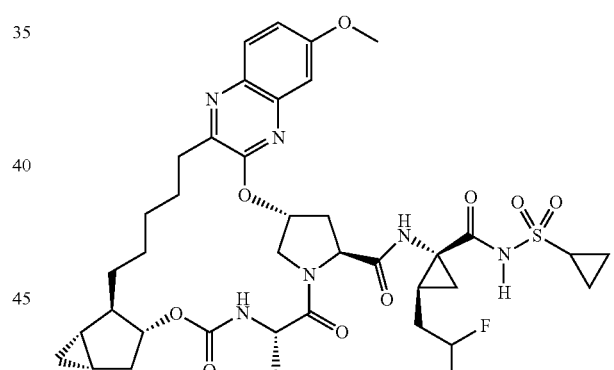

Example 3

Example 3 was prepared in a similar fashion to Example 1, substituting Intermediate A7 for Intermediate A9 in Step 8. Example 3 (52 mg) was isolated as a TFA salt. Analytical HPLC RetTime: 8.82 min. LCMS-ESI$^+$ (m/z): [M+H]$^+$ calcd for $C_{41}H_{55}F_2N_6O_9S$: 845.37. found: 845.96. $^1$H-NMR (400 MHz, CD$_3$OD) δ 9.18 (s, 1H), 7.78 (dd, J=8.1, 1.5 Hz, 1H), 7.26-7.16 (m, 2H), 6.07 (t, J=3.6 Hz, 1H), 5.89 (tt, J=56.5, 4.1 Hz, 1H), 4.99 (d, J=7.5 Hz, 1H), 4.45 (dd, J=11.1, 5.9 Hz, 2H), 4.32 (s, 1H), 4.11 (dd, J=11.9, 3.8 Hz, 1H), 3.92 (s, 3H), 3.04-2.86 (m, 2H), 2.86-2.68 (m, 1H), 2.47 (dd, J=13.8, 6.3 Hz, 1H), 2.34-2.07 (m, 4H), 1.95 (dd, J=11.0, 4.4 Hz, 1H), 1.79 (dd, J=27.1, 9.7 Hz, 3H), 1.71-1.47 (m, 6H), 1.47-1.18 (m, 8H), 1.18-0.92 (m, 12H), 0.64-0.43 (m, 2H).

Example 4

Preparation of (1R,4S,4aR,8S,11S,13R,25aR)-8-tert-butyl-N-[(1R,2R)-1-[(cyclopropylsulfonyl)carbamoyl]-2-(difluoromethyl)cyclopropyl]-17-methoxy-6,9-dioxo-2,3,4,4a,6,7,8,9,12,13,21,22,23,24,25,25a-hexadecahydro-1H,11H-1, 4:10,13-dimethanoquinoxalino[2,3-k][1,10,3,6]benzodioxadiazacyclononadecine-11-carboxamide

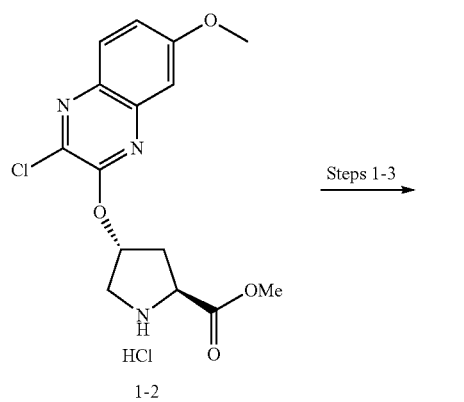

1-2

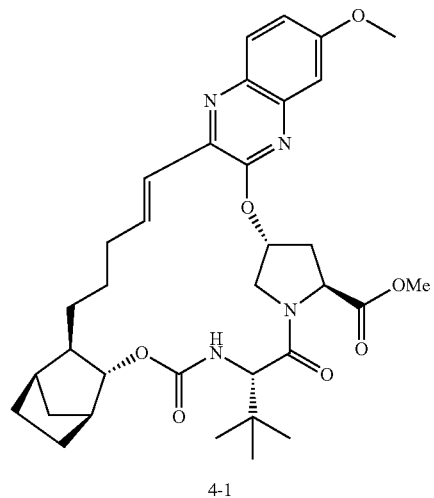

4-1 and

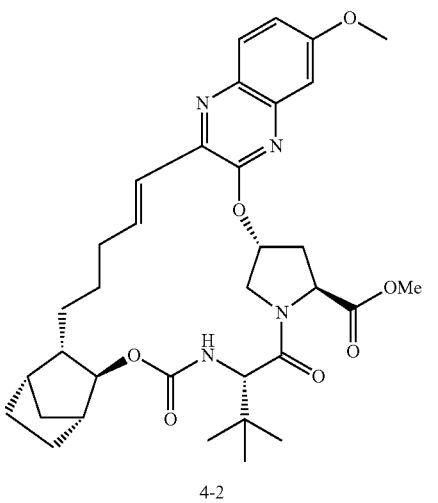

4-2

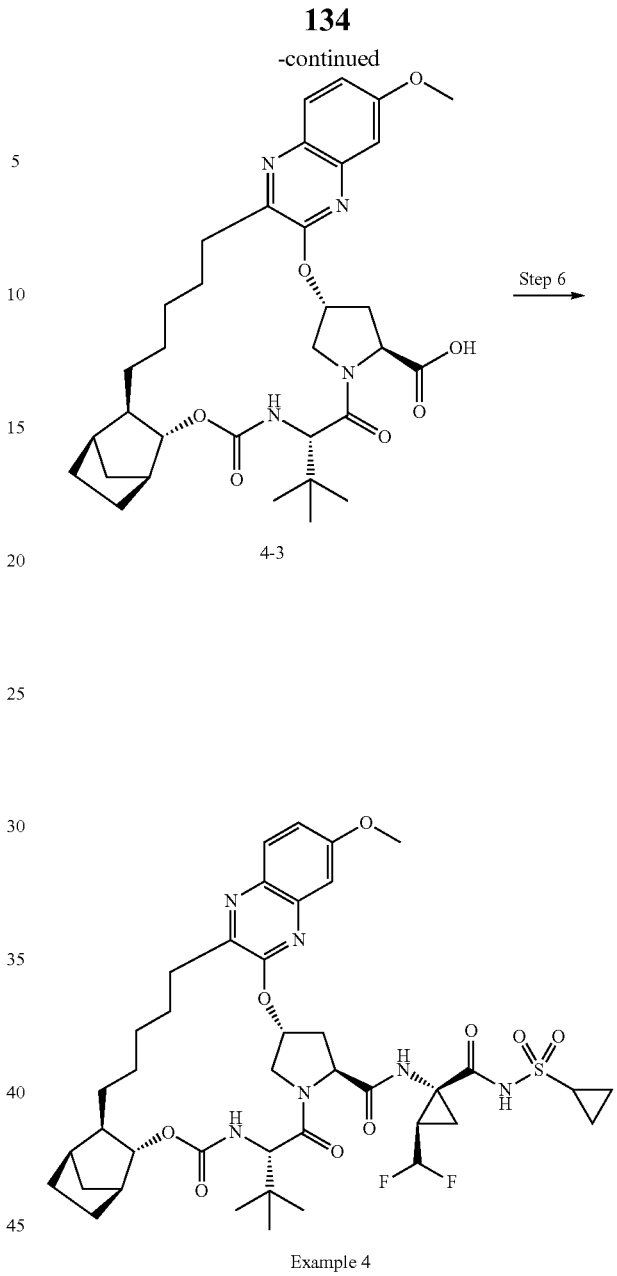

4-3

Example 4

Step 1-3. Preparation of 4-1 and 4-2: Proline hydrochloride 1-2 (1.3 mmol) was dissolved along with 1:1 Intermediate mixture B1 and B2 (1.29 mmol) and DIPEA (1.0 mL, 5.7 mmol) in DMF (6.5 mL). HATU (597 mg, 1.57 mmol) was added in one portion. The reaction was stirred 80 min at rt and was diluted with saturated aqueous NaHCO$_3$ (30 mL) and EtOAc (50 mL). The phases were separated and the organic phase was washed with water (30 mL) and brine (30 mL). The organic phase was dried over anhydrous Na$_2$SO$_4$, filtered and concentrated in vacuo to a crude residue that was purified by silica gel chromatography to provide a residue (732 mg; LCMS-ESI$^+$ (m/z): [M+H]$^+$ calcd for C$_{34}$H$_{46}$ClN$_4$O$_7$: 657.3. found: 657.0). A stirred mixture of this residue, PdCl$_2$(dppf).CH$_2$Cl$_2$ (68 mg, 0.083 mmol) and potassium vinyltrifluoroborate (304 mg, 2.27 mmol) in EtOH (10 mL) was sparged with Ar for several minutes. Triethylamine (330 μL, 2.35 mmol) was added and the mixture was heated to 75° C. for 60 min. The reaction mixture was cooled to ambient temperature, diluted with EtOAc, and washed with water and brine. The organics were dried over anhydrous Na$_2$SO$_4$, filtered and concentrated in vacuo to afford a crude residue that was purified by silica gel chromatography (20% to 30% EtOAc in hexanes) to afford a yellow oil (676 mg; LCMS-ESI$^+$ (m/z): [M+H]$^+$ calcd for C$_{36}$H$_{49}$N$_4$O$_7$: 649.4. found: 649.1). This residue (626 mg, 0.965 mmol) was dissolved in DCE (250 mL) and the solution was sparged with Ar for 15 min. Zhan 1B catalyst (75 mg, 0.050 mmol) was added as a solution in DCE (10 mL) and the resulting solution stirred at 85° C. under Ar for 1.5 h. The reaction mixture was then concentrated in vacuo and the resulting residue purified by silica gel chromatography (20% to 40% EtOAc in hexanes) to afford intermediate 4-1 (LCMS-ESI$^+$ (m/z): [M+H]$^+$ calcd for C$_{34}$H$_{45}$N$_4$O$_7$: 621.3. found: 621.1) and 4-2 (LCMS-ESI$^+$ (m/z): [M+H]$^+$ calcd for C$_{34}$H$_{45}$N$_4$O$_7$: 621.3. found: 621.1).

Steps 4 and 5: Preparation of 4-3: To a solution of 4-1 (205 mg, 0.330 mmol) in 1:1 EtOAc:EtOH (5 mL) was added Pd/C (10 wt % Pd, 68 mg). The reaction vessel was purged twice with H$_2$ and was stirred at rt under 1 atm H$_2$ for 3 h. The reaction mixture was filtered through a pad of Celite with EtOAc and concentrated in vacuo to afford a crude residue (188 mg, LCMS-ESI$^+$ (m/z): [M+H]$^+$ calcd for C$_{34}$H$_{47}$N$_4$O$_7$: 623.3. found: 623.2). This residue was dissolved in THF (4.3 mL) and H$_2$O (1.7 mL). LiOH.H$_2$O (79 mg, 1.9 mmol) was added and the mixture was stirred at rt for 14.5 h. The reaction was quenched with 1 M aqueous HCl (2 mL) and was diluted with EtOAc (30 mL) and 1 M aqueous HCl (20 mL). The phases were separated, and the aqueous phase was extracted with EtOAc (30 mL). The combined organic phase was dried over anhydrous Na$_2$SO$_4$, filtered and concentrated in vacuo to afford 4-1 that was used directly in the following step without further purification. LCMS-ESI$^-$ (m/z): [M−H]$^-$ calcd for C$_{33}$H$_{43}$N$_4$O$_7$: 607.3. found: 607.0.

Step 6: Preparation of Example 4: To a suspension of acid 4-3 (66.5 mg, 0.109 mmol) and Intermediate A9 (35 mg, 0.12 mmol) in MeCN (1.6 mL) was added DIPEA (80 µL, 0.46 mmol). To the resulting solution was added HATU (52 mg, 0.137 mmol). The reaction was stirred at rt for 60 min and was diluted with EtOAc (15 mL), 1 M aqueous HCl (10 mL) and brine (5 mL). The phases were separated and the aqueous phase was extracted with EtOAc (20 mL). The combined organic phase was dried over anhydrous Na$_2$SO$_4$, filtered, and concentrated in vacuo to afford a crude residue. Purification by silica gel chromatography (15% to 30% acetone in hexanes) provided an amorphous residue that was lyophilized from water and MeCN to provide Example 4. Analytical HPLC RetTime: 8.95 min. LCMS-ESI$^+$ (m/z): [M+H]$^+$ calcd for C$_{41}$H$_{55}$F$_2$N$_6$O$_9$S: 845.4. found: 845.2. $^1$H-NMR (300 MHz, CDCl$_3$) δ 10.28 (s, 1H), 7.82 (d, J=9.1 Hz, 1H), 7.19 (dd, J=9.1, 2.8 Hz, 1H), 7.11 (d, J=2.3 Hz, 2H), 6.19-5.72 (m, 2H), 5.37 (d, J=10.1 Hz, 1H), 4.48 (d, J=10.1 Hz, 1H), 4.42-4.24 (m, 3H), 4.05 (dd, J=11.6, 3.7 Hz, 1H), 3.92 (s, 3H), 2.96-2.81 (m, 2H), 2.73-2.59 (m, 2H), 2.43-2.30 (m, 1H), 2.20-2.04 (m, 3H), 1.96-1.70 (m, 3H), 1.70-0.96 (m, 27H).

Example 5

Preparation of (1R,4S,4aR,8S,11S,13R,25aR)-8-tert-butyl-N-[(1R,2R)-2-(difluoromethyl)-1-{[(1-methyl-cyclopropyl)sulfonyl]carbamoyl}cyclopropyl]-17-methoxy-6,9-dioxo-2,3,4,4a,6,7,8,9,12,13,21,22,23,24,25,25a-hexadecahydro-1H,11H-1, 4:10,13-dimethanoquinoxalino[2,3-k][1,10,3,6]benzodioxadiazacyclononadecine-11-carboxamide

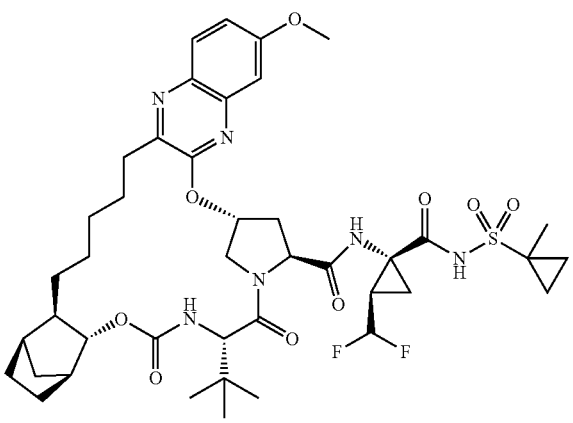

Example 5

Example 5 (59.3 mg) was prepared in a similar fashion to Example 4, substituting Intermediate A10 for Intermediate A9 in Step 6. Analytical HPLC RetTime: 8.86 min. LCMS-ESI$^+$ (m/z): [M+H]$^+$ calcd for C$_{42}$H$_{57}$F$_2$N$_6$O$_9$S: 859.4; found: 859.3. $^1$H-NMR (400 MHz, CDCl$_3$) δ 9.85 (s, 1H), 7.83 (d, J=9.1 Hz, 1H), 7.29 (s, 1H), 7.19 (dd, J=9.1, 2.7 Hz, 1H), 7.12 (d, J=2.7 Hz, 1H), 6.17-5.67 (m, 2H), 5.40 (d, J=10.1 Hz, 1H), 4.53-4.26 (m, 4H), 4.04 (dd, J=12.1, 4.5 Hz, 1H), 3.93 (s, 3H), 2.95-2.83 (m, 1H), 2.74-2.60 (m, 2H), 2.46-2.32 (m, 1H), 2.20-2.09 (m, J=9.0 Hz, 2H), 2.00-1.17 (m, 22H), 1.06 (s, 9H), 0.92-0.77 (m, 3H).

Example 6

Preparation of (1S,4R,4aS,8S,11S,13R,25aS)-8-tert-butyl-N-[(1R,2R)-1-[(cyclopropylsulfonyl)carbamoyl]-2-(difluoromethyl)cyclopropyl]-17-methoxy-6,9-dioxo-2,3,4,4a,6,7,8,9,12,13,21,22,23,24,25,25a-hexadecahydro-1H,11H-1, 4:10,13-dimethanoquinoxalino[2,3-k][1,10,3,6]benzodioxadiazacyclononadecine-11-carboxamide

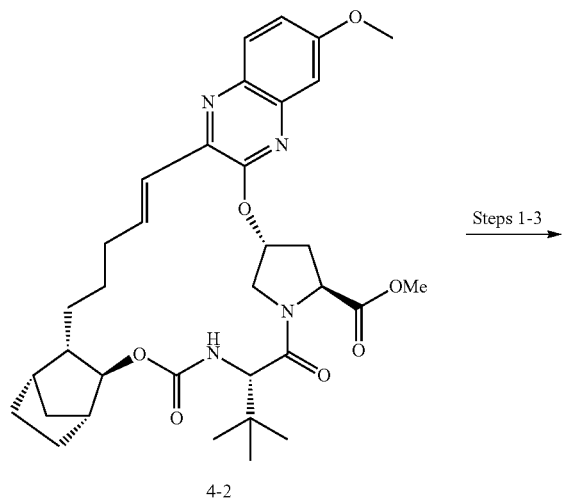

4-2

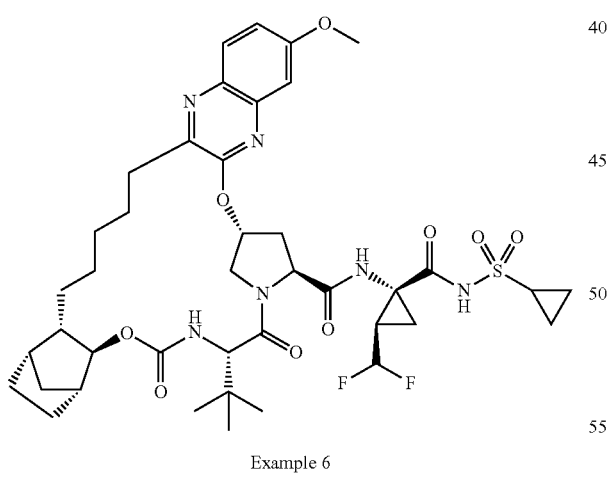

Example 6

Steps 1-3: Preparation of Example 6: To a solution of 4-2 (160 mg, 0.26 mmol) in 1:1 EtOAc:EtOH (4 mL) was added Pd/C (10 wt % Pd, 55 mg). The reaction vessel was purged twice with $H_2$ and was stirred at rt under 1 atm $H_2$ for 5.5 h. The reaction mixture was filtered through a pad of Celite with EtOAc and concentrated in vacuo to afford a crude residue (155 mg, LCMS-ESI$^+$ (m/z): [M+H]$^+$ calcd for $C_{34}H_{47}N_4O_7$: 623.3. found: 623.2). This residue was then dissolved in THF (4.3 mL) and $H_2O$ (1.7 mL). LiOH·$H_2O$ (64 mg, 1.5 mmol) was added and the mixture was stirred at rt for 14.5 h. The reaction was quenched with 1 M aqueous HCl (2 mL) and was diluted with EtOAc (30 mL) and 1 M aqueous HCl (20 mL). The phases were separated, and the aqueous phase was extracted with EtOAc (30 mL). The combined organic phase was dried over anhydrous $Na_2SO_4$, filtered and concentrated in vacuo to afford a residue (139 mg; LCMS-ESI$^+$ (m/z): [M+H]$^+$ calcd for $C_{33}H_{45}N_4O_7$: 609.3. found: 608.9) that was used directly in the following step without further purification. To a suspension of the product from the previous step (54 mg, 0.089 mmol) and Intermediate A9 (28.4 mg, 0.098 mmol) in MeCN (1.5 mL) was added DIPEA (70 µL, 0.40 mmol). To the resulting solution was added HATU (43.5 mg, 0.114 mmol). The reaction was stirred at rt for 120 min and was diluted with EtOAc (15 mL), 1 M aqueous HCl (10 mL), water (10 mL), and brine (5 mL). The phases were separated and the aqueous phase was extracted with EtOAc (20 mL). The combined organic phase was dried over anhydrous $Na_2SO_4$, filtered, and concentrated in vacuo to afford a crude residue. Purification by silica gel chromatography (17% to 40% acetone in hexanes) provided an amorphous residue that was lyophilized from water and MeCN to provide Example 6. Analytical HPLC RetTime: 8.85 min. LCMS-ESI$^+$ (m/z): [M+H]$^+$ calcd for $C_{41}H_{55}F_2N_6O_9S$: 845.4. found: 845.2. $^1$H-NMR (300 MHz, CDCl$_3$) δ 9.80 (s, 1H), 9.05 (s, 1H), 7.88-7.78 (m, 1H), 7.24-7.17 (m, 2H), 6.95 (d, J=9.9 Hz, 1H), 6.08-5.96 (m, 1H), 5.95-5.50 (m, 1H), 4.66 (dd, J=8.3, 3.8 Hz, 1H), 4.41-4.30 (m, 2H), 4.00 (s, 1H), 3.95 (s, 3H), 3.81 (dd, J=10.5, 4.1 Hz, 1H), 3.12-2.86 (m, 2H), 2.79 (t, J=6.1 Hz, 2H), 2.57-2.41 (m, 1H), 2.31 (d, J=4.5 Hz, 1H), 2.13-1.91 (m, 3H), 1.87-0.96 (m, 28H), 0.93-0.81 (m, 1H).

Example 7

Preparation of (1aR,1bS,5S,8S,10R,22aR,23aR)-5-tert-butyl-N-[(1R,2R)-1-[(cyclopropylsulfonyl)carbamoyl]-2-(difluoromethyl)cyclopropyl]-14-methoxy-3,6-dioxo-1a,1b,3,4,5,6,9,10,18,19,20,21,22,22a,23,23a-hexadecahydro-1H,8H-7,10-methanocyclopropa[3',40]cyclopenta[1',2':18,19][1,10,3,6]dioxadiazacyclononadecino[11,12-b]quinoxaline-8-carboxamide 1-2

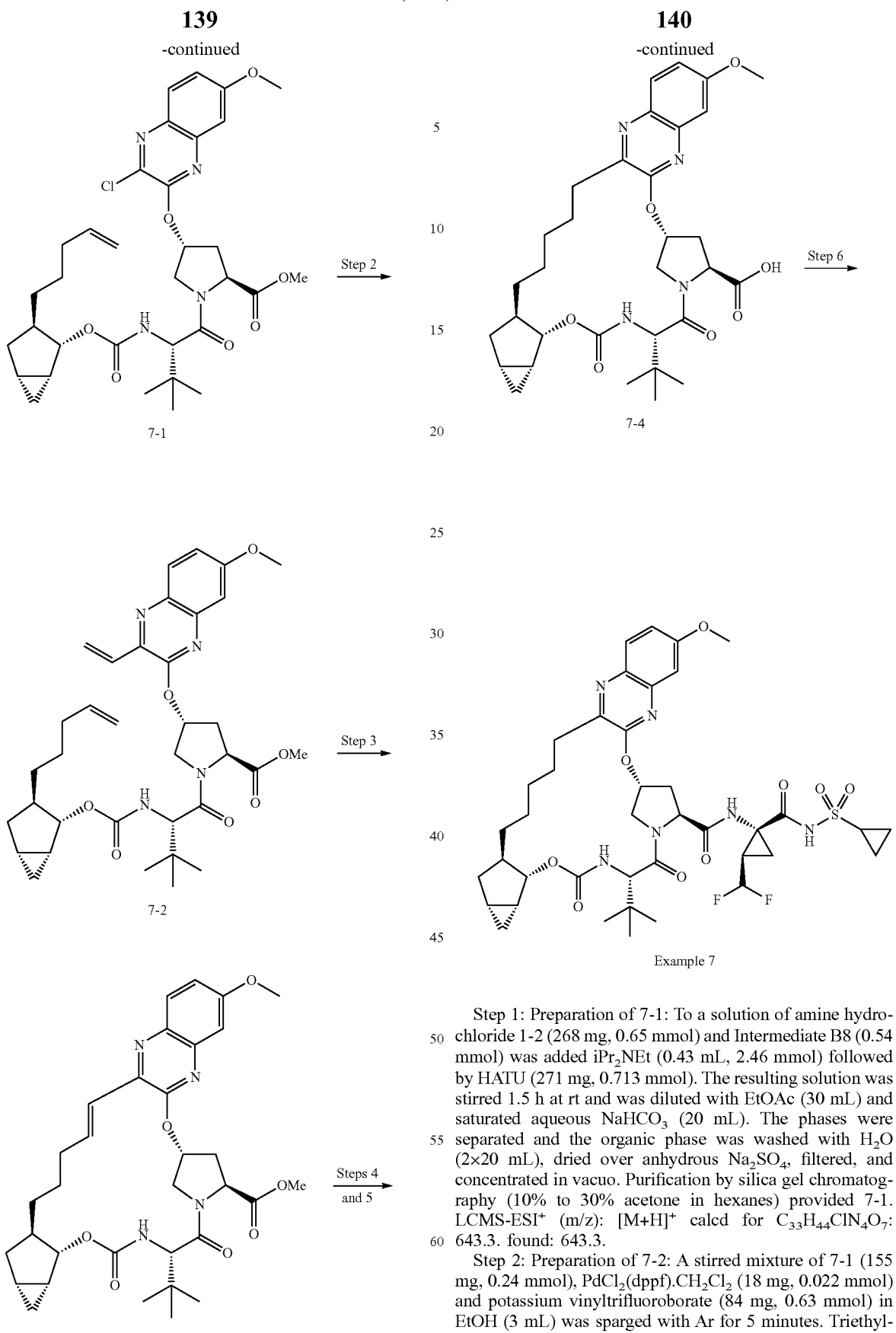

Example 7

Step 1: Preparation of 7-1: To a solution of amine hydrochloride 1-2 (268 mg, 0.65 mmol) and Intermediate B8 (0.54 mmol) was added iPr$_2$NEt (0.43 mL, 2.46 mmol) followed by HATU (271 mg, 0.713 mmol). The resulting solution was stirred 1.5 h at rt and was diluted with EtOAc (30 mL) and saturated aqueous NaHCO$_3$ (20 mL). The phases were separated and the organic phase was washed with H$_2$O (2×20 mL), dried over anhydrous Na$_2$SO$_4$, filtered, and concentrated in vacuo. Purification by silica gel chromatography (10% to 30% acetone in hexanes) provided 7-1. LCMS-ESI$^+$ (m/z): [M+H]$^+$ calcd for C$_{33}$H$_{44}$ClN$_4$O$_7$: 643.3. found: 643.3.

Step 2: Preparation of 7-2: A stirred mixture of 7-1 (155 mg, 0.24 mmol), PdCl$_2$(dppf).CH$_2$Cl$_2$ (18 mg, 0.022 mmol) and potassium vinyltrifluoroborate (84 mg, 0.63 mmol) in EtOH (3 mL) was sparged with Ar for 5 minutes. Triethylamine (90 µL, 0.64 mmol) was added and the mixture was stirred at 70° C. for 65 min. The reaction mixture was cooled to ambient temperature, diluted with EtOAc (30 mL), and

141 washed with water (30 mL). The organic phase was dried over anhydrous Na₂SO₄, filtered and concentrated in vacuo to afford a crude residue that was purified by silica gel chromatography (20% to 40% EtOAc in hexanes) to afford 7-2. LCMS-ESI⁺ (m/z): [M+H]⁺ calcd for $C_{35}H_{47}N_4O_7$: 635.3. found: 635.2.

Step 3: Preparation of 7-3: Vinyl quinoxaline 7-2 (119 mg, 0.187 mmol) was dissolved in DCE (60 mL) and the solution was sparged with Ar for 10 min. Zhan 1B catalyst (16 mg, 0.022 mmol) was added as a solution in DCE (1 mL) and the resulting solution was stirred at 85° C. under Ar for 45 min. The reaction mixture was then concentrated in vacuo and was purified by silica gel chromatography (20% to 40% EtOAc in hexanes) to afford 7-3. LCMS-ESI⁺ (m/z): [M+H]⁺ calcd for $C_{33}H_{43}N_4O_7$: 607.3. found: 607.3.

Steps 4 and 5: Preparation of 7-4: To a solution of 7-3 (74 mg, 0.12 mmol) in 1:1 EtOAc:EtOH (3 mL) was added Pd/C (10 wt % Pd, 45 mg). The reaction vessel was purged twice with H₂ and was stirred at rt under 1 atm H₂ for 2 h. The reaction mixture was filtered through a pad of Celite with EtOAc and concentrated in vacuo to afford a crude residue used directly in the following step. (LCMS-ESI⁺ (m/z): [M+H]⁺ calcd for $C_{33}H_{45}N_4O_7$: 609.3. found: 608.9). This residue was dissolved in THF (1.5 mL), H₂O (0.75 mL) and MeOH (0.75 mL). LiOH.H₂O (52 mg, 1.2 mmol) was added and the mixture was stirred at 45° C. for 70 min. The reaction was then quenched with 1 M aqueous HCl (1.1 mL) and was diluted with CH₂Cl₂ (20 mL) and 0.3 M aqueous HCl (20 mL). The phases were separated, and the aqueous phase was extracted with CH₂Cl₂ (30 mL). The combined organic phase was dried over anhydrous MgSO₄, filtered and concentrated in vacuo to afford 7-4. LCMS-ESI⁺ (m/z): [M+H]⁺ calcd for $C_{32}H_{43}N_4O_7$: 595.3. found: 595.2.

Step 6: Preparation of Example 7: To a suspension of acid 7-4 (36.6 mg, 0.0615 mmol) and Intermediate A9 (25 mg, 0.086 mmol) in MeCN (1.5 mL) was added DIPEA (56 µL, 0.32 mmol). To the resulting solution was added HATU (35.5 mg, 0.093 mmol). The reaction was stirred at rt for 90 min and was diluted with EtOAc (20 mL) and 0.2 M aqueous HCl (20 mL). The phases were separated and the aqueous phase was extracted with EtOAc (20 mL). The combined organic phase was dried over anhydrous Na₂SO₄, filtered, and concentrated in vacuo to afford a crude residue. Purification by silica gel chromatography (10% to 45% acetone in hexanes) provided an amorphous residue that was lyophilized from water and MeCN to provide Example 7. Analytical HPLC RetTime: 8.67 min. LCMS-ESI⁺ (m/z): [M+H]⁺ calcd for $C_{40}H_{53}F_2N_6O_9S$: 831.4. found: 831.3. ¹H-NMR (300 MHz, CDCl₃) δ 10.28 (s, 1H), 7.82 (d, J=9.1 Hz, 1H), 7.20 (dd, J=9.1, 2.8 Hz, 1H), 7.13 (d, J=2.7 Hz, 1H), 7.04 (s, 1H), 6.20-5.72 (m, 2H), 5.45 (d, J=9.8 Hz, 1H), 5.21-5.10 (m, 1H), 4.41 (d, J=9.8 Hz, 1H), 4.34 (dd, J=10.9, 6.6 Hz, 1H), 4.20 (d, J=12.0 Hz, 1H), 4.04 (dd, J=11.8, 3.3 Hz, 1H), 3.94 (s, 3H), 3.05-2.84 (m, 2H), 2.70-2.55 (m, 2H), 2.47-2.31 (m, 1H), 2.14-2.07 (m, 1H), 1.99-0.80 (m, 28H), 0.66-0.56 (m, 1H), 0.42 (dd, J=13.0, 7.8 Hz, 1H).

142

Example 8

Preparation of (1aR,1bS,5S,8S,10R,22aR,23aR)-5-tert-butyl-N-[(1R,2R)-2-(difluoromethyl)-1-{[(1-methylcyclopropyl)sulfonyl]carbamoyl}cyclopropyl]-14-methoxy-3,6-dioxo-1a,1b,3,4,5,6,9,10,18,19,20,21,22,22a, 23,23a-hexadecahydro-1H,8H-7,10-methanocyclopropa[3',4']cyclopenta [1',2':18,19][1,10,3,6]dioxadiazacyclononadecino[11,12-b]quinoxaline-8-carboxamide

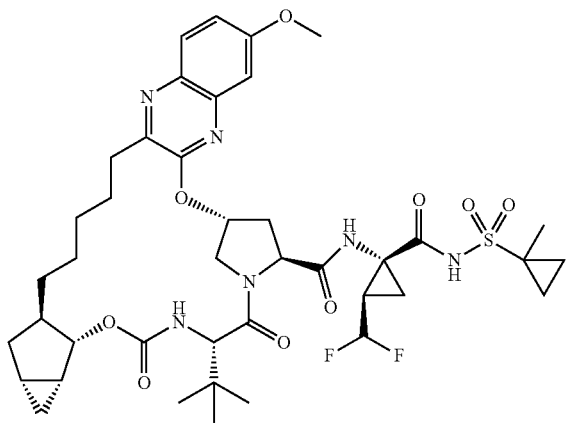

Example 8

Example 8 was prepared in a similar fashion to Example 7, substituting Intermediate A10 for Intermediate A9 in Step 6. Analytical HPLC RetTime: 8.79 min. LCMS-ESI⁺ (m/z): [M+H]⁺ calcd for $C_{41}H_{55}F_2N_6O_9S$: 845.4. found: 845.2. ¹H-NMR (300 MHz, CDCl₃) δ 9.85 (s, 1H), 7.82 (d, J=9.0 Hz, 1H), 7.20 (dd, J=9.1, 2.7 Hz, 1H), 7.13 (d, J=2.7 Hz, 1H), 7.08 (s, 1H), 6.17-5.68 (m, 2H), 5.51 (d, J=9.8 Hz, 1H), 5.17 (t, J=5.9 Hz, 1H), 4.47-4.33 (m, 2H), 4.24 (d, J=11.9 Hz, 1H), 4.03 (dd, J=11.9, 3.5 Hz, 1H), 3.94 (s, 3H), 3.05-2.88 (m, 1H), 2.72-2.57 (m, 2H), 2.48-2.33 (m, 1H), 2.11-2.04 (m, 1H), 2.01-1.84 (m, 2H), 1.82-1.13 (m, 17H), 1.06 (s, 9H), 0.93-0.77 (m, 3H), 0.65-0.55 (m, 1H), 0.49-0.37 (m, 1H).

Example 9
Preparation of (1aS,2aR,6S,9S,11R,23aR,23bS)-6-tert-butyl-N-[(1R,2R)-1-[(cyclopropylsulfonyl)carbamoyl]-2-(difluoromethyl)cyclopropyl]-19,19-difluoro-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide
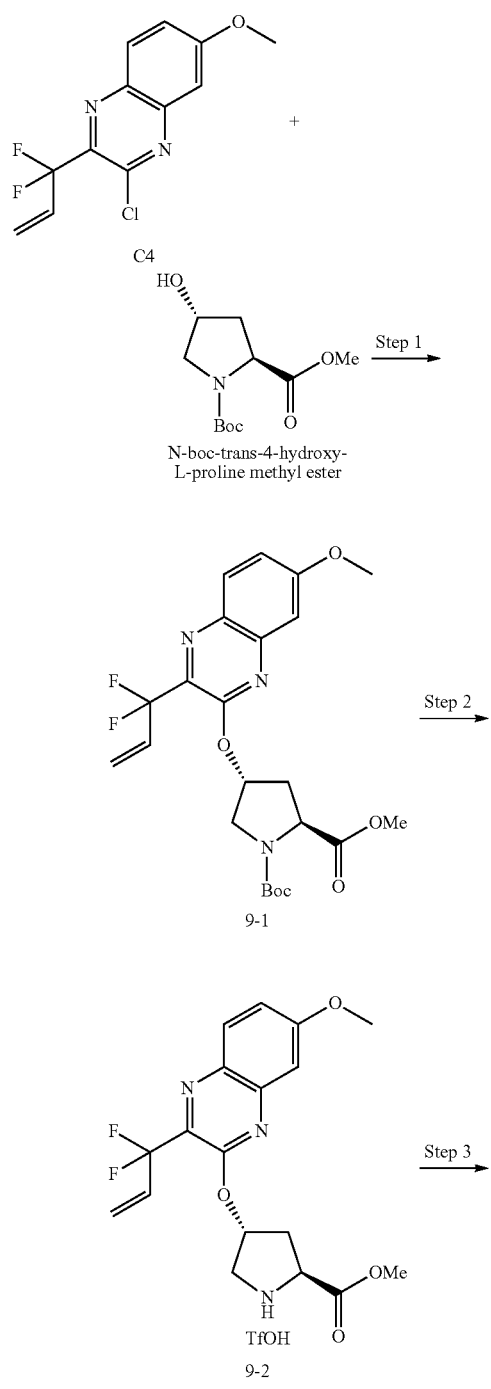
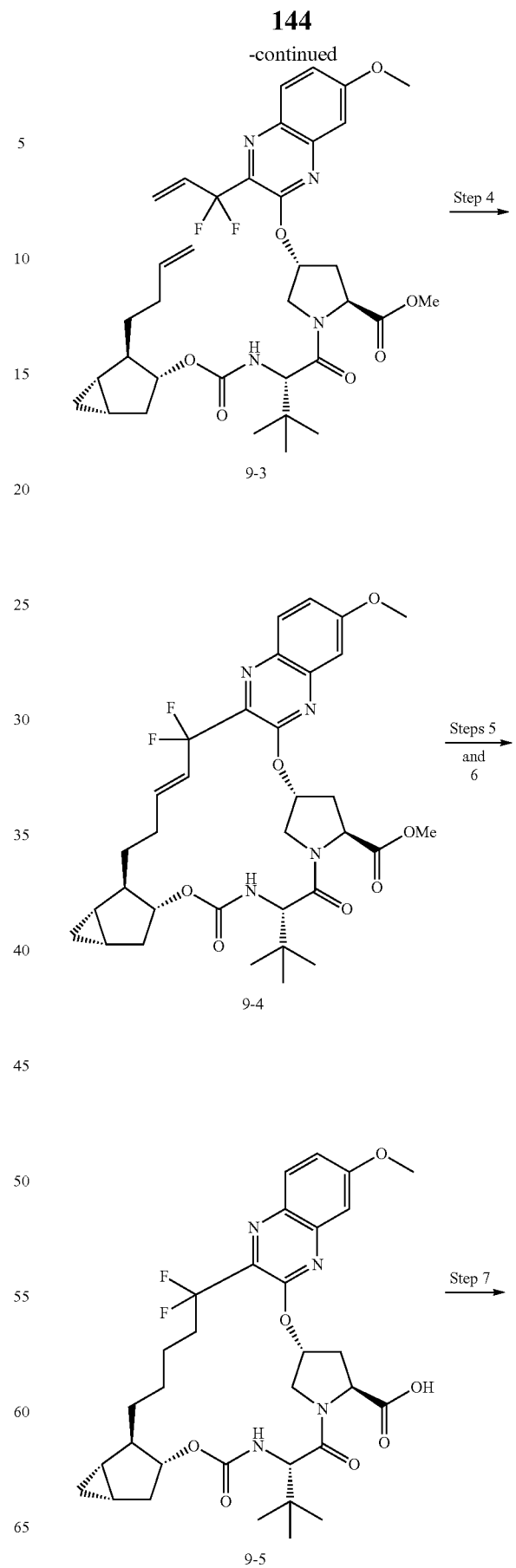

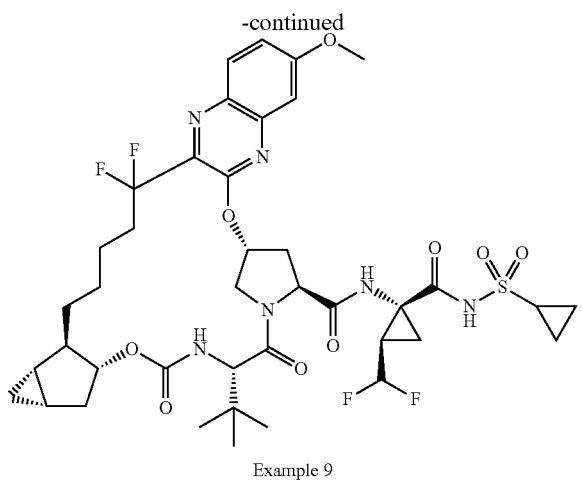

Example 9

Step 1: Preparation of 9-1: Intermediate C4 (361 mg, 1.33 mmol), N-Boc-trans-4-hydroxy-L-proline methyl ester (489 mg, 2.00 mmol, AIMS fine chemicals) and cesium carbonate (651 mg, 2.00 mmol) were taken in $CH_3CN$ (5 mL) and heated to 80° C. overnight. Reaction was cooled to rt, diluted with ethyl acetate (15 mL) and filtered through pad of Celite. Residue was washed with ethyl acetate and filtrate was concentrated in vacuo. Residue was purified by silica gel chromatography (0-100% EtOAc/hex) to produce 9-1. LCMS-ESI$^+$ (m/z): [M+H]$^+$ calcd for $C_{23}H_{28}F_2N_3O_6$: 480.19. found: 480.30.

Step 2: Preparation of 9-2: To a solution of 9-1 (392 mg, 0.82 mmol) in dichloromethane (3 mL) was slowly added trimethylsilyl trifluoromethanesulfonate (212 µL, 1.23 mmol) at 23° C. under an Ar atmosphere. After 20 minutes, the resulting mixture was concentrated in vacuo to give intermediate 9-2 as a triflic acid salt, which was used subsequently without further purification. LCMS-ESI$^+$ (m/z): [M+H]$^+$ calcd for $C_{18}H_{20}F_2N_3O_4$: 380.14. found: 380.22.

Step 3: Preparation of 9-3: To a solution of 9-2 (432 mg, 0.82 mmol) in DMF (2 mL) were added Intermediate B5 (275 mg, 0.89 mmol), HATU (467 mg, 1.23 mmol) and iPr$_2$NEt (0.71 mL, 4.09 mmol) at 23° C. After 40 hours, the reaction mixture was diluted with water (50 mL) and extracted with ethyl acetate (3×20 mL). Combined organic layers were washed with water (50 mL), brine (25 mL), dried over anhydrous MgSO$_4$ and concentrated in vacuo. The resulting residue was purified by silica gel chromatography (0-100% EtOAc/hex) to give 9-3. LCMS-ESI$^+$ (m/z): [M+H]$^+$ calcd for $C_{36}H_{46}F_2N_4O_7$: 671.32. found: 671.51.

Step 4: Preparation of 9-4: To a solution of 9-3 (300 mg, 0.45 mmol) in degassed DCE (100 mL) was added Zhan 1B catalyst (33 mg, 0.045 mmol) followed by additional degassing for 10 min. The resulting solution was refluxed under Ar for 75 min. The reaction mixture was then concentrated in vacuo and purified by silica gel chromatography with 0-100% EtOAc/hex to produce 9-4. LCMS-ESI$^+$ (m/z): [M+H]$^+$ calcd for $C_{33}H_{41}F_2N_4O_7$: 643.29. found: 643.44.

Steps 5 and 6: Preparation of 9-5: To a solution of 9-4 (220 mg, 0.34 mmol) in EtOH (7 mL) was added Pd/C (10 wt % Pd, 38 mg). The atmosphere of the reaction was replaced with H$_2$ and the reaction stirred at rt under 1 atm H$_2$ overnight. The reaction mixture was filtered through a pad of Celite and washed with EtOH and concentrated in vacuo to afford a crude residue which was resubmitted to reaction conditions for an additional 2 d. The reaction mixture was filtered through a pad of Celite and washed with EtOH and concentrated in vacuo to afford a crude residue that was used subsequently without further purification. (LCMS-ESI$^+$ (m/z): [M+H]$^+$ calcd for $C_{33}H_{43}F_2N_4O_7$: 645.30. found: 645.51). This residue was dissolved in THF (3 mL), H$_2$O (1 mL) and MeOH (1 mL). LiOH.H$_2$O (71 mg, 1.7 mmol) was added and the mixture was stirred at 23° C. for 2 h. Solvents were removed in vacuo and the residue taken up in ethyl acetate (10 mL) and 1 M HCl (10 mL). The aqueous layer was extracted with ethyl acetate (10 mL). Combined organic layers were dried over anhydrous MgSO$_4$ and concentrated in vacuo to afford a residue of 9-5 which was used subsequently without further purification. LCMS-ESI$^+$ (m/z): [M+H]$^+$ calcd for $C_{32}H_{41}F_2N_4O_7$: 631.29. found: 631.46).

Step 7: Preparation of Example 9: To a suspension of 9-5 (56.8 mg, 0.090 mmol) and Intermediate A9 (39.3 mg, 0.135 mmol) in MeCN (3 mL) was added HATU (55 mg, 0.144 mmol) and DIPEA (78 µL, 0.45 mmol) at 23° C. After 20 min, the solution was directly purified by reverse phase HPLC (Gemini 5u C18 110 Å column, 50-100% ACN/H$_2$O+ 0.1% TFA) and lyophilized to afford the TFA salt of Example 9. Analytical HPLC RetTime: 8.87 min. LCMS-ESI$^+$ (m/z): [M+H]$^+$ calcd for $C_{40}H_{51}F_4N_6O_9S$: 867.33. found: 867.45. $^1$H-NMR (400 MHz, CD$_3$OD) δ 9.46 (s, 1H), 7.93 (d, J=9.1 Hz, 1H), 7.33 (d, J=2.8 Hz, 1H), 7.30 (d, J=2.8 Hz, 1H), 7.28 (d, J=2.7 Hz, 1H), 6.16 (t, J=3.6 Hz, 1H), 5.89 (td, J=55.7, 6.8 Hz, 1H), 4.93 (t, J=9.8 Hz, 1H), 4.49-4.37 (m, 2H), 4.32 (s, 1H), 4.13 (dd, J=11.9, 3.9 Hz, 1H), 3.96 (d, J=4.9 Hz, 3H), 3.04-2.91 (m, 1H), 2.64-2.51 (m, 1H), 2.64-2.51 (m, 1H), 2.32-2.15 (m, 2H), 2.11-1.90 (m, 4H), 1.87-1.62 (m, 4H), 1.61-1.36 (m, 4H), 1.37-1.23 (m, 4H), 1.14-1.02 (m, 11H), 0.60-0.47 (m, 2H).

Example 10

Preparation of (1aS,2aR,6S,9S,11R,23aR,23bS)-6-tert-butyl-N-[(1R,2R)-2-(difluoromethyl)-1-{[(1-methylcyclopropyl)sulfonyl]carbamoyl}cyclopropyl]-19,19-difluoro-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

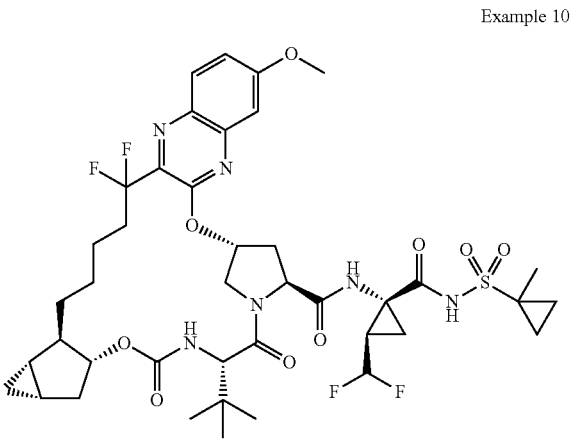 [SMILES: COc1ccc2nc3c(nc2c1)O[C@@H]1C[C@@H](C(=O)N[C@]2(C(=O)NS(=O)(=O)C4(C)CC4)C[C@H]2C(F)F)N(C1)C(=O)[C@H](C(C)(C)C)NC(=O)O[C@@H]1C[C@@H]2C[C@@H]2[C@H]1CCCCC3(F)F]

Example 10

Example 10 was prepared in a similar fashion to Example 9, substituting Intermediate A10 for Intermediate A9 in Step 7. Example 10 was isolated as a TFA salt. Analytical HPLC RetTime: 8.91 min. LCMS-ESI+ (m/z): [M–H]+ calcd for $C_{41}H_{51}F_2N_6O_9S$: 879.35. found: 879.63. $^1$H-NMR (400 MHz, CD$_3$OD) δ 9.43 (s, 1H), 7.93 (d, J=9.1 Hz, 1H), 7.32 (d, J=2.8 Hz, 1H), 7.30 (d, J=2.8 Hz, 1H), 7.27 (d, J=2.7 Hz, 1H), 6.15 (t, J=3.6 Hz, 1H), 5.87 (td, J=55.7, 6.9 Hz, 1H), 4.94 (d, J=7.5 Hz, 1H), 4.51-4.38 (m, 2H), 4.32 (s, 1H), 4.13 (dd, J=11.9, 3.9 Hz, 1H), 3.96 (s, 3H), 2.65-2.39 (m, 2H), 2.34-2.14 (m, 2H), 2.12-1.88 (m, 4H), 1.87-1.63 (m, 4H), 1.62-1.43 (m, 8H), 1.62-1.43 (m, 2H), 1.09-1.03 (m, 10H), 0.96-0.87 (m, 2H), 0.54 (qd, J=8.3, 4.9 Hz, 2H).

Example 11

Preparation of (1aS,2aR,6S,9S,11R,23aR,23bS)-6-tert-butyl-N-[(1R,2R)-2-(difluoromethyl)-1-{[(1-methylcyclopropyl)sulfonyl] carbamoyl}cyclopropyl]-15-fluoro-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

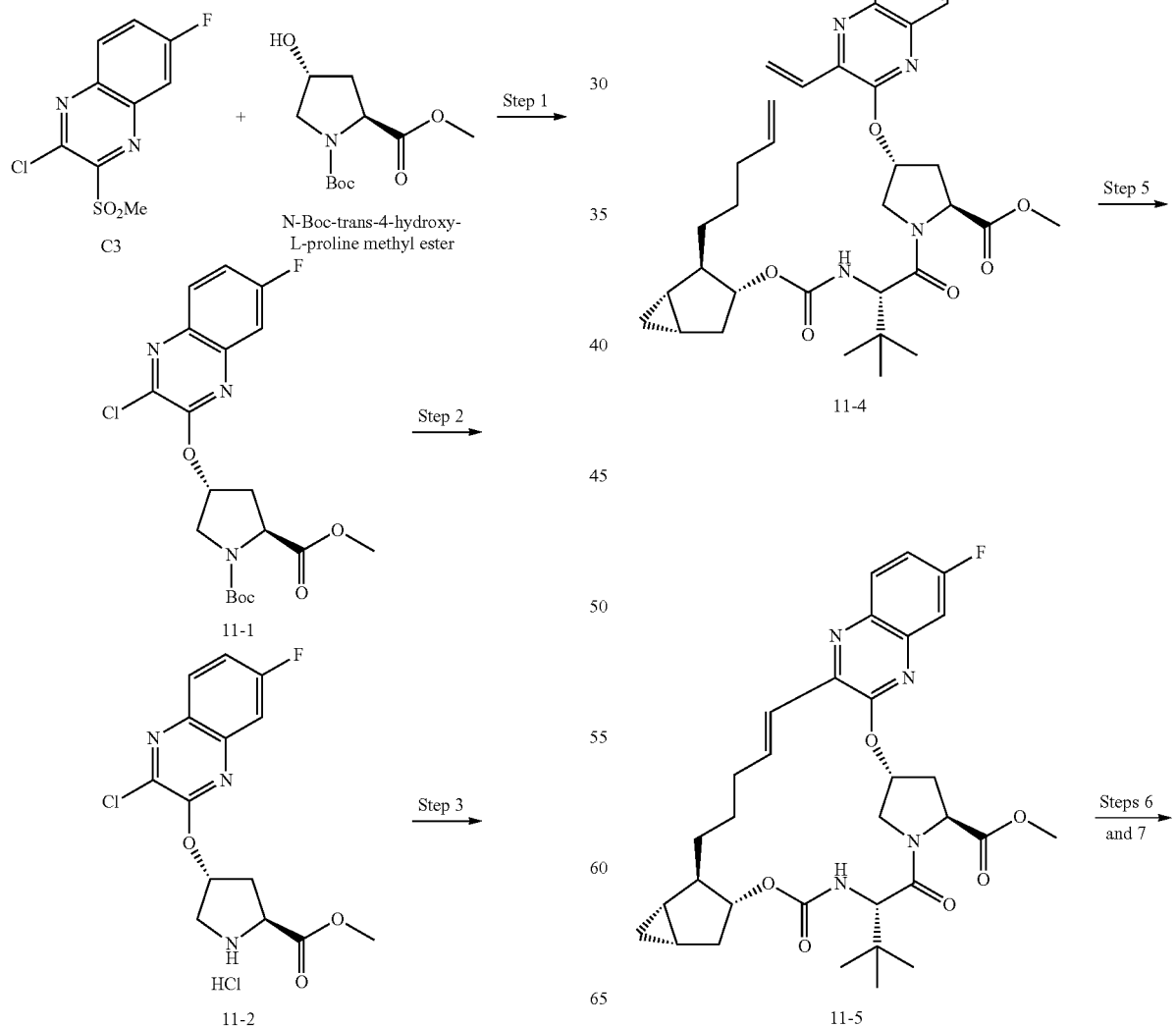

-continued

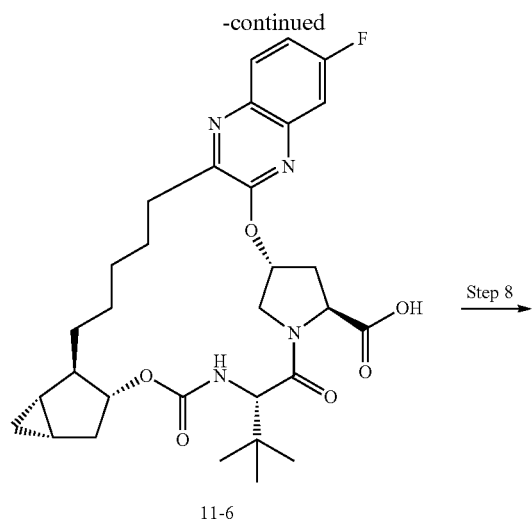

11-6

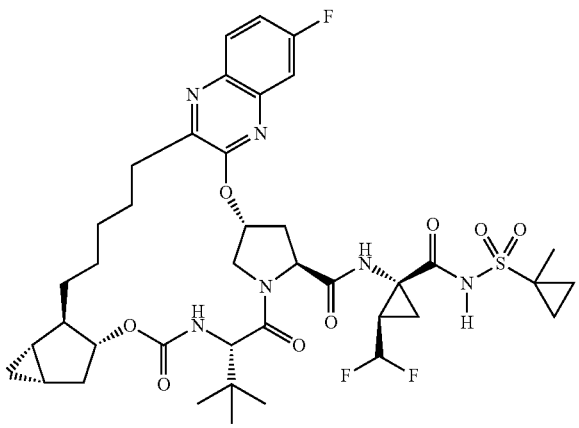

Example 11

Step 1. Preparation of 11-1. Intermediate C3 (506 mg, 1.94 mmol) was combined with N-Boc-trans-4-hydroxy-L-proline methyl ester (524 mg, 2.13 mmol) and Cs$_2$CO$_3$ (759 mg, 2.33 mmol) then suspended in MeCN (10 mL). The stirred reaction mixture was stirred at rt for 72 h then filtered over Celite and concentrated in vacuo. The crude residue was purified by silica gel chromatography to afford 11-1. LCMS-ESI$^+$ (m/z): [M-Boc+2H]$^+$ calcd for C$_{14}$H$_{14}$ClFN$_3$O$_3$: 326.07. found: 326.68.

Step 2. Preparation of 11-2. Carbamate 11-1 (409 mg, 0.960 mmol) was dissolved in DCM (10 mL) and treated with HCl (4.0 M in dioxane, 5 mL, 20 mmol). After stirring at rt for 1.5 h, the reaction mixture was concentrated in vacuo to afford amine hydrochloride 11-2 which was carried on without further purification. LCMS-ESI$^+$ (m/z): [M+H]$^+$ calcd for C$_{14}$H$_{14}$ClFN$_3$O$_3$: 326.07. found: 326.52.

Step 3. Preparation of 11-3. Amine hydrochloride 11-2 (0.960 mmol) and Intermediate B3 (229 mg, 0.704 mmol) were combined and treated with BEP (231 mg, 0.845 mmol), EtOAc (4.5 mL), NMP (0.5 mL) and DIPEA (0.61 mL, 3.5 mmol). The stirred mixture was heated to 50° C. for 2.5 h. After cooling to rt, the reaction mixture was diluted with EtOAc and washed successively with saturated aqueous NaHCO$_3$ and brine. The organic phase was dried over anhydrous MgSO$_4$, filtered and concentrated in vacuo. The crude residue was purified by silica gel chromatography to afford amide 11-3. LCMS-ESI$^+$ (m/z): [M+H]$^+$ calcd for C$_{32}$H$_{41}$ClFN$_4$O$_6$: 631.27. found: 631.98.

Step 4. Preparation of 11-4. Chloroquinoxaline 11-3 (336 mg, 0.532 mmol) was treated with potassium vinyltrifluoroborate (107 mg, 0.799 mmol), Pd(dppf)Cl$_2$.DCM (43 mg, 0.053 mmol), EtOH (5 mL) and Et$_3$N (0.11 mL, 0.80 mmol). The reaction mixture was stirred at reflux for 3.5 h then cooled to rt and diluted with EtOAc. The organic phase was washed with water and brine then dried over anhydrous MgSO$_4$, filtered and concentrated in vacuo. The crude residue was purified by silica gel chromatography to afford vinylquinoxaline 11-4. LCMS-ESI$^+$ (m/z): [M+H]$^+$ calcd for C$_{34}$H$_{44}$FN$_4$O$_6$: 623.32. found: 623.45.

Step 5. Preparation of 11-5. Vinylquinoxaline 11-4 (191 mg, 0.307 mmol) was dissolved in DCE (61 mL) and treated with Zhan Catalyst-1B (21 mg, 0.031 mmol). The mixture was degassed with bubbling N$_2$ for 20 min the heated to reflux for 1.5 h. The reaction mixture was concentrated in vacuo and the crude residue was purified by silica gel chromatography to afford macrocycle 11-5. LCMS-ESI$^+$ (m/z): [M+H]$^+$ calcd for C$_{32}$H$_{40}$FN$_4$O$_6$: 595.29. found: 595.46.

Steps 6 and 7. Preparation of 11-6. Macrocycle 11-5 (155 mg, 0.261 mmol) was dissolved in EtOH (20 mL) and EtOAc (5 mL). Pd/C (10 wt % Pd, 47 mg) was added and H$_2$ was bubbled through the suspension for 4 min. The stirred reaction mixture was maintained under 1 atm of H$_2$ for 52 min before being filtered over Celite and concentrated in vacuo. This residue was used subsequently without further purification. (LCMS-ESI$^+$ (m/z): [M+H]$^+$ calcd for C$_{32}$H$_{42}$FN$_4$O$_6$: 597.31. found: 597.36). This residue (0.261 mmol theoretical) was treated with THF (10 mL) and LiOH (1.0 M in H$_2$O, 10 mL, 10 mmol). The mixture was stirred for 12.5 h then poured into a separatory containing 40 mL 10% aqueous HCl. The aqueous layer was extracted 3× with DCM. The combined organics were dried over anhydrous MgSO$_4$, filtered and concentrated in vacuo to afford carboxylic acid 11-6 which was used subsequently without further purification. LCMS-ESI$^+$ (m/z): [M+H]$^+$ calcd for C$_{31}$H$_{40}$FN$_4$O$_6$: 583.29. found: 583.29.

Step 8. Preparation of Example 11. Carboxylic acid 11-6 (110 mg, 0.189 mmol) was treated with Intermediate A10 (86 mg, 0.28 mmol), TBTU (73 mg, 0.23 mmol), DMAP (28 mg, 0.23 mmol), DCM (2 mL) and DIPEA (0.16 mL, 0.95 mmol). The reaction mixture was stirred for 2.5 h, followed by concentration in vacuo. The crude residue was purified by HPLC to afford Example 11 as a TFA salt. Analytical HPLC RetTime: 9.05 min. LCMS-ESI$^+$ (m/z): [M+H]$^+$ calcd for C$_{40}$H$_{52}$F$_3$N$_6$O$_8$S: 833.35. found: 833.17. $^1$H-NMR (400 MHz, CD$_3$OD) δ 9.31 (s, 1H), 7.94 (dd, J=9.1, 5.8 Hz, 1H), 7.47 (dd, J=9.6, 2.7 Hz, 1H), 7.40 (td, J=8.8, 2.8 Hz, 1H), 6.08 (t, J=3.6 Hz, 1H), 5.87 (td, J=55.7, 6.7 Hz, 1H), 4.99 (d, J=7.6 Hz, 1H), 4.51-4.38 (m, 2H), 4.33 (s, 1H), 4.12 (dd, J=11.9, 3.8 Hz, 1H), 3.08-2.91 (m, 1H), 2.89-2.73 (m, 1H), 2.50 (dd, J=13.9, 6.6 Hz, 1H), 2.25 (ddd, J=18.5, 12.7, 5.4 Hz, 2H), 2.10-1.92 (m, 3H), 1.92-1.72 (m, 2H), 1.72-1.15 (m, 15H), 1.06 (d, J=10.1 Hz, 10H), 0.97-0.88 (m, 2H), 0.58 (q, J=4.1 Hz, 1H), 0.55-0.45 (m, 1H).

Example 12

Preparation of (1aS,2aR,6S,9S,11R,23aR,23bS)-6-tert-butyl-N-[(1R,2R)-1-[(cyclopropylsulfonyl)carbamoyl]-2-(difluoromethyl)cyclopropyl]-15-fluoro-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

Example 13

Preparation of (1aS,2aR,6S,9S,11R,20E,23aR,23bS)-6-tert-butyl-15-cyano-N-[(1R,2R)-2-(difluoromethyl)-1-{[(1-methylcyclopropyl)sulfonyl]carbamoyl}cyclopropyl]-19,19-difluoro-4,7-dioxo-1a,2,2a,4,5,6,7,10,11,19,22,23,23a,23b-tetradecahydro-1H,9H-8,11-methanocyclopropa[4',5']cyclopenta[1',2'18,19][1,10,3,6]dioxadiazacyclononadecino[11,12-b]quinoxaline-9-carboxamide

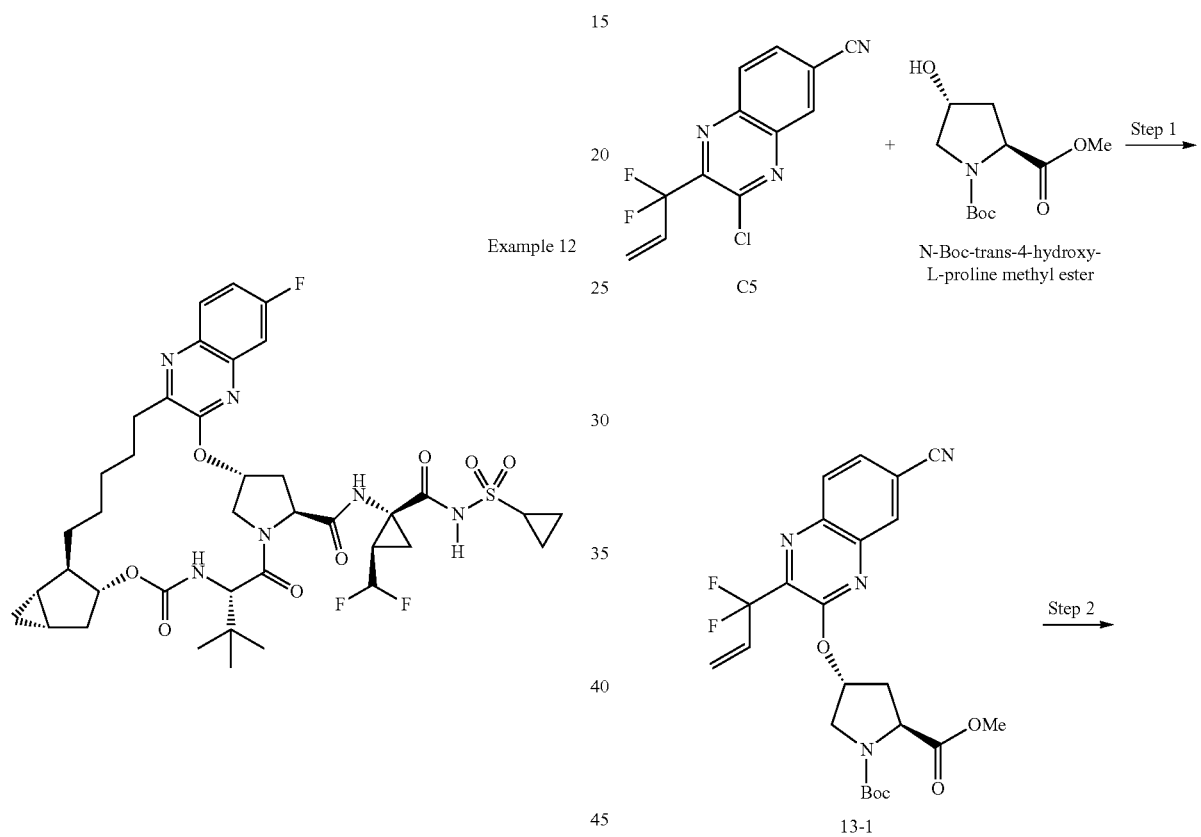

Example 12

Example 12 was prepared in a similar fashion to Example 11, substituting Intermediate A9 for Intermediate A10 in Step 8. Following purification by preparatory HPLC, the TFA salt of Example 12 (24 mg) was isolated. Analytical HPLC RetTime: 8.95 min. LCMS-ESI⁺ (m/z): [M+H]⁺ calcd for $C_{39}H_{50}F_3N_6O_8S$: 819.34. found: 819.34. $^1$H-NMR (400 MHz, CD$_3$OD) δ 9.35 (s, 1H), 7.94 (dd, J=9.1, 5.8 Hz, 1H), 7.46 (dd, J=9.6, 2.7 Hz, 1H), 7.39 (td, J=8.7, 2.8 Hz, 1H), 6.08 (t, J=3.5 Hz, 1H), 5.90 (td, J=55.9, 6.8 Hz, 1H), 4.99 (d, J=7.5 Hz, 1H), 4.50-4.36 (m, 2H), 4.32 (s, 1H), 4.12 (dd, J=11.8, 3.8 Hz, 1H), 3.05-2.91 (m, 2H), 2.88-2.69 (m, 1H), 2.49 (dd, J=14.1, 6.3 Hz, 1H), 2.33-2.11 (m, 2H), 2.11-1.91 (m, 3H), 1.84 (dd, J=11.6, 7.1 Hz, 1H), 1.75 (d, J=14.6 Hz, 1H), 1.70-1.15 (m, 12H), 1.15-1.09 (m, 2H), 1.06 (d, J=11.2 Hz, 11H), 0.57 (q, J=4.2 Hz, 1H), 0.54-0.45 (m, 1H).

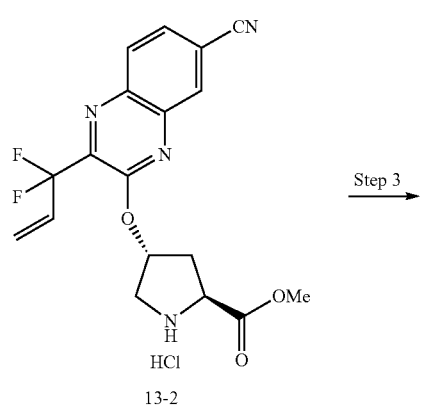

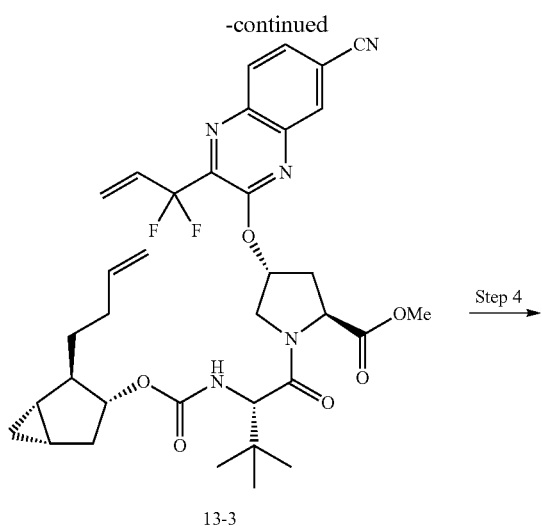

13-3

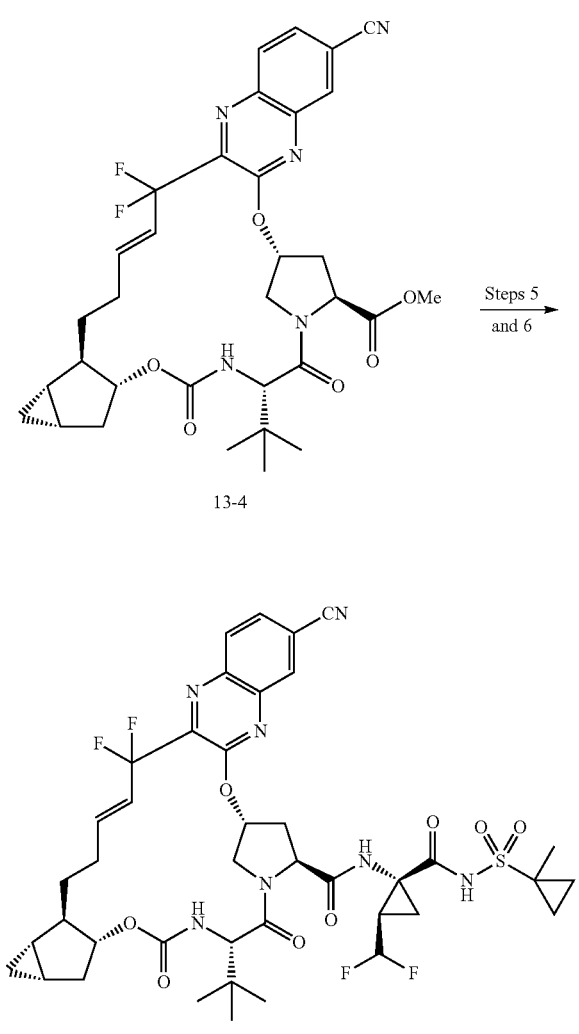

13-4

Example 13

Step 1: Preparation of 13-1: Intermediate C5 (213 mg, 0.8 mmol), N-Boc-trans-4-hydroxy-L-proline methyl ester (394 mg, 1.2 mmol) and cesium carbonate (391 mg, 1.2 mmol) were combined in $CH_3CN$ (4 mL) and heated to 80° C. for 3 h. The reaction was cooled to rt, diluted with ethyl acetate (15 mL) and filtered through a pad of Celite. The Celite pad was washed with ethyl acetate and the filtrate was concentrated in vacuo. The resulting residue was purified by silica gel chromatography to produce 13-1. LCMS-ESI$^+$ (m/z): [M+H]$^+$ calcd for $C_{23}H_{25}F_2N_4O_5$: 475.47. found: 475.10.

Step 2: Preparation of 13-2: To a solution of 13-1 (300 mg, 0.63 mmol) in DCM (2 mL) was slowly added HCl in dioxane (4 M, 1 mL, 4 mmol) at rt. After 2.5 h, the resulting mixture was concentrated in vacuo to give proline 13-2 as an HCl salt, which was used subsequently without further purification. LCMS-ESI$^+$ (m/z): [M+H]$^+$ calcd for $C_{18}H_{17}F_2N_4O_3$: 375.35. found: 375.10.

Step 3: Preparation of 13-3: To a solution of 13-2 (320 mg, 0.8 mmol) in DMF (2 mL) were added Intermediate B5 (275 mg, 0.89 mmol), HATU (467 mg, 1.23 mmol) and $iPr_2NEt$ (0.71 mL, 4.09 mmol) at rt. After 16 h, the reaction mixture was diluted with water (50 mL) and extracted with EtOAc (3×20 mL). The combined organic layers were washed with water (50 mL), brine (25 mL), dried over anhydrous $MgSO_4$, filtered and concentrated in vacuo. The resulting residue was purified by silica gel chromatography to give 13-3. LCMS-ESI$^+$ (m/z): [M]$^+$ calcd for $C_{35}H_{41}F_2N_5O_6$: 665.73. found: 665.93.

Step 4: Preparation of 13-4: To a solution of diene 13-3 (290 mg, 0.43 mmol) in degassed DCE (80 mL) was added Zhan 1B catalyst (32 mg, 0.043 mmol) followed by additional degassing for 10 min. The resulting solution was refluxed under Ar for 2 h. The reaction mixture was then cooled to rt, concentrated in vacuo and purified by silica gel chromatography to produce macrocycle 13-4. LCMS-ESI$^+$ (m/z): [M]$^+$ calcd for $C_{33}H_{37}F_2N_5O_6$: 637.67. found: 637.95.

Steps 5 and 6: Preparation of Example 13: To a solution of 13-4 (200 mg, 0.31 mmol) in THF (1 mL), 1 N LiOH (1 mL) was added and the mixture was stirred at 23° C. for 2 h. Solvents were removed in vacuo and the residue taken up in EtOAc (10 mL) and 1 M HCl (10 mL). The aqueous layer was extracted with EtOAc (10 mL). The combined organic layers were dried over anhydrous $MgSO_4$ and concentrated in vacuo to afford a residue that was used subsequently without further purification. To a suspension of this residue (50 mg, 0.08 mmol) and Intermediate A10 (36 mg, 0.12 mmol) in MeCN (1 mL) was added HATU (46 mg, 0.12 mmol) and DIPEA (70 μL, 0.4 mmol) at rt. After 1 h, the solution was directly purified by reverse phase HPLC and lyophilized to afford the TFA salt of Example 13. Analytical HPLC RetTime: 8.55 min. LCMS-ESI$^+$ (m/z): [M]$^+$ calcd for $C_{41}H_{47}F_4N_7O_8S$: 873.91. found: 873.89. $^1$H-NMR (400 MHz, $CD_3OD$) δ 9.38 (s, 1H), 8.30 (d, 1H), 8.18 (d, 1H), 7.90 (dd, 1H), 6.30-6.15 (m, 3H), 5.83 (m, 1H), 4.93 (d, 1H), 4.61 (d, 1H), 4.45-4.38 (m, 2H), 4.12 (m, 1H), 2.55-2.48 (m, 2H), 2.28-2.18 (m, 3H), 2.01-1.90 (m, 3H), 1.79 (m, 1H), 1.59-1.33 (m, 10H), 1.05-0.91 (m, 11H), 0.88 (m, 2H). 0.62-0.47 (m, 2H).

Example 14

Preparation of (1aS,2aR,6S,9S,11R,23aR,23bS)-6-tert-butyl-15-cyano-N-[(1R,2R)-2-(difluoromethyl)-1-{[(1-methylcyclopropyl)sulfonyl]carbamoyl}cyclopropyl]-19,19-difluoro-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

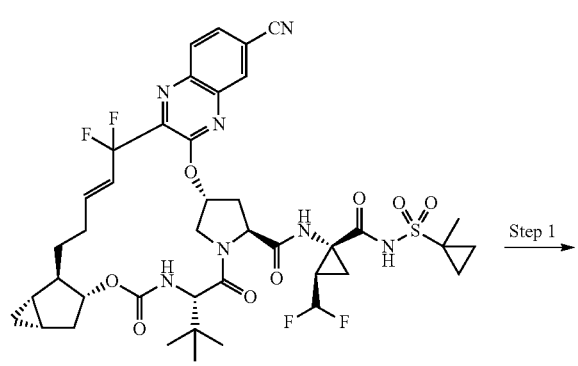

Example 13

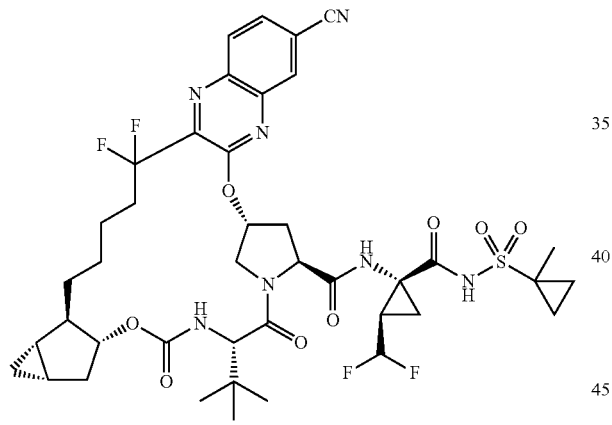

Example 14

Step 1: Preparation of Example 14: To a solution of Example 13 (88 mg, 0.1 mmol) in EtOH (1 mL) was added Pd/C (10 wt % Pd, 20 mg). The reaction vessel was purged twice with $H_2$ and was stirred at rt under 1 atm $H_2$ for 6 h. The reaction mixture was filtered through a pad of Celite and the filtrate concentrated in vacuo. The crude material was redissolved in dioxane (2.5 mL) and treated with DDQ (34 mg, 0.15 mmol). After 1 h, the solution was directly purified by reverse phase HPLC and lyophilized to afford the TFA salt of Example 14. Analytical HPLC RetTime: 8.64 min. LCMS-ESI$^+$ (m/z): [M]$^+$ calcd for $C_{41}H_{49}F_4N_7O_8S$: 875.93. found: 875.98. $^1$H-NMR (400 MHz, CD$_3$OD) δ 8.32 (s, 1H), 8.20 (d, 1H), 7.90 (d, 1H), 6.90 (d, 1H), 6.17 (d, 1H), 5.87 (m, 1H), 4.90 (m, 1H), 4.45 (m, 2H), 4.28 (m, 1H), 4.12 (m, 2H), 3.70-3.50 (m, 3H), 2.55-2.48 (m, 2H), 2.28-2.18 (m, 3H), 2.01-1.90 (m, 3H), 1.79 (m, 1H), 1.59-1.33 (m, 10H), 1.05-0.91 (m, 11H), 0.89 (m, 2H). 0.57-0.51 (m, 2H).

Example 15

Preparation of (1aS,2aR,6S,9S,11R,23aR,23bS)-6-tert-butyl-N-[(1R,2R)-1-[(cyclopropylsulfonyl)carbamoyl]-2-(difluoromethyl)cyclopropyl]-15,16,19,19-tetrafluoro-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

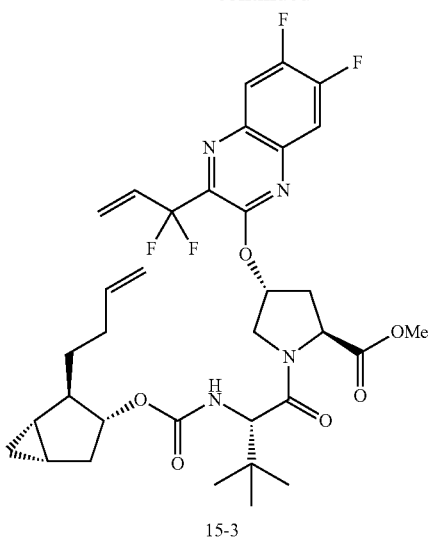

15-3

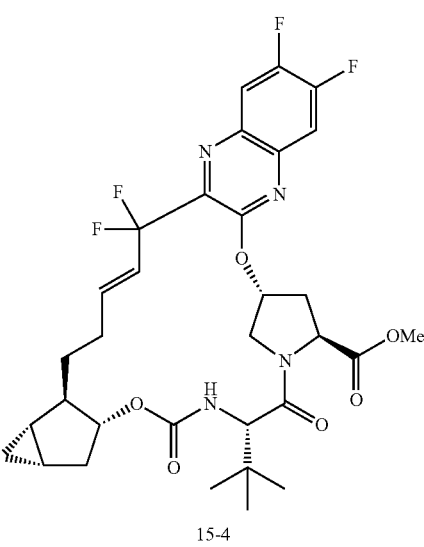

15-4

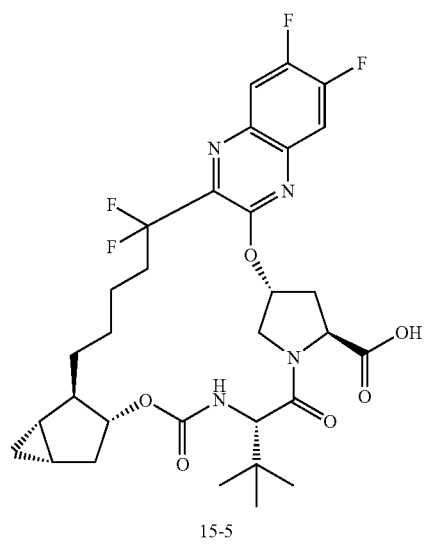

15-5

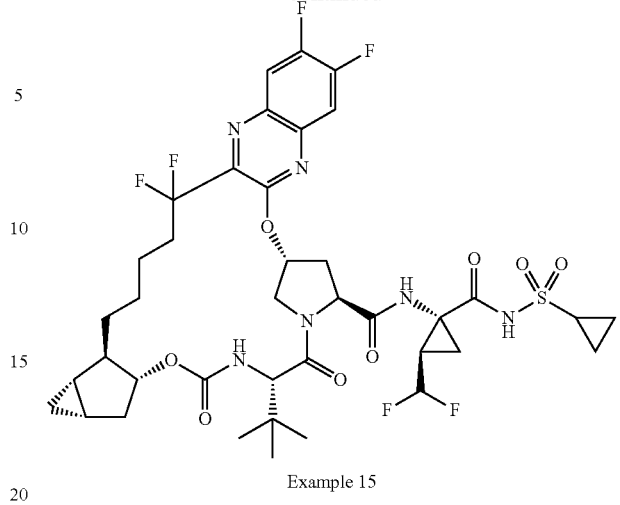

Example 15

Step 1: Preparation of 15-1: Intermediate C6 (575 mg, 2.22 mmol), Intermediate D1 (1.55 g, 3.34 mmol) and cesium carbonate (2 g, 6.14 mmol) were combined in NMP (10 mL) and heated to 70° C. overnight. The reaction mixture was cooled to rt, diluted with ethyl acetate (50 mL), washed with water (100 mL), brine (50 mL) and dried over anhydrous MgSO$_4$. Following filtration, the resulting solution was concentrated in vacuo. The resulting residue was purified via silica gel chromatography to produce 15-1. LCMS-ESI$^+$ (m/z): [M+Na]$^+$ calcd for $C_{22}H_{23}F_4N_3NaO_5$: 508.15. found: 508.2.

Step 2: Preparation of 15-2: To a solution of 15-1 (392 mg, 0.82 mmol) in dichloromethane (3 mL) was added 4 N HCl in dioxane (3 mL). The resulting mixture was allowed to stir overnight at rt and was concentrated in vacuo to give 15-2 as an HCl salt, which was used subsequently without further purification. LCMS-ESI$^+$ (m/z): [M+H]$^+$ calcd for $C_{17}H_{16}F_4N_3O_3$: 386.11. found: 386.1.

Step 3: Preparation of 15-3: To a solution of 15-2 (393 mg, 0.93 mmol) in DMF (3 mL) were added Intermediate B5 (240 mg, 0.78 mmol), HATU (324 mg, 0.853 mmol) and iPr$_2$NEt (1.35 mL, 7.76 mmol) at 23° C. After 18 hours, the reaction mixture was diluted with water (50 mL) and extracted with ethyl acetate (3×25 mL). The combined organic layers were washed with water (50 mL), brine (50 mL), dried over anhydrous MgSO$_4$ and concentrated in vacuo. The resulting residue was purified via silica gel chromatography to give 15-3. LCMS-ESI$^+$ (m/z): [M+H]$^+$ calcd for $C_{34}H_{41}F_4N_4O_6$: 677.30. found: 677.04.

Step 4: Preparation of 15-4: To a solution of 15-3 (450 mg, 0.665 mmol) in degassed DCE (133 mL) was added Zhan 1B catalyst (52 mg, 0.067 mmol). The resulting solution was refluxed under N$_2$ for 3 hours. The reaction mixture was then concentrated in vacuo and was purified via silica gel chromatography to produce 15-4. LCMS-ESI$^+$ (m/z): [M+H]$^+$ calcd for $C_{32}H_{37}F_4N_4O_6$: 649.25. found: 649.2.

Steps 5 and 6: Preparation of 15-5: To a solution of 15-4 (270 mg, 0.42 mmol) in EtOH (8 mL) was added Pd/C (10 wt % Pd, 270 mg). The atmosphere of the reaction was replaced with H$_2$ and the reaction stirred at rt under 1 atm H$_2$ for 3 h. The reaction mixture was filtered through a pad of Celite and washed with EtOH and concentrated in vacuo to afford a crude residue that was used subsequently without further purification. (LCMS-ESI$^+$ (m/z): [M+H]$^+$ calcd for $C_{32}H_{37}F_4N_4O_6$: 651.28. found: 651.3). This residue was dissolved in THF (2 mL) and MeOH (1 mL). Aqueous 2 N lithium hydroxide solution (1 mL) was added and the mixture was stirred at 23° C. for 2 h. Solvents were removed in vacuo and the residue taken up in ethyl acetate (10 mL) and 1 M HCl (10 mL). The aqueous layer was extracted with ethyl acetate (10 mL). The combined organic layers were dried over anhydrous MgSO₄ and concentrated in vacuo to afford a residue of 15-5 which was used subsequently without further purification. LCMS-ESI⁺ (m/z): [M+H]⁺ calcd for $C_{31}H_{37}F_4N_4O_6$: 637.26. found: 637.3).

Step 7: Preparation of Example 15: To a suspension of 15-5 (37 mg, 0.058 mmol) and Intermediate A9 (21.2 mg, 0.073 mmol) in DMF (3 mL) was added HATU (28 mg, 0.73 mmol) and DIPEA (126 µL, 0.73 mmol) at 23° C. T reaction mixture was allowed to stir overnight, then purified via HPLC and lyophilized to afford the TFA salt of Example 15. Analytical HPLC RetTime: 8.87 min. LCMS-ESI⁺ (m/z): [M+H]⁺ calcd for $C_{39}H_{47}F_6N_6O_8S$: 873.31. found: 873.09. ¹H-NMR (400 MHz, CDCl₃) δ 10.39 (s, 1H), 7.88 (dd, J=9.4, 8.8 Hz, 1H), 7.61 (dd, J=10.3, 7.7 Hz, 1H), 6.73 (s, 1H), 6.15 (s, 1H), 5.97 (td, J=55.5, 6.9 Hz, 1H), 5.23 (d, J=9.5 Hz, 1H), 4.90 (d, J=7.4 Hz, 1H), 4.50 (d, J=12.2 Hz, 1H), 4.37-4.20 (m, 2H), 4.07 (dd, J=11.8, 3.6 Hz, 1H), 2.94 (td, J=8.3, 4.1 Hz, 1H) 2.62-2.25 (m, 2H), 2.62-2.25 (m, 2H), 2.29-2.08 (m, 2H), 2.07-1.69 (m, 6H), 1.70-1.50 (m, 2H), 1.51-1.15 (m, 6H), 1.07 (s, 9H), 1.05-0.77 (m, 2H), 0.57-0.46 (m, 1H), 0.46-0.35 (m, 1H).

Example 16

Preparation of (1aS,2aR,6S,9S,11R,23aR,23bS)-6-tert-butyl-N-[(1R,2R)-1-[(cyclopropylsulfonyl)carbamoyl]-2-(difluoromethyl)cyclopropyl]-15-(difluoromethoxy)-19,19-difluoro-4,7-dioxo-1a,2,2a,4,5,6,7,10,11,19,20,21,22,23,23a,23b-hexadecahydro-1H,9H-8,11-methanocyclopropa[4',5']cyclopenta [1',2':18,19][1,10,3,6]dioxadiazacyclononadecino[11,12-b]quinoxaline-9-carboxamide

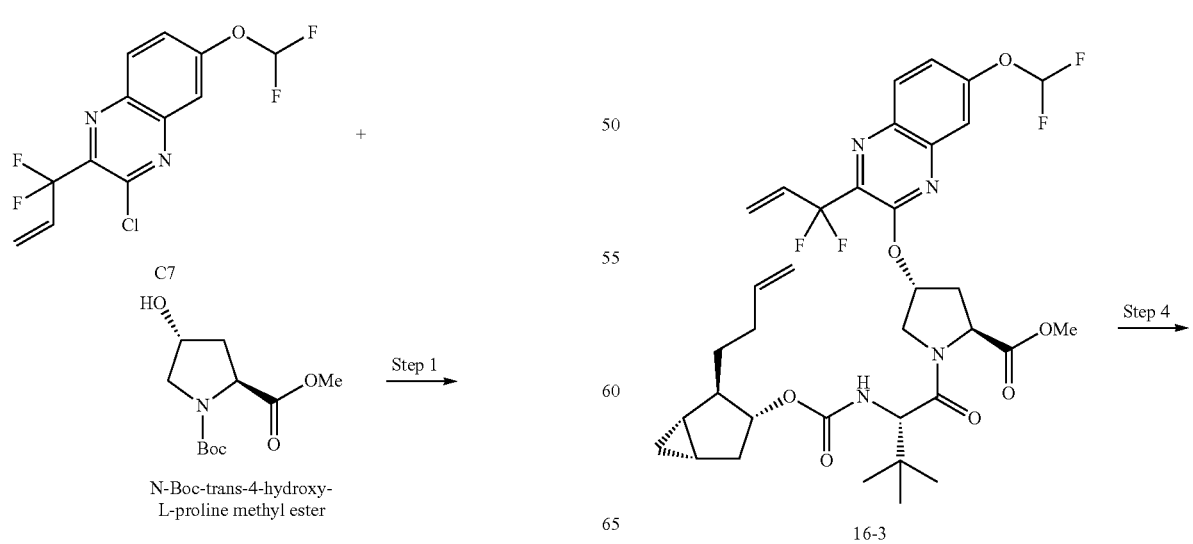

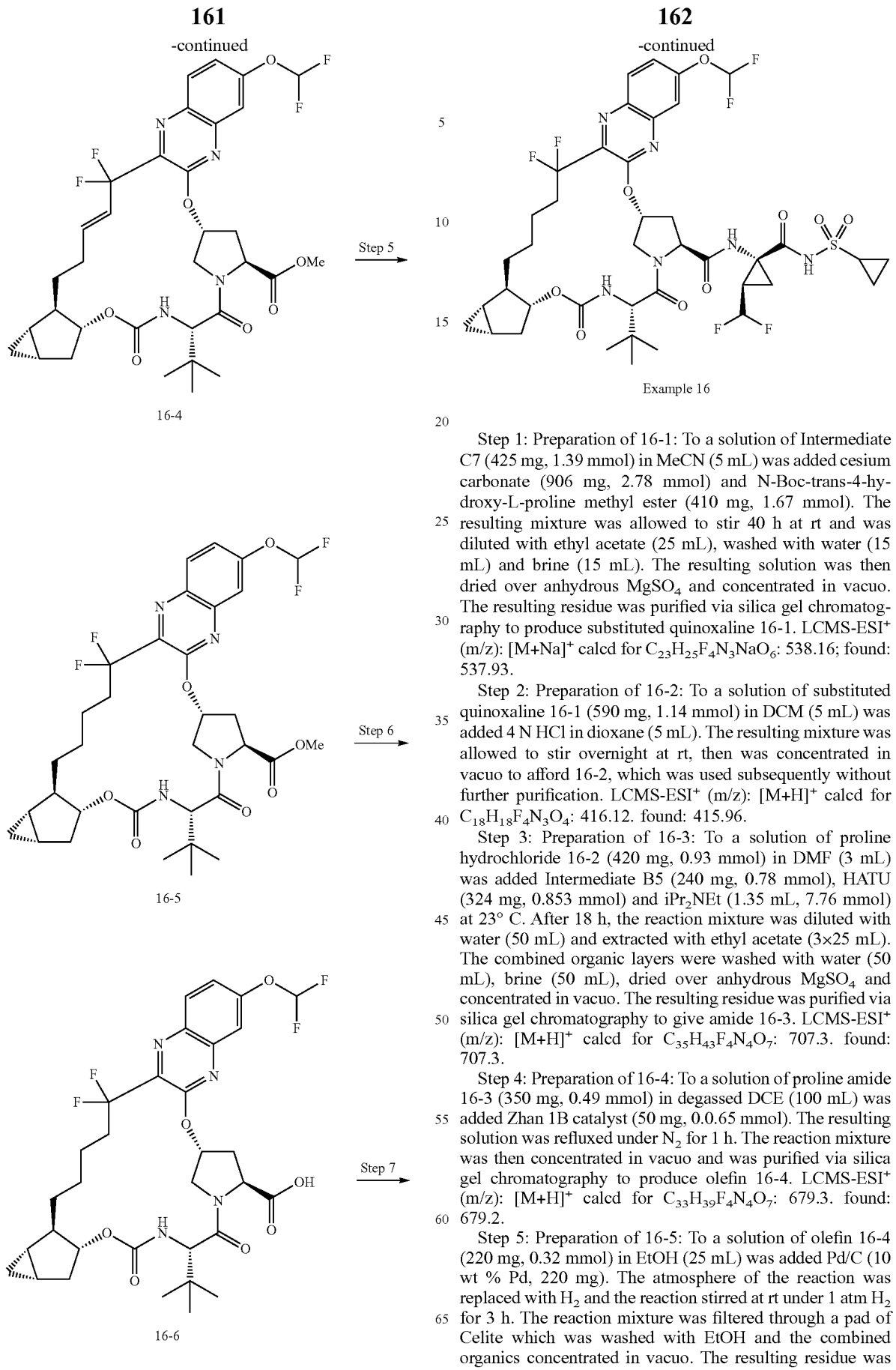

Step 1: Preparation of 16-1: To a solution of Intermediate C7 (425 mg, 1.39 mmol) in MeCN (5 mL) was added cesium carbonate (906 mg, 2.78 mmol) and N-Boc-trans-4-hydroxy-L-proline methyl ester (410 mg, 1.67 mmol). The resulting mixture was allowed to stir 40 h at rt and was diluted with ethyl acetate (25 mL), washed with water (15 mL) and brine (15 mL). The resulting solution was then dried over anhydrous $MgSO_4$ and concentrated in vacuo. The resulting residue was purified via silica gel chromatography to produce substituted quinoxaline 16-1. LCMS-ESI$^+$ (m/z): [M+Na]$^+$ calcd for $C_{23}H_{25}F_4N_3NaO_6$: 538.16; found: 537.93.

Step 2: Preparation of 16-2: To a solution of substituted quinoxaline 16-1 (590 mg, 1.14 mmol) in DCM (5 mL) was added 4 N HCl in dioxane (5 mL). The resulting mixture was allowed to stir overnight at rt, then was concentrated in vacuo to afford 16-2, which was used subsequently without further purification. LCMS-ESI$^+$ (m/z): [M+H]$^+$ calcd for $C_{18}H_{18}F_4N_3O_4$: 416.12. found: 415.96.

Step 3: Preparation of 16-3: To a solution of proline hydrochloride 16-2 (420 mg, 0.93 mmol) in DMF (3 mL) was added Intermediate B5 (240 mg, 0.78 mmol), HATU (324 mg, 0.853 mmol) and iPr$_2$NEt (1.35 mL, 7.76 mmol) at 23° C. After 18 h, the reaction mixture was diluted with water (50 mL) and extracted with ethyl acetate (3×25 mL). The combined organic layers were washed with water (50 mL), brine (50 mL), dried over anhydrous $MgSO_4$ and concentrated in vacuo. The resulting residue was purified via silica gel chromatography to give amide 16-3. LCMS-ESI$^+$ (m/z): [M+H]$^+$ calcd for $C_{35}H_{43}F_4N_4O_7$: 707.3. found: 707.3.

Step 4: Preparation of 16-4: To a solution of proline amide 16-3 (350 mg, 0.49 mmol) in degassed DCE (100 mL) was added Zhan 1B catalyst (50 mg, 0.0.65 mmol). The resulting solution was refluxed under $N_2$ for 1 h. The reaction mixture was then concentrated in vacuo and was purified via silica gel chromatography to produce olefin 16-4. LCMS-ESI$^+$ (m/z): [M+H]$^+$ calcd for $C_{33}H_{39}F_4N_4O_7$: 679.3. found: 679.2.

Step 5: Preparation of 16-5: To a solution of olefin 16-4 (220 mg, 0.32 mmol) in EtOH (25 mL) was added Pd/C (10 wt % Pd, 220 mg). The atmosphere of the reaction was replaced with $H_2$ and the reaction stirred at rt under 1 atm $H_2$ for 3 h. The reaction mixture was filtered through a pad of Celite which was washed with EtOH and the combined organics concentrated in vacuo. The resulting residue was purified via HPLC to give 16-5. LCMS-ESI⁺ (m/z): [M+H]⁺ calcd for $C_{33}H_{41}F_4N_4O_7$: 681.3. found: 681.3.

Step 6: Preparation of 16-6. Proline ester 16-5 was dissolved in THF (2 mL) and MeOH (1 mL). Aqueous 2 N LiOH solution (1 mL) was added and the mixture was stirred at 23° C. for 1 h. Solvents were removed in vacuo and the residue taken up in ethyl acetate (10 mL) and 1 M HCl (10 mL). Following extraction with ethyl acetate (10 mL), the combined organic layers were dried over anhydrous MgSO₄ and concentrated in vacuo to afford a residue of 16-6 which was used subsequently without further purification. LCMS-ESI⁺ (m/z): [M+H]⁺ calcd for $C_{32}H_{39}F_4N_4O_7$: 667.3. found: 667.3.

Step 7: Preparation of Example 16: To a suspension of carboxylic acid 16-6 (67.9 mg, 0.102 mmol) and Intermediate A9 (37 mg, 0.128 mmol) in DMF (1 mL) was added HATU (49 mg, 0.128 mmol) and DIPEA (177 µL, 1.02 mmol) at 23° C. The reaction mixture was allowed to stir overnight, then purified via HPLC and lyophilized to afford the TFA salt of Example 16. Analytical HPLC RetTime: 8.75 min. LCMS-ESI⁺ (m/z): [M+H]⁺ calcd for $C_{40}H_{49}F_6N_6O_9S$: 903.32. found: 903.14. ¹H-NMR (400 MHz, CDCl₃) δ 10.22 (s, 1H), 7.95-7.77 (m, 2H), 7.57 (dd, J=9.1, 2.4 Hz, 1H), 7.06 (s, 1H), 6.77 (t, J=72.9 Hz, 1H), 6.16 (s, 1H), 5.92 (td, J=55.7, 7.2 Hz, 1H), 5.26 (d, J=9.2 Hz, 1H), 4.89 (d, J=7.5 Hz, 1H), 4.53 (d, J=11.7 Hz, 1H), 4.33 (dd, J=11.0, 6.2 Hz, 1H), 4.26 (d, J=9.1 Hz, 1H), 4.08 (dd, J=11.7, 3.7 Hz, 1H), 2.98-2.78 (m, 1H), 2.57-2.27 (m, 2H), 2.25-2.12 (m, 1H), 2.12-2.04 (m, 1H), 2.03-1.94 (m, 3H), 1.94-1.81 (m, 2H), 1.82-1.66 (m, 2H), 1.64-1.42 (m, 3H), 1.42-1.18 (m, 6H), 1.07 (s, 9H), 1.05-0.93 (m, 2H), 0.58-0.46 (m, 1H), 0.46-0.36 (m, 1H).

Example 17

Preparation of (1aS,2aR,6S,9S,11R,23aR,23bS)-6-tert-butyl-N-[(1R,2R)-1-[(cyclopropylsulfonyl)carbamoyl]-2-(difluoromethyl)cyclopropyl]-19,19-difluoro-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide

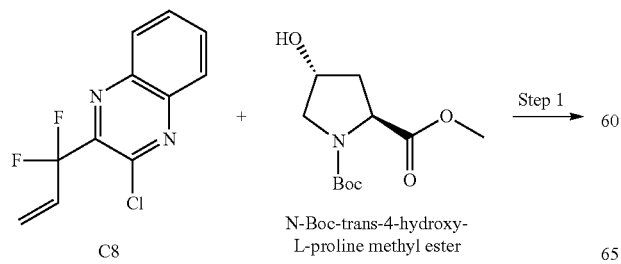

C8 + N-Boc-trans-4-hydroxy-L-proline methyl ester  →  Step 1

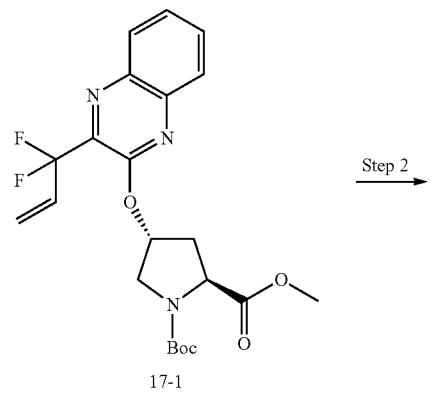

17-1  →  Step 2

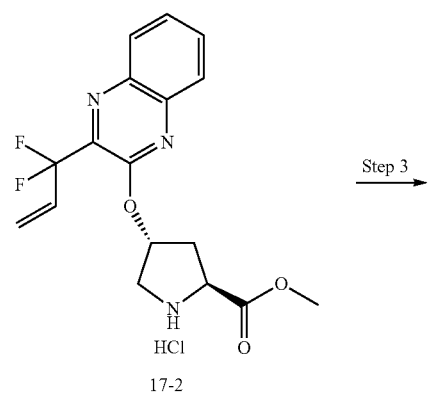

17-2  →  Step 3

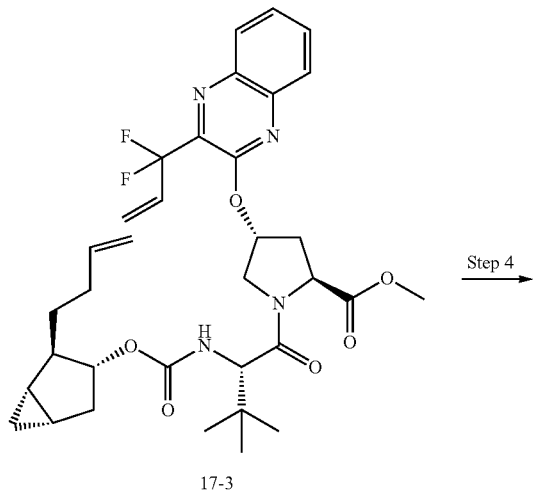

17-3  →  Step 4

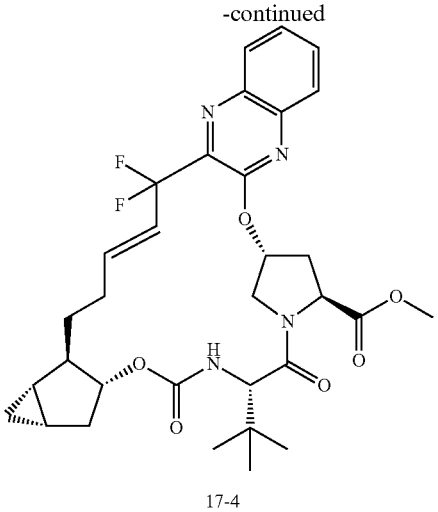

17-4

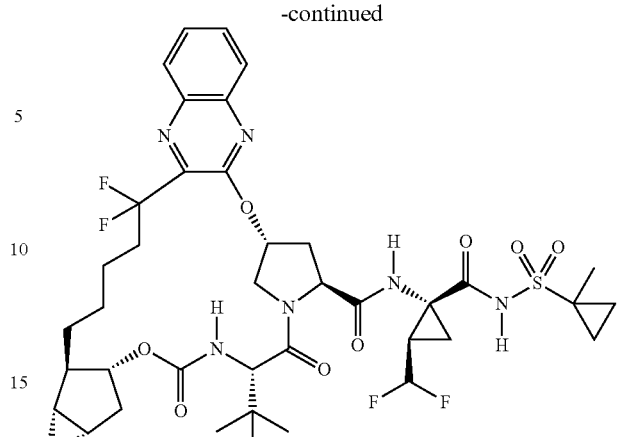

Example 17

Step 1. Preparation of 17-1: A mixture containing Intermediate C8 (0.94 g, 3.92 mmol), N-Boc-trans-4-hydroxy-L-proline methyl ester (1.48 g, 4.71 mmol), and Cs$_2$CO$_3$ (1.92 g, 5.88 mmol) in MeCN (10 mL) was stirred vigorously at 85° C. under an atmosphere of Ar for 2 h. The reaction was then filtered through a pad of Celite and the filtrate concentrated in vacuo. The crude material was purified by silica gel chromatography to provide 17-1. LCMS-ESI$^+$ (m/z): [M+H]$^+$ calcd for C$_{22}$H$_{25}$F$_2$N$_3$O$_5$: 449.2. found: 450.7.

Step 2. Preparation of 17-2: To a solution of substituted quinoxaline 17-1 in DCM (10 mL) was added hydrochloric acid in dioxane (4 M, 25 mL, 98.4 mmol) and the reaction stirred at rt for 5 h. The crude reaction was concentrated in vacuo to give 17-2 that was used in subsequent steps without further purification. LCMS-ESI$^+$ (m/z): [M+H]$^+$ calcd for C$_{17}$H$_{17}$F$_2$N$_3$O$_5$: 349.1. found: 350.1.

Step 3. Preparation of 17-3: To a solution of proline HCl salt 17-2 (1.00 g, 2.59 mmol) in DMF (26 mL) were added Intermediate B5 (0.82 g, 2.85 mmol) in DMF, HATU (1.18 g, 3.11 mmol) and DIPEA (2.48 mL, 14.26 mmol) at 23° C. After 40 h, the reaction was diluted with water (50 mL) and extracted with ethyl acetate (3×20 mL). Combined organic layers were washed with water (50 mL), brine (25 mL), dried over anhydrous Na$_2$SO$_4$ and concentrated in vacuo. The crude material was purified by silica gel chromatography to provide 17-3. LCMS-ESI$^+$ (m/z): [M+H]$^+$ calcd for C$_{34}$H$_{42}$F$_2$N$_4$O$_6$: 640.31. found: 641.36.

Step 4. Preparation of 17-4: To a solution of diene 17-3 (1.38 g, 2.25 mmol) in degassed DCE (430 mL) was added Zhan 1B catalyst (158 mg, 0.215 mmol) and degassed for an additional 1 h. The resulting reaction mixture was refluxed under Ar for 1 h, cooled to rt and concentrated in vacuo. The crude material was purified by silica gel chromatography to provide macrocycle 17-4. LCMS-ESI$^+$ (m/z): [M+H]$^+$ calcd for C$_{32}$H$_{38}$F$_2$N$_4$O$_6$: 612.28. found: 613.31.

Step 5. Preparation of 17-5: To a solution of macrocycle 17-4 (1.18 g, 1.92 mmol) in EtOH (7 mL) was added Pd/C (10 wt % Pd, 500 mg). The reaction vessel was purged twice with H$_2$ and was stirred at rt under 1 atm H$_2$ overnight. The reaction mixture was then heated to 50° C. and stirred for an additional 24 h. The reaction mixture was filtered through a pad of Celite and concentrated in vacuo. The crude material was redissolved in dioxane (25 mL) and treated with DDQ (525 mg, 2.31 mmol). After 1 h, the solvent was removed in vacuo and the resulting residue purified by silica gel chromatography to provide the macrocycle 17-5. LCMS-ESI⁺ (m/z): [M+H]⁺ calcd for $C_{32}H_{40}F_2N_4O_6$: 614.29. found: 615.17).

Step 6. Preparation of 17-6: Macrocycle 17-5 (1.0 g, 1.63 mmol) was dissolved in THF (25 mL). LiOH (1.0 M, 25 mL, 25 mmol) was added and the reaction mixture was stirred for 5 h at rt. The reaction was concentrated in vacuo and then diluted with ethyl acetate (100 mL) and 1 M HCl (60 mL). The layers were separated and the aqueous layer extracted with ethyl acetate (50 mL). The combined organic layer was dried over anhydrous $Na_2SO_4$ and concentrated in vacuo to provide 17-6 as a residue that was used without further purification. LCMS-ESI⁺ (m/z): [M+H]⁺ calcd for $C_{31}H_{38}F_2N_4O_6$: 600.28. found: 601.16).

Step 7. Preparation of Example 17: To a suspension of carboxylic acid 17-6 (350 mg, 0.583 mmol) and Intermediate A10 (259 mg, 0.850 mmol) in MeCN (7 mL) was added HATU (323 mg, 0.850 mmol) and DIPEA (542 μL, 3.11 mmol) at 23° C. After 45 min, the solution was concentrated and purified by reverse phase HPLC, then silica gel chromatography. TFA was added and the sample lyophilized to provide the TFA salt of Example 17. Analytical HPLC RetTime: 8.77 min. LCMS-ESI⁺ (m/z): [M+H]⁺ calcd for $C_{40}H_{51}F_4N_6O_8S$: 851.93. found: 851.31. ¹H-NMR (400 MHz, CDCl3) δ 9.83 (s, 1H), 8.13 (d, 1H), 7.86 (d, 1H), 7.77 (dd, 1H), 7.67 (dd, 1H), 7.17 (s, 1H), 6.22 (t, 1H), 5.91 (td, 1H), 4.89 (d, 1H), 4.52 (d, 1H), 4.38-4.33 (m, 1H), 4.26 (d, 1H), 4.08 (dd, 1H), 2.51-2.34 (m, 3H), 2.10-1.94 (m, 5H), 1.87-1.29 (m, 15H), 1.08-1.01 (m, 10H), 0.87 (m, 2H), 0.53-0.50 (m, 1H), 0.44-0.43 (m, 1H).

Example 18

Preparation of (1aS,2aR,6S,9S,11R,23aR,23bS)-6-tert-butyl-N-[(1R,2R)-2-(difluoromethyl)-1-{[(1-methylcyclopropyl)sulfonyl]carbamoyl}cyclopropyl]-19,19-difluoro-4,7-dioxo-1a,2,2a,4,5,6,7,10,11,19,20,21,22,23,23a, 23b-hexadecahydro-1H,9H-8,11-methanocyclopropa[4′,5′]cyclopenta[1′,2′:18,19][1,10,3,6]dioxadiazacyclononadecino[11,12-b]quinoxaline-9-carboxamide Example 18

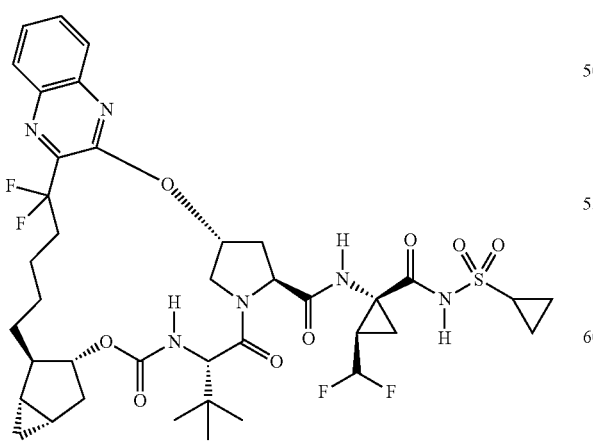

Example 18 was prepared in a similar fashion to Example 17, substituting Intermediate A9 for Intermediate A10 in Step 7. Example 18 (234 mg) was isolated as a TFA salt. Analytical HPLC RetTime: 8.87 min. LCMS-ESI⁺ (m/z): [M+H]⁺ calcd for $C_{39}H_{49}F_4N_6O_8S$: 837.33. found: 837.26. ¹H-NMR (400 MHz, CDCl3) δ 10.21 (s, 1H), 8.13 (d, 1H), 7.86 (d, 1H), 7.77 (dd, 1H), 7.67 (dd, 1H), 7.24 (s, 1H), 6.22 (t, 1H), 5.91 (dt, 1H), 5.36 (d, 1H), 4.89 (d, 1H), 4.51 (d, 1H), 4.37-4.33 (m, 1H), 4.27 (d, 1H), 4.08 (dd, 1H), 2.93-2.87 (m, 1H), 2.50-2.32 (m, 3H), 2.10-1.91 (m, 5H), 1.80-1.25 (m, 13H), 1.08-1.01 (m, 10H), 0.53-0.50 (m, 1H), 0.44-0.43 (m, 1H).

Example 19

Preparation of (1aS,2aR,6S,9S,11R,23aR,23bS)-6-tert-butyl-15-chloro-N-[(1R,2R)-1-[(cyclopropylsulfonyl)carbamoyl]-2-(difluoromethyl)cyclopropyl]-4,7-dioxo-1a,2,2a,4,5,6,7,10,11,19,20,21,22,23,23a,23b-hexadecahydro-1H,9H-8,11-methanocyclopropa[4′,5′]cyclopenta[1′,2′:18,19][1,10,3,6]dioxadiazacyclononadecino[11,12-b]quinoxaline-9-carboxamide

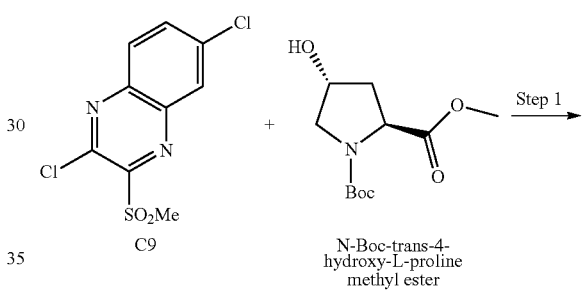

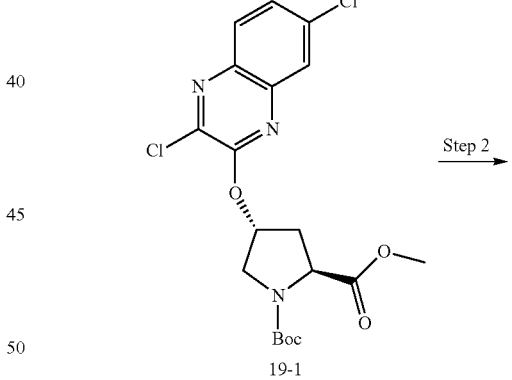

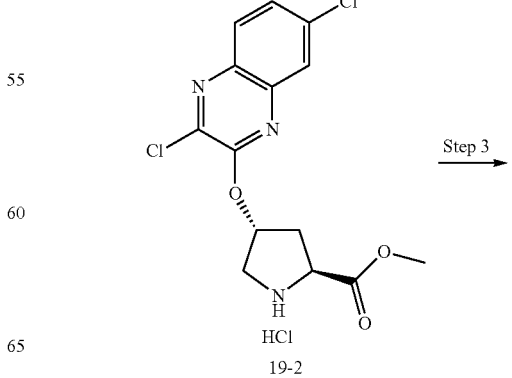

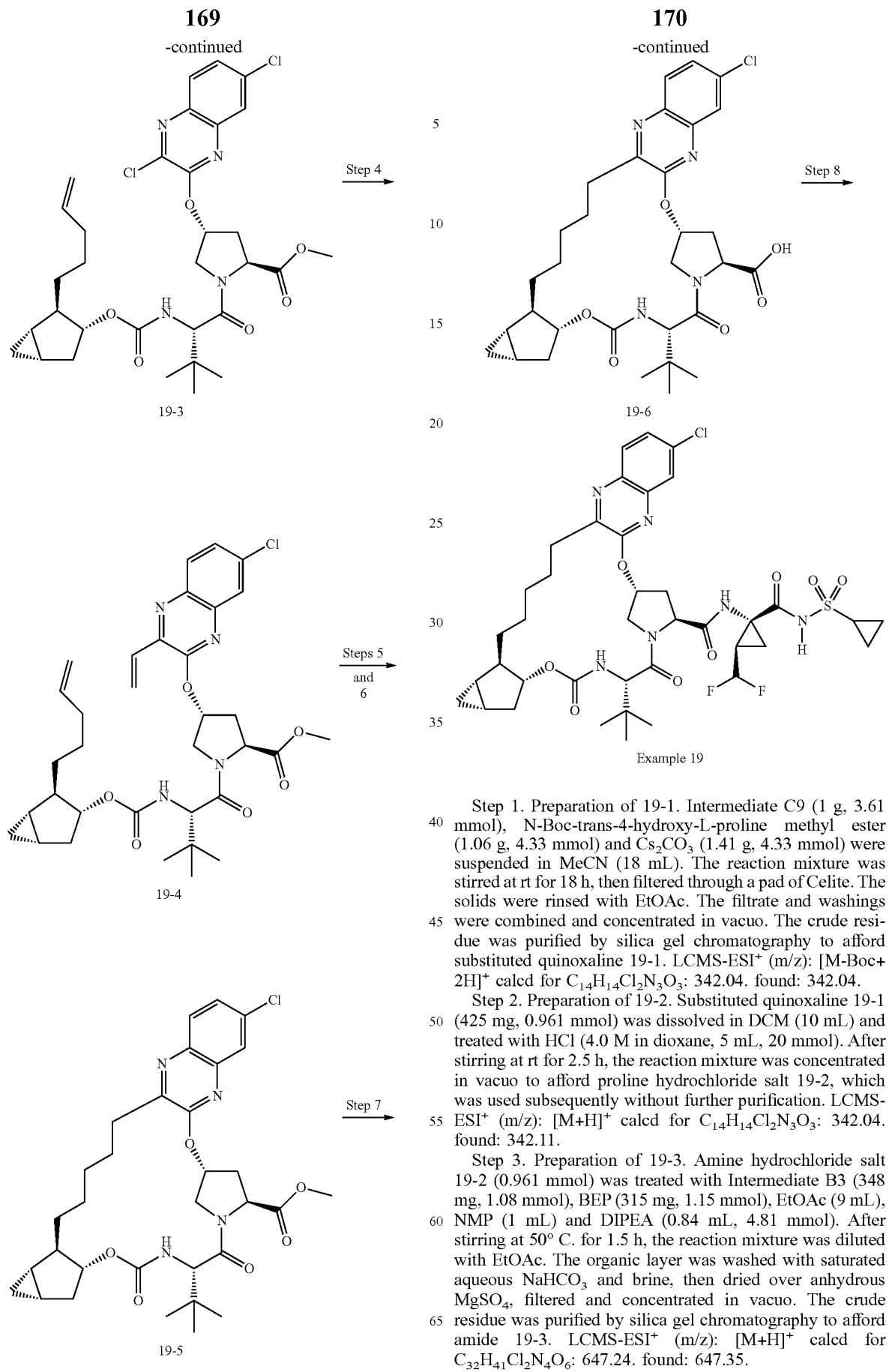

Example 19

Step 1. Preparation of 19-1. Intermediate C9 (1 g, 3.61 mmol), N-Boc-trans-4-hydroxy-L-proline methyl ester (1.06 g, 4.33 mmol) and $Cs_2CO_3$ (1.41 g, 4.33 mmol) were suspended in MeCN (18 mL). The reaction mixture was stirred at rt for 18 h, then filtered through a pad of Celite. The solids were rinsed with EtOAc. The filtrate and washings were combined and concentrated in vacuo. The crude residue was purified by silica gel chromatography to afford substituted quinoxaline 19-1. LCMS-ESI$^+$ (m/z): [M-Boc+2H]$^+$ calcd for $C_{14}H_{14}Cl_2N_3O_3$: 342.04. found: 342.04.

Step 2. Preparation of 19-2. Substituted quinoxaline 19-1 (425 mg, 0.961 mmol) was dissolved in DCM (10 mL) and treated with HCl (4.0 M in dioxane, 5 mL, 20 mmol). After stirring at rt for 2.5 h, the reaction mixture was concentrated in vacuo to afford proline hydrochloride salt 19-2, which was used subsequently without further purification. LCMS-ESI$^+$ (m/z): [M+H]$^+$ calcd for $C_{14}H_{14}Cl_2N_3O_3$: 342.04. found: 342.11.

Step 3. Preparation of 19-3. Amine hydrochloride salt 19-2 (0.961 mmol) was treated with Intermediate B3 (348 mg, 1.08 mmol), BEP (315 mg, 1.15 mmol), EtOAc (9 mL), NMP (1 mL) and DIPEA (0.84 mL, 4.81 mmol). After stirring at 50° C. for 1.5 h, the reaction mixture was diluted with EtOAc. The organic layer was washed with saturated aqueous $NaHCO_3$ and brine, then dried over anhydrous $MgSO_4$, filtered and concentrated in vacuo. The crude residue was purified by silica gel chromatography to afford amide 19-3. LCMS-ESI$^+$ (m/z): [M+H]$^+$ calcd for $C_{32}H_{41}Cl_2N_4O_6$: 647.24. found: 647.35.

Step 4. Preparation of 19-4. Chloroquinoxaline 19-3 (281 mg, 0.434 mmol) was treated with potassium vinyltrifluoroborate (87 mg, 0.651 mmol), Pd(dppf)Cl$_2$·DCM adduct (35 mg, 0.043 mmol), EtOH (4 mL) and Et$_3$N (0.091 mL, 0.65 mmol). The stirred reaction mixture was heated to reflux for 1 h, then cooled to rt and diluted with EtOAc. The organic mixture was washed with H$_2$O and brine, then dried over anhydrous MgSO$_4$, filtered and concentrated in vacuo. The crude residue was purified by silica gel chromatography to afford vinyl quinoxaline 19-4. LCMS-ESI$^+$ (m/z): [M+H]$^+$ calcd for C$_{34}$H$_{44}$ClN$_4$O$_6$: 639.29; found: 639.86.

Steps 5 and 6. Preparation of 19-5. Vinyl quinoxaline 19-4 (203 mg, 0.318 mmol) was combined with Zhan Catalyst-1B (21 mg, 0.032 mmol) in DCE (64 mL). The suspension was degassed for 20 min with bubbling N$_2$ then heated to reflux for 40 min. After cooling to rt, the mixture was concentrated in vacuo. The crude mixture was purified by silica gel chromatography to afford macrocycle 19-5 (110 mg; LCMS-ESI$^+$ (m/z): [M+H]$^+$ calcd for C$_{32}$H$_{40}$ClN$_4$O$_6$: 611.26. found: 611.30). This residue (109 mg, 0.178 mmol) was dissolved in EtOAc (40 mL) and treated with 5% Rh/Al$_2$O$_3$ (40 mg). H$_2$ was bubbled through the suspension for 1 min then the reaction mixture was allowed to stir under an H$_2$ atmosphere for 1 h. After this period, more 5% Rh/Al$_2$O$_3$ (80 mg) was added to the reaction mixture. H$_2$ was bubbled through the suspension for 1 min and the reaction mixture was allowed to stir under an H$_2$ atmosphere for an additional 1 h. The reaction mixture was filtered through Celite, then concentrated in vacuo to produce the methyl ester 19-5 which was carried on without further purification. LCMS-ESI$^+$ (m/z): [M+H]$^+$ calcd for C$_{32}$H$_{42}$ClN$_4$O$_6$: 613.28. found: 613.29.

Step 7. Preparation of 19-6. Methyl ester 19-5 (0.187 mmol) was treated with THF (10 mL) and LiOH (1.0 M in H$_2$O, 10 mL, 10 mmol). The reaction mixture was stirred for 3 h then concentrated in vacuo to remove THF. The remaining suspension was poured into 10% HCl. The aqueous layer was then extracted 3× with DCM. The combined organics were dried over anhydrous MgSO$_4$, filtered and concentrated in vacuo to afford carboxylic acid 19-6 which was carried on without further purification. LCMS-ESI$^+$ (m/z): [M+H]$^+$ calcd for C$_{31}$H$_{40}$ClN$_4$O$_6$: 599.26. found: 599.04.

Step 8. Preparation of Example 19. In DMF (2 mL), carboxylic acid 19-6 (110 mg, 0.184 mmol) was combined with A9 (80 mg, 0.28 mmol), HATU (84 mg, 0.22 mmol) and DIPEA (0.16 mL, 0.92 mmol). The reaction mixture was stirred at rt for 1 h then quenched by addition of 1 mL H$_2$O. The aqueous suspension was filtered and purified by HPLC to afford Example 19 as a TFA salt. This material contained an impurity, thus it was dissolved in EtOAc and the organic solution was washed 2× with saturated aqueous NaHCO$_3$ in order to free base the material. The organic layer was dried over MgSO$_4$, filtered and concentrated in vacuo. The resulting residue was purified by silica gel chromatography to afford Example 19. Analytical HPLC RetTime: 9.30 min. LCMS-ESI$^+$ (m/z): [M+H]$^+$ calcd for C$_{39}$H$_{50}$ClF$_2$N$_6$O$_8$S: 835.31. found: 835.44. $^1$H-NMR (400 MHz, CD$_3$OD) δ 7.93-7.84 (m, 1H), 7.83-7.76 (m, 1H), 7.61-7.51 (m, 1H), 6.87 (d, J=9.3 Hz, 1H), 5.95 (m, J=62.1, 31.3, 5.0 Hz, 2H), 4.99 (d, J=7.5 Hz, 1H), 4.52-4.37 (m, 2H), 4.32 (d, J=9.3 Hz, 1H), 4.11 (dd, J=11.9, 3.8 Hz, 1H), 3.08-2.90 (m, 2H), 2.81 (ddd, J=14.0, 11.6, 4.6 Hz, 1H), 2.50 (dd, J=13.9, 6.2 Hz, 1H), 2.37-2.12 (m, 2H), 1.97 (ddd, J=15.4, 10.2, 3.6 Hz, 3H), 1.85 (dd, J=12.0, 7.7 Hz, 1H), 1.75 (d, J=14.6 Hz, 1H), 1.71-1.20 (m, 13H), 1.17-0.97 (m, 12H), 0.97-0.79 (m, 1H), 0.57 (dd, J=8.6, 4.1 Hz, 1H), 0.54-0.45 (m, 1H).

Example 20

Preparation of (1aS,2aR,6S,9S,11R,23aR,23bS)-6-tert-butyl-N-[(1R,2S)-2-(2,2-difluoroethyl)-1-{[(1-methylcyclopropyl)sulfonyl]carbamoyl}cyclopropyl]-19,19-difluoro-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoxaline-9-carboxamide Example 20

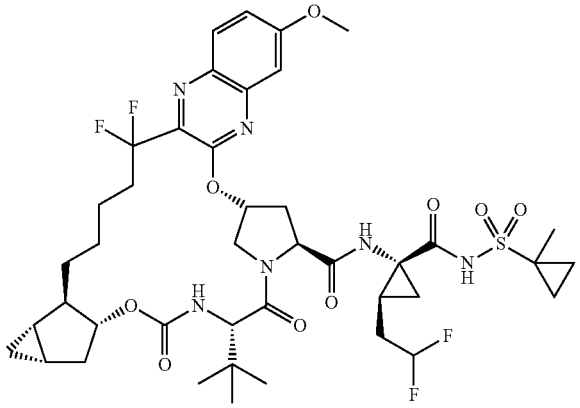

Example 20 was prepared in a similar fashion to Example 9, substituting Intermediate A8 for Intermediate A9 in Step 7. Example 20 (9.4 mg) was isolated as a TFA salt. Analytical HPLC RetTime: 8.90 min. LCMS-ESI$^+$ (m/z): [M+H]$^+$ calcd for C$_{42}$H$_{55}$F$_2$N$_6$O$_9$S: 895.36. found: 895.64. $^1$H-NMR (400 MHz, CD$_3$OD) δ 9.23 (s, 1H), 7.93 (d, J=9.0 Hz, 1H), 7.39-7.24 (m, 2H), 6.15 (s, 1H), 5.89 (tt, J=57.4, 4.2 Hz, 1H), 4.94 (d, J=7.5 Hz, 1H), 4.45 (dd, J=11.2, 5.8 Hz, 2H), 4.32 (s, 1H), 4.13 (dd, J=12.0, 3.7 Hz, 1H), 3.96 (s, 3H), 2.63-2.44 (m, 2H), 2.31-1.91 (m, 6H), 1.84-1.70 (m, 2H), 1.71-1.25 (m, 15H), 1.06 (s, 10H), 0.96-0.84 (m, 2H), 0.59-0.48 (m, 2H).

Example 21
Preparation of (1aS,2aR,6S,9S,11R,23aR,23bS)-6-tert-butyl-N-[(1R,2R)-1-[(cyclopropylsulfonyl)carbamoyl]-2-(difluoromethyl)cyclopropyl]-15-methoxy-4,7-dioxo-1a,2,2a,4,5,6,7,10,11,19,20,21,22,23,23a,23b-hexadecahydro-1H,9H-8,11-methanocyclopropa[4',5']cyclopenta[1',2':18,19][1,10,3,6]dioxadiazacyclononadecino[11,12-b]quinoline-9-carboxamide
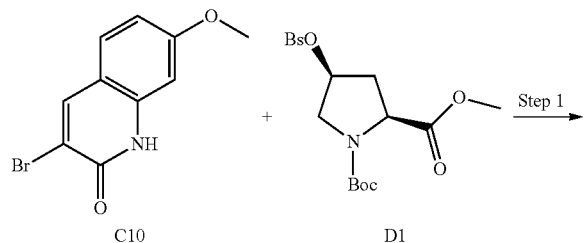
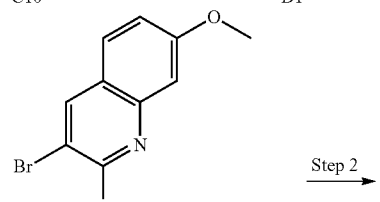
21-1
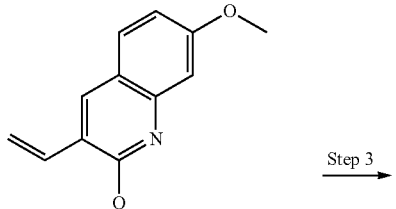
21-2
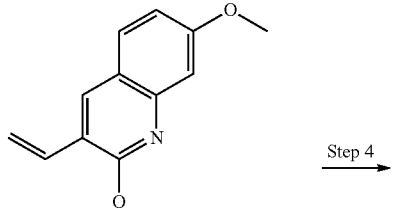
21-3
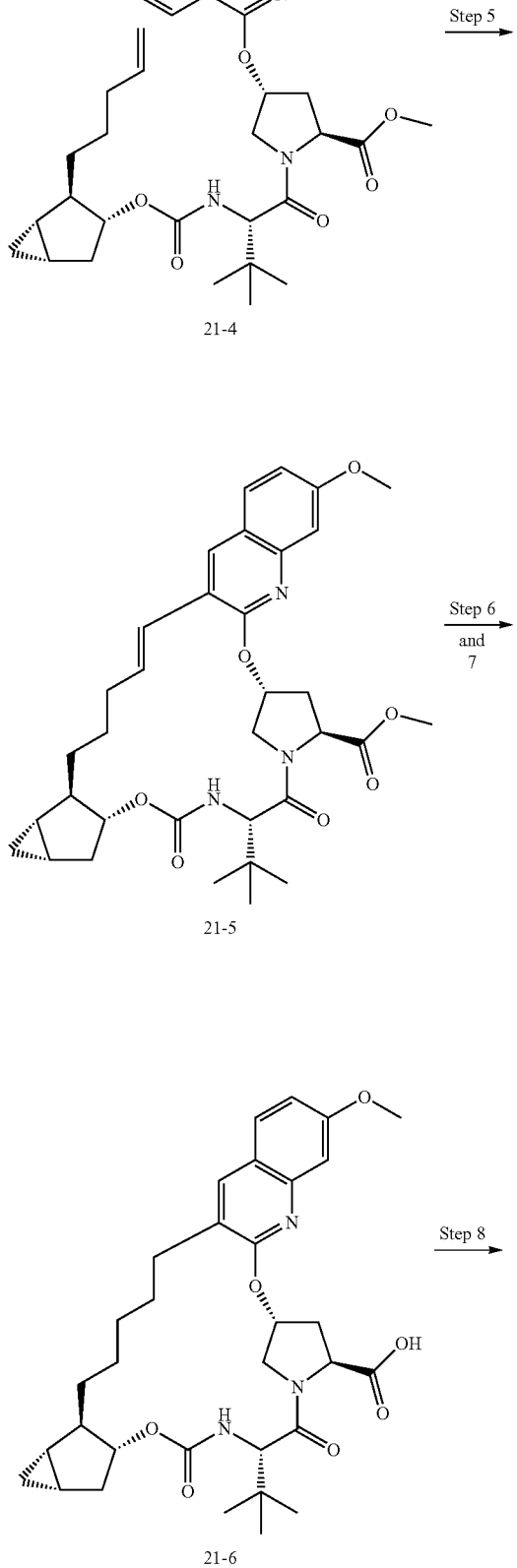

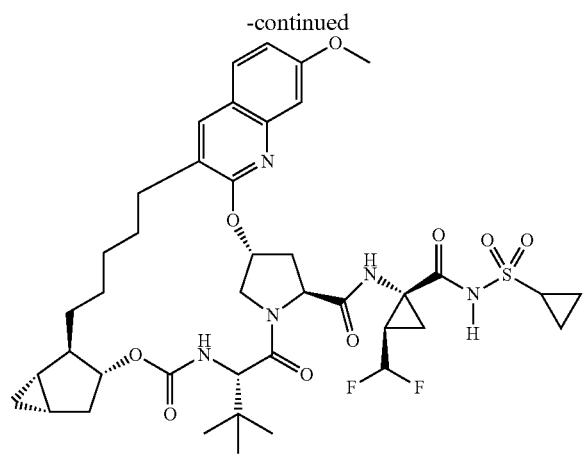

Example 21

Step 1. Preparation of 21-1. Intermediate C10 (1 g, 3.92 mmol) was combined with Intermediate D1 (1.51 g, 3.24 mmol) and Cs$_2$CO$_3$ (1.92 g, 5.88 mmol) as a suspension in NMP (30 mL) and warmed to 40° C. After 16 h the reaction was cooled to rt, diluted with EtOAc and washed successively with H$_2$O, saturated aqueous NaHCO$_3$, and brine. The organic phase was dried over anhydrous MgSO$_4$, filtered and concentrated in vacuo to afford 21-1 which was used subsequently without further purification. LCMS-ESI$^+$ (m/z): [M+H]$^+$ calcd for C$_{21}$H$_{26}$BrN$_2$O$_6$: 481.10. found: 480.95.

Step 2. Preparation of 21-2. Bromoquinoline 21-1 (1.48 g, 3.07 mmol) was treated with potassium vinyltrifluoroborate (618 mg, 4.61 mmol), Pd(dppf)Cl$_2$.DCM (125 mg, 0.15 mmol), EtOH (30 mL) and Et$_3$N (0.63 mL, 4.61 mmol). The reaction mixture was stirred at reflux for 1.5 h then cooled to rt and diluted with EtOAc. The organic phase was washed with water and brine then dried over anhydrous MgSO$_4$, filtered and concentrated in vacuo. The crude residue was purified by silica gel chromatography (10% to 40% EtOAc/Hex) to afford vinylquinoline 21-2. LCMS-ESI$^+$ (m/z): [M+H]$^+$ calcd for C$_{23}$H$_{29}$N$_2$O$_6$: 429.20. found: 429.44.

Step 3. Preparation of 21-3. Vinyl quinoline 21-2 (920 mg, 2.15 mmol) was dissolved in DCM (5 mL) and MeOH (1 mL) and treated with HCl (4.0 M in dioxane, 5 mL). After stirring at rt for 3 h, the reaction mixture was concentrated in vacuo to afford amine hydrochloride 21-3 which was carried on without further purification. LCMS-ESI$^+$ (m/z): [M+H]$^+$ calcd for C$_{18}$H$_{21}$N$_2$O$_4$: 329.15. found: 329.2.

Step 4. Preparation of 21-4. Amine hydrochloride 21-3 (358 mg, 0.96 mmol) and Intermediate B3 (310 mg, 0.96 mmol) were combined and treated with BEP (289 mg, 1.06 mmol), EtOAc (9 mL), NMP (1 mL) and DIPEA (0.50 mL, 2.88 mmol). After stirring at 40° C. for 1.5 h, additional DIPEA (0.2 mL, 1.15 mmol) was added and the mixture was stirred an additional 30 min. After cooling to rt, the reaction mixture was diluted with EtOAc and washed successively with saturated aqueous NaHCO$_3$ and brine. The organic phase was dried over anhydrous MgSO$_4$, filtered and concentrated in vacuo. The crude residue was purified by silica gel chromatography (10% to 40% EtOAc/Hex) to afford amide 21-4. LCMS-ESI$^+$ (m/z): [M+H]$^+$ calcd for C$_{36}$H$_{48}$N$_3$O$_7$: 634.35. found: 634.47.

Step 6. Preparation of 21-5. Vinylquinoline 21-4 (358 mg, 0.56 mmol) was dissolved in DCE (100 mL) and treated with Zhan Catalyst-1B (41 mg, 0.06 mmol). The mixture was degassed with bubbling N$_2$ for 30 min the heated to reflux for 45 min. The reaction mixture was concentrated in vacuo and the crude residue was purified by silica gel chromatography (0% to 30% EtOAc/Hex) to afford macrocycle 21-5. LCMS-ESI$^+$ (m/z): [M+H]$^+$ calcd for C$_{34}$H$_{44}$N$_3$O$_7$: 606.32; found: 606.16.

Steps 6 and 7. Preparation of 21-6. Macrocycle 21-5 (235 mg, 0.39 mmol) was dissolved in EtOH (6 mL). Pd/C (10 wt % Pd, 200 mg) was added and H$_2$ was bubbled through the suspension for 2 min. The stirred reaction mixture was maintained under 1 atm of H$_2$ for 45 min before being filtered over Celite and concentrated in vacuo. This residue was used subsequently without further purification. (LCMS-ESI$^+$ (m/z): [M+H]$^+$ calcd for C$_{32}$H$_{42}$FN$_4$O$_6$: 597.31. found: 597.36). This residue (0.39 mmol theoretical) was treated with THF (3 mL), H$_2$O (3 mL), and LiOH (28 mg, 1.17 mmol). The mixture was stirred for 1 h then diluted with EtOAc. The mixture was acidified to pH 3 with 1 N HCl and extracted 3× with EtOAc. The combined organics were washed with brine and dried over anhydrous MgSO$_4$, filtered and concentrated in vacuo to afford carboxylic acid 21-6 which was used subsequently without further purification. LCMS-ESI$^+$ (m/z): [M+H]$^+$ calcd for C$_{33}$H$_{44}$N$_3$O$_7$: 594.32. found: 594.50.

Step 8. Preparation of Example 21. Carboxylic acid 21-6 (175 mg, 0.30 mmol) was treated with Intermediate A9 (113 mg, 0.39 mmol), TBTU (140 mg, 0.44 mmol), DMAP (55 mg, 0.45 mmol), DCM (5 mL) and DIPEA (0.16 mL, 0.90 mmol). The reaction mixture was stirred for 1.5 h, and additional DIPEA (0.10 mL, 0.55 mmol) was added. After stirring for 30 min, the mixture was diluted with EtOAc, washed with saturated aqueous NaHCO$_3$, and brine. The organic phase was dried over anhydrous MgSO$_4$, filtered and concentrated in vacuo. The crude residue was purified by HPLC to afford Example 21 as a TFA salt. Analytical HPLC RetTime: 9.17 min. LCMS-ESI$^+$ (m/z): [M+H]$^+$ calcd for C$_{41}$H$_{54}$F$_2$N$_5$O$_9$S: 830.36. found: 830.55. $^1$H-NMR (400 MHz, CD$_3$OD) δ 9.36 (s, 1H), 7.84 (s, 1H), 7.62 (d, J=8.9 Hz, 1H), 7.19 (d, J=2.4 Hz, 1H), 7.02 (dd, J=8.9, 2.5 Hz, 1H), 6.11 (t, J=3.6 Hz, 1H), 5.90 (td, J=55.8, 6.6 Hz, 1H), 5.49 (s, 1H), 5.03 (d, J=7.6 Hz, 1H), 4.40 (dd, J=12.0, 6.9 Hz, 3H), 4.10 (dd, J=11.6, 3.9 Hz, 1H), 3.90 (s, 3H), 3.06-2.91 (m, 1H), 2.74 (m, 1H), 2.60-2.40 (m, 2H), 2.30-2.13 (m, 2H), 2.09-1.89 (m, 5H), 1.81-1.18 (m, 13H), 1.16-1.09 (m, 2H), 1.05 (d, J=14.4 Hz, 9H), 0.62-0.45 (m, 2H).

Example 22

Preparation of (33R,35S,91S,93R,94R,95S,5S)-5-(tert-butyl)-N-((1R,2R)-2-(difluoromethyl)-1-(((1-methylcyclopropyl)sulfonyl)carbamoyl)cyclopropyl)-4,7-dioxo-2,8-dioxa-6-aza-1(2,3)-benzo[f]quinoxalina-3(3,1)-pyrrolidina-9(3,4)-bicyclo[3.1.0]hexanacyclotetradecaphane-35-carboxamide

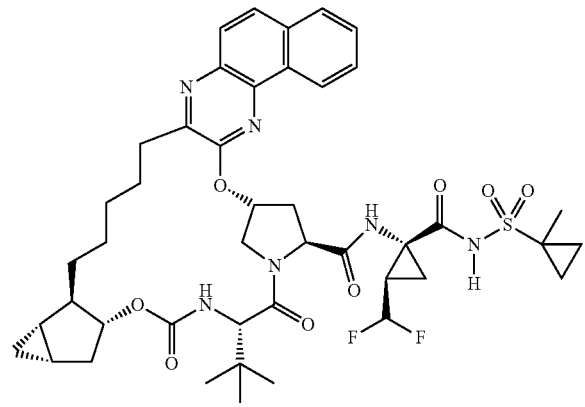

Example 22

Example 22 was prepared similarly to example 11, substituting intermediate C13 for intermediate C3 in step 1. Example 22 was isolated as a TFA salt (53 mg). Analytic HPLC RetTime: 9.63 min. LCMS-ESI$^+$ (m/z): [M+H]$^+$ calcd for $C_{44}H_{55}F_2N_6O_8S$: 865.38. found: 865.51.

Example 23

Preparation of (33R,35S,91S,93R,94R,95S,5S)-5-(tert-butyl)-17-cyano-N-((1R,2R)-2-(difluoromethyl)-1-(((1-methylcyclopropyl)sulfonyl)carbamoyl)cyclopropyl)-4,7-dioxo-2,8-dioxa-6-aza-1(2,3)-quinoxalina-3(3,1)-pyrrolidina-9(3,4)-bicyclo[3.1.0]hexanacyclotetradecaphane-35-carboxamide

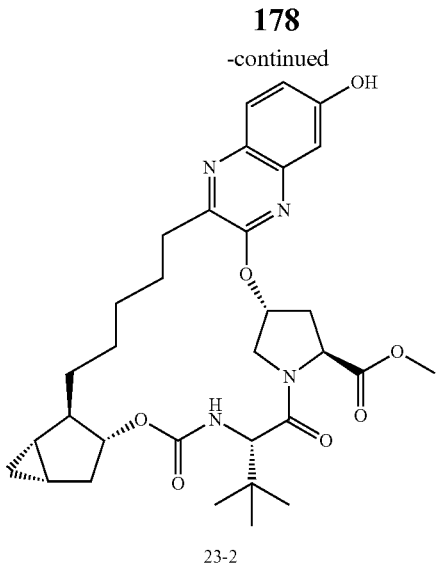

23-2

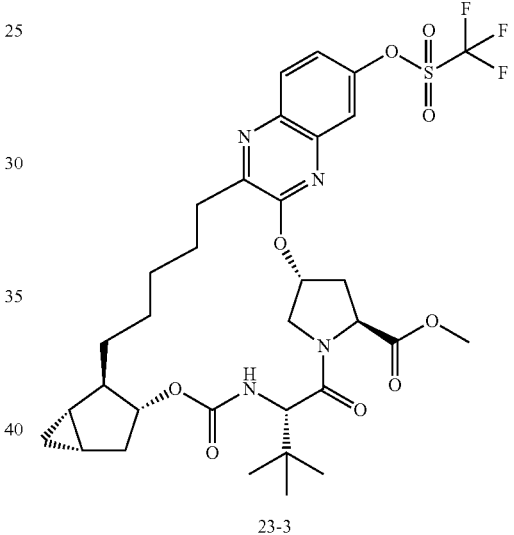

23-3

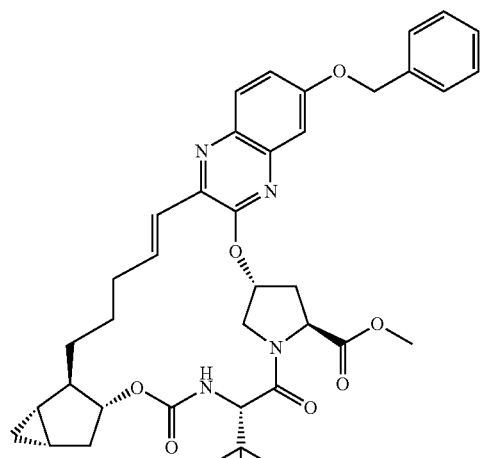

23-1

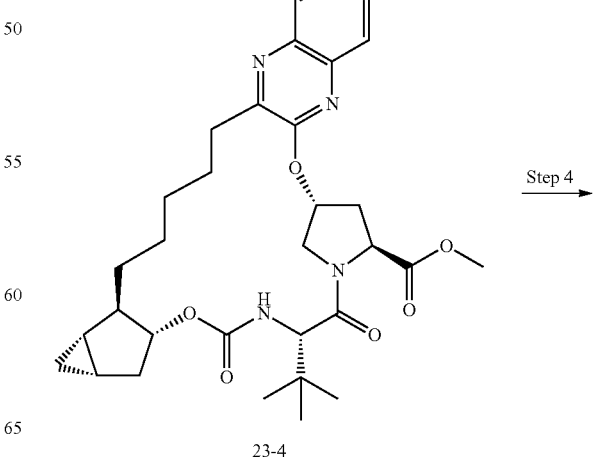

23-4

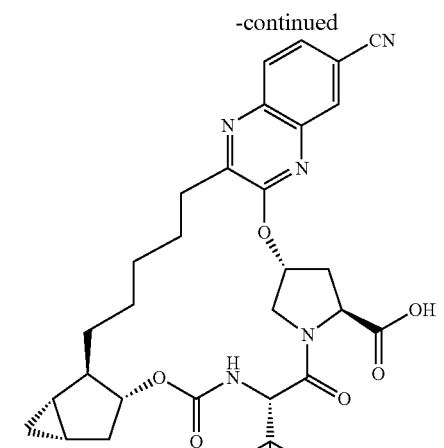

23-5

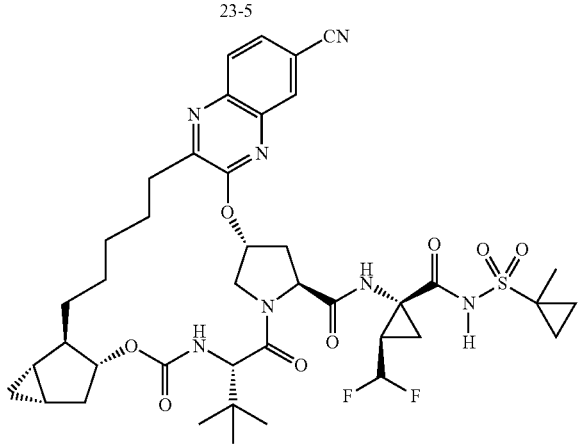

Example 23

Intermediate 23-1 was prepared as for Intermediate 11-5, using intermediate C11 in place of Intermediate C3 in step 1. LCMS-ESI+ (m/z): [M+H]+ calcd for $C_{39}H_{47}N_4O_2$: 683.34. found: 683.39.

Step 1. Preparation of 23-2: A mixture of Intermediate 23-1 (318 mg, 0.466 mmol), in 46 mL ethanol and 46 mL ethyl acetate was hydrogenated over 318 mg of 10% palladium on carbon. After 4 hours, the mixture was filtered over Celite and the filtrate was concentrated was concentrated under reduced pressure. The resulting residue was purified by silica gel chromatography (5-60% ethyl acetate in hexanes) to yield 23-2 (245 mg). LCMS-ESI+ (m/z): [M+H]+ calcd for $C_{32}H_{43}N_4O_7$: 595.31. found: 595.23.

Step 2. Preparation of 23-3: A mixture of Intermediate 23-2 (245 mg, 0.412 mmol), in 1.6 mL of dichloromethane was chilled in an ice bath before addition of triethylamine (0.459 mL, 3.3 mmol)) and then trifluoromethanesulfonic anhydride (0.104 mL, 0.618 mmol). The mixture was allowed to stir and come to room temperature. Once complete, the reaction was quenched with water and the product was extracted into ethyl acetate. The organic layer was dried over anhydrous sodium sulphate, filtered, and concentrated under reduced pressure. The resulting residue was purified by silica gel chromatography (25-75% ethyl acetate in hexanes) to yield 23-3 (245 mg). LCMS-ESI+ (m/z): [M+H]+ calcd for $C_{33}H_{42}F_3N_4O_9S$: 727.26. found: 727.33.

Step 3. Preparation of 23-4: A mixture of Intermediate 23-3 (158 mg, 0.217 mmol), tetrakis(triphenylphosphine) palladium 2.0 M in ether (25.12 mg, 0.02 mmol), and zinc cyanide, 98% (51.07 mg, 0.43 mmol) in 1 mL of dimethylformamide was degassed with argon for 10 minutes, then heated at 80° C. for 30 minutes. The mixture was then concentrated under reduced pressure. The resulting residue was purified by silica gel chromatography (5-70% ethyl acetate in hexanes) to yield 23-4 (122 mg). LCMS-ESI+ (m/z): [M+H]+ calcd for $C_{33}H_{42}N_5O_6$: 604.31. found: 604.03.

Step 4. Preparation of 23-5: A mixture of Intermediate 23-4 (120 mg, 0.199 mmol) in 1.5 mL tetrahydrofuran and 1.0 mL water was treated with lithium hydroxide monohydrate (33.36 mg, 0.8 mmol). After 6 hours, 1 mL of 2 N hydrochloric acid was added and the mixture was concentrated under reduced pressure. The resulting residue was partitioned between water and ethyl acetate, adding 2 N hydrochloric acid dropwise to ensure acidity. The organic phase was dried over anhydrous sodium sulphate, filtered, concentrated to yield 23-5 (101 mg). LCMS-ESI+ (m/z): [M+H]+ calcd for $C_{32}H_{40}N_5O_6$: 590.30. found: 590.15.

Step 5. Preparation of 23-6: To a suspension of carboxylic acid 23-5 (95 mg, 0.161 mmol) and Intermediate A10 (59 mg, 0.193 mmol) in DMF (0.8 mL) was added HATU (74 mg, 0.193 mmol) and DIPEA (113 µL, 0.644 mmol) at 23° C. After 10 min, the solution was treated with 0.5 mL formic acid and purified by reverse phase HPLC to provide the TFA salt of Example 23. Analytical HPLC RetTime: 8.86 min. LCMS-ESI+ (m/z): [M+H]+ calcd for $C_{41}H_{52}F_4N_7O_8S$: 840.177; found: 840.29.

Example 24

Preparation of (1aS,2aR,6S,9S,11R,24aR,24bS)-6-tert-butyl-N-[(1R,2R)-2-(difluoromethyl)-1-{[(1-methylcyclopropyl)sulfonyl]carbamoyl}cyclopropyl]-4,7,18-trioxo-1a,2,2a,4,5,6,7,10,11,20,21,22,23,24,24a,24b-hexadecahydro-1H,9H,18H-8,11-methanocyclopropa[4',5']cyclopenta[1',2':18,19][1,10,3,6,12]dioxatriazacyclonona decino[11,12-b]quinazoline-9-carboxamide

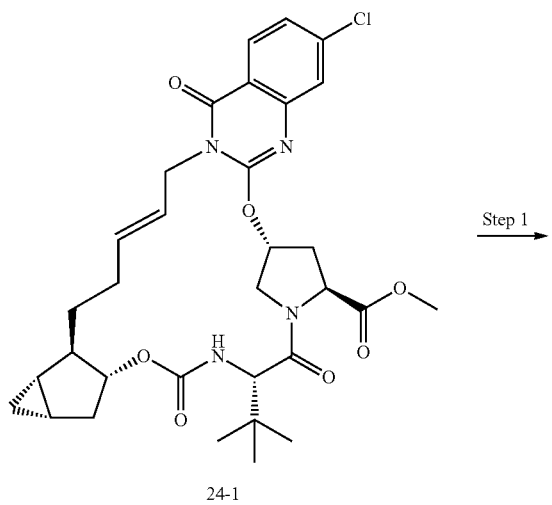

24-1

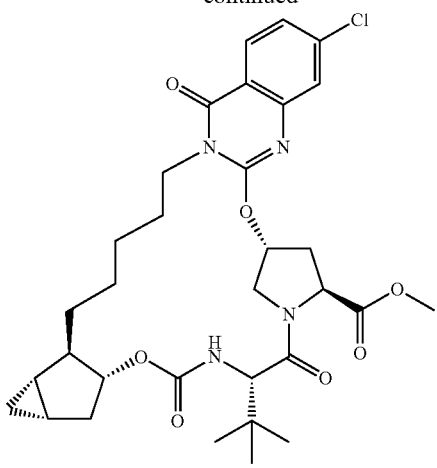

25-1
see example 25 and 26

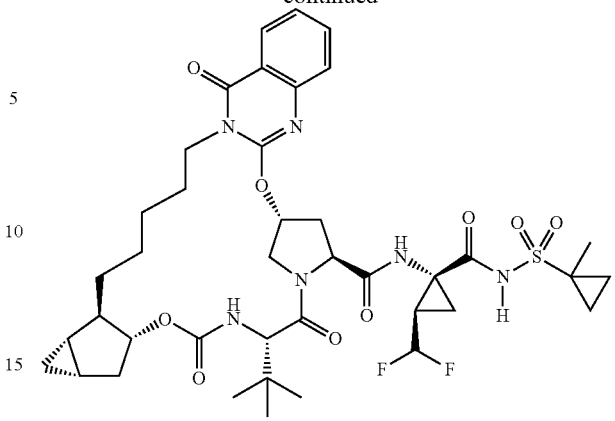

Example 24

Intermediate 24-1 was prepared as for Intermediate 17-4, using intermediate C12 in place of Intermediate C8 in step 1. LCMS-ESI+ (m/z): [M+H]+ calcd for $C_{32}H_{40}ClN_4O_7$: 627.26. found: 627.10.

Step 1: Preparation of 25-1 and 24-2. Macrocyclic olefin 24-1 (0.574 g, 0.915 mmol) was dissolved in 100 mL ethyl acetate. After degassing with Ar, 5% Rh/Al (0.12 g, 115 mmol) was added and the mixture was hydrogenated for 24 hours at 1 atm. Filtration through Celite, concentration, and silica gel chromatography (10%-25% ethyl acetate in hexanes gradient) provided intermediate 24-2 (24 mg) and intermediate 25-1 (385 mg). For 25-1, LCMS-ESI+ (m/z): [M+H]+ calcd for $C_{32}H_{42}ClN_4O_7$: 629.27. found: 629.28. For 24-2, LCMS-ESI+ (m/z): [M+H]+ calcd for $C_{32}H_{43}N_4O_7$: 595.31. found: 594.91.

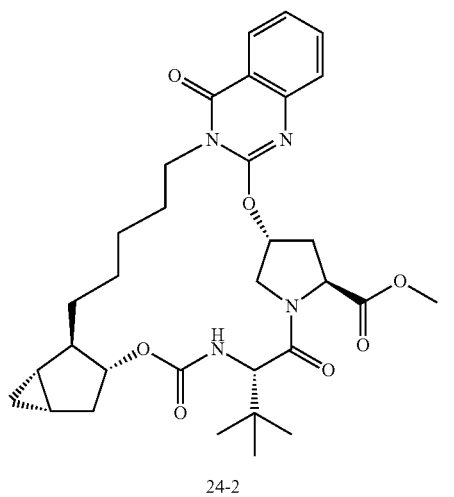

24-2

Step 2. Preparation of 24-3: A mixture of Intermediate 24-2 (24 mg) in 1 mL methanol was treated 0.25 mL of 1N lithium hydroxide. After 2 hours, the mixture was concentrated under reduced pressure and partitioned between water and ethyl acetate. The organic phase was dried over anhydrous sodium sulphate, filtered, concentrated to yield 24-3 (25 mg). LCMS-ESI+ (m/z): [M+H]+ calcd for $C_{31}H_{41}N_4O_7$: 581.30. found: 581.03.

Step 3. Preparation of Example 24: To a suspension of carboxylic acid 24-3 (25 mg, 0.044 mmol) and Intermediate A10 (16 mg, 0.053 mmol) in DMF (0.2 mL) was added HATU (20 mg, 0.053 mmol) and DIPEA (31 μL, 0.176 mmol) at 23° C. After 10 min, the solution was treated with 0.5 mL formic acid and purified by reverse phase HPLC to provide the TFA salt of Example 24 (11.7 mg).

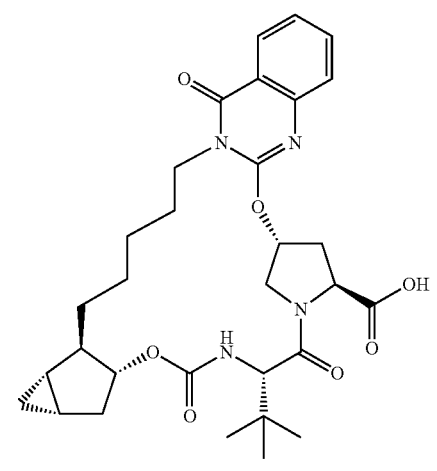

24-3

Analytical HPLC RetTime: 8.72 min. LCMS-ESI+ (m/z): [M+H]+ calcd for $C_{40}H_{53}F_2N_6O_9S$: 831.95. found: 831.36.

Example 25
Preparation of (1aS,2aR,6S,9S,11R,24aR,24bS)-6-tert-butyl-15-cyano-N-[(1R,2R)-2-(difluoromethyl)-1-{[(1-methylcyclopropyl)sulfonyl]carbamoyl}cyclopropyl]-4,7,18-trioxo-1a,2,2a,4,5,6,7,10,11,20,21,22,23,24,24a,24b-hexadecahydro-1H,9H,18H-8,11-methanocyclopropa[4',5']cyclopenta[1',2':18,19][1,10,3,6,12]dioxatriazacyclonona decino[11,12-b]quinazoline-9-carboxamide
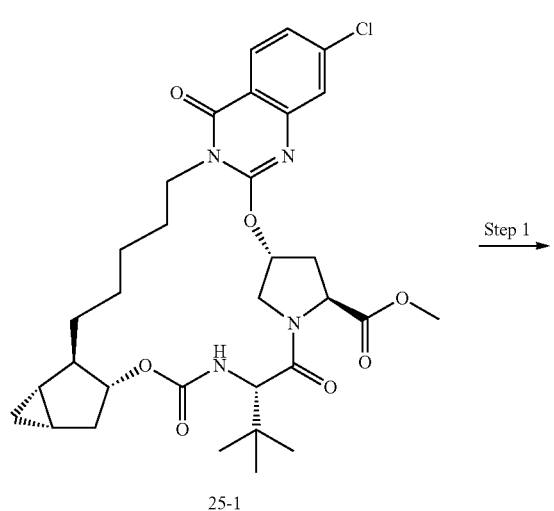
25-1
Step 1 →
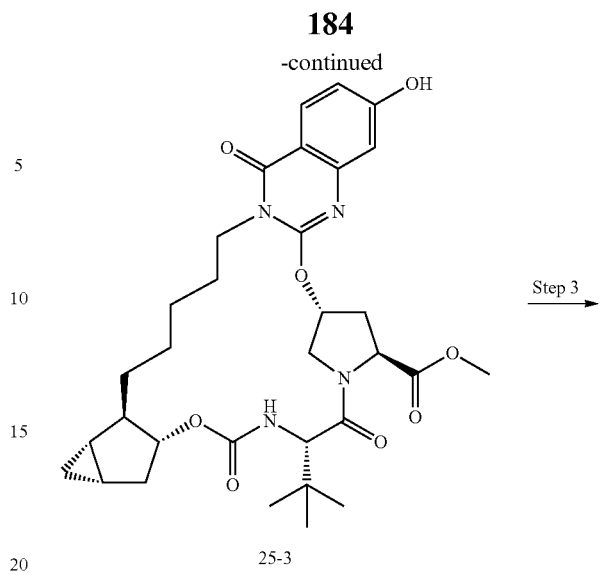
25-3
Step 3 →
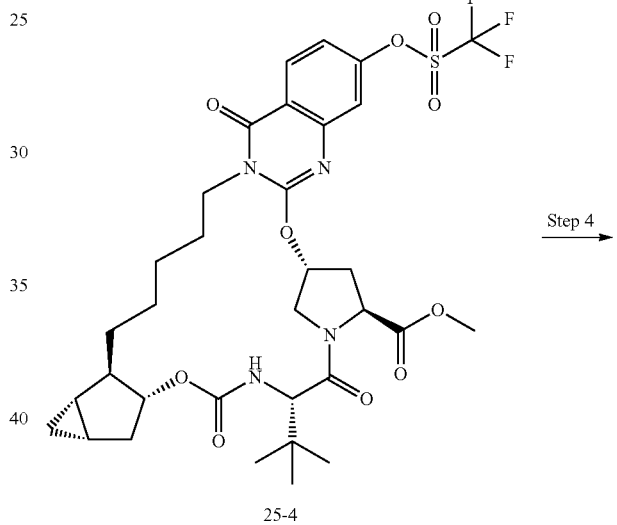
25-4
Step 4 →
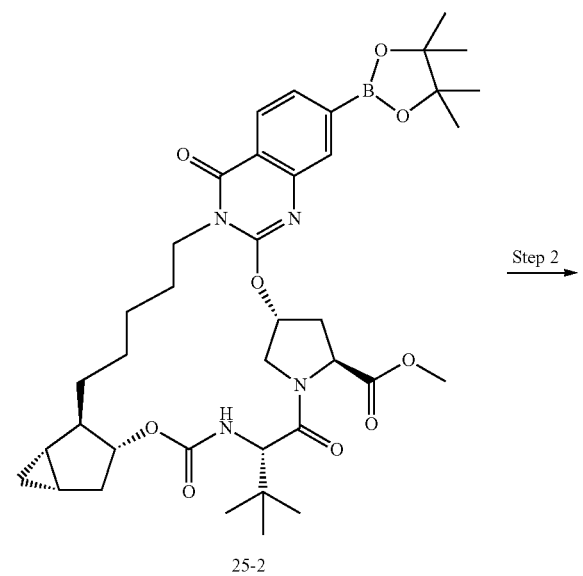
25-2
Step 2 →
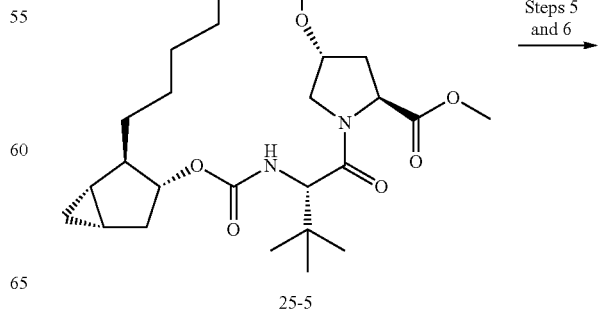
25-5
Steps 5 and 6 →

-continued

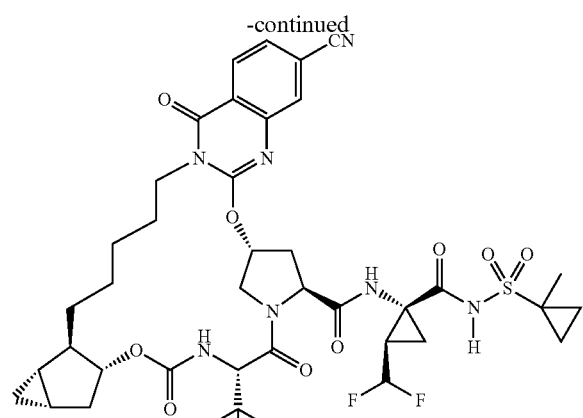

Example 25

Step 1. Preparation of 25-2. Intermediate 25-1 (0.315 g, 0.501 mmol), Bis (Pinacolato) Diboron (0.25 g, 1 mmol), and potassium acetate (0.15 g, 1.5 mmol) was dissolved in 5 mL 1,4-dioxane and degassed with Ar for 15 minutes. Then tris(dibenzylideneacetone) dipalladium (0) (0.02 g, 0.02 mmol) and 2-(dicyclohexylphosphino)-2',4',6'-triisopropylbiphenyl (0.02 g, 0.05 mmol) was added and the mixture was heated at 90° C. for 45 minutes. The mixture was concentrated and purified by silica gel chromatography (5%-80% ethyl acetate in hexanes gradient) to provide intermediate 25-2 (0.456 g). LCMS-ESI$^+$ (m/z): [M+H]$^+$ calcd for $C_{38}H_{54}BN_4O_9$: 721.40. found: 721.20.

Step 2. Preparation of 25-3. A solution of 25-2 (0.360 g, 0.5 mmol) in 4 mL THF and 4 mL of 0.5 N sodium hydroxide was treated with hydrogen peroxide (35%, 485.48 mg, 5 mmol) and triethylamine (0.81 ml, 5.81 mmol). After 5 minutes, the reaction was quenched with 1N HCl and extracted with ethyl acetate. The organic layer was dried over Na$_2$SO$_4$, filtered and concentrated. Silica gel chromatography using a 5%-100% ethyl acetate in hexanes gradient gave 25-3 (224 mg). LCMS-ESI$^+$ (m/z): [M+H]$^+$ calcd for $C_{32}H_{43}N_4O_8$: 611.31; found: 611.14.

Step 3. Preparation of 25-4. An ice cold solution of 25-3 (0.104 g, 0.17 mmol) and triethylamine (0.19 ml, 1.362 mmol) in 1 mL DCM was treated with trifluoromethanesulfonic anhydride solution, 1M in methylene chloride (0.043 ml, 0.26 mmol) dropwise. After stirring for 3 hours, the reaction was quenched with water and extracted with ethyl acetate. The organic layer was washed with water and brine, dried over Na$_2$SO$_4$, filtered and concentrated. Silica gel chromatography using a 25%-75% ethyl acetate in hexanes gradient gave 25-4 (126 mg). LCMS-ESI$^+$ (m/z): [M+H]$^+$ calcd for $C_{33}H_{42}F_3N_4O_{10}S$: 743.26. found: 743.06.

Step 4. Preparation of 25-5. Degassed a mixture of macrocycle triflate 25-4 (126 mg, 0.17 mmol), tetrakis (triphenylphosphine)palladium (19.6 mg, 0.017 mmol), zinc cyanide, 98% (39.9 mg, 0.34 mmol) in 1.7 mL DMF for 10 minutes. The reaction was heated at 80° C. for 30 minutes. The reaction was concentrated. The crude product was purified by silica gel chromatography using a gradient of 5%-70% ethyl acetate in hexanes to give intermediate 25-5 (94 mg). LCMS-ESI$^+$ (m/z): [M+H]$^+$ calcd for $C_{33}H_{42}N_5O_7$: 620.31. found: 620.09.

Steps 5 and 6. Preparation of Example 25. A solution of 25-5 (94 mg, 0.015 mmol) in 1.5 mL THF and 1 mL water was treated with lithium hydroxide monohydrate (25 mg, 0.061 mmol) and stirred for 1.5 hours at room temperature.

The mixture was acidified with 1N hydrochloric acid and extracted with ethyl acetate. The organic phase was separated, dried over anhydrous sodium sulphate, filtered and concentrated to give 87 mg of the crude carboxylic acid. This residue was treated with HATU (65.5 mg, 0.172 mmol) and 0.8 mL DMF, then A10 (53 mg, 0.172 mmol) and DIPEA (0.1 ml, 0.58 mmol) were added. After 25 min, several drops of formic acid and methanol to total volume of 1.2 mL was added and the product was purified by reverse phase HPLC to give the TFA salt of Example 25 (75 mg). Analytic HPLC RetTime: 8.65 min. LCMS-ESI$^+$ (m/z): [M+H]$^+$ calcd for $C_{41}H_{52}F_2N_7O_9S$: 856.35. found: 855.95.

Example 26

Preparation of (1aS,2aR,6S,9S,11R,24aR,24bS)-6-tert-butyl-N-[(1R,2R)-2-(difluoromethyl)-1-{[(1-methylcyclopropyl)sulfonyl] carbamoyl}cyclopropyl]-15-methoxy-4,7,18-trioxo-1a,2,2a,4,5,6,7,10,11,20,21,22,23,24,24a,24b-hexadecahydro-1H,9H,18H-8,11-methanocyclopropa [4',5']cyclopenta[1',2':18,19][1,10,3,6,12] dioxatriazacyclonona decino[11,12-b]quinazoline-9-carboxamide

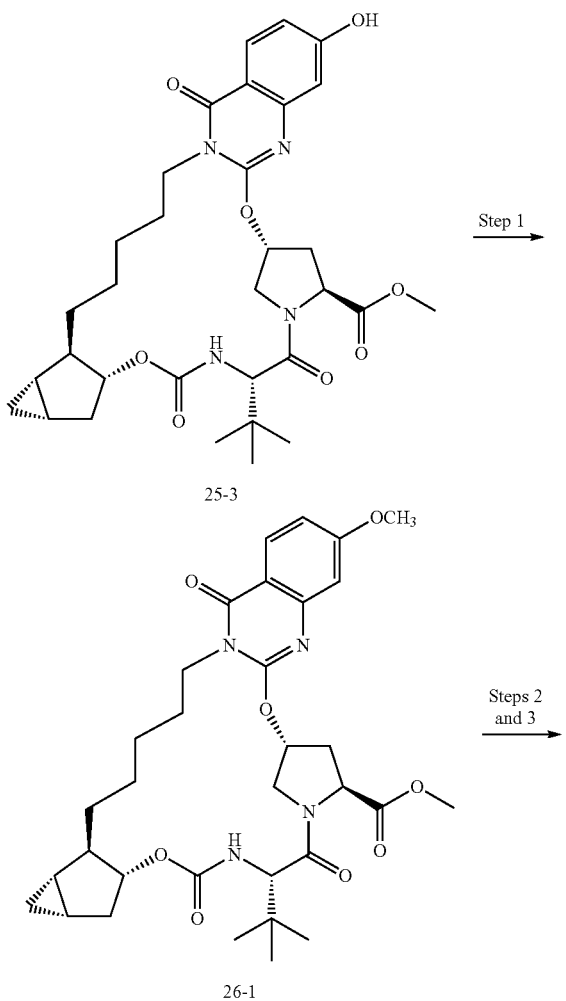

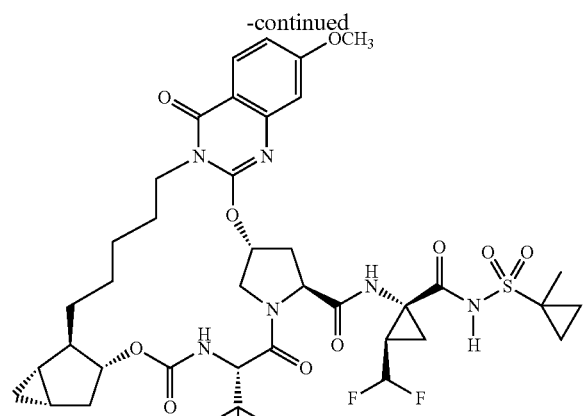

Example 26

Step 1. Preparation of 26-1. To a solution of 25-3 (110 mg, 0.18 mmol) in 2 mL methanol was added iodomethane (0.03 ml, 0.54 mmol) and potassium carbonate (74.68 mg, 0.54 mmol). The mixture was heated at 80° C. for 30 minutes, then was diluted with ethyl acetate and washed with water and brine. The organic phase was concentrated to give crude 26-1, 105 mg (93.3%) which was carried on directly to the step 2. LCMS-ESI$^+$ (m/z): [M+H]$^+$ calcd for $C_{33}H_{45}N_4O_8$: 625.32. found: 625.18.

Steps 2 and 3. Preparation of Example 26. To a solution of 26-1 (105 mg, 0.17 mmol) in 1 mL THF, 1 mL methanol and 1 mL water was added lithium hydroxide monohydrate (28 mg, 0.67 mmol). After 3.5 hours, the reaction was acidified with 1N HCl and extracted into ethyl acetate. The organic phase was dried over anhydrous sodium sulfate, filtered and concentrated, then further dried under vacuum to give 103 mg of the crude carboxylic acid. This residue was treated with HATU (76 mg, 0.20 mmol) and 1.7 mL DMF, then A10 (61 mg, 0.20 mmol) and DIPEA (0.117 ml, 0.668 mmol) were added. After 1 hour, several drops of formic acid and methanol to total volume of 1.2 mL was added and the product was purified by reverse phase HPLC to give the TFA salt of Example 26 (23 mg). Analytic HPLC RetTime: 8.67 min. LCMS-ESI$^+$ (m/z): [M+H]$^+$ calcd for $C_{41}H_{55}N_6O_{10}S$: 861.37. found: 861.08.

Biological Activity

Expression and Purification of Genotype 1a, 2a, and 3 NS3 Proteases

Generation of NS3 Protease Expression Plasmids

The coding sequence of the genotype 1b (con-1 strain) HCV NS3 protease domain was PCR amplified from a plasmid encoding the 1389luc-ubi-neo/NS3-3'/ET replicon (Reblikon, Mainz, Germany). The 5'-PCR primer was designed to encode an N-terminal $K_3$ hexahistidine tag and to insert an in-frame recombinant Tobacco Etch virus (rTEV) protease cleavage site into the NS3 coding sequence. The resulting DNA fragment was cloned into the pET28 protein expression vector (Invitrogen, Carlsbad, Calif.) yielding the p28-N6H-Tev-NS3(181)1b.

The coding sequences for the genotype 3 HCV protease domain was amplified by RT-PCR using a Titan One Tube RT-PCR Kit (Roche, Indianapolis, Ind.) and RNA extracted from HCV-positive human serum (BBI Diagnostics, MA) using a QIAmp UltraSens Virus Kit (Qiagen, Valencia, Calif.). 5' PCR primers were designed to encode N-terminal hexahistidine tags and to insert in-frame rTEV protease cleavage sites into the NS3 protease coding sequences. The resulting DNA fragments were cloned into pET28 yielding the expression vectors p28-N6H-Tev-NS3(181)1a and p28-N6H-Tev-NS3(181)3, respectively.

NS3 Protease Protein Expression

BL21AI bacteria (Invitrogen, Carlsbad, Calif.) were transformed with genotype 1b or 3 NS3 expression vectors and used to inoculate a 20 L fermentation vessel (Sartorius BBI System Inc., Bethlehem, Pa.), containing 18 L of fresh 2YT medium supplemented with 50 μg/ml kanamycin. When cell densities reached an $OD_{600}$ of 1, the temperature of the cultures was reduced from 37° C. to 28° C. and induction was immediately initiated by the addition of 30 μM $ZnSO_4$, 14 mM L-arabinose and 1 mM Isopropyl β-D-thiogalactoside (IPTG) final concentrations. Cells were harvested by centrifugation four hours post-induction and were stored as frozen pellets at −80° C. prior to NS3 protein purification.

Purification of NS3 Proteases

Purification of Genotype 1b NS3 Protease
Cell pellets were thawed and resuspended at 10 ml/g cells in lysis buffer containing 50 mM tris pH 7.6, 300 mM NaCl, 0.1% 3-[(3-Cholamidopropyl)dimethylammonio]-1-propanesulfonate (CHAPS), 5% glycerol, and 2 mM β-mercaptoethanol. Cell suspensions were then sonicated, filtered through cheesecloth, and passed three times through a microfluidizer at 18,000 pounds/in$^2$. The resulting lysates were centrifuged at 15500 rpm for 45 minutes and supernatants were loaded onto a HisTrap HP column (GE Lifesciences) pre-equilibrated with five volumes of Ni buffer A (50 mM tris pH 7.6, 300 mM NaCl, 0.1% CHAPS, 5% glycerol, 2 mM β-mercaptoethanol, 50 mM imidazole-HCl). Proteins were eluted with a 0-100% gradient of Ni buffer A plus 500 mM imidazole-HCl and fractions were collected and pooled. The HisTrap pool was diluted 1:10 with SP-A buffer (50 mM tris pH 7.0, 10% glycerol, 2 mM dithiothreitol (DTT)) and loaded onto a HiTrap SP-HP column (GE Lifesciences) equilibrated with SP-A buffer. NS3 protease was eluted with a 0-100% SP-B buffer (SP-A buffer plus 1 M NaCl) gradient. Concentrated pools of NS3-containing SP fractions were aliquoted, snap frozen in liquid nitrogen and stored at −80° C.

Purification of Genotype 3 NS3 Protease
Bacterial pellets collected from the expression of genotype 3 HCV NS3 protease were homogenized in Lysis Buffer (25 mM tris, pH 7.5 buffer containing 150 mM NaCl and 1 mM phenylmethanesulfonyl fluoride (PMSF)) and passed through a microfluidizer at 18,000 pounds/in$^2$. Homogenized cell lysates were centrifuged at 30,000×g for 30 minutes at 4° C. The resulting P1 pellets were washed with Wash Buffer I (25 mM tris, pH 7.5 containing 1% CHAPS) followed by centrifugation at 10,000×g for 30 minutes at 4° C. The resulting P2 pellets were washed with Wash Buffer 11(50 mM CAPS buffer, pH 10.8, containing 2M NaCl and 2 M urea) followed by centrifugation at 30,000×g for minutes at 4° C. The resulting P3 pellets were resuspended in Solubilization Buffer (20 ml of 25 mM tris, pH 7.5 containing 150 mM NaCl and 8 M urea) and incubated at 4° C. for one hour. Solubilized proteins were passed through a 0.45 micron filter. Protein concentrations were measured and the solutions were adjusted to 40 mM DTT, incubated for 30 minutes at 4° C. and then quickly diluted into Refolding Buffer (25 mM tris, pH 8.5, 0.8 M Guanidine-HCl, 0.4 M L-Arginine, 10 mM ZnSO$_4$) while stirring. Protein solutions were incubated at 4° C. overnight to allow refolding. Refolded proteases were centrifuged at 30,000×g for 10 minutes to remove residual precipitates. Final protein concentrations were then measured and the NS3 proteases were aliquoted, snap frozen in liquid nitrogen and stored at −80° C.

Ki Determination for Genotypes 1b and 3a NS3 Protease.

Purified NS3 protease domain (amino acids 1-181) of the genotype 1b and 3a virus were generated as above. The internally quenched fluorogenic depsipeptide substrate Ac-DED(Edans)-EEAbuψ[COO]ASK(Dabcyl)-NH$_2$ and a synthetic peptide containing the hydrophobic core residues of the NS4A protein cofactor (KKGSWIVGRIILSGRKK; NS4A peptide) were obtained from Anaspec, Inc. (San Jose, Calif.). Other chemicals and biochemicals were of reagent grade or better and were purchased from standard suppliers.

Reactions were run at room temperature in buffer consisting of 50 mM HEPES, 40% glycerol, 0.05% Triton X-100, 10 mM DTT, and 10% DMSO. The final assay solutions contained 50 pM NS3 genotype 1b protease or 200 pM genotype 3a protease, 20 μM NS4A peptide, and 4 μM substrate (genotype 1b) or 2 μM substrate (genotype 3a). Inhibitor concentrations varied from 100 nM to 5 pM in 3-fold dilutions, and no-inhibitor controls were included.

Compound dilutions were made in DMSO at 20× final concentration. Reaction mixtures were prepared in 96-well assay plates. A solution of enzyme and NS4A peptide in assay buffer (25 μL volume with both reagents at 4× final concentration) was mixed with 45 μL assay buffer and 5 μL of either inhibitor or DMSO, and pre-incubated at room temperature for 1 hour. The reaction was started by addition of 25 μL substrate solution at 4× final concentration. Plates were mixed vigorously for 5-10 seconds and reactions were allowed to proceed for 90 minutes. Fluorescence was measured every 30 s between 90 and 120 minutes reaction time using a Tecan InfiniTe M1000 or PerkinElmer Envision multimode plate reader with an excitation wavelength of 340 nm and an emission wavelength of 490 nm.

Rates were calculated from the progress curves at steady state, in the time frame of 90-120 minutes after addition of substrate. To determine the $K_i$, rates were plotted as a function of inhibitor concentration, and the data were fit with equation 1 (Morrison, J. F., *Biochimica et Biophysica Acta* 1969, 185, 269-286) to calculate $K_i^{app}$ using GraphPad Prism 5. Active fraction of enzyme was determined by active site titration with known potent inhibitors. $K_i$ was calculated from $K_i^{app}/(1+[[S]/K_m])$.

$$\frac{v}{v_0} = \frac{[E]_t - [I]_t - K_i^{app} + \sqrt{([E]_t - [I]_t - K_i^{app})^2 + 4[E]_t K_i^{app}}}{2[E]_t} \quad (1)$$

Evaluation of Cell-Based Anti-HCV Activity:

Antiviral potency (EC$_{50}$) was determined in both stable subgenomic HCV replicon cell lines and transient-transfected HCV replicon cells. The term half maximal effective concentration (EC$_{50}$) refers to the concentration of a drug which induces a response halfway between the baseline and maximum after the exposure time specified below.

Stable subgenomic HCV replicons for genotype 1a, 1b, 2a, 3a, and 4a were established in Huh-7-derived cells as described by Lohmann et al (Lohmann V, Korner F, Koch J, et al Replication of subgenomic hepatitis C virus RNAs in a hepatoma cell line. Science 1999; 285:119-3). Each stable cell line contains a bicistronic HCV replicon that encodes a humanized *Renilla luciferase* (hRLuc) reporter gene fused to a selectable neomycin-resistance gene, followed by an EMCV IRES and the NS3-NS5B coding region of HCV. Selection for cells constitutively expressing the HCV replicon was achieved in the presence of the selection antibiotic, neomycin (G418). Luciferase activity was measured as a marker for intracellular HCV replication levels.

The genotype 1a stable replicon was derived from the H77 HCV strain and contained adaptive mutations P1496L and S2204I. The genotype 1b stable replicon was derived from the Con1 HCV strain and contained adaptive mutations E1202G, T1280I, and K1846T. The genotype 2a stable replicon was derived from the JFH-1 HCV strain and did not require adaptive mutations. The genotype 3a stable replicon was derived from the S52 HCV strain and contained adaptive mutations P1121 L, A1198T and S2210I (equivalent to S2204I in genotype 1). The genotype 4a stable replicon was derived from the ED43 HCV strain and contained adaptive mutations Q1691R and S2204I. All replicon cell lines were propagated in Huh-7-derived cells and maintained in Dulbecco's modified Eagle's Medium (DMEM) supplemented with 10% fetal bovine serum (FBS) and 0.5 mg/ml G418.

Transient-transfected HCV replicons were established for genotype 1a, 1b, 3a and NS3/4a protease inhibitor resistant variants D168A in genotype 1b or R155K in genotype 1a. Transient-transfected replicons are also bicistronic subgenomic replicons but do not contain the neomycin selectable marker present in stable replicons. These replicons encode the poliovirus IRES followed by the hRLuc reporter gene, the EMCV IRES and finally the NS3-NS5B coding region of HCV. The genotype 1a (H77) and 1b (Cont) wild-type replicons were derived from the same strain and contained the same adaptive mutations as listed above. The genotype 3a transient replicon was derived from the S52 HCV strain as above, but contained slightly different adaptive mutations P1112L, K1615E and S2210I. Specifically, the secondary adaptive mutation A1198T (A166T) in the protease domain of the stable genotype 3a replicon was replaced with K1615E (K583E) in the NS3 helicase, with no effect on replication efficiency. Removal of A166T located in the protease domain minimizes the impact of this variant on inhibitors targeting the protease domain and represents a protease domain closer to wild type for genotype 3a. Resistant replicons encoding N5314 protease inhibitor mutations were introduced into the 1b or 1a wild-type NS3 gene by site directed mutagenesis. In vitro transcribed RNAs from all transient replicons were transfected into naive Huh-7-derived cell lines by electroporation. Luciferase activity was measured as a marker for intracellular HCV replication levels To perform EC$_{50}$ assays, cells from each HCV replicon were dispensed into 384-well plates. Compounds were dissolved in DMSO at a concentration of 10 mM and diluted in DMSO using an automated pipetting instrument. Three-fold serially diluted compounds were directly added to the cells using an automated instrument. DMSO was used as a negative (solvent; no inhibition) control, and a combination of three HCV inhibitors including a protease inhibitor; an NS5A inhibitor and a nucleoside inhibitor was used at concentrations >100×EC$_{50}$ as a positive control (100% inhibition). Seventy-two hours later, cells were lysed and *Renilla luciferase* activity were quantified as recommended by the manufacturer (Promega-Madison, Wis.). Non-linear regression was performed to calculate EC$_K$, values.

Results are Shown in Tables 1 and 2:

TABLE 1

Biological Activity Values For Stable Subgenomic HCV Replicon Cell Lines

| Example | Ki 1B (nM) | Ki 3A (nM) | $EC_{50}$ 1A RLUC (nM) | $EC_{50}$ 1B RLUC (nM) | $EC_{50}$ 2A RLUC (nM) | $EC_{50}$ 3A RLUC (nM) | $EC_{50}$ 4A RLUC (nM) |
|---|---|---|---|---|---|---|---|
| 1 | 0.02 | 0.03 | 1.1 | 0.99 | 2.5 | 23 | 1.0 |
| 2 | 0.02 | 0.04 | 1.1 | 1.0 | 1.82 | 17 | 1.2 |
| 3 | 0.03 | 0.21 | 3.8 | 3.2 | 15 | 194 | 3.4 |
| 4 | 0.02 | 0.21 | 4.3 | 2.6 | 18 | 429 | 3.1 |
| 5 | 0.02 | 0.27 | 5.0 | 3.5 | 14 | 473 | 3.9 |
| 6 | 0.01 | 1.2 | 723 | 581 | 294 | 3845 | 433 |
| 7 | 0.05 | 9.5 | 95 | 82 | 199 | 3299 | 55 |
| 8 | 0.04 | 8.5 | 76 | 55 | 110 | 2450 | 33 |
| 9 | 0.02 | 0.02 | 1.7 | 1.5 | 2.3 | 6.6 | 1.4 |
| 10 | 0.02 | 0.02 | 1.6 | 1.4 | 1.6 | 4.9 | 1.3 |
| 11 | 0.02 | 0.09 | 1.4 | 1.3 | 2.0 | 61 | 1.2 |
| 12 | 0.02 | 0.09 | 1.7 | 1.3 | 2.6 | 89 | 1.4 |
| 13 | 0.02 | 0.03 | 3.4 | 3.0 | 1.4 | 7.2 | 3.6 |
| 14 | 0.01 | 0.01 | 1.4 | 1.1 | 1.4 | 5.0 | 1.4 |
| 15 | 0.03 | 0.05 | 3.5 | 3.4 | 3.3 | 30 | 2.6 |
| 16 | 0.03 | 0.13 | 3.8 | 4.2 | 2.3 | 127 | 2.3 |
| 17 | 0.01 | 0.02 | 5.8 | 4.7 | 2.7 | 26 | 4.8 |
| 18 | 0.01 | 0.02 | 4.8 | 4.1 | 2.6 | 18 | 4.2 |
| 19 | 0.02 | 0.06 | 1.4 | 1.3 | 3.1 | 82 | 1.8 |
| 20 | 0.04 | 0.07 | 6.0 | 5.9 | 5.0 | 46 | 5.0 |
| 21 | 0.02 | 0.10 | 1.6 | 0.95 | 3.5 | 115 | 1.4 |
| 22 | | | | 5.064 | | | |
| 23 | | | | 2.926 | | | |
| 24 | | | | 3.022 | | | |
| 25 | | | | 2.723 | | | |
| 26 | | | | 1.832 | | | |

TABLE 2

Biological Activity Values For Transient-Transfected HCV Replicon Cell Lines

| Example | $EC_{50}$ 3A WT* (nM) | $EC_{50}$ 1A WT* (nM) | $EC_{50}$ 1A R155K† (nM) | $EC_{50}$ 1B WT* (nM) | $EC_{50}$ 1B D168A‡ (nM) |
|---|---|---|---|---|---|
| 1 | 7.1 | 1.0 | 1.5 | 0.61 | 4.6 |
| 2 | 5.1 | 1.1 | 1.4 | 0.74 | 3.2 |
| 3 | 67 | 5.1 | 11 | 2.9 | 50 |
| 4 | 63 | 2.6 | 27 | 1.2 | 112 |
| 5 | 64 | 4.2 | 35 | 2.1 | 161 |
| 7 | 928 | 72 | 180 | 53 | 1069 |
| 8 | 817 | 72 | 148 | 33 | 712 |
| 9 | 2.5 | 1.3 | 1.1 | 0.71 | 1.1 |
| 10 | 2.3 | 1.4 | 1.3 | 0.75 | 1.0 |
| 11 | 9.7 | 1.4 | 1.9 | 0.78 | 8.6 |
| 12 | 22.0 | 0.8 | 1.9 | 0.64 | 15.6 |
| 13 | 2.8 | 2.8 | 2.0 | 0.99 | 1.1 |
| 14 | 1.4 | 0.9 | 0.69 | 0.55 | 0.65 |
| 15 | 11 | 1.6 | 1.2 | 1.3 | 4.7 |
| 16 | 50 | 1.8 | 2.0 | 1.6 | 7.9 |
| 17 | 7.1 | 3.3 | 2.9 | 1.3 | 2.7 |
| 18 | 4.9 | 3.6 | 2.6 | 1.6 | 2.6 |
| 19 | 17 | 1.3 | 1.9 | 1.1 | 16 |
| 20 | 12 | 5.2 | 5.0 | 4.1 | 6.3 |
| 21 | 36 | 1.5 | 1.4 | 0.61 | 22 |
| 22 | 5.5 | 1.7 | 2.7 | 2.0 | 18 |
| 23 | 9.5 | 1.2 | 2.3 | 0.9 | 11 |
| 24 | 7.6 | 1.7 | 1.5 | 0.8 | 3.3 |
| 25 | 7.5 | 1.8 | 2.0 | 0.70 | 4.4 |
| 26 | 4.5 | 0.8 | 1.0 | 0.4 | 0.9 |

*WT = wild type
†NS3/4a protease inhibitor resistant variants R155K in genotype 1a
‡NS3/4a protease inhibitor resistant variants D168A in genotype 1b The data in Tables 1 and 2 represent an average over time of each assays for each compound. For certain compounds, multiple assays have been conducted over the life of the project.

Pharmaceutical Compositions

The following illustrate representative pharmaceutical dosage forms, containing a compound of formula I, II, or III ('Compound X'), for therapeutic or prophylactic use in humans.

| (i) Tablet 1 | mg/tablet |
|---|---|
| Compound X= | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X= | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X= | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0 N Sodium hydroxide solution (pH adjustment to 7.0-7.5) | q.s. |
| Water for injection | q.s. ad 1 mL |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A compound selected from the group consisting of:

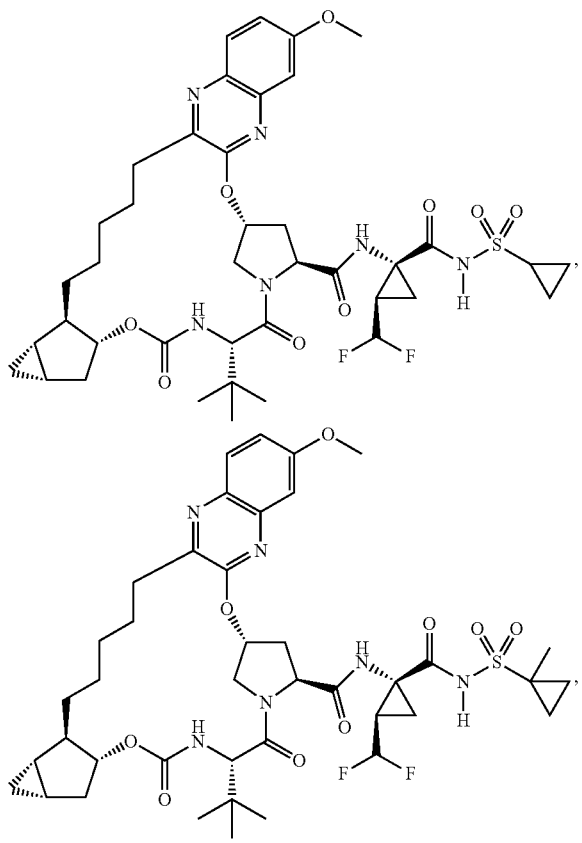

195
-continued
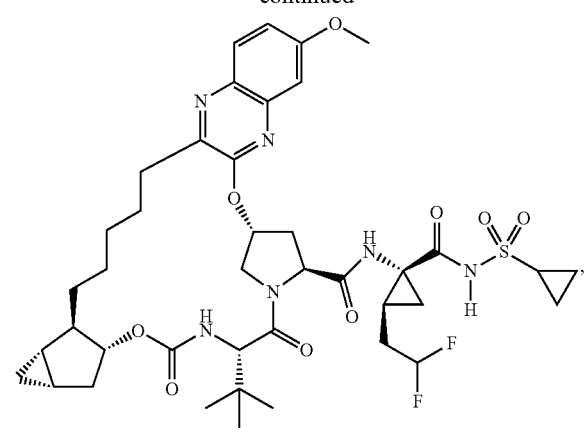
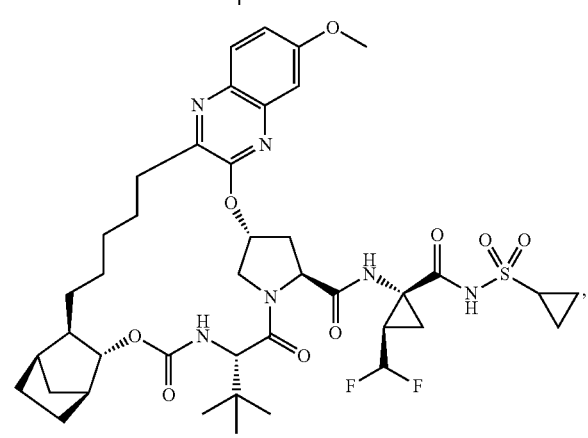
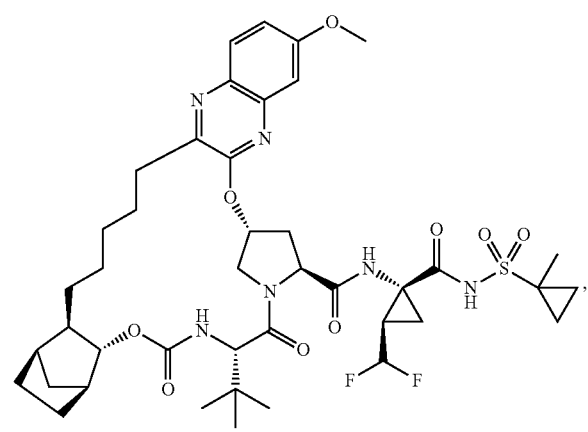
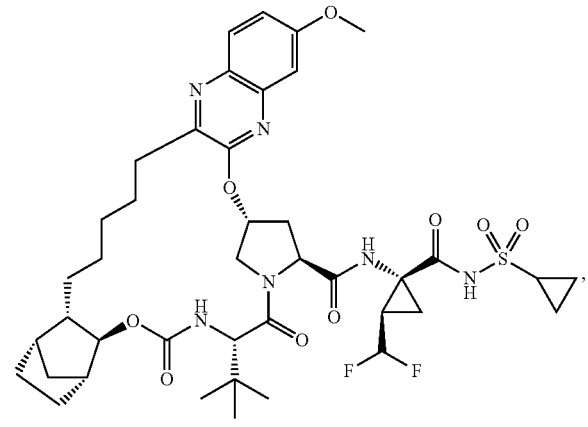
196
-continued
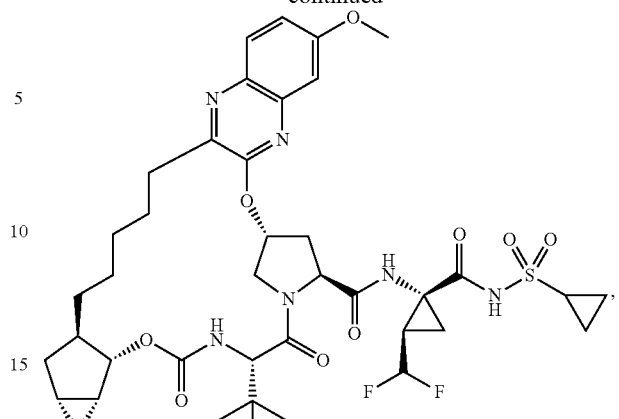
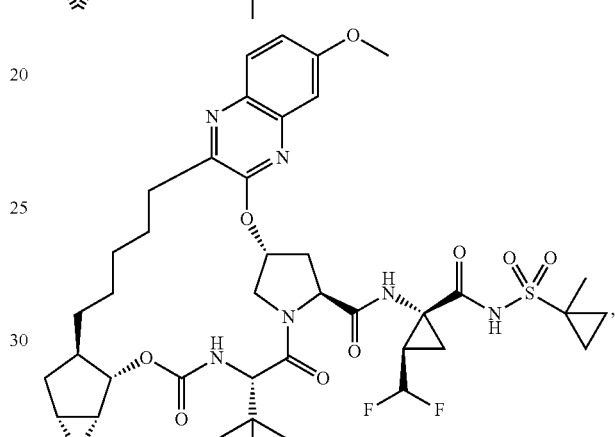
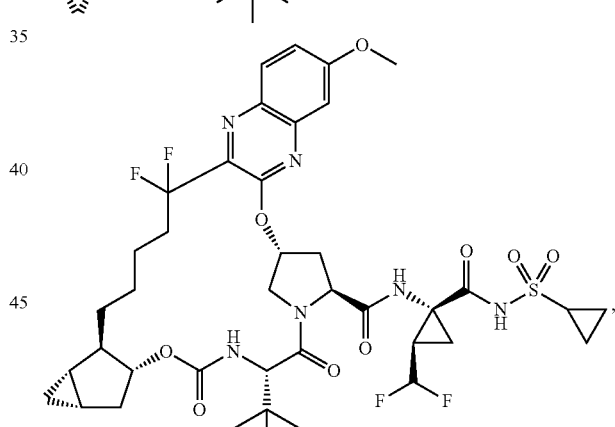
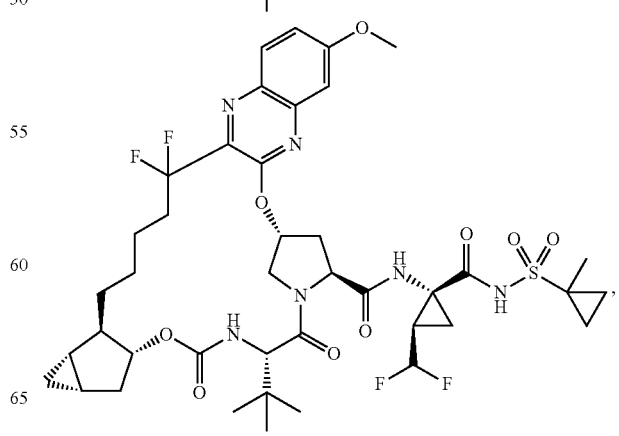

197
-continued
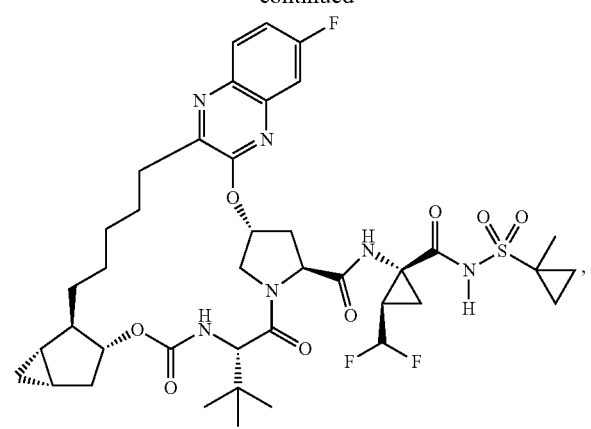
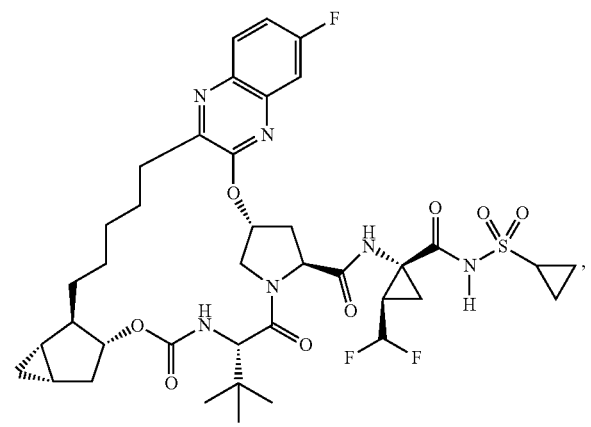
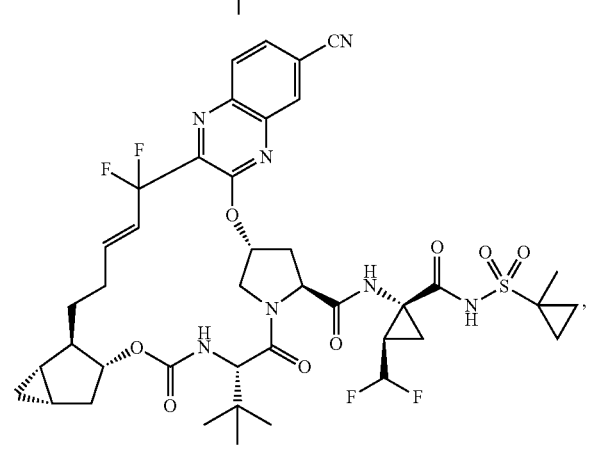
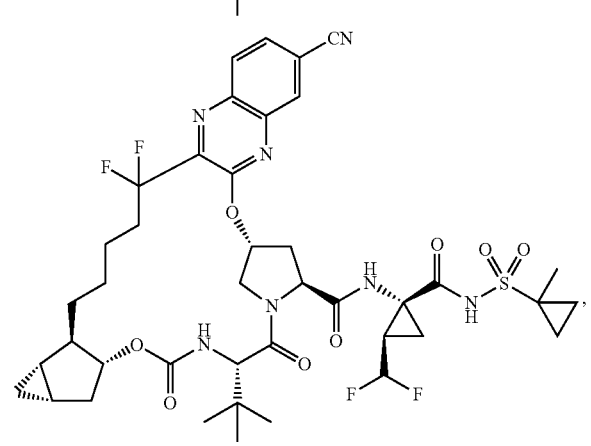
198
-continued
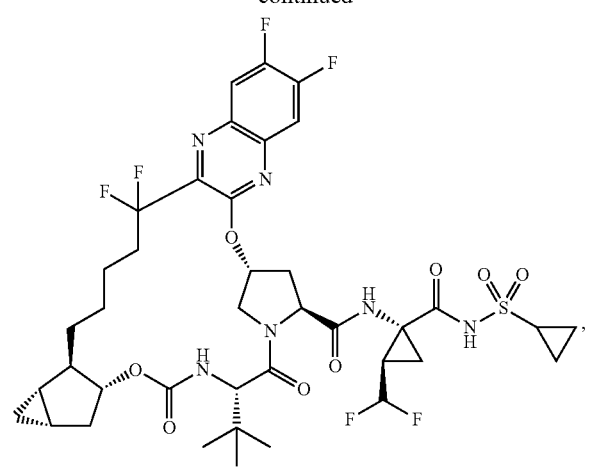
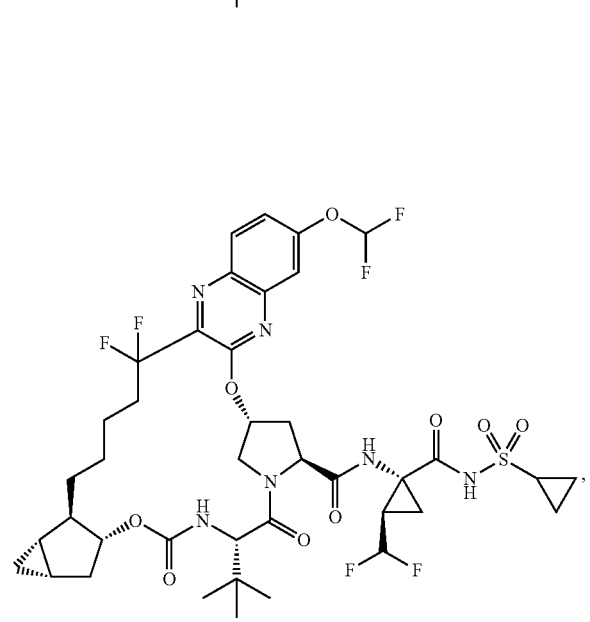
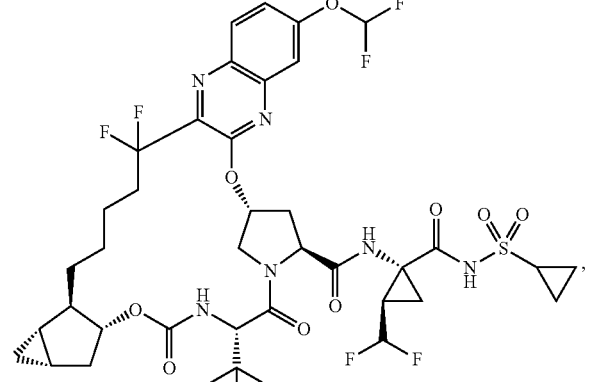

-continued
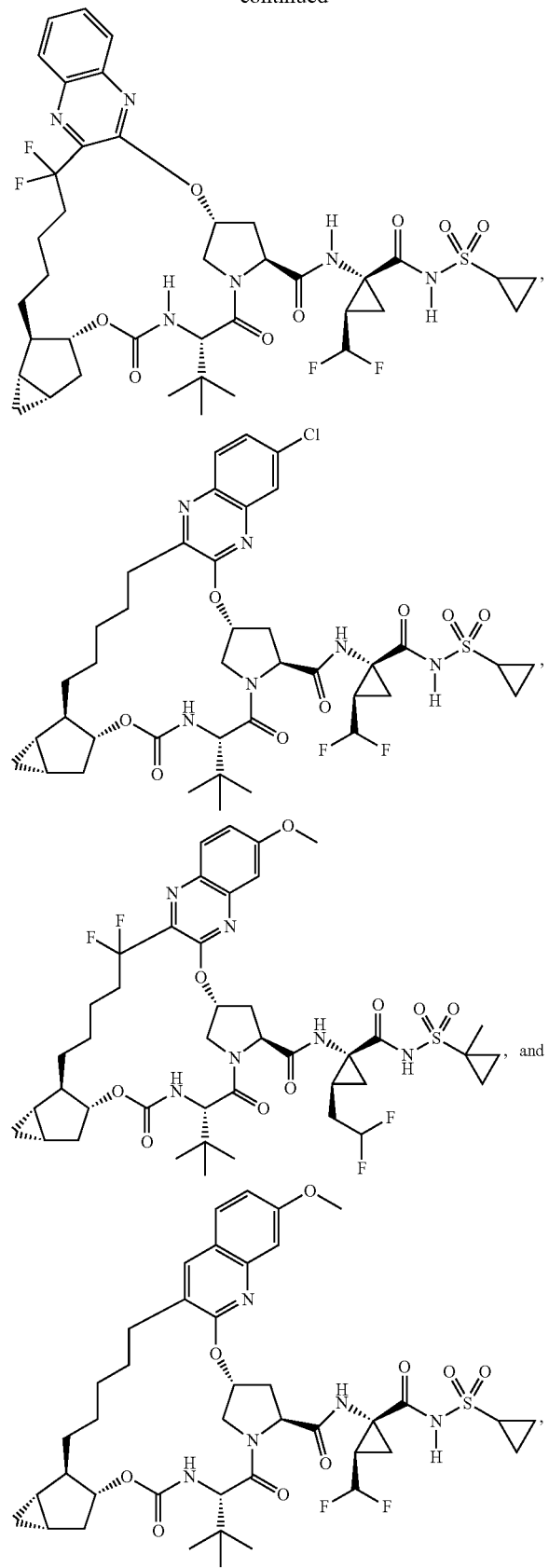
or a pharmaceutically acceptable salt thereof.
2. A compound selected from the group consisting of:
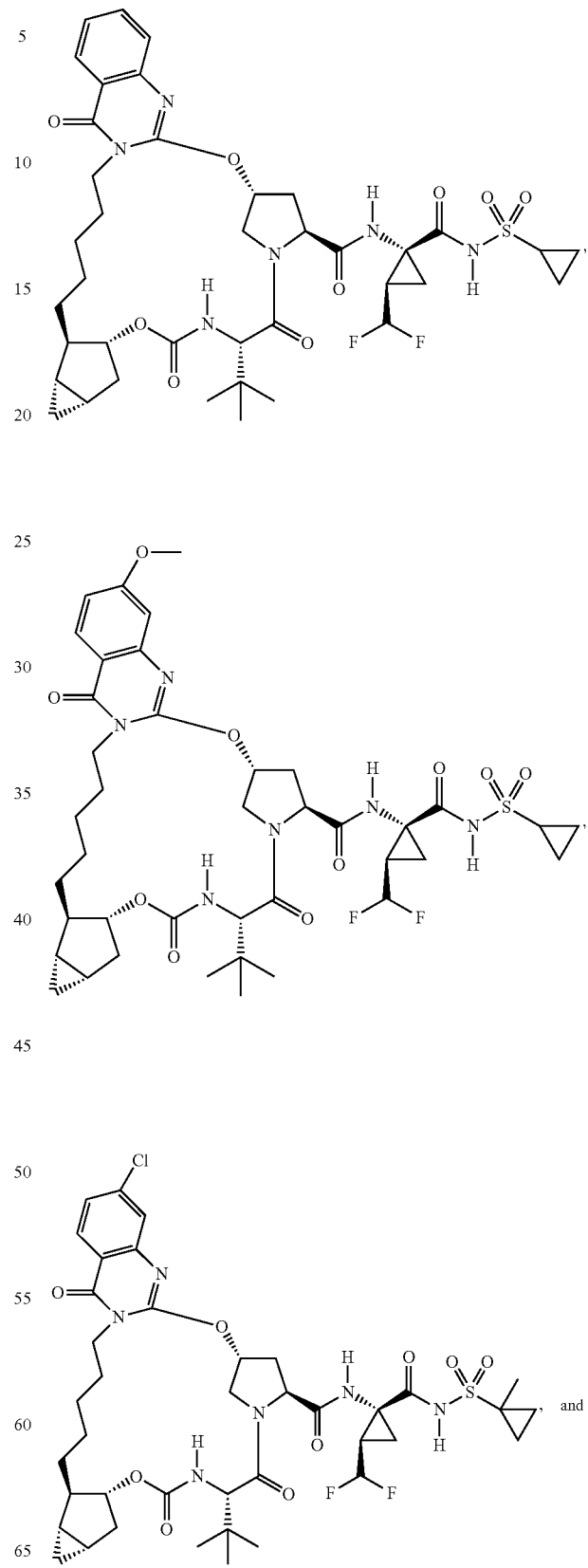

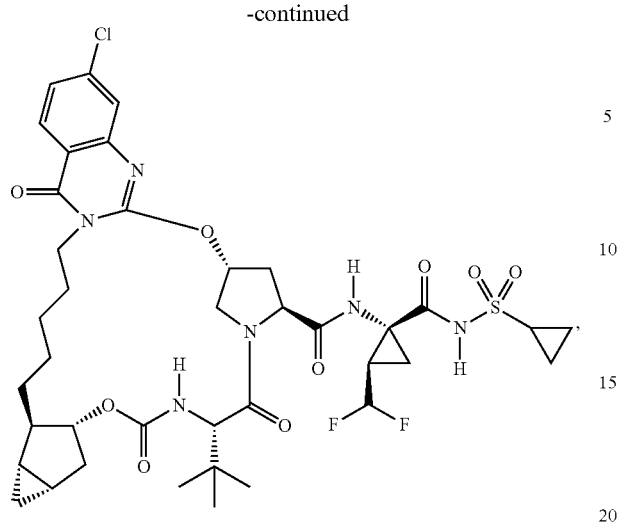
or a pharmaceutically acceptable salt thereof.
3. A pharmaceutical composition comprising a compound of claim 1, and a pharmaceutically acceptable excipient.
4. A method of treating HCV in a patient in need thereof, comprising administering to said patient a compound of claim 1.
* * * * *